(12) United States Patent
Bramhill et al.

(10) Patent No.: US 9,458,454 B2
(45) Date of Patent: *Oct. 4, 2016

(54) VIABLE GRAM NEGATIVE BACTERIA WITH REDUCED PROTEOLYTIC ACTIVITY LACKING OUTER MEMBRANE AGONISTS OF TLR4/MD-2

(75) Inventors: David Bramhill, Tucson, AZ (US); Uwe Mamat, Wahlstedt (DE)

(73) Assignee: Research Corporation Technologies, Inc., Tucson, AZ (US)

( * ) Notice: Subject to any disclaimer, the term of this patent is extended or adjusted under 35 U.S.C. 154(b) by 16 days.

This patent is subject to a terminal disclaimer.

(21) Appl. No.: 14/343,974

(22) PCT Filed: Sep. 7, 2012

(86) PCT No.: PCT/US2012/054139
§ 371 (c)(1),
(2), (4) Date: Mar. 10, 2014

(87) PCT Pub. No.: WO2013/036756
PCT Pub. Date: Mar. 14, 2013

(65) Prior Publication Data
US 2014/0221251 A1 Aug. 7, 2014

Related U.S. Application Data

(60) Provisional application No. 61/533,017, filed on Sep. 9, 2011.

(51) Int. Cl.
| | |
|---|---|
| C12N 1/00 | (2006.01) |
| C12N 15/10 | (2006.01) |
| C12N 9/52 | (2006.01) |
| C12N 15/70 | (2006.01) |
| C12N 15/78 | (2006.01) |
| C12P 19/34 | (2006.01) |
| C12P 21/00 | (2006.01) |

(52) U.S. Cl.
CPC ............ *C12N 15/1037* (2013.01); *C12N 9/52* (2013.01); *C12N 15/70* (2013.01); *C12N 15/78* (2013.01); *C12P 19/34* (2013.01); *C12P 21/00* (2013.01)

(58) Field of Classification Search
None
See application file for complete search history.

(56) References Cited

FOREIGN PATENT DOCUMENTS

| WO | 2007/084633 A2 | 7/2007 |
| WO | 2011/113003 A1 | 9/2011 |

OTHER PUBLICATIONS

Meredith, T.C. et al., "Redefining the Requisite Lipopolysaccharide Structure in *Echerichia coli*" ACS Chemical Biology (Feb. 2006) pp. 33-42, vol. 1, No. 1.

Wang, X. et al., "Lipopolysaccharide: Biosynthetic pathway and structure modification" Progress in Lipid Research (Apr. 2010) pp. 97-107, vol. 49, No. 2.
Supplementary European Search Report dated Feb. 2, 2015 issued in European Application No. EP 12829962.5.
Meredith, T.C. et al., "Identification of GutQ from *Escherichia coli* as a D-arabinose 5-phosphate isomerase" J Bacteriol (Oct. 2005) pp. 6936-2942, vol. 187, No. 20.
Qureshi, S.T. et al., "Endotoxin-tolerant Mice Have Mutations in Toll-like Receptor 4 (Tlr4)" J. Exp. Med. (Feb. 15, 1999) pp. 615-625, vol. 189, No. 4.
Shimazu, R. et al., "MD-2, a Molecule that Confers Lipopolysaccharide Responsiveness on Toll-like Receptor 4" J. Exp. Med. (Jun. 7, 1999) pp. 1777-1782, vol. 189, No. 11.
Poltorak, A. et al., "Defective LPS signaling in C3H/HeJ and C57BL/10ScCr mice: mutations in Tlr4 gene" Science (Dec. 11, 1998) pp. 2085-2088, vol. 282.
Cognet, I. et al, "Expression of recombinant proteins in a lipid A mutant of *Escherichia coli* BL21 with a strongly reduced capacity to induce dendritic cell activation and maturation" Journal of Immunological Methods (Jan. 15, 2003) pp. 199-210, vol. 272, No. 1-2.
Blattner, F.R. et al., "The Complete Genome Sequence of *Escherichia coli* K-12" Science (Sep. 5, 1997) pp. 1453-1462, vol. 277, No. 5331.
Riley, M. et al., "*Escherichia coli* K-12: a cooperatively developed annotation snapshot—2005" Nucleic Acids Res (Jan. 5, 2006) pp. 1-9, vol. 34, No. 1.
Chow, J. et al., "Toll-like receptor-4 mediates lipopolysaccharide-induced signal transduction" J Biol Chem (Apr. 16, 1999) pp. 10689-10692, vol. 274, No. 16.
Chang, J. et al., "Differential host response to LPS variants in amniochorion and the TLR4IMD-2 system in Macaca nemestrina" Placenta (Sep. 2010) pp. 811-817, vol. 31, No. 9.
Rallabhandi, P. et al., "Analysis of proteinase-activated receptor 2 and TLR4 signal transduction" J Biol Chem (Sep. 5, 2008) pp. 24314-24325, vol. 283, No. 36.

(Continued)

*Primary Examiner* — Jennifer Graser
(74) *Attorney, Agent, or Firm* — Scully, Scott, Murphy & Presser, P.C.

(57) ABSTRACT

Viable Gram-negative bacteria or components thereof comprising outer membranes that substantially lack a ligand, such as Lipid A or 6-acyl lipidpolysaccharide, that acts as an agonist of TLR4/MD-2. The bacteria may comprise reduced activity of arabinose-5-phosphate isomerases and one or more suppressor mutations, for example in a transporter thereby increasing the transporter's capacity to transport lipid IVA or in membrane protein YhjD. One or more genes (e.g., lpxL, lpxM, pagP, lpxP, and/or eptA) may be substantially deleted and/or one or more enzymes (e.g., LpxL, LpxM, PagP, LpxP, and/or EptA) may be substantially inactive. The bacteria may be competent to take up extracellular DNA, may be donor bacteria, or may be members of a library. The present invention also features methods of creating and utilizing such bacteria.

19 Claims, 95 Drawing Sheets

(56) References Cited

OTHER PUBLICATIONS

Lohmann, K.L. et al., "The equine TLR4IMD-2 complex mediates recognition of lipopolysaccharide from Rhodobacter sphaeroides as an agonist" J Endotoxin Res (2007) pp. 235-242, vol. 13, No. 4.

International Search Report dated Dec. 20, 2012 issued in International Application No. PCT/US2012/054139.

Phue, J.N. et al., "Modified *Escherichia coli* B (BL21), a Superior Producer of Plasmid DNA Compared with *Escherichia coli* K (DH5α)" Biotechnology and Bioengineering (Nov. 1, 2008) pp. 831-836, vol. 101, No. 4.

European Communication dated Oct. 8, 2015 received from European Application No. 12 829 962.5.

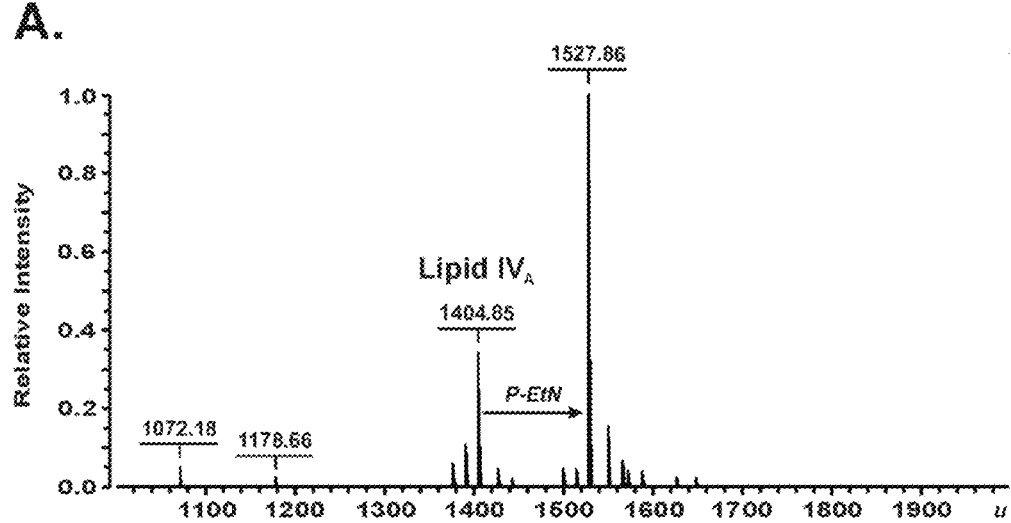
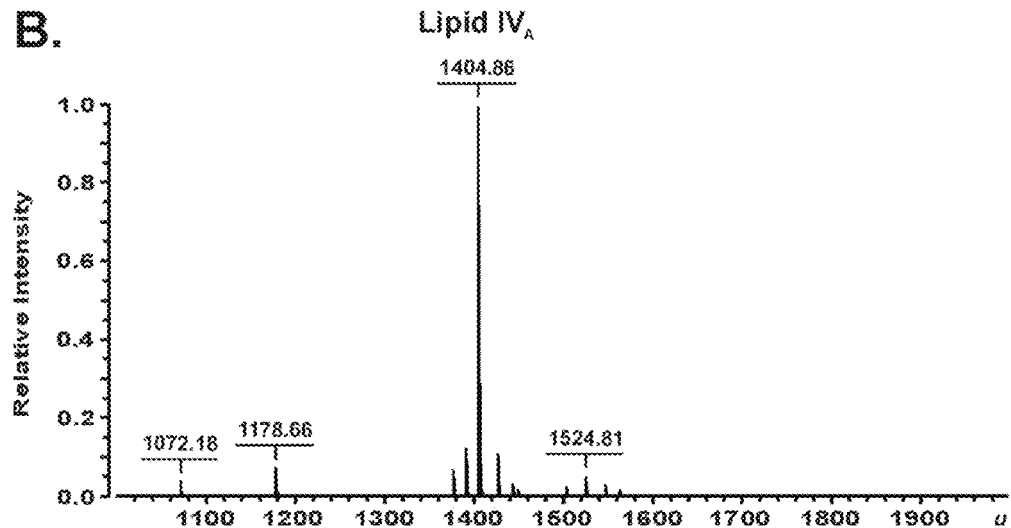
Figure 11

*Escherichia coli* KPM316 (*msbA52 ΔkdsD ΔgutQ ΔlpxL ΔlpxM ΔpagP ΔlpxP ΔeptA*)

The sequence of the sense strand of the organism is the *E coli* reference sequence with the following alterations:

*msbA52* replaces the wild type allele of *msbA*, wherein a C at 965895 is replaced by a T, resulting in a Serine instead of Proline at amino acid 18 in the MsbA protein.

SEQ ID NO: 5:

965844                                                                C>T 965895

ATGCATAACGACAAAGATCTCTCTACGTGGCAGACATTCCGCCGACTGTGGTCAACCATTGCG
CCTTTCAAAGCGGGTCTGATCGTGGCGGGCGTAGCGTTAATCCTCAACGCAGCCAGCGATACCT
TCATGTTATCGCTCCTTAAGCCACTTCTTGATGATGGCTTTGGTAAAACAGATCGCTCCGTGCT
GGTGTGGATGCCGCTGGTGGTGATCGGGCTGATGATTTTACGTGGTATCACCAGCTATGTCTCC
AGCTACTGTATCTCCTGGGTATCAGGAAAGGTGGTAATGACCATGCGTCGCCGCCTGTTTGGTC
ACATGATGGGAATGCCAGTTTCATTCTTTGACAAACAGTCAACGGGTACGCTGTTGTCACGTAT
TACCTACGATTCCGAACAGGTTGCTTCTTCTTCTTCCGGCGCACTGATTACTGTTGTGCGTGAA
GGTGCGTCGATCATCGGCCTGTTCATCATGATGTTCTATTACAGTTGGCAACTGTCGATCATTT
TGATTGTGCTGGCACCGATTGTTTCGATTGCGATTCGCGTTGTATCGAAGCGTTTTCGCAACAT
CAGTAAAAACATGCAGAACACCATGGGGCAGGTGACCACCAGCGCAGAACAAATGCTGAAGGGC
CACAAAGAAGTATTGATTTTCGGTGGTCAGGAAGTGGAAACGAAACGCTTTGATAAAGTCAGCA
ACCGAATGCGTCTTCAGGGGATGAAAATGGTTTCAGCCTCTTCCATCTCTGATCCGATCATTCA
GCTGATCGCCTCTTTGGCGCTGGCGTTTGTTCTGTATGCGGCGAGCTTCCCAAGTGTCATGGAT
AGCCTGACTGCCGGTACGATTACCGTTGTTTTCTCTTCAATGATTGCACTGATGCGTCCGCTGA
AATCGCTGACCAACGTTAACGCCCAGTTCCAGCGCGGTATGGCGGCTTGTCAGACGCTGTTTAC
CATTCTGGACAGTGAGCAGGAGAAAGATGAAGGTAAGCGCGTGATCGAGCGTGCGACTGGCGAC
GTGGAATTCCGCAATGTCACCTTTACTTATCCGGGACGTGACGTACCTGCATTGCGTAACATCA
ACCTGAAAATTCCGGCAGGGAAGACGGTTGCTCTGGTTGGACGCTCTGGTTCGGGTAAATCAAC
CATCGCCAGCCTGATCACGCGTTTTTACGATATTGATGAAGGCGAAATCCTGATGGATGGTCAC
GATCTGCGCGAGTATACCCTGGCGTCGTTACGTAACCAGGTTGCTCTGGTGTCGCAGAATGTCC
ATCTGTTTAACGATACGGTTGCTAACAACATTGCTTACGCACGGACTGAACAGTACAGCCGTGA
GCAAATTGAAGAAGCGGCGCGTATGGCCTACGCCATGGACTTCATCAATAAGATGGATAACGGT
CTCGATACAGTGATTGGTGAAAACGGCGTGCTGCTCTCTGGCGGTCAGCGTCAGCGTATTGCTA
TCGCTCGAGCCTTGTTGCGTGATAGCCCGATTCTGATTCTGGACGAAGCTACCTCGGCTCTGGA
TACCGAATCCGAACGTGCGATTCAGGCGGCACTGGATGAGTTGCAGAAAAACCGTACCTCTCTG
GTGATTGCCCACCGCTTGTCTACCATTGAAAAGGCAGACGAAATCGTGGTCGTCGAGGATGGTG
TCATTGTGGAACGCGGTACGCATAACGATTTGCTTGAGCACCGCGGCGTTTACGCGCAACTTCA
CAAAATGCAGTTTGGCCAATGA

*ΔgutQ*

Nucleotides 2827846 to 2828789 are deleted from the reference sequence and the following sequence is incorporated into KPM316 (the terminal nucleotides, shown at the ends of the sequence, are present in KPM316 and correspond to bases of the MG1655 genome: C at 2827845 and G at 2828790):

SEQ ID NO: 6:

2827845
CGTGTAGGCTGGAGCTGCTTCGAAGTTCCTATACTTTCTAGAGAATAGGAACTTCGGAATAGGA
AGGTCGACGGATCCCCGGAATG
                    2828790

Figure 12B

*ΔkdsD*

Nucleotides 3339288 to 3340264 are deleted from the reference sequence and the following sequence is incorporated into KPM316 (the terminal nucleotides, shown at the ends of the sequence, are present in KPM316 and correspond to bases of the MG1655 genome: T at 3339287 and C at 3340265):

SEQ ID NO: 7:

3339287
TGTGTAGGCTGGAGCTGCTTCGAAGTTCCTATACTTTCTAGAGAATAGGAACTTCGGAATAGGA
ACTAAGGAGGATATTCATATGC
                    3340265

Figure 12C

*ΔlpxL*
(coding sequence of *lpxL* is complement of the reference nucleic acid strand)
Nucleotides 1114958 to 11155744 are deleted from the reference sequence and the following sequence is incorporated into KPM316 (the terminal nucleotides, shown at the ends of the sequence, are present in KPM316 and correspond to bases of the MG1655 genome: C at 1114957 and C at 1115745):

SEQ ID NO: 8:

1114957
C̲TATGAATATCCTCCTTAGTTCCTATTCCGAAGTTCCTATTCTCTAGAAAGTATAGGAACTTCG
AAGCAGCTCCAGCCTACACC̲
             1115745

Figure 12D

*ΔlpxM*
(coding sequence of *lpxM* is complement of the reference nucleic acid strand)
Nucleotides 1937303 to 1938151 are deleted from the reference sequence and the following sequence is incorporated into KPM316 (the terminal nucleotides, shown at the ends of the sequence, are present in KPM316 and correspond to bases of the MG1655 genome: G at 1937302 and G at 1938152):

SEQ ID NO: 9:

1937302
G̲TATGAATATCCTCCTTAGTTCCTATTCCGAAGTTCCTATTCTCTAGAAAGTATAGGAACTTCG
AAGCAGCTCCAGCCTACACG̲
            1938152

Figure 12E

ΔpagP

Nucleotides 655780 to 656340 are deleted from the reference sequence and the following sequence is incorporated into KPM316 (the terminal nucleotides, shown at the ends of the sequence, are present in KPM316 and correspond to bases of the MG1655 genome: A at 655779 and G at 656341):

SEQ ID NO: 10:

655779

A̲GTGTAGGCTGGAGCTGCTTCGAAGTTCCTATACTTTCTAGAGAATAGGAACTTCGGAATAGGA
ACTAAGGAGGATATTCATATGG̲
       656341

Figure 12F

ΔlpxP

Nucleotides 2493667 to 2494587 are deleted from the reference sequence and the following sequence is incorporated into KPM316 (the terminal nucleotides, shown at the ends of the sequence, are present in KPM316 and correspond to bases of the MG1655 genome: T at 2493666 and C at 2494588):

SEQ ID NO: 11:

2493666
T̲GTGTAGGCTGGAGCTGCTTCGAAGTTCCTATACTTTCTAGAGAATAGGAACTTCGGAATAGGA
ACTAAGGAGGATATTCATATGC̲
       2494588

Figure 12G

*Escherichia coli* KPM318 (*msbA52* Δ*kdsD* Δ*gutQ* Δ*lpxL* Δ*lpxM* Δ*pagP* Δ*lpxP* Δ*eptA*)

The sequence of the sense strand of the organism is the *E coli* reference sequence with the following alterations:

*msbA52* replaces the wild type allele of *msbA*, wherein a C at 965895 is replaced by a T, resulting in a Serine instead of Proline at amino acid 18 in the MsbA protein.

SEQ ID NO: 5:

965844                                              C>T 965895

ATGCATAACGACAAAGATCTCTCTACGTGGCAGACATTCCGCCGACTGTGGTCAACCATTGCG
CCTTTCAAAGCGGGTCTGATCGTGGCGGGCGTAGCGTTAATCCTCAACGCAGCCAGCGATACCT
TCATGTTATCGCTCCTTAAGCCACTTCTTGATGATGGCTTTGGTAAAACAGATCGCTCCGTGCT
GGTGTGGATGCCGCTGGTGGTGATCGGGCTGATGATTTTACGTGGTATCACCAGCTATGTCTCC
AGCTACTGTATCTCCTGGGTATCAGGAAAGGTGGTAATGACCATGCGTCGCCGCCTGTTTGGTC
ACATGATGGGAATGCCAGTTTCATTCTTTGACAAACAGTCAACGGGTACGCTGTTGTCACGTAT
TACCTACGATTCCGAACAGGTTGCTTCTTCTTCTTCCGGCGCACTGATTACTGTTGTGCGTGAA
GGTGCGTCGATCATCGGCCTGTTCATCATGATGTTCTATTACAGTTGGCAACTGTCGATCATTT
TGATTGTGCTGGCACCGATTGTTTCGATTGCGATTCGCGTTGTATCGAAGCGTTTTCGCAACAT
CAGTAAAAACATGCAGAACACCATGGGGCAGGTGACCACCAGCGCAGAACAAATGCTGAAGGGC
CACAAAGAAGTATTGATTTTCGGTGGTCAGGAAGTGGAAACGAAACGCTTTGATAAAGTCAGCA
ACCGAATGCGTCTTCAGGGGATGAAAATGGTTTCAGCCTCTTCCATCTCTGATCCGATCATTCA
GCTGATCGCCTCTTTGGCGCTGGCGTTTGTTCTGTATGCGGCGAGCTTCCCAAGTGTCATGGAT
AGCCTGACTGCCGGTACGATTACCGTTGTTTTCTCTTCAATGATTGCACTGATGCGTCCGCTGA
AATCGCTGACCAACGTTAACGCCCAGTTCCAGCGCGGTATGGCGGCTTGTCAGACGCTGTTTAC
CATTCTGGACAGTGAGCAGGAGAAAGATGAAGGTAAGCGCGTGATCGAGCGTGCGACTGGCGAC
GTGGAATTCCGCAATGTCACCTTTACTTATCCGGGACGTGACGTACCTGCATTGCGTAACATCA
ACCTGAAAATTCCGGCAGGGAAGACGGTTGCTCTGGTTGGACGCTCTGGTTCGGGTAAATCAAC
CATCGCCAGCCTGATCACGCGTTTTTACGATATTGATGAAGGCGAAATCCTGATGGATGGTCAC
GATCTGCGCGAGTATACCCTGGCGTCGTTACGTAACCAGGTTGCTCTGGTGTCGCAGAATGTCC
ATCTGTTTAACGATACGGTTGCTAACAACATTGCTTACGCACGGACTGAACAGTACAGCCGTGA
GCAAATTGAAGAAGCGGCGCGTATGGCCTACGCCATGGACTTCATCAATAAGATGGATAACGGT
CTCGATACAGTGATTGGTGAAAACGGCGTGCTGCTCTCTGGCGGTCAGCGTCAGCGTATTGCTA
TCGCTCGAGCCTTGTTGCGTGATAGCCCGATTCTGATTCTGGACGAAGCTACCTCGGCTCTGGA
TACCGAATCCGAACGTGCGATTCAGGCGGCACTGGATGAGTTGCAGAAAAACCGTACCTCTCTG
GTGATTGCCCACCGCTTGTCTACCATTGAAAAGGCAGACGAAATCGTGGTCGTCGAGGATGGTG
TCATTGTGGAACGCGGTACGCATAACGATTTGCTTGAGCACCGCGGCGTTTACGCGCAACTTCA
CAAAATGCAGTTTGGCCAATGA

ΔgutQ

Nucleotides 2827846 to 2828789 are deleted from the reference sequence and the following sequence is incorporated into KPM318 (the terminal nucleotides, shown at the ends of the sequence, are present in KPM318 and correspond to bases of the MG1655 genome: C at 2827845 and G at 2828790):

SEQ ID NO: 6:

2827845
<u>C</u>GTGTAGGCTGGAGCTGCTTCGAAGTTCCTATACTTTCTAGAGAATAGGAACTTCGGAATAGGA
AGGTCGACGGATCCCCGGAAT<u>G</u>
                  2828790

Figure 13B

ΔkdsD

Nucleotides 3339288 to 3340264 are deleted from the reference sequence and the following sequence is incorporated into KPM318 (the terminal nucleotides, shown at the ends of the sequence, are present in KPM318 and correspond to bases of the MG1655 genome: T at 3339287 and C at 3340265):

SEQ ID NO: 7:

3339287
<u>T</u>GTGTAGGCTGGAGCTGCTTCGAAGTTCCTATACTTTCTAGAGAATAGGAACTTCGGAATAGGA
ACTAAGGAGGATATTCATATG<u>C</u>
                  3340265

Figure 13C

Δ*lpxL*
(coding sequence of *lpxL* is complement of the reference nucleic acid strand)
Nucleotides 1114958 to 11155744 are deleted from the reference sequence and the following sequence is incorporated into KPM318 (the terminal nucleotides, shown at the ends of the sequence, are present in KPM318 and correspond to bases of the MG1655 genome: C at 1114957 and C at 1115745):

SEQ ID NO: 8:

1114957
CTATGAATATCCTCCTTAGTTCCTATTCCGAAGTTCCTATTCTCTAGAAAGTATAGGAACTTCG
AAGCAGCTCCAGCCTACACC
              1115745

Figure 13D

Δ*lpxM*
(coding sequence of *lpxM* is complement of the reference nucleic acid strand)
Nucleotides 1937303 to 1938151 are deleted from the reference sequence and the following sequence is incorporated into KPM318 (the terminal nucleotides, shown at the ends of the sequence, are present in KPM318 and correspond to bases of the MG1655 genome: G at 1937302 and G at 1938152):

SEQ ID NO: 9:

1937302
GTATGAATATCCTCCTTAGTTCCTATTCCGAAGTTCCTATTCTCTAGAAAGTATAGGAACTTCG
AAGCAGCTCCAGCCTACACG
              1938152

Figure 13E

*ΔpagP*

Nucleotides 655780 to 656340 are deleted from the reference sequence and the following sequence is incorporated into KPM318 (the terminal nucleotides, shown at the ends of the sequence, are present in KPM318 and correspond to bases of the MG1655 genome: A at 655779 and G at 656341):

SEQ ID NO: 10:

655779

<u>A</u>GTGTAGGCTGGAGCTGCTTCGAAGTTCCTATACTTTCTAGAGAATAGGAACTTCGGAATAGGA
ACTAAGGAGGATATTCATATG<u>G</u>
                    656341

Figure 13F

*ΔlpxP*

Nucleotides 2493667 to 2494587 are deleted from the reference sequence and the following sequence is incorporated into KPM318 (the terminal nucleotides, shown at the ends of the sequence, are present in KPM318 and correspond to bases of the MG1655 genome: T at 2493666 and C at 2494588):

SEQ ID NO: 11:

2493666
<u>T</u>GTGTAGGCTGGAGCTGCTTCGAAGTTCCTATACTTTCTAGAGAATAGGAACTTCGGAATAGGA
ACTAAGGAGGATATTCATATG<u>C</u>
                      2494588

Figure 13G

ΔeptA
(coding sequence is complement of the reference nucleic acid strand)

Nucleotides 4331974 to 4333613 are deleted from the reference sequence and the following sequence is incorporated into KPM318 (the terminal nucleotides, shown at the ends of the sequence, are present in KPM318 and correspond to bases of the MG1655 genome: T at 4331973 and C at 4333614):

SEQ ID NO: 12:

4331973
<u>T</u>CATATGAATATCCTCCTTAGTTCCTATTCCGAAGTTCCTATTCTCTAGAAAGTATAGGAACTT
CGAAGCAGCTCCAGCCTACAC<u>C</u>
                    4333614

Figure 13H

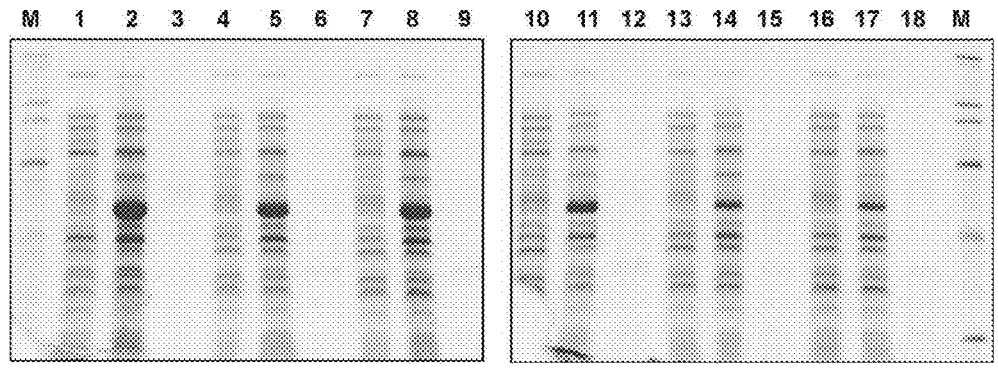

1. BW30270/pMAL-c2 – uninduced
2. BW30270/pMAL-c2 – protein extract, induced (3h)
3. BW30270/pMAL-c2 – culture supernatant, induced (overnight)
4. KPM318/pMAL-c2 – uninduced
5. KPM318/pMAL-c2 – protein extract, induced (3h)
6. KPM318/pMAL-c2 – culture supernatant, induced (overnight)
7. KPM318-9/pMAL-c2 – uninduced
8. KPM318-9/pMAL-c2 – protein extract, induced (3h)
9. KPM318-9/pMAL-c2 – culture supernatant, induced (overnight)
10. KPM318-10/pMAL-c2 – uninduced
11. KPM318-10/pMAL-c2 – protein extract, induced (3h)
12. KPM318-10/pMAL-c2 – culture supernatant, induced (overnight)
13. KPM318-19/pMAL-c2 – uninduced
14. KPM318-19/pMAL-c2 – protein extract, induced (3h)
15. KPM318-19/pMAL-c2 – culture supernatant, induced (overnight)
16. KPM318-23/pMAL-c2 – uninduced
17. KPM318-23/pMAL-c2 – protein extract, induced (3h)
18. KPM318-23/pMAL-c2 – culture supernatant, induced (overnight)

Figure 33

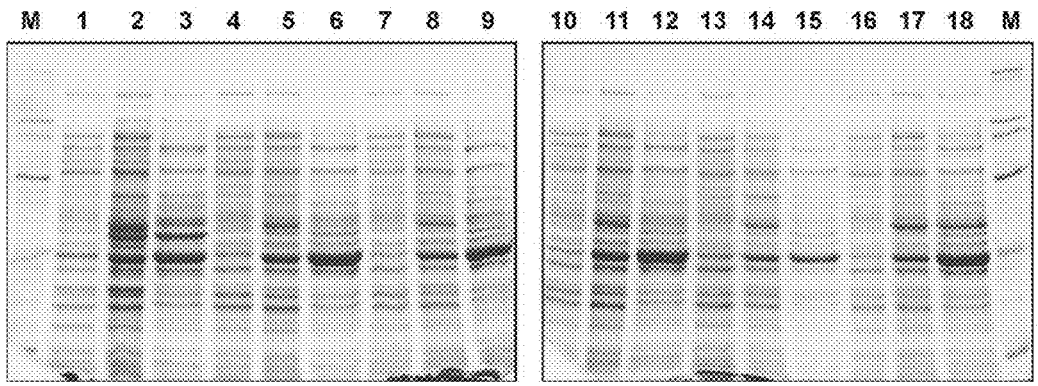

1. BW30270/pMAL-p2 - uninduced
2. BW30270/pMAL-p2 – protein extract, induced (3h)
3. BW30270/pMAL-p2 – culture supernatant, induced (overnight)
4. KPM318/pMAL-p2 - uninduced
5. KPM318/pMAL-p2 – protein extract, induced (3h)
6. KPM318/pMAL-p2 – culture supernatant, induced (overnight)
7. KPM318-9/pMAL-p2 – uninduced
8. KPM318-9/pMAL-p2 – protein extract, induced (3h)
9. KPM318-9/pMAL-p2 – culture supernatant, induced (overnight)
10. KPM318-10/pMAL-p2 – uninduced
11. KPM318-10/pMAL-p2 – protein extract, induced (3h)
12. KPM318-10/pMAL-p2 – culture supernatant, induced (overnight)
13. KPM318-19/pMAL-p2 – uninduced
14. KPM318-19/pMAL-p2 – protein extract, induced (3h)
15. KPM318-19/pMAL-p2 – culture supernatant, induced (overnight)
16. KPM318-23/pMAL-p2 – uninduced
17. KPM318-23/pMAL-p2 – protein extract, induced (3h)
18. KPM318-23/pMAL-p2 – culture supernatant, induced (overnight)

Figure 34

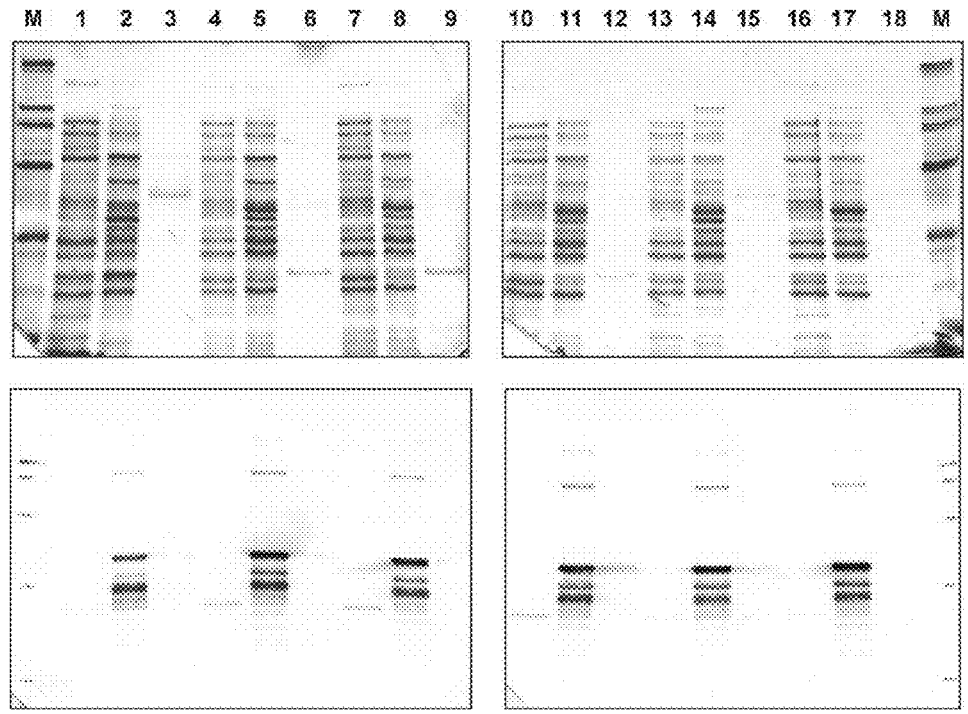

1. BW30270/pMAL-c2 - uninduced
2. BW30270/pMAL-c2 – protein extract, induced (overnight)
3. BW30270/pMAL-c2 – culture supernatant, induced (overnight)
4. KPM318/pMAL-c2 - uninduced
5. KPM318/pMAL-c2 – protein extract, induced (overnight)
6. KPM318/pMAL-c2 – culture supernatant, induced (overnight)
7. KPM318-9/pMAL-c2 – uninduced
8. KPM318-9/pMAL-c2 – protein extract, induced (overnight)
9. KPM318-9/pMAL-c2 – culture supernatant, induced (overnight)
10. KPM318-10/pMAL-c2 – uninduced
11. KPM318-10/pMAL-c2 – protein extract, induced (overnight)
12. KPM318-10/pMAL-c2 – culture supernatant, induced (overnight)
13. KPM318-19/pMAL-c2 – uninduced
14. KPM318-19/pMAL-c2 – protein extract, induced (overnight)
15. KPM318-19/pMAL-c2 – culture supernatant, induced (overnight)
16. KPM318-23/pMAL-c2 – uninduced
17. KPM318-23/pMAL-c2 – protein extract, induced (overnight)
18. KPM318-23/pMAL-c2 – culture supernatant, induced (overnight)

Figure 35

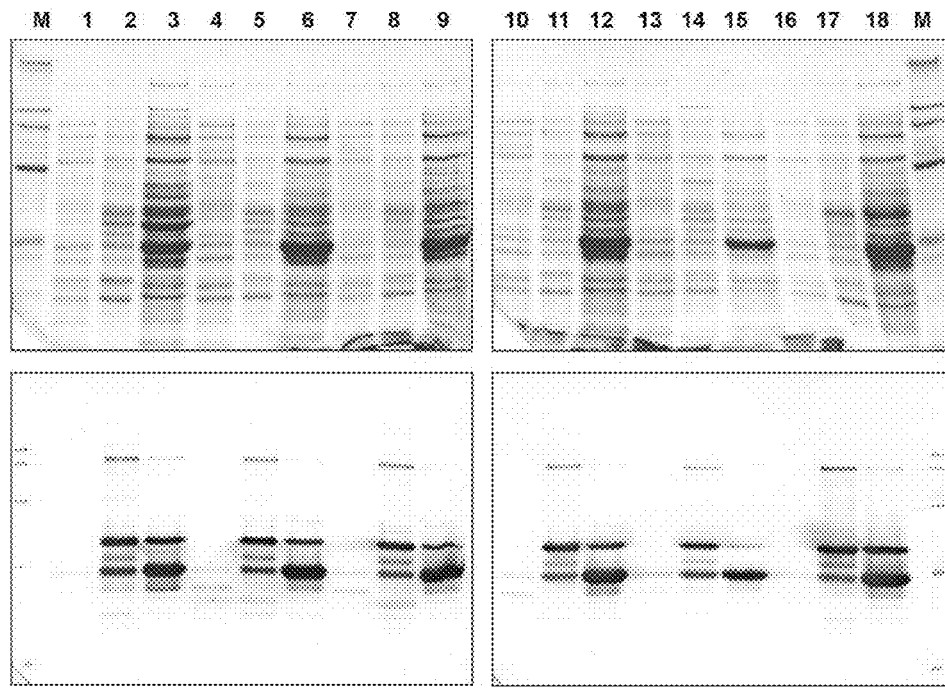

1. BW30270/pMAL-p2 – uninduced
2. BW30270/pMAL-p2 – protein extract, induced (overnight)
3. BW30270/pMAL-p2 – culture supernatant, induced (overnight)
4. KPM318/pMAL-p2 – uninduced
5. KPM318/pMAL-p2 – protein extract, induced (overnight)
6. KPM318/pMAL-p2 – culture supernatant, induced (overnight)
7. KPM318-9/pMAL-p2 – uninduced
8. KPM318-9/pMAL-p2 – protein extract, induced (overnight)
9. KPM318-9/pMAL-p2 – culture supernatant, induced (overnight)
10. KPM318-10/pMAL-p2 – uninduced
11. KPM318-10/pMAL-p2 – protein extract, induced (overnight)
12. KPM318-10/pMAL-p2 – culture supernatant, induced (overnight)
13. KPM318-19/pMAL-p2 – uninduced
14. KPM318-19/pMAL-p2 – protein extract, induced (overnight)
15. KPM318-19/pMAL-p2 – culture supernatant, induced (overnight)
16. KPM318-23/pMAL-p2 – uninduced
17. KPM318-23/pMAL-p2 – protein extract, induced (overnight)
18. KPM318-23/pMAL-p2 – culture supernatant, induced (overnight)

Figure 36

1. Protein extract – uninduced
2. Culture supernatant – uninduced
3. Protein extract – induced (3h)
4. Culture supernatant – induced (3h)
5. Protein extract – induced (6h)
6. Culture supernatant – induced (6h)
7. Protein extract – induced (12h)
8. Culture supernatant – induced (12h)
9. Protein extract – induced (24h)
10. Culture supernatant – induced (24h)

1. Protein extract – uninduced
2. Culture supernatant – uninduced
3. Protein extract – induced (3h)
4. Culture supernatant – induced (3h)
5. Protein extract – induced (6h)
6. Culture supernatant – induced (6h)
7. Protein extract – induced (12h)
8. Culture supernatant – induced (12h)
9. Protein extract – induced (24h)
10. Culture supernatant – induced (24h)

1. BW30270/pJexpress404:51149 - uninduced
2. BW30270/pJexpress404:51149 - induced (3 h)
3. BW30270/pJexpress404:51149 - induced (6 h)
4. BW30270/pJexpress404:51149 - induced (12 h)
5. BW30270/pJexpress404:51149 - induced (24 h)
6. KPM318/pJexpress404:51149 - uninduced
7. KPM318/pJexpress404:51149 - induced (3 h)
8. KPM318/pJexpress404:51149 - induced (6 h)
9. KPM318/pJexpress404:51149 - induced (12 h)
10. KPM318/pJexpress404:51149 - induced (24 h)

1. KPM318-9/pJexpress404:51149 - uninduced
2. KPM318-9/pJexpress404:51149 - induced (3 h)
3. KPM318-9/pJexpress404:51149 - induced (6 h)
4. KPM318-9/pJexpress404:51149 - induced (12 h)
5. KPM318-9/pJexpress404:51149 - induced (24 h)
6. KPM318-10/pJexpress404:51149 - uninduced
7. KPM318-10/pJexpress404:51149 - induced (3 h)
8. KPM318-10/pJexpress404:51149 - induced (6 h)
9. KPM318-10/pJexpress404:51149 - induced (12 h)
10. KPM318-10/pJexpress404:51149 - induced (24 h)

1. KPM318-19/pJexpress404:51149 – uninduced
2. KPM318-19/pJexpress404:51149 - induced (3 h)
3. KPM318-19/pJexpress404:51149 - induced (6 h)
4. KPM318-19/pJexpress404:51149 - induced (12 h)
5. KPM318-19/pJexpress404:51149 - induced (24 h)

1. BW30270/pJexpress404:51150 - uninduced
2. BW30270/pJexpress404:51150 - induced (3 h)
3. BW30270/pJexpress404:51150 - induced (6 h)
4. BW30270/pJexpress404:51150 - induced (12 h)
5. BW30270/pJexpress404:51150 - induced (24 h)
6. KPM318/pJexpress404:51150 - uninduced
7. KPM318/pJexpress404:51150 - induced (3 h)
8. KPM318/pJexpress404:51150 - induced (6 h)
9. KPM318/pJexpress404:51150 - induced (12 h)
10. KPM318/pJexpress404:51150 - induced (24 h)

1. KPM318-9/pJexpress404:51150 - uninduced
2. KPM318-9/pJexpress404:51150 - induced (3 h)
3. KPM318-9/pJexpress404:51150 - induced (6 h)
4. KPM318-9/pJexpress404:51150 - induced (12 h)
5. KPM318-9/pJexpress404:51150 - induced (24 h)
6. KPM318-10/pJexpress404:51150 - uninduced
7. KPM318-10/pJexpress404:51150 - induced (3 h)
8. KPM318-10/pJexpress404:51150 - induced (6 h)
9. KPM318-10/pJexpress404:51150 - induced (12 h)
10. KPM318-10/pJexpress404:51150 - induced (24 h)

1. KPM318-19/pJexpress404:51150 – uninduced
2. KPM318-19/pJexpress404:51150 - induced (3 h)
3. KPM318-19/pJexpress404:51150 - induced (6 h)
4. KPM318-19/pJexpress404:51150 - induced (12 h)
5. KPM318-19/pJexpress404:51150 - induced (24 h)

1. BW30270/pJexpress404:51150 – uninduced
2. BW30270/pJexpress404:51150 - induced (3 h)
3. BW30270/pJexpress404:51150 - induced (6 h)
4. BW30270/pJexpress404:51150 - induced (12 h)
5. BW30270/pJexpress404:51150 - induced (24 h)
6. KPM318/pJexpress404:51150 - uninduced
7. KPM318/pJexpress404:51150 - induced (3 h)
8. KPM318/pJexpress404:51150 - induced (6 h)
9. KPM318/pJexpress404:51150 - induced (12 h)
10. KPM318/pJexpress404:51150 - induced (24 h)

1. KPM318-9/pJexpress404:51150 - uninduced
2. KPM318-9/pJexpress404:51150 - induced (3 h)
3. KPM318-9/pJexpress404:51150 - induced (6 h)
4. KPM318-9/pJexpress404:51150 - induced (12 h)
5. KPM318-9/pJexpress404:51150 - induced (24 h)
6. KPM318-10/pJexpress404:51150 - uninduced
7. KPM318-10/pJexpress404:51150 - induced (3 h)
8. KPM318-10/pJexpress404:51150 - induced (6 h)
9. KPM318-10/pJexpress404:51150 - induced (12 h)
10. KPM318-10/pJexpress404:51150 - induced (24 h)

1. KPM318-19/pJexpress404:51150 – uninduced
2. KPM318-19/pJexpress404:51150 – induced (3 h)
3. KPM318-19/pJexpress404:51150 – induced (6 h)
4. KPM318-19/pJexpress404:51150 – induced (12 h)
5. KPM318-19/pJexpress404:51150 – induced (24 h)

1. BW30270/pJexpress404:51149 - uninduced
2. BW30270/pJexpress404:51149 - induced (3 h)
3. BW30270/pJexpress404:51149 - induced (6 h)
4. BW30270/pJexpress404:51149 - induced (12 h)
5. BW30270/pJexpress404:51149 - induced (24 h)
6. KPM318/pJexpress404:51149 - uninduced
7. KPM318/pJexpress404:51149 - induced (3 h)
8. KPM318/pJexpress404:51149 - induced (6 h)
9. KPM318/pJexpress404:51149 - induced (12 h)
10. KPM318/pJexpress404:51149 - induced (24 h)

1. KPM318-9/pJexpress404:51149 - uninduced
2. KPM318-9/pJexpress404:51149 - induced (3 h)
3. KPM318-9/pJexpress404:51149 - induced (6 h)
4. KPM318-9/pJexpress404:51149 - induced (12 h)
5. KPM318-9/pJexpress404:51149 - induced (24 h)
6. KPM318-10/pJexpress404:51149 - uninduced
7. KPM318-10/pJexpress404:51149 - induced (3 h)
8. KPM318-10/pJexpress404:51149 - induced (6 h)
9. KPM318-10/pJexpress404:51149 - induced (12 h)
10. KPM318-10/pJexpress404:51149 - induced (24 h)

1. KPM318-19/pJexpress404:51149 – uninduced
2. KPM318-19/pJexpress404:51149 - induced (3 h)
3. KPM318-19/pJexpress404:51149 - induced (6 h)
4. KPM318-19/pJexpress404:51149 - induced (12 h)
5. KPM318-19/pJexpress404:51149 - induced (24 h)

1. BW30270/pJexpress404:51150 - uninduced
2. BW30270/pJexpress404:51150 - induced (3 h)
3. BW30270/pJexpress404:51150 - induced (6 h)
4. BW30270/pJexpress404:51150 - induced (12 h)
5. BW30270/pJexpress404:51150 - induced (24 h)
6. KPM318/pJexpress404:51150 - uninduced
7. KPM318/pJexpress404:51150 - induced (3 h)
8. KPM318/pJexpress404:51150 - induced (6 h)
9. KPM318/pJexpress404:51150 - induced (12 h)
10. KPM318/pJexpress404:51150 - induced (24 h)

1. KPM318-9/pJexpress404:51150 - uninduced
2. KPM318-9/pJexpress404:51150 - induced (3 h)
3. KPM318-9/pJexpress404:51150 - induced (6 h)
4. KPM318-9/pJexpress404:51150 - induced (12 h)
5. KPM318-9/pJexpress404:51150 - induced (24 h)
6. KPM318-10/pJexpress404:51150 - uninduced
7. KPM318-10/pJexpress404:51150 - induced (3 h)
8. KPM318-10/pJexpress404:51150 - induced (6 h)
9. KPM318-10/pJexpress404:51150 - induced (12 h)
10. KPM318-10/pJexpress404:51150 - induced (24 h)

1. KPM318-19/pJexpress404:51150 – uninduced
2. KPM318-19/pJexpress404:51150 - induced (3 h)
3. KPM318-19/pJexpress404:51150 - induced (6 h)
4. KPM318-19/pJexpress404:51150 - induced (12 h)
5. KPM318-19/pJexpress404:51150 - induced (24 h)

1. BW30270/pJexpress404:51150 – uninduced
2. BW30270/pJexpress404:51150 - induced (3 h)
3. BW30270/pJexpress404:51150 - induced (6 h)
4. BW30270/pJexpress404:51150 - induced (12 h)
5. BW30270/pJexpress404:51150 - induced (24 h)
6. KPM318/pJexpress404:51150 - uninduced
7. KPM318/pJexpress404:51150 - induced (3 h)
8. KPM318/pJexpress404:51150 - induced (6 h)
9. KPM318/pJexpress404:51150 - induced (12 h)
10. KPM318/pJexpress404:51150 - induced (24 h)

1. KPM318-9/pJexpress404:51150 - uninduced
2. KPM318-9/pJexpress404:51150 - induced (3 h)
3. KPM318-9/pJexpress404:51150 - induced (6 h)
4. KPM318-9/pJexpress404:51150 - induced (12 h)
5. KPM318-9/pJexpress404:51150 - induced (24 h)
6. KPM318-10/pJexpress404:51150 - uninduced
7. KPM318-10/pJexpress404:51150 - induced (3 h)
8. KPM318-10/pJexpress404:51150 - induced (6 h)
9. KPM318-10/pJexpress404:51150 - induced (12 h)
10. KPM318-10/pJexpress404:51150 - induced (24 h)

1. KPM318-19/pJexpress404:51150 – uninduced
2. KPM318-19/pJexpress404:51150 - induced (3 h)
3. KPM318-19/pJexpress404:51150 - induced (6 h)
4. KPM318-19/pJexpress404:51150 - induced (12 h)
5. KPM318-19/pJexpress404:51150 - induced (24 h)

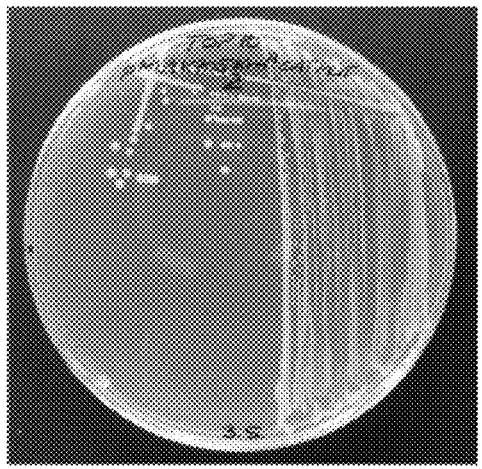
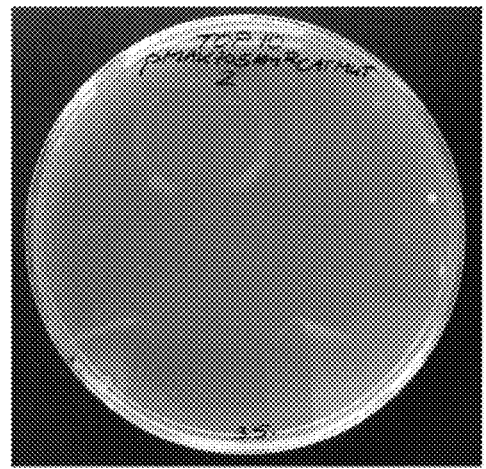
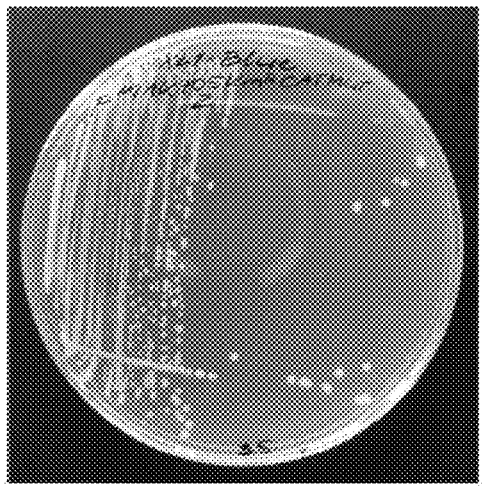
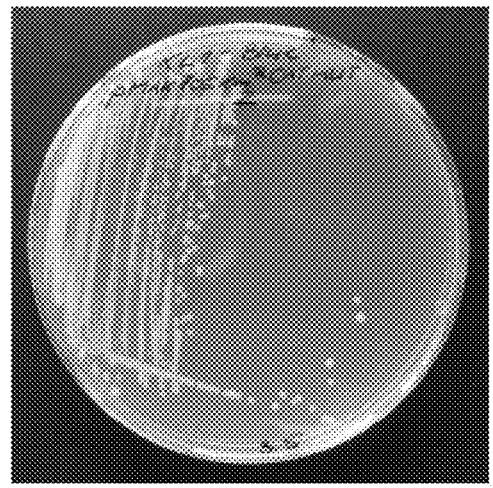
Figure 64

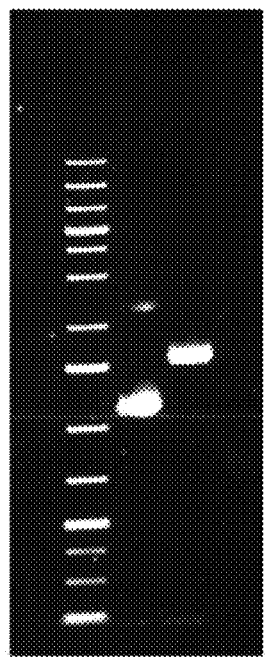
expected size of the Km-cassette: 1571 bp
expected size of the Cm-cassette: 1108 bp
Figure 68A
Figure 68A
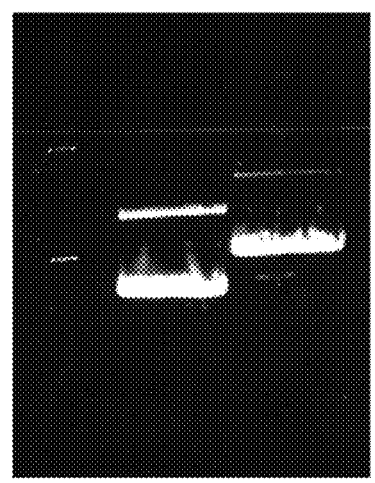
Figure 68B

Gel 1:

1. BL21(DE3)
2. BL21(DE3) msbA L11/pKD46 ΔlpxL::Km 1
3. BL21(DE3) msbA L11/pKD46 ΔlpxL::Km 2
4. BL21(DE3) msbA L11/pKD46 ΔlpxL::Km 3
5. BL21(DE3) msbA L11/pKD46 ΔlpxL::Km 4
6. BL21(DE3) msbA L11/pKD46 ΔlpxL::Km 5
7. BL21(DE3) msbA L11/pKD46 ΔlpxL::Cm 6
8. BL21(DE3) msbA L11/pKD46 ΔlpxL::Cm 7
9. BL21(DE3) msbA L11/pKD46 ΔlpxL::Cm 8
10. BL21(DE3) msbA L11/pKD46 ΔlpxL::Cm 9
11. BL21(DE3) msbA L11/pKD46 ΔlpxL::Cm 10
12. BL21(DE3) msbA L11/pKD46 ΔlpxL::Cm 11
13. BL21(DE3) msbA L11/pKD46 ΔlpxL::Cm 12
14. BL21(DE3) msbA L11/pKD46 ΔlpxL::Km 13
15. BL21(DE3) msbA L11/pKD46 ΔlpxL::Cm 14
16. BL21(DE3) msbA L11/pKD46 ΔlpxL::Cm 15
17. BL21(DE3) msbA L11/pKD46 ΔlpxL::Km 16

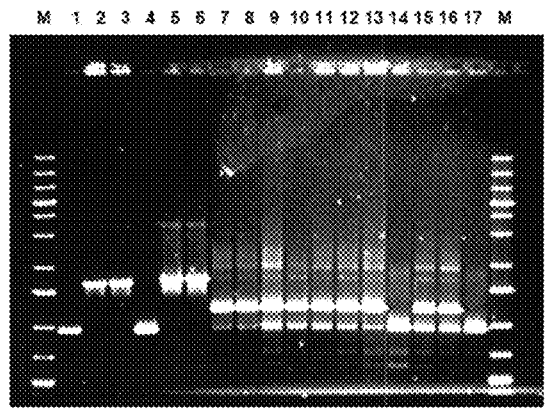

expected size of the PCR products:
1. lpxL wild-type gene: 955 bp
2. ΔlpxL::Km$^+$: 1604 bp
3. ΔlpxL::Cm$^+$: 1140 bp

Figure 69

Gel 2:

1. BL21(DE3)
2. BL21(DE3) *msbA* L18/pKD46 Δ*lpxL*::Km 1
3. BL21(DE3) *msbA* L18/pKD46 Δ*lpxL*::Km 2
4. BL21(DE3) *msbA* L18/pKD46 Δ*lpxL*::Km 3
5. BL21(DE3) *msbA* L18/pKD46 Δ*lpxL*::Km 4
6. BL21(DE3) *msbA* L18/pKD46 Δ*lpxL*::Km 5
7. BL21(DE3) *msbA* L18/pKD46 Δ*lpxL*::Km 6
8. BL21(DE3) *msbA* L18/pKD46 Δ*lpxL*::Km 7
9. BL21(DE3) *msbA* L18/pKD46 Δ*lpxL*::Km 8
10. BL21(DE3) *msbA* L18/pKD46 Δ*lpxL*::Km 9
11. BL21(DE3) *msbA* L18/pKD46 Δ*lpxL*::Km 10
12. BL21(DE3) *msbA* L18/pKD46 Δ*lpxL*::Km 11
13. BL21(DE3) *msbA* L18/pKD46 Δ*lpxL*::Km 12
14. BL21(DE3) *msbA* L18/pKD46 Δ*lpxL*::Km 13
15. BL21(DE3) *msbA* L18/pKD46 Δ*lpxL*::Cm 14
16. BL21(DE3) *msbA* L18/pKD46 Δ*lpxL*::Cm 15
17. BL21(DE3) *msbA* L18/pKD46 Δ*lpxL*::Cm 16

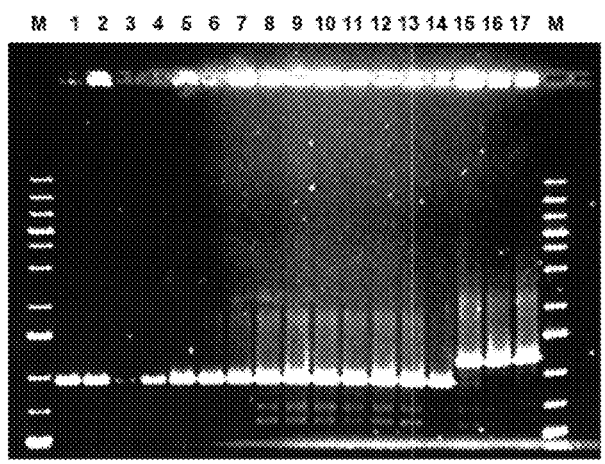

Figure 70

Gel 3:
1. BL21(DE3)
2. BL21(DE3) *msbA* L1/pKD46 Δ*lpxL*::Km 1
3. BL21(DE3) *msbA* L1/pKD46 Δ*lpxL*::Km 2
4. BL21(DE3) *msbA* L1/pKD46 Δ*lpxL*::Km 3
5. BL21(DE3) *msbA* L1/pKD46 Δ*lpxL*::Km 4
6. BL21(DE3) *msbA* L1/pKD46 Δ*lpxL*::Km 5
7. BL21(DE3) *msbA* L1/pKD46 Δ*lpxL*::Cm 6
8. -
9. BL21(DE3) *msbA* L14/pKD46 Δ*lpxL*::Km 1
10. BL21(DE3) *msbA* L14/pKD46 Δ*lpxL*::Km 2
11. BL21(DE3) *msbA* L14/pKD46 Δ*lpxL*::Km 3
12. BL21(DE3) *msbA* L14/pKD46 Δ*lpxL*::Km 4
13. BL21(DE3) *msbA* L14/pKD46 Δ*lpxL*::Km 5
14. BL21(DE3) *msbA* L14/pKD46 Δ*lpxL*::Km 6
15. BL21(DE3) *msbA* L14/pKD46 Δ*lpxL*::Cm 7
16. BL21(DE3) *msbA* L14/pKD46 Δ*lpxL*::Cm 8
17. BL21(DE3) *msbA* L14/pKD46 Δ*lpxL*::Km 9

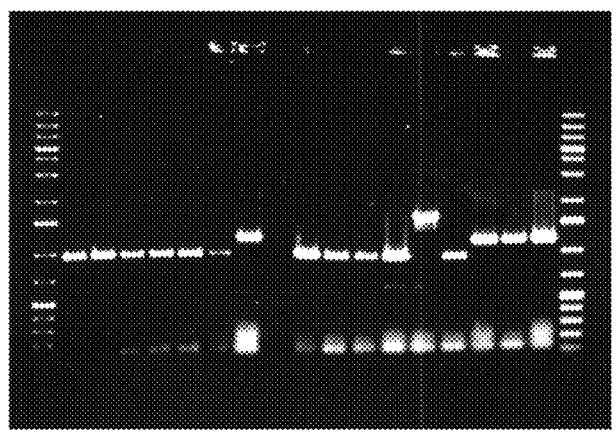

Figure 71

Gel 4:

1. BL21(DE3)
2. BL21(DE3) msbA L15/pKD46 ΔlpxL::Km 1
3. BL21(DE3) msbA L15/pKD46 ΔlpxL::Km 2
4. BL21(DE3) msbA L15/pKD46 ΔlpxL::Km 3
5. BL21(DE3) msbA L15/pKD46 ΔlpxL::Cm 4
6. BL21(DE3) msbA L15/pKD46 ΔlpxL::Cm 5
7. BL21(DE3) msbA L15/pKD46 ΔlpxL::Cm 6
8. BL21(DE3) msbA L15/pKD46 ΔlpxL::Cm 7
9. BL21(DE3) msbA L15/pKD46 ΔlpxL::Cm 8
10. BL21(DE3) msbA L15/pKD46 ΔlpxL::Cm 9
11. BL21(DE3) msbA L15/pKD46 ΔlpxL::Cm 10
12. BL21(DE3) msbA L15/pKD46 ΔlpxL::Cm 11
13. BL21(DE3) msbA L15/pKD46 ΔlpxL::Cm 12
14. BL21(DE3) msbA L15/pKD46 ΔlpxL::Cm 13
15. BL21(DE3) msbA L15/pKD46 ΔlpxL::Cm 14
16. BL21(DE3) msbA L15/pKD46 ΔlpxL::Cm 15
17. BL21(DE3) msbA L15/pKD46 ΔlpxL::Cm 16

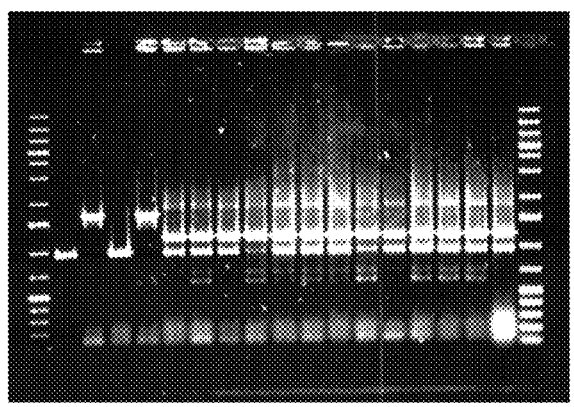

Figure 72

Gel 1:

1. BL21(DE3)/pKD46 (control)
2. BL21(DE3) *msbA* L11 Δ*lpxL*::Km 1 (control)
3. BL21(DE3) *msbA* L11 Δ*lpxL*(Km⁻)/pCP20 1
4. BL21(DE3) *msbA* L11 Δ*lpxL*(Km⁻)/pCP20 6

Gel 2:

1. BL21(DE3)/pKD46 (control 1)
2. BL21(DE3) *msbA* L1 Δ*lpxL*::Cm 6 (control 2)
3. BL21(DE3) *msbA* L1 Δ*lpxL*(Cm⁻)/pCP20 1
4. BL21(DE3) *msbA* L14 Δ*lpxL*::Km 5 (control 3)
5. BL21(DE3) *msbA* L14 Δ*lpxL*(Km⁻)/pCP20 1
6. BL21(DE3) *msbA* L14 Δ*lpxL*(Km⁻)/pCP20 2
7. BL21(DE3) *msbA* L15 Δ*lpxL*::Km 3 (control 4)
8. BL21(DE3) *msbA* L15 Δ*lpxL*(Km⁻)/pCP20 2
9. BL21(DE3) *msbA* L15 Δ*lpxL*(Km⁻)/pCP20 6

Gel 3:

1. BL21(DE3)/pKD46 (control 1)
2. BL21(DE3) msbA L14 ΔlpxL::Km 5 (control 2)
3. BL21(DE3) msbA L14 ΔlpxL(Km⁻)/ pCP20 3
4. BL21(DE3) msbA L14 ΔlpxL(Km⁻)/ pCP20 4
5. BL21(DE3) msbA L14 ΔlpxL(Km⁻)/ pCP20 5
6. BL21(DE3) msbA L14 ΔlpxL(Km⁻)/ pCP20 6
7. BL21(DE3) msbA L18 ΔlpxL::Cm 15 (control 3)
8. BL21(DE3) msbA L18 ΔlpxL(Cm⁻)/pCP20 1
9. BL21(DE3) msbA L18 ΔlpxL(Cm⁻)/pCP20 2

1. BL21 (DE3) *msbA* L14 Δ*lpxL*/pKD46 (control 1)
2. BL21 (DE3) *msbA* L14 Δ*lpxL* (Δ*kdsD*::Km$^+$)/pKD46 1
3. BL21 (DE3) *msbA* L14 Δ*lpxL* (Δ*kdsD*::Km$^+$)/pKD46 2
4. BL21 (DE3) *msbA* L14 Δ*lpxL* (Δ*kdsD*::Km$^+$)/pKD46 3
5. BL21 (DE3) *msbA* L14 Δ*lpxL* (Δ*kdsD*::Km$^+$)/pKD46 4
6. BL21 (DE3) *msbA* L14 Δ*lpxL* (Δ*kdsD*::Km$^+$)/pKD46 5
7. BL21 (DE3) *msbA* L14 Δ*lpxL* (Δ*kdsD*::Km$^+$)/pKD46 6
8. BL21 (DE3) *msbA* L14 Δ*lpxL* (Δ*kdsD*::Km$^+$)/pKD46 7
9. BL21 (DE3) *msbA* L14 Δ*lpxL* (Δ*kdsD*::Km$^+$)/pKD46 8
10. BL21 (DE3) *msbA* L1 Δ*lpxL*/pKD46 (control 2)
11. BL21 (DE3) *msbA* L1 Δ*lpxL* (Δ*kdsD*::Km$^+$)/pKD46 1
12. BL21 (DE3) *msbA* L1 Δ*lpxL* (Δ*kdsD*::Km$^+$)/pKD46 2
13. BL21 (DE3) *msbA* L1 Δ*lpxL* (Δ*kdsD*::Km$^+$)/pKD46 3
14. BL21 (DE3) *msbA* L1 Δ*lpxL* (Δ*kdsD*::Km$^+$)/pKD46 4
15. BL21 (DE3) *msbA* L1 Δ*lpxL* (Δ*kdsD*::Km$^+$)/pKD46 5
16. BL21 (DE3) *msbA* L1 Δ*lpxL* (Δ*kdsD*::Km$^+$)/pKD46 6
17. BL21 (DE3) *msbA* L1 Δ*lpxL* (Δ*kdsD*::Km$^+$)/pKD46 7
18. BL21 (DE3) *msbA* L1 Δ*lpxL* (Δ*kdsD*::Km$^+$)/pKD46 8
19. BL21 (DE3) *msbA* L1 Δ*lpxL* (Δ*kdsD*::Km$^+$)/pKD46 9
20. BL21 (DE3) *msbA* L1 Δ*lpxL* (Δ*kdsD*::Km$^+$)/pKD46 10
21. BL21 (DE3) *msbA* L1 Δ*lpxL* (Δ*kdsD*::Km$^+$)/pKD46 11
22. BL21 (DE3) *msbA* L1 Δ*lpxL* (Δ*kdsD*::Km$^+$)/pKD46 12
23. BL21 (DE3) *msbA* L1 Δ*lpxL* (Δ*kdsD*::Km$^+$)/pKD46 13
24. BL21 (DE3) *msbA* L1 Δ*lpxL* (Δ*kdsD*::Km$^+$)/pKD46 14
25. BL21 (DE3) *msbA* L1 Δ*lpxL* (Δ*kdsD*::Km$^+$)/pKD46 15
26. BL21 (DE3) *msbA* L1 Δ*lpxL* (Δ*kdsD*::Km$^+$)/pKD46 16
27. BL21 (DE3) *msbA* L1 Δ*lpxL* (Δ*kdsD*::Km$^+$)/pKD46 17
28. BL21 (DE3) *msbA* L1 Δ*lpxL* (Δ*kdsD*::Km$^+$)/pKD46 18
29. BL21 (DE3) *msbA* L1 Δ*lpxL* (Δ*kdsD*::Km$^+$)/pKD46 19

Figure 79 continued

1. BL21 (DE3) *msbA* L1 Δ*lpxL*/pKD46 (control 2)
2. BL21 (DE3) *msbA* L1 Δ*lpxL* (Δ*kdsD*::Km$^+$)/pKD46 20
3. BL21 (DE3) *msbA* L1 Δ*lpxL* (Δ*kdsD*::Km$^+$)/pKD46 21
4. BL21 (DE3) *msbA* L1 Δ*lpxL* (Δ*kdsD*::Km$^+$)/pKD46 22
5. BL21 (DE3) *msbA* L1 Δ*lpxL* (Δ*kdsD*::Km$^+$)/pKD46 23
6. BL21 (DE3) *msbA* L1 Δ*lpxL* (Δ*kdsD*::Km$^+$)/pKD46 24
7. BL21 (DE3) *msbA* L1 Δ*lpxL* (Δ*kdsD*::Km$^+$)/pKD46 25
8. BL21 (DE3) *msbA* L1 Δ*lpxL* (Δ*kdsD*::Km$^+$)/pKD46 26
9. BL21 (DE3) *msbA* L1 Δ*lpxL* (Δ*kdsD*::Km$^+$)/pKD46 27
10. BL21 (DE3) *msbA* L1 Δ*lpxL* (Δ*kdsD*::Km$^+$)/pKD46 28
11. BL21 (DE3) *msbA* L1 Δ*lpxL* (Δ*kdsD*::Km$^+$)/pKD46 29
12. BL21 (DE3) *msbA* L1 Δ*lpxL* (Δ*kdsD*::Km$^+$)/pKD46 30
13. BL21 (DE3) *msbA* L1 Δ*lpxL* (Δ*kdsD*::Km$^+$)/pKD46 31
14. BL21 (DE3) *msbA* L1 Δ*lpxL* (Δ*kdsD*::Km$^+$)/pKD46 32
15. BL21 (DE3) *msbA* L1 Δ*lpxL* (Δ*kdsD*::Km$^+$)/pKD46 33
16. BL21 (DE3) *msbA* L1 Δ*lpxL* (Δ*kdsD*::Km$^+$)/pKD46 34
17. BL21 (DE3) *msbA* L1 Δ*lpxL* (Δ*kdsD*::Km$^+$)/pKD46 35
18. BL21 (DE3) *msbA* L1 Δ*lpxL* (Δ*kdsD*::Km$^+$)/pKD46 36
19. BL21 (DE3) *msbA* L1 Δ*lpxL* (Δ*kdsD*::Km$^+$)/pKD46 37
20. BL21 (DE3) *msbA* L1 Δ*lpxL* (Δ*kdsD*::Km$^+$)/pKD46 38
21. BL21 (DE3) *msbA* L1 Δ*lpxL* (Δ*kdsD*::Km$^+$)/pKD46 39
22. BL21 (DE3) *msbA* L1 Δ*lpxL* (Δ*kdsD*::Km$^+$)/pKD46 40
23. BL21 (DE3) *msbA* L1 Δ*lpxL* (Δ*kdsD*::Km$^+$)/pKD46 41
24. BL21 (DE3) *msbA* L1 Δ*lpxL* (Δ*kdsD*::Km$^+$)/pKD46 42

Figure 80 continued

1. BL21(DE3) *msbA* L1 Δ*lpxL*/pKD46 (control 1)
2. BL21(DE3) *msbA* L1 Δ*lpxL* (Δ*kdsD*::Km$^+$) 11/pKD46 (control 2)
3. BL21(DE3) *msbA* L1 Δ*lpxL* Δ*kdsD* (Km$^-$)/pFLP2 1
4. BL21(DE3) *msbA* L1 Δ*lpxL* Δ*kdsD* (Km$^-$)/pFLP2 2
5. BL21(DE3) *msbA* L1 Δ*lpxL* Δ*kdsD* (Km$^-$)/pFLP2 3
6. BL21(DE3) *msbA* L1 Δ*lpxL* Δ*kdsD* (Km$^-$)/pFLP2 4
7. BL21(DE3) *msbA* L1 Δ*lpxL* Δ*kdsD* (Km$^-$)/pFLP2 5
8. BL21(DE3) *msbA* L1 Δ*lpxL* Δ*kdsD* (Km$^-$)/pFLP2 6
9. BL21(DE3) *msbA* L1 Δ*lpxL* Δ*kdsD* (Km$^-$)/pFLP2 8

1. BL21(DE3) *msbA* L14 Δ*lpxL*/pKD46 (control 3)
2. BL21(DE3) *msbA* L14 Δ*lpxL* (Δ*kdsD*::Km$^+$) 11/pKD46 (control 4)
3. BL21(DE3) *msbA* L14 Δ*lpxL* Δ*kdsD* (Km$^-$)/pFLP2 19
4. BL21(DE3) *msbA* L14 Δ*lpxL* Δ*kdsD* (Km$^-$)/pFLP2 29

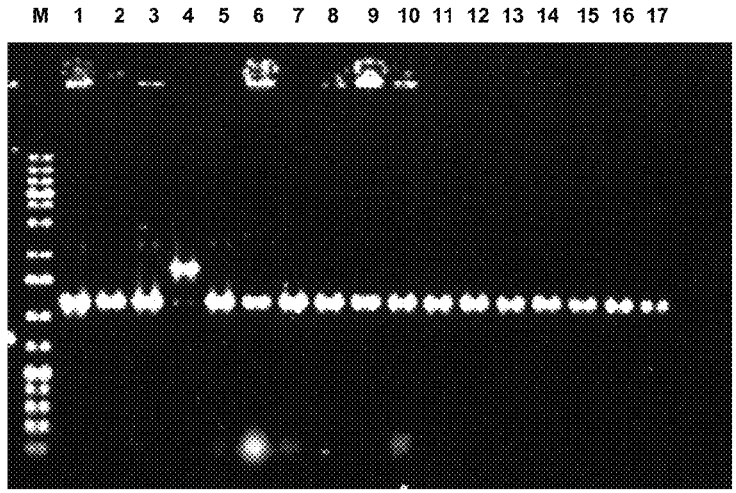

1. BL21 (DE3) msbA L1 ΔlpxL ΔkdsD/pKD46 (control)
2. BL21 (DE3) msbA L1 ΔlpxL ΔkdsD (ΔgutQ::Km⁺)/pKD46 1
3. BL21 (DE3) msbA L1 ΔlpxL ΔkdsD (ΔgutQ::Km⁺)/pKD46 2
4. BL21 (DE3) msbA L1 ΔlpxL ΔkdsD (ΔgutQ::Km⁺)/pKD46 3
5. BL21 (DE3) msbA L1 ΔlpxL ΔkdsD (ΔgutQ::Km⁺)/pKD46 4
6. BL21 (DE3) msbA L1 ΔlpxL ΔkdsD (ΔgutQ::Km⁺)/pKD46 5
7. BL21 (DE3) msbA L1 ΔlpxL ΔkdsD (ΔgutQ::Km⁺)/pKD46 6
8. BL21 (DE3) msbA L1 ΔlpxL ΔkdsD (ΔgutQ::Km⁺)/pKD46 7
9. BL21 (DE3) msbA L1 ΔlpxL ΔkdsD (ΔgutQ::Km⁺)/pKD46 8
10. BL21 (DE3) msbA L1 ΔlpxL ΔkdsD (ΔgutQ::Km⁺)/pKD46 9
11. BL21 (DE3) msbA L1 ΔlpxL ΔkdsD (ΔgutQ::Km⁺)/pKD46 10
12. BL21 (DE3) msbA L1 ΔlpxL ΔkdsD (ΔgutQ::Km⁺)/pKD46 11
13. BL21 (DE3) msbA L1 ΔlpxL ΔkdsD (ΔgutQ::Km⁺)/pKD46 12
14. BL21 (DE3) msbA L1 ΔlpxL ΔkdsD (ΔgutQ::Km⁺)/pKD46 13
15. BL21 (DE3) msbA L1 ΔlpxL ΔkdsD (ΔgutQ::Km⁺)/pKD46 14
16. BL21 (DE3) msbA L1 ΔlpxL ΔkdsD (ΔgutQ::Km⁺)/pKD46 15
17. BL21 (DE3) msbA L1 ΔlpxL ΔkdsD (ΔgutQ::Km⁺)/pKD46 16

Figure 84

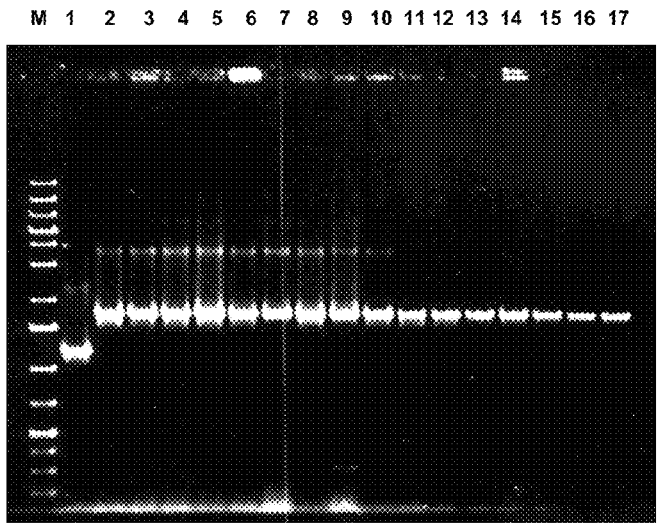

1. BL21 (DE3) *msbA* L1 Δ*lpxL* Δ*kdsD*/pKD46 (control)
2. BL21 (DE3) *msbA* L1 Δ*lpxL* Δ*kdsD* (Δ*gutQ*::Km⁺)/pKD46 (3) 1
3. BL21 (DE3) *msbA* L1 Δ*lpxL* Δ*kdsD* (Δ*gutQ*::Km⁺)/pKD46 (3) 2
4. BL21 (DE3) *msbA* L1 Δ*lpxL* Δ*kdsD* (Δ*gutQ*::Km⁺)/pKD46 (3) 3
5. BL21 (DE3) *msbA* L1 Δ*lpxL* Δ*kdsD* (Δ*gutQ*::Km⁺)/pKD46 (3) 4
6. BL21 (DE3) *msbA* L1 Δ*lpxL* Δ*kdsD* (Δ*gutQ*::Km⁺)/pKD46 (3) 5
7. BL21 (DE3) *msbA* L1 Δ*lpxL* Δ*kdsD* (Δ*gutQ*::Km⁺)/pKD46 (3) 6
8. BL21 (DE3) *msbA* L1 Δ*lpxL* Δ*kdsD* (Δ*gutQ*::Km⁺)/pKD46 (3) 7
9. BL21 (DE3) *msbA* L1 Δ*lpxL* Δ*kdsD* (Δ*gutQ*::Km⁺)/pKD46 (3) 8
10. BL21 (DE3) *msbA* L1 Δ*lpxL* Δ*kdsD* (Δ*gutQ*::Km⁺)/pKD46 (3) 9
11. BL21 (DE3) *msbA* L1 Δ*lpxL* Δ*kdsD* (Δ*gutQ*::Km⁺)/pKD46 (3) 10
12. BL21 (DE3) *msbA* L1 Δ*lpxL* Δ*kdsD* (Δ*gutQ*::Km⁺)/pKD46 (3) 11
13. BL21 (DE3) *msbA* L1 Δ*lpxL* Δ*kdsD* (Δ*gutQ*::Km⁺)/pKD46 (3) 12
14. BL21 (DE3) *msbA* L1 Δ*lpxL* Δ*kdsD* (Δ*gutQ*::Km⁺)/pKD46 (3) 13
15. BL21 (DE3) *msbA* L1 Δ*lpxL* Δ*kdsD* (Δ*gutQ*::Km⁺)/pKD46 (3) 14
16. BL21 (DE3) *msbA* L1 Δ*lpxL* Δ*kdsD* (Δ*gutQ*::Km⁺)/pKD46 (3) 15
17. BL21 (DE3) *msbA* L1 Δ*lpxL* Δ*kdsD* (Δ*gutQ*::Km⁺)/pKD46 (3) 16

Figure 85

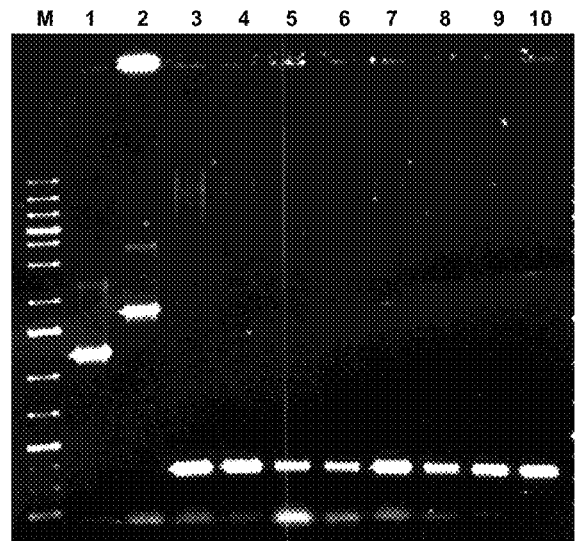

1. BL21 (DE3) *msbA* L1 Δ*lpxL* Δ*kdsD*/pKD46 (control 1)
2. BL21 (DE3) *msbA* L1 Δ*lpxL* Δ*kdsD* (Δ*gutQ*::Km$^+$) 3 (control 2)
3. BL21(DE3) *msbA* L1 Δ*lpxL* Δ*kdsD* Δ*gutQ* (Km$^-$)/pFLP2 9
4. BL21(DE3) *msbA* L1 Δ*lpxL* Δ*kdsD* Δ*gutQ* (Km$^-$)/pFLP2 10
5. BL21(DE3) *msbA* L1 Δ*lpxL* Δ*kdsD* Δ*gutQ* (Km$^-$)/pFLP2 11
6. BL21(DE3) *msbA* L1 Δ*lpxL* Δ*kdsD* Δ*gutQ* (Km$^-$)/pFLP2 12
7. BL21(DE3) *msbA* L1 Δ*lpxL* Δ*kdsD* Δ*gutQ* (Km$^-$)/pFLP2 13
8. BL21(DE3) *msbA* L1 Δ*lpxL* Δ*kdsD* Δ*gutQ* (Km$^-$)/pFLP2 14
9. BL21(DE3) *msbA* L1 Δ*lpxL* Δ*kdsD* Δ*gutQ* (Km$^-$)/pFLP2 15
10. BL21(DE3) *msbA* L1 Δ*lpxL* Δ*kdsD* Δ*gutQ* (Km$^-$)/pFLP2 16

SEQUENCE LISTING

```
<160> NUMBER OF SEQ ID NOS: 24

<210> SEQ ID NO 1
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 1
atatggatcc ttacatggcg atagctagac tgg                            33

<210> SEQ ID NO 2
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 2
atataagctt gaagaactcc agcatgagat cc                             32

<210> SEQ ID NO 3
<211> LENGTH: 47
<212> TYPE: DNA
<213> ORGANISM: Artificial Sequence
<220> FEATURE:
<223> OTHER INFORMATION: Snythetic Oligonucleotide

<400> SEQUENCE: 3
gagaaaaaaa tcactggata tacctaggtt gatatatccc aatggca             47

<210> SEQ ID NO 4
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 4
cagtactgtt gtaattcatt aagcattctg ccgacatgga agccatc             47

<210> SEQ ID NO 5
<211> LENGTH: 1749
<212> TYPE: DNA
<213> ORGANISM: Escherichia coli

<400> SEQUENCE: 5
atgcataacg acaaagatct ctctacgtgg cagacattcc gccgactgtg gtcaaccatt    60
gcgcctttca agcgggtct gatcgtggcg ggcgtagcgt taatcctcaa cgcagccagc   120
```

| | |
|---|---|
| gataccttca tgttatcgct ccttaagcca cttcttgatg atggctttgg taaaacagat | 180 |
| cgctccgtgc tggtgtggat gccgctggtg gtgatcgggc tgatgatttt acgtggtatc | 240 |
| accagctatg tctccagcta ctgtatctcc tgggtatcag aaaggtggt aatgaccatg | 300 |
| cgtcgccgcc tgtttggtca catgatggga atgccagttt cattctttga caaacagtca | 360 |
| acgggtacgc tgttgtcacg tattacctac gattccgaac aggttgcttc ttcttcttcc | 420 |
| ggcgcactga ttactgttgt gcgtgaaggt cgtcgatca tcggcctgtt catcatgatg | 480 |
| ttctattaca gttggcaact gtcgatcatt tgattgtgc tggcaccgat tgtttcgatt | 540 |
| gcgattcgcg ttgtatcgaa gcgttttcgc aacatcagta aaaacatgca gaacaccatg | 600 |
| gggcaggtga ccaccagcgc agaacaaatg ctgaagggcc acaagaagt attgattttc | 660 |
| ggtggtcagg aagtggaaac gaaacgcttt gataaagtca gcaaccgaat gcgtcttcag | 720 |
| gggatgaaaa tggtttcagc ctcttccatc tctgatccga tcattcagct gatcgcctct | 780 |
| ttggcgctgg cgtttgttct gtatgcggcg agcttcccaa gtgtcatgga tagcctgact | 840 |
| gccggtacga ttaccgttgt tttctcttca atgattgcac tgatgcgtcc gctgaaatcg | 900 |
| ctgaccaacg ttaacgccca gttccagcgc ggtatggcgg cttgtcagac gctgtttacc | 960 |
| attctggaca gtgagcagga gaaagatgaa ggtaagcgcg tgatcgagcg tgcgactggc | 1020 |
| gacgtggaat ccgcaatgt caccttact tatccgggac gtgacgtacc tgcattgcgt | 1080 |
| aacatcaacc tgaaaattcc ggcagggaag acggttgctc tggttggacg ctctggttcg | 1140 |
| ggtaaatcaa ccatcgccag cctgatcacg cgttttacg atattgatga aggcgaaatc | 1200 |
| ctgatggatg gtcacgatct gcgcgagtat accctggcgt cgttacgtaa ccaggttgct | 1260 |
| ctggtgtcgc agaatgtcca tctgtttaac gatacggttg ctaacaacat tgcttacgca | 1320 |
| cggactgaac agtacagccg tgagcaaatt gaagaagcgg cgcgtatggc ctacgccatg | 1380 |
| gacttcatca ataagatgga taacggtctc gatacagtga ttggtgaaaa cggcgtgctg | 1440 |
| ctctctggcg gtcagcgtca gcgtattgct atcgctcgag ccttgttgcg tgatagcccg | 1500 |
| attctgattc tggacgaagc tacctcggct ctggataccg aatccgaacg tgcgattcag | 1560 |
| gcggcactgg atgagttgca gaaaaaccgt acctctctgg tgattgccca ccgcttgtct | 1620 |
| accattgaaa aggcagacga aatcgtggtc gtcgaggatg gtgtcattgt ggaacgcggt | 1680 |
| acgcataacg atttgcttga gcaccgcggc gtttacgcgc aacttcacaa aatgcagttt | 1740 |
| ggccaatga | 1749 |

<210> SEQ ID NO 6
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 6

| | |
|---|---|
| cgtgtaggct ggagctgctt cgaagttcct atactttcta gagaatagga acttcggaat | 60 |
| aggaaggtcg acggatcccc ggaatg | 86 |

<210> SEQ ID NO 7
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 7
tgtgtaggct ggagctgctt cgaagttcct atactttcta gagaatagga acttcggaat    60
aggaactaag gaggatattc atatgc    86

<210> SEQ ID NO 8
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 8
ctatgaatat cctccttagt tcctattccg aagttcctat tctctagaaa gtataggaac    60
ttcgaagcag ctccagccta cacc    84

<210> SEQ ID NO 9
<211> LENGTH: 84
<212> TYPE: DNA
<213> ORGANISM: Artificial Sequence
<220> FEATURE:
<223> OTHER INFORMATION: Synthetic Oligonucleotide

<400> SEQUENCE: 9
gtatgaatat cctccttagt tcctattccg aagttcctat tctctagaaa gtataggaac    60
ttcgaagcag ctccagccta cacg    84

<210> SEQ ID NO 10
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 10
agtgtaggct ggagctgctt cgaagttcct atactttcta gagaatagga acttcggaat    60
aggaactaag gaggatattc atatgg    86

<210> SEQ ID NO 11
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 11
tgtgtaggct ggagctgctt cgaagttcct atactttcta gagaatagga acttcggaat    60
aggaactaag gaggatattc atatgc    86

<210> SEQ ID NO 12
<211> LENGTH: 86
<212> TYPE: DNA
<213> ORGANISM: Artificial Sequence
<220> FEATURE:
<223> OTHER INFORMATION: Synthetic Oligonucleotide

<400> SEQUENCE: 12
tcatatgaat atcctcctta gttcctattc cgaagttcct attctctaga aagtatagga    60
acttcgaagc agctccagcc tacacc    86

<210> SEQ ID NO 13
<211> LENGTH: 23

```
<212> TYPE: DNA
<213> ORGANISM: Artificial Sequence
<220> FEATURE:
<223> OTHER INFORMATION: Synthetic Oligonucleotide

<400> SEQUENCE: 13
gtcgataagc tgattaccga cgc                                             23

<210> SEQ ID NO 14
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 14
gtgaaactat tcgtcaggca ctgg                                            24

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
ctactgcgta tgcattgcag                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
tcgtaatctt ctgccgtagc                                                 20

<210> SEQ ID NO 17
<211> LENGTH: 73
<212> TYPE: DNA
<213> ORGANISM: Artificial Sequence
<220> FEATURE:
<223> OTHER INFORMATION: Synthetic Oligonucleotide

<400> SEQUENCE: 17
gcgatgttgt actggttatc gccaatactc gttgaataac tggaaacgca ttgtgtaggc     60
tggagctgct tcg                                                        73

<210> SEQ ID NO 18
<211> LENGTH: 72
<212> TYPE: DNA
<213> ORGANISM: Artificial Sequence
<220> FEATURE:
<223> OTHER INFORMATION: Synthetic Oligonucleotide

<400> SEQUENCE: 18
gcgacgcacc tgctttgctc attgttgttt atccttgaat ctttacacta cggatatgaa     60
tatcctcctt ag                                                         72

<210> SEQ ID NO 19
<211> LENGTH: 22
<212> TYPE: DNA
<213> ORGANISM: Artificial Sequence
<220> FEATURE:
```

```
<223> OTHER INFORMATION: Synthetic Oligonucleotide

<400> SEQUENCE: 19
gactacagcg tgatgttgct gg                                              22

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
tcgacatcga ggatcagcag ac                                              22

<210> SEQ ID NO 21
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 21
gatcgatgtg atcataaccg gagagagcaa tgagtgaagc gtgtaggctg gagctgcttc     60

<210> SEQ ID NO 22
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 22
cggctggcga aacgtctggg attgaaggat taaataatcc attccgggga tccgtcgacc     60

<210> SEQ ID NO 23
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 23
gtcgataagc tgattaccga cgc                                             23

<210> SEQ ID NO 24
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 24
gtgaaactat tcgtcaggca ctgg                                            24
```

VIABLE GRAM NEGATIVE BACTERIA WITH REDUCED PROTEOLYTIC ACTIVITY LACKING OUTER MEMBRANE AGONISTS OF TLR4/MD-2

CROSS REFERENCE TO RELATED APPLICATION

This application claims priority from U.S. Provisional Application No. 61/533,017, filed Sep. 9, 2011.

INCORPORATION BY REFERENCE OF SEQUENCE LISTING

The Sequence Listing in an ASCII text file, named as 28631_SequenceListing.txt of 8 KB, created on Mar. 10, 2014, and submitted to the U.S. Patent and Trademark Office via EFS-Web, is incorporated herein by reference.

FIELD OF THE INVENTION

The present invention is directed to Gram-negative bacteria with substantially reduced bacterial proteolytic activity lacking a ligand that acts as an agonist of TLR4/MD-2 signalling, wherein the TLR4/MD2 signalling is substantially abrogated. The present invention is also directed to methods of generating such Gram-negative bacteria and uses thereof.

BACKGROUND OF THE INVENTION

Lipopolysaccharide (LPS) is the main outer membrane surface-associated component in Gram-negative bacteria and is associated with an array of pathological and physiological activities in mammalian host immune responses. LPS-mediated toxicity caused by these bacteria is generally due to lipid A, the hydrophobic moiety of LPS, which can function as an agonist of Toll-like receptor 4 (TLR4)/MD-2. Lipid A comprises two bisphosphorylated glucosamine residues with six acyl chains attached.

Kdo (3-deoxy-D<small>D</small>-manno-octulosonate) is considered an essential component of LPS, and it is believed that the minimal LPS structure required for growth of *E. coli* is two Kdo residues attached to lipid A ($Kdo_2$-lipid A; Re-LPS). Biosynthesis of Kdo begins with API (D<small>D</small>-arabinose 5-phosphate isomerase), which coverts D<small>D</small>-ribulose 5-phosphate (Ru5P) into A5P (D-arabinose 5-phosphate). In *E. coli* K-12, there are two API genes, kdsD and gutQ. Next, A5P is condensed with phosphoenolpyruvate (PEP) to form Kdo 8-phosphate (Kdo8P), which is then hydrolyzed forming Kdo. Kdo is subsequently activated as the sugar nucleotide CMP-Kdo, which is ultimately transferred to lipid $IV_A$ forming $Kdo_2$-lipid $IV_A$. The Kdo-dependent acyltransferases LpxL and LpxM transfer laurate and myristate, respectively, to $Kdo_2$-lipid $IV_A$ to form $Kdo_2$-lipid A (Re-LPS).

The strain *E. coli* K-12 TCM15, which has both API genes (kdsD and gutQ) deleted and thus lacks Kdo, is not viable unless supplied with exogenous A5P (e.g., see Meredith and Woodard, Identification of GutQ from *Escherichia coli* as a D-arabinose 5-phosphate isomerase, J Bacteriol 187:6936, 2005). The present invention features viable Gram-negative bacteria that substantially lack a ligand that acts as an agonist of TLR4/MD-2. Additional information regarding TLR4/MD-2 may be found at, for example, Qureshi et al., J. Exp. Med., Vol. 189, No. 4, Feb. 15, 1999, Pages 615-625; Shimazu et al., J. Exp. Med., Volume 189, Number 11, Jun. 7, 1999, Pages 1777-1782; Poltorak et al., Science 282, 2085 (1998), the disclosures of which are incorporated in their entirety by reference herein to the extent that the disclosures are consistent with the present invention. The ligand, for example, may comprise lipid A or a 6-acyl lipid. The viable Gram-negative bacteria comprise suppressor mutations, which enable viability despite lacking otherwise essential Kdo. Mamat et al. have described suppressor mutations in the yhjD and msbA genes non-conditional of *E. coli* TCM15 derivatives (see Mol Microbiol 67(3):633, 2008).

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY

The present invention features viable Gram-negative bacteria comprising an outer membrane that substantially lacks a ligand (e.g., lipid A, 6-acyl lipopolysaccharide, etc.) that acts as an agonist of TLR4/MD2, especially that lacks an agonist of human TLR4/MD2. The ligand may activate a production of costimulatory immune response molecules in a mammal (e.g., inducing macrophages to synthesize mediators of inflammation). In some embodiments, the Gram-negative bacterium is an *Escherichia coli* strain [e.g., KPM22, KPM22 L1, KPM22 L11, KPM22 L13, KPM22 L14, KPM22 L15, KPM22 L18, KPM22 L20, KPM316, KPM318, KPM334 through KPM362, BL21 (DE3)] or a *Pseudomonas* strain.

The viable Gram-negative bacterium may further comprise reduced activity of functional arabinose-5-phosphate (A5P) isomerases KdsD and GutQ. In some embodiments, the remaining activity of the arabinose-5-phosphate isomerases with reduced activity is insufficient to provide substrate for the Kdo biosynthetic pathway (e.g., zero or inadequate substrate for the Kdo biosynthetic pathway as would be understood by one of ordinary skill). In some embodiments, this is achieved by complete deletion of both genes. In the present KPM318 and some earlier lpxL lpxM deletions allow full restoration of Kdo synthesis (by growing on A5P) while limiting the lipid form to lipid $IV_A$, when grown in the presence of A5P as supplement.

In some embodiments, the viable Gram-negative bacterium further comprises one or more suppressor mutations, for example a suppressor mutation in a transporter (e.g., MsbA such as MsbA-P50S, MsbA-P18S, MsbA-T283A, MsbA-R310S, or MsbA-L48F) thereby increasing the transporter's capacity to transport lipid $IV_A$, a suppressor mutation affecting membrane protein YhjD (e.g., YhjD-R134C), a suppressor mutation that enables growth at 42 degrees Celsius, etc.

In some embodiments, one or more genes (e.g., lpxL, lpxM, pagP, lpxP, and/or eptA) are substantially deleted and/or one or more enzymes (e.g., LpxL, LpxM, PagP, LpxP, and/or EptA) are substantially inactive. For example, the viable Gram-negative bacterium may comprise a site-specific recombinase scar sequence at a site of a partial or complete deletion of one or more genes (e.g., lpxL, lpxM, pagP, lpxP, eptA). *E. coli* strains may include but are not limited to: KPM279, KPM280, KPM288, KPM290, KPM296, KPM300, KPM303, KPM310, KPM312, KPM314, KPM316, KPM317, KPM318, KPM334 through KPM362. In some embodiments, a gene encoding for a DNA restriction enzyme and/or a DNA methylation enzyme and/or a gene encoding for RecA and/or EndA is mutated or deleted.

In some embodiments, one or more proteases (e.g., OmpT) are substantially deleted through a loss of function mutation to reduce bacterial proteolytic activity. In some embodiments, insertion sequences (e.g., IS186) are included upstream of the coding region of the protease to reduce expression of one or more proteases by reducing the activity of the promoter. In some embodiments, E. coli strains of the present invention may include but are not limited to BL21 (DE3).

The bacterium may exhibit various growth characteristics. For example, in some embodiments, the bacterium can grow exponentially at 42 degrees Celsius. For example, in some embodiments, the bacterium exhibits an exponential phase doubling time of less than about 35 minutes, less than about 40 minutes, or less than about 45 minutes at above 37 degrees Celsius. In some embodiments, the bacterium remains viable in a salt concentration between about 0.1 M and 0.9 M.

In some embodiments, the bacterium comprises a means of conferring resistance to an antibiotic. In some embodiments, the bacterium comprises an F plasmid, an F' plasmid, or a gene encoding for F pilus production. In some embodiments, the bacterium can propagate bacteriophages fd, M13, or bacteriophages related to fd or M13. In some embodiments, the bacterium is competent to take up extracellular DNA (e.g., electrocompetent).

The present invention also features outer membranes derived from such Gram-negative bacteria, the outer membranes substantially lacking a ligand that is an agonist of TLR4/MD2. For example, the outer membrane may be derived from the Gram-negative bacteria described herein. The present invention also features viable Gram-negative bacteria (e.g., Gram-negative bacteria described herein such as E. coli and/or Pseudomonas) lacking an O-acyl transferase that can acylate a lipid A precursor of lipid A or Lipid IV$_A$. O-acyl transferases may include LpxL, LpxM, LpxP, and PagP.

In some embodiments, a Gram-negative bacterium as described herein is a donor bacterium. For example, the Gram-negative donor bacterium may comprise a DNA cassette comprising a gene (e.g., lpxL, lpxM, pagP, lpxP, eptA) having an open reading frame deletion and a means of conferring resistance to an antibiotic (e.g., kanamycin, penicillin, neomycin, tetracycline, chloramphenicol, or ampicillin), wherein the cassette is flanked by sites that are a target for a site-specific recombinase enzyme.

The present invention also features methods of selecting Gram-negative bacteria capable of exponential growth at a temperature above 40 degrees Celsius, wherein the Gram-negative bacterium substantially lacks a ligand that acts as an agonist of TLR4/MD2. In some embodiments, the method comprises growing a strain that substantially lacks the ligand that acts as an agonist of the TLR4/MD2 receptor and has a suppressor mutation that allows growth between about 30 to 40 degrees Celsius (e.g., a strain described herein); plating the strain on a suitable nutrient medium; and incubating the plated strain at 42 degrees Celsius until single colonies of bacteria appear.

The present invention also features methods of constructing a bacterium substantially lacking a gene such as lpxL, lpxM, pagP, lpxP, and eptA. The method comprises obtaining a viable Gram-negative bacterium comprising an outer membrane that substantially lacks a ligand that acts as an agonist of a TLR4/MD2 receptor (e.g., a strain described herein). In some embodiments, the viable Gram-negative bacterium comprises a DNA cassette comprising a modified gene (e.g., a modified antibiotic resistance gene), wherein the modified gene is a modified target gene having an open reading frame deletion. The DNA cassette may further comprise a means of conferring resistance to an antibiotic and/or may be flanked by appropriate target sites for a site-specific recombinase. The method further comprises subjecting the bacterium to P1 vir transduction and replacing the target gene with the modified gene (e.g., a modified antibiotic resistance gene) via homologous recombination. In some embodiments, the method further comprises deleting the antibiotic resistance gene by transient introduction of a site-specific recombinase capable of acting on sequences that flank the antibiotic resistance gene, thereby deleting the resistance gene and leaving a scar characteristic of the site-specific recombinase.

The present invention also features methods of producing a DNA sample and/or a protein sample substantially free of a ligand that acts as an agonist of TLR4/MD2. The method comprises obtaining a Gram-negative bacterium comprising an outer membrane that substantially lacks the ligand that acts as an agonist of the TLR4/MD2 receptor (e.g., a strain described herein), wherein the bacterium is competent to take up extracellular DNA. For producing the DNA sample, the method further comprises introducing a DNA vector to the bacterium, wherein the bacterium amplifies the DNA vector, and harvesting a DNA sample from the bacterium via a standard DNA isolation protocol. Such DNA isolation protocols are well known to one of ordinary skill in the art.

For producing the protein sample, the method may comprise introducing a DNA vector expression construct to the bacterium, wherein the vector comprises both a gene encoding a protein of interest expressed from a functional promoter and a selectable marker gene, growing the bacterium and allowing or inducing the bacterium to express the protein of interest, and harvesting the bacterium and treating the bacterium to release the protein of interest. In some embodiments, the bacterium comprises a mutation or deletion in one or more genes such as lolA, lolB and/or lpp. In some embodiments, for producing the protein sample, the method may comprise introducing a DNA vector expression construct to the bacterium, wherein the vector comprises both a gene encoding a protein of interest expressed from a functional promoter and a selectable marker gene, growing the bacterium and allowing or inducing the bacterium to express the protein of interest, and removing the bacterium from the culture medium to leave the protein of interest in the culture medium.

The present invention also features a library of bacteria substantially free of a ligand that acts as an agonist of the TLR4/MD2 receptor (e.g., a strain described herein), wherein the library of bacteria expresses a series of variants of a protein. The library of bacteria may be useful for screening the protein variants for activity in a mammalian cell based assay. In some embodiments, the members of the library are generated by phage display or by mutagenesis of a plasmid vector expressing a prototype member of the library.

Preferably, the bacteria are able to grow at least as rapidly in rich media supplemented with arabinose-5-phosphate as they grow in the same rich media lacking arabinose-5-phosphate, allowing a choice of outer membrane composition dependent upon the arabinose-5-phosphate without the supplement leading to a slower growth rate. Growth with supplement should be at least 95% of the unsupplemented growth rate and preferably a faster rate than the unsupplemented rate.

The viable Gram-negative bacteria described herein, various components thereof, reagents, and/or materials, may be available in the form of a kit. For example, in some embodiments, the kit comprises a viable Gram-negative bacterium having an outer membrane substantially free of a ligand that acts as an agonist of TLR4/MD2 (e.g., a strain described herein), wherein the bacterium is competent to take up extracellular DNA.

DEFINITIONS

The term "viable non-toxic Gram-negative bacteria" refers to viable Gram-negative bacterial strains comprising an outer membrane substantially free of a ligand that acts as an agonist of TLR4/MD2.

The terms "cells" and "host cells" and "recombinant host cells", which are used interchangeably herein, refer to cells that are capable of or have been transformed with a vector, typically an expression vector. The host cells used herein may be Gram-negative bacteria. It is understood that such terms refer not only to the particular subject cell, but to the progeny or potential progeny of such a cell. Because certain modifications may occur in succeeding generations due to either mutation or environmental influences, such progeny may not, in fact, be identical to the parent cell, but are still included within the scope of the term as used herein.

The terms "media" and "culture medium" is recognized in the art, and refers generally to any substance or preparation used for the cultivation of living cells.

The term "derived from," as used, for example, in the context of deriving lipid $IV_A$ from a strain of Gram-negative bacteria, refers to lipid $IV_A$ that can be obtained from the bacteria or the protein, and is intended to include fragments or portions of proteins.

The term "defective", as used herein, with regard to a gene or gene expression, may mean that the gene is not a wild type gene and that the organism does not have a wild type genotype and/or a wild type phenotype. The defective gene, genotype or phenotype may be the consequence of a mutation in that gene, or of a gene that regulates the expression of that gene (e.g., transcriptional or post-transcriptional), such that its normal expression is disrupted or extinguished. "Disrupted gene expression" is intended to include both complete inhibition and decreased gene expression (e.g., as in a leaky mutation), below wild type gene expression.

The term "Gram-negative bacteria" is recognized in the art, and refers generally to bacteria that do not retain Gram stain (e.g., the deposition of a colored complex between crystal violet and iodine). In an exemplary Gram stain, cells are first fixed to a slide by heat and stained with a basic dye (e.g., crystal violet), which is taken up by all bacteria (i.e., both Gram-negative and Gram-positive). The slides are then treated with an iodine-KI mixture to fix the stain, washed with acetone or alcohol, and finally counterstained with a paler dye of different color (e.g., safranin). Gram-positive organisms retain the initial violet stain, while Gram-negative organisms are decolorized by the organic solvent and hence show the counterstain. Gram-negative bacteria and cell lines include, but are not limited to, *Escherichia* spp., *Shigella* spp., *Salmonella* spp., *Campylobacter* spp., *Neisseria* spp., *Haemophilus* spp., *Aeromonas* spp., *Francisella* spp., *Yersinia* spp., *Klebsiella* spp., *Bordetella* spp., *Legionella* spp., *Citrobacter* spp., *Chlamydia* spp., *Brucella* spp., *Pseudomonas* spp., *Helicobacter* spp. and *Vibrio* spp.

The term "mutant Gram-negative bacteria", "LPS mutant Gram-negative bacteria", "kdsD and gutQ mutant Gram-negative bacteria", "API mutant Gram-negative bacteria" or similar terms, as used herein, includes Gram-negative bacteria of the invention that have been mutated one or more times in, for example, one or more of the gutQ, kdsD, kdsA, kdsB, waaA, msbA, yhjD genes, of any other biosynthetic, processing, or trafficking gene thereby producing an outer membrane substantially lacking LPS or other ligand that acts as an agonist of TLR4/MD2.

An "immunogenic portion of a molecule" refers to a portion of the molecule that is capable of eliciting an immune reaction against the molecule in a subject.

The term "isolated" as applied to LPS or lipid $IV_A$ molecules, refers to LPS or lipid $IV_A$ which has been isolated (e.g., partial or complete isolation) from other bacterial components, in particular from the outer membrane.

As used herein, the term "portion" when used in reference to a sequence (e.g., an amino acid sequence of a protein, a nucleic acid sequence of a gene) represents any amount of the referenced sequence (e.g., 0.001%, 0.1%, 1%, 10%, 30%, 50%, 75%, 80%, 85%, 90%, 95%, 98%, 99.999% of an amino acid sequence or nucleic acid sequence).

The term "modulation" as used herein refers to both upregulation (i.e., activation or stimulation, e.g., by agonizing or potentiating) and downregulation (i.e., inhibition or suppression, e.g., by antagonizing, decreasing or inhibiting). The term "inducible" refers in particular to gene expression which is not constitutive but which takes place in response to a stimulus (e.g., temperature, heavy metals or other medium additive).

The term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs and as applicable to the embodiment being described, single (sense or antisense) and double-stranded polynucleotides.

As used herein, the term "transfection" means the introduction of a nucleic acid (e.g., via an expression vector) into a recipient cell by nucleic acid-mediated gene transfer. "Transformation", as used herein, refers to a process in which a cell's genotype is changed as a result of the cellular uptake of exogenous DNA or RNA. In an illustrative embodiment, a transformed cell is one that expresses a mutant form of one or more of the kdsD and gutQ genes. A transformed cell can also be one that expresses a nucleic acid that interferes with the expression of a gutQ, kdsD, kdsA, kdsB, waaA, msbA, yhjD gene of any other biosynthetic, processing, or trafficking gene.

As used herein, the term "transgene" means a nucleic acid (e.g., a mutant kdsD, gutQ, kdsA, kdsB, waaA, msbA, yhjD gene of any other biosynthetic, processing, or trafficking gene, or an antisense transcript thereto) that has been introduced into a cell. A transgene could be partly or entirely heterologous, e.g., foreign, to the transgenic animal or cell into which it is introduced, or, can be homologous to an endogenous gene of the organism or- cell into which it is introduced, but which is designed to be inserted, or is inserted, into the animal or cell's genome in such a way as to alter the genome of the cell into which it is inserted. A transgene can also be present in a cell in the form of an episome.

The term "treating" a subject for a condition or disease, as used herein, is intended to encompass curing, as well as ameliorating at least one symptom of the condition or disease.

The term "vector" refers to a nucleic acid molecule, which is capable of transporting another nucleic acid to which it has been linked. Vectors capable of directing the expression of genes to which they are operatively linked are referred to herein as "expression vectors."

The term "expression system" as used herein refers to an expression vector under conditions whereby an mRNA may be transcribed and/or an mRNA may be translated into protein, structural RNA, or other cellular component. The expression system may be an in vitro expression system, which is commercially available or readily made according to art known techniques, or may be an in vivo expression system, such as a eukaryotic or prokaryotic cell containing the expression vector. In general, expression vectors of utility in recombinant DNA techniques are often in the form of "plasmids" which refer generally to circular double stranded DNA loops that, in their vector form, are not bound to the chromosome. In the present specification, "plasmid" and "vector" are used interchangeably as the plasmid is the most commonly used form of vector. However, the invention is intended to include such other forms of expression vectors which serve equivalent functions and are well known in the art or which become known in the art subsequently hereto (e.g., cosmid, phagemid and bacteriophage vectors).

In some embodiments, the term "viable" means that the cells are able to grow and divide exponentially for multiple generations (e.g., more than 10 generations) in a suitable nutrient medium, without supplementation, and that the cells can be stored under typical storage conditions for that cell type and subsequently re-grown. For example, in some embodiments, supplementation of arabinose 5-phosphate is not required for viability of the presently claimed bacteria.

In some embodiments, the term "viable" means that the claimed cells of the present invention have similar growth characteristics as compared to wild type or parental cells in a rich media. In some embodiments, similar growth characteristics means the growth rate of the claimed cells is more than 60% of the wild type or parental cells (wherein the growth of the wild type is set as being 100%). In some embodiments, similar growth characteristics means the growth rate of the claimed cells is more than 70% of the wild type or parental cells (wherein the growth of the wild type is set as being 100%). In some embodiments, similar growth characteristics means the growth rate of the claimed cells is more than 80% of the wild type or parental cells (wherein the growth of the wild type is set as being 100%). In some embodiments, similar growth characteristics means the growth rate of the claimed cells is more than 90% of the wild type or parental cells (wherein the growth of the wild type is set as being 100%). In some embodiments, similar growth characteristics means the growth rate of the claimed cells is more than 95% of the wild type or parental cells (wherein the growth of the wild type is set as being 100%).

In some embodiments, the term "viable" means that the claimed cells of the present invention can grow at or more than a temperature of about 39 degrees celcius. In some embodiments, the term "viable" means that the claimed cells of the present invention can grow at or more than a temperature of about 40 degrees celcius. In some embodiments, the term "viable" means that the claimed cells of the present invention can grow at or more than a temperature of about 41 degrees celcius. In some embodiments, the term "viable" means that the claimed cells of the present invention can grow at or more than a temperature of about 42 degrees celcius. In some embodiments, the term "viable" means that the claimed cells of the present invention can grow at or more than a temperature of 43 degrees celcius.

The term "substantially abrogated" as it relates to TLR4/MD-2 signalling means that the induction of a cellular signaling process by membrane and/or membrane extracts from a mutant bacterial strain is significantly reduced by more than 90% as compared to that induced by the membrane and/or membrane extracts from the parental bacterial strain, wherein the mutant strain has an alteration in one or more LPS anabolic pathway components and wherein the parental strain has no LPS biochemical pathway modifications. In some embodiments, the term "substantially abrogated" means that the induction of a cellular signaling process by membrane and/or membrane extracts from a mutant bacterial strain is reduced by more than 95% as compared to that induced by the membrane and/or membrane extracts from the parental bacterial strain. In some embodiments, the term "substantially abrogated" means that the induction of a cellular signaling process by membrane and/or membrane extracts from a mutant bacterial strain is reduced by more than 97% as compared to that induced by the membrane and/or membrane extracts from the parental bacterial strain. In some embodiments, the parental strain is BL21 (DE3). In some embodiments, the percentage abrogation described above is defined at a stimulation of a membrane and/or membrane extract prepared at more than 10 ng/mL. In some embodiments, the percentage abrogation described above is defined at a stimulation of a membrane and/or membrane extract prepared at more than 100 ng/mL. In some embodiments, the percentage abrogation described above is defined at a stimulation of a membrane and/or membrane extract prepared at more than 1000 ng/mL. In some embodiments, the percentage abrogation described above is defined at a stimulation of a membrane extract prepared at more than 2000 ng/mL. In some embodiments, the percentage abrogation described above is defined at a stimulation of a membrane and/or membrane extract prepared at more than 5000 ng/mL.

In some embodiments, cellular signaling processes include measurement of cytokine levels. In some embodiments, the induction of a signaling process refers to induction of TNF alpha, IL-8, and CD86 expression. Standard protocols for cellular signaling processes are known to one of ordinary skill in the art, including, for example Cognet et al, Journal of Immunological Methods 272 (2003) 199-210, the disclosure of which is incorporated in its entirety by reference herein.

In some embodiments, the term "substantially abrogated" means that the induction of a cellular signaling process by a membrane and/or membrane extract from a mutant bacterial strain is reduced by more than 1100 fold as compared to that induced by the membrane and/or membrane extract from a parental bacterial strain. In some embodiments, the term "substantially abrogated" means that the induction of a cellular signaling process by a membrane and/or membrane extract from a mutant bacterial strain is reduced by more than 200 fold as compared to that induced by the a membrane and/or membrane extract from the parental bacterial strain. In some embodiments, the term "substantially abrogated" means that the induction of a cellular signaling process by a membrane and/or membrane extract from a mutant bacterial strain is reduced by more than 300 fold as compared to that induced by the a membrane and/or membrane extract from the parental bacterial strain. In some embodiments, the term "substantially abrogated" means that the induction of a cellular signaling process by a membrane and/or membrane extract from a mutant bacterial strain is reduced by more than 400 fold as compared to that induced by the a membrane and/or membrane extract from the parental bacterial strain. In some embodiments, the term "substantially abrogated" means that the induction of a cellular signaling process by a membrane and/or membrane extract from a mutant bacterial strain is reduced by more than 500 fold as compared to that induced by the a membrane and/or membrane extract from a parental bacterial strain.

The term "substantially reduced" as it relates to proteolytic activity means that the proteolytic activity is reduced by more than 90% as compared to the proteolytic activity of bacterial strains expressing wild-type OpmT. The term "substantially reduced" as it relates to proteolytic activity means that the proteolytic activity is reduced by more than 95% as compared to the proteolytic activity of bacterial strains expressing wild-type OpmT. The term "substantially reduced" as it relates to proteolytic activity means that the proteolytic activity is reduced by more than 98% as compared to the proteolytic activity of bacterial strains expressing wild-type OpmT.

The term "substantially reduced" as it relates to proteolytic activity means that the proteolytic activity is reduced by more than 90% as compared to the proteolytic activity of bacterial strains expressing wild-type Lon protease. The term "substantially reduced" as it relates to proteolytic activity means that the proteolytic activity is reduced by more than 95% as compared to the proteolytic activity of bacterial strains expressing wild-type Lon protease. The term "substantially reduced" as it relates to proteolytic activity means that the proteolytic activity is reduced by more than 98% as compared to the proteolytic activity of bacterial strains expressing wild-type Lon protease.

The term "substantially reduced" as it relates to proteolytic activity means that the proteolytic activity is reduced by more than 90% as compared to the proteolytic activity of K-12 strains. The term "substantially reduced" as it relates to proteolytic activity means that the proteolytic activity is reduced by more than 95% as compared to the proteolytic activity of K12 strains. The term "substantially reduced" as it relates to proteolytic activity means that the proteolytic activity is reduced by more than 98% as compared to the proteolytic activity of K12 strains.

The term "endotoxin signaling activity" as it relates to TLR4/MD-2 signaling means that TLR4/MD-2 signaling is activated to induce a signaling cascade that results in the induction of the expression of inflammatory mediators in mammalian cells.

BRIEF DESCRIPTION OF THE DRAWINGS

FIG. 11 Charge deconvoluted electrospray-ionization Fourier-transformed ion cyclotron (ESI FT-ICR) mass spectra in negative ion mode of LPS molecules isolated from *E. coli* strains KPM316 (A) and KPM318 (B). The mass numbers given refer to the monoisotopic peaks of the neutral molecules. The peak at 1178.66 u is most likely a triacylated degradation product of lipid $IV_A$ (1404.86 u) produced during LPS isolation as it is not consistent with a known pathway intermediate.

FIG. 12A-G The sequence for *Escherichia coli* KPM316 (msbA52 ΔkdsD ΔgutQ ΔlpxL ΔlpxM ΔpagP ΔlpxP). msbA52 replaces the wild type allele of msbA, wherein a C at 965895 is replaced by a T, resulting in a Serine instead of Proline at amino acid 18 in the MsbA protein. The following were deleted from the parental strain: ΔgutQ (FIG. 12B), ΔkdsD (FIG. 12C), ΔlpxL (FIG. 12D), ΔlpxM (FIG. 12E), ΔpagP (FIG. 12F), and ΔlpxP (FIG. 12G).

FIG. 13A-H *Escherichia coli* KPM318 (msbA52 ΔkdsD ΔgutQ ΔlpxL ΔlpxM ΔpagP ΔlpxP ΔeptA). msbA52 replaces the wild type allele of msbA, wherein a C at 965895 is replaced by a T, resulting in a Serine instead of Proline at amino acid 18 in the MsbA protein (FIG. 13A). The following were deleted from the parental strain: ΔgutQ (FIG. 13B), ΔkdsD (FIG. 13C), ΔlpxL (FIG. 13D), ΔlpxM (FIG. 13E), ΔpagP (FIG. 13F), ΔlpxP (FIG. 13G), and ΔeptA (FIG. 13H).

FIG. 33 SDS-PAGE analysis of protein extracts (10 µg each) and culture media (10 µl each). The protein extracts were prepared from uninduced cells and cells after an induction time of 3 hr. The culture media were obtained from cells grown under conditions of overnight IPTG induction. The samples were resolved using 10% polyacrylamide gels and stained with Coomassie blue. Molecular Mass protein markers (Broad Range—Bio-Rad) were run in lanes M.

FIG. 34 SDS-PAGE analysis of protein extracts (10 µg each) and culture media (10 µl each). The protein extracts were prepared from uninduced cells and cells after an induction time of 3 hr. The culture media were obtained from cells grown under conditions of overnight IPTG induction. The samples were resolved using 10% polyacrylamide gels and stained with Coomassie blue. Molecular mass protein markers (Broad Range—Bio-Rad) were run in lanes M.

FIG. 35 SDS-PAGE analysis (upper panel) of protein extracts (8 µg each) and culture media (10 µl each). The protein extracts were prepared from uninduced cells and cells after overnight induction. The culture media were obtained from cells grown under conditions of overnight IPTG induction. The samples were resolved using 10% polyacrylamide gels and stained with Coomassie blue. For the immunoblots (lower panel), 8 µg of each protein extract and 2.5 µl of each culture supernatant were subjected to SDS-PAGE. The blotted membranes were probed with anti- MalE and alkaline phosphatase-conjugated goat anti-mouse IgG (H+L) antibodies, and developed in the presence of nitroblue tetrazolium (NBT) and 5-bromo-4-chloro-3-indolylphosphate (BCIP) substrate. Molecular mass protein markers (Broad Range—Bio-Rad) were run in lanes M.

FIG. 36 SDS-PAGE analysis (upper panel) of protein extracts (8 μg each) and culture media (10 μl each). The protein extracts were prepared from uninduced cells and cells after overnight induction. The culture media were obtained from cells grown under conditions of overnight IPTG induction. The samples were resolved using 10% polyacrylamide gels and stained with Coomassie blue. For the immunoblots (lower panel), 8 μg of each protein extract and 2.5 μl of each culture supernatant were subjected to SDS-PAGE. The blotted membranes were probed with anti-MalE and alkaline phosphatase-conjugated goat anti-mouse IgG (H+L) antibodies, and developed in the presence of nitroblue tetrazolium (NBT) and 5-bromo-4-chloro-3-indolylphosphate (BCIP) substrate. Molecular mass protein markers (Broad Range—Bio-Rad) were run in lanes M.

FIG. 64 The E. coli strains TOP10 and XL1-Blue were transformed with plasmid pMAK705 $Km^R$ CATMUT. The resulting strains TOP10/pMAK705 $Km^R$ CATMUT and XL1-Blue/pMAK705 $Km^R$CATMUT were streaked on both LB+30 µg/ml kanamycin and LB+30 µg/ml kanamycin+15 µg/ml chloramphenicol plates.

FIG. 68A shows the PCR products for the Km (1571 bp) and Cm insertion (1108 bp) cassettes.

FIG. 68B shows the DpnI-digested samples used for gel purification.

FIG. 69 shows verification of the ΔlpxL mutations in kanamycin- and chloramphenicol-resistant transformants of E. coli strains BL21(DE3) and BL21(DE3) msbA L11/pKD46

FIG. 70 shows verification of the ΔlpxL mutations in kanamycin- and chloramphenicol-resistant transformants of E. coli strains BL21(DE3) and BL21(DE3) msbA L18/pKD46

FIG. 71 shows verification of the ΔlpxL mutations in kanamycin- and chloramphenicol-resistant transformants of E. coli strains BL21(DE3) and BL21(DE3) msbA L1/pKD46 and BL21(DE3) msbA L14/pKD46.

FIG. 72 shows verification of the ΔlpxL mutations in kanamycin- and chloramphenicol-resistant transformants of E. coli strains BL21(DE3) and BL21(DE3) msbA L15/pKD46.

FIG. 84 shows verification of the ΔgutQ mutations in kanamycin-resistant transformants of E. coli strain BL21 (DE3) msbA L1 ΔlpxL ΔkdsD (ΔgutQ::Km⁺)/pKD46.

FIG. 85 shows verification of the ΔgutQ mutations in kanamycin-resistant transformants of E. coli strain BL21 (DE3) msbA L1 ΔlpxL ΔkdsD (ΔgutQ::Km⁺)/pKD46.

FIG. 86 shows verification of the kanamycin resistance cassette loss in E. coli strain BL21(DE3) msbA L14 ΔlpxL ΔkdsD ΔgutQ (Km⁻)/pFLP2.

DESCRIPTION OF PREFERRED EMBODIMENTS

Figure 1:
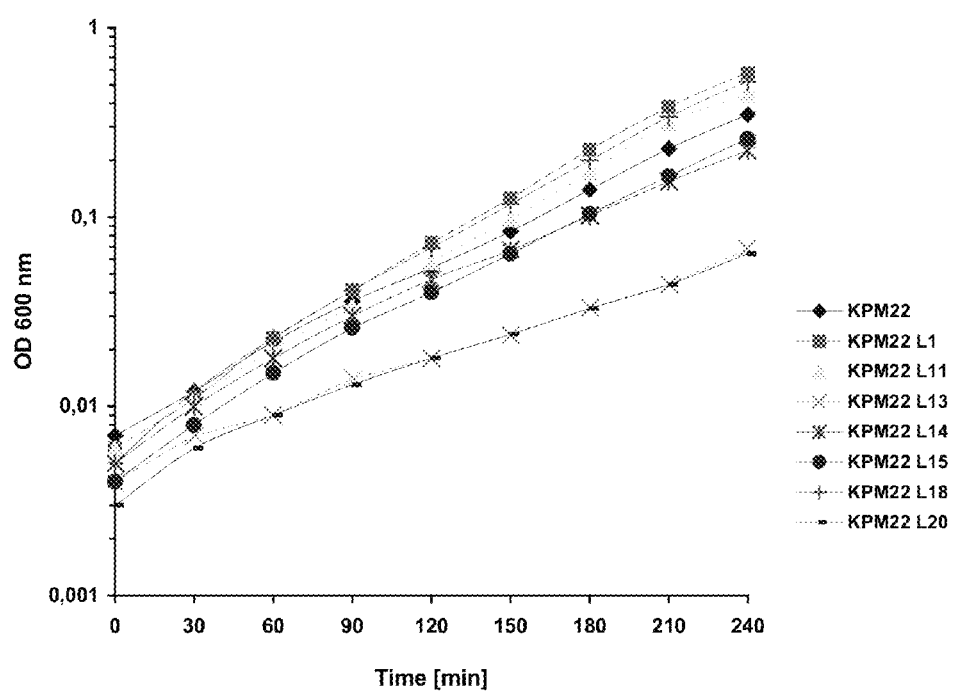
FIG. 1 shows growth curves of E. coli KPM22 and the KPM22-like strains KPM22 L1, KPM22 L11, KPM22 L13, KPM22 L14, KPM22 L15, KPM22 L18, and KPM22 L20. Generation times were determined in LB medium with shaking at 200 rpm at 37° C. Generation times (under these conditions) were calculated to be as follows: KPM22 40 min, KPM22 L1 37 min, KPM22L11 39 min, KPM22 L13 59 min, KPM22 L14 44 min, KPM22 L15 40 min, KPM22 L18 36 min, and KPM22 L20 55 min.

Lipid A, a component of lipopolysaccharide (LPS) which comprises two bisphosphorylated glucosamine residues to which six acyl chains are attached, functions as an agonist of Toll-like receptor 4 (TLR4/MD-2). TLR4/MD-2 is present on several immune system cells, for example macrophages, monocytes, and dendritic cells. Activation of TLR4/MD-2 via LPS/Lipid A can lead to activation of costimulatory immune response components and molecules, ultimately causing endotoxicity. For example, when LPS becomes bound to TLR4/MD-2 (in humans), cytokine production can be activated, complement can be activated, and coagulation can be activated. Cytokines may include interleukin IL-1, IL-6, IL-8, tumor necrosis factor (TNF) (e.g., TNFα), and platelet activating factor. Such cytokines can stimulate production of mediators of inflammation and septic shock (e.g., prostaglandins, leukotrienes). Complement C3a and C5a can cause histamine release leading to vasodilation and/or affect neutrophil chemotaxis. Blood-clotting Factor XII can activate several responses resulting in thrombosis, plasmin activation (fibrinolysis, hemorrhaging), and the like.

Gram-negative bacteria normally comprise a majority of 6-acyl LPS in their outer membranes. The present invention features viable Gram-negative bacteria comprising an outer membrane that substantially lacks components (e.g., ligands) that act as agonists of Toll-like receptor 4 (TLR4)/MD-2. The components (e.g., ligands) may comprise lipid A, a 6-acyl lipid (e.g., 6-acyl LPS), the like, or a combination thereof. In contrast to normal LPS (or lipid A, 6-acyl lipid), lipid $IV_A$, or 4-acyl LPS binds less tightly to human TLR4/MD-2 and acts as a mild antagonist to TLR-4/MD2 rather than as an agonist. In some embodiments, the ligand substantially lacking in the outer membrane comprises a lipid $IV_A$, or derivatives of lipid $IV_A$.

As used herein, the term "substantially lacks" means that the outer membrane has from about zero of the agonist ligand up to a level of such ligand that does not induce a response above about 25% of the maximal signal in the HEK-Blue assay when 20 µg of outer membrane is added to a single assay well. In some embodiments, a HEK-Blue assay that may be used in accordance with the present invention may be obtained from InvivoGen, 3950 Sorrento Valley Blvd., Suite 100, San Diego, Calif. 92121 (USA), catalog #hkb-htlr4, and the assay protocol is submitted in FIG. 92. For example, in some embodiments, outer membrane that substantially lacks a ligand that acts as an agonist of Toll-like receptor 4 (TLR4/MD-2) means that the outer membrane does not have the ligand at all. In some embodiments, the outer membrane may have a low amount of agonist for TLR4/MD-2 present at a level that is below the detection limit in a HEK-Blue cell-based assay when tested as a membrane extract at up to 20 µg per well. The human cell line HEK-Blue is engineered to be very sensitive to TLR4/MD-2 signaling, and this assay will give a very strong signal when only 20 pg of LPS is present per well. In some embodiments, a very low signal (e.g., less than about 25% of the maximal value) is seen even at a level of 20 µg of outer membrane per well.

The Gram-negative bacteria of the present invention include but are not limited to Escherichia coli. For example, distantly related Gram-negative species such as Pseudomonas species may also be engineered to grow while lacking TLR4/MD2 agonist as a component of their outer membrane. In some embodiments the Escherichia coli strain is K-12, W3110, MG1655, B/r, BL21, O157:h7, 042, 101-1, 1180, 1357, 1412, 1520, 1827-70, 2362-75, 3431, 53638, 83972, 929-78, 98NK2, ABU 83972, B, B088, B171, B185, B354, B646, B7A, C, c7122, CFT073, DH1, DH5α, E110019, E128010, E74/68, E851/71, EAEC 042, EPECa11, EPECa12, EPECa14, ETEC, H10407, F11, F18+, FVEC1302, FVEC1412, GEMS_EPEC1, HB101, HT115, KO11, LF82, LT-41, LT-62, LT-68, MS 107-1, MS 119-7, MS 124-1, MS 145-7, MS 79-2, MS 85-1, NCTC 86, Nissle 1917, NT:H19, NT:H40, NU14, O103:H2, O103:HNM, O103:K+, O104:H12, O108:H25, O109:H9, O111:H−, O111:H19, O111:H2, O111:H21, O111:NM, O115:H−, O115:HNM, O115:K+, O119:H6, O119:UT, O124:H40, O127a:H6, O127:H6, O128:H2, O131:H25, O136:H−, O139:H28 (strain E24377A/ETEC), O13:H11, O142:H6, O145:H−, O153:H21, O153:H7, O154:H9, O157:12, O157:H−, O157:H12, O157:H43, O157:H45, O157:H7 EDL933, O157:NM, O15:NM, O177:H11,>O17:K52:H18 (strain UMN026/ExPEC), O180:H−, O1:K1/APEC, O26, O26:H−, O26:H11, O26:H11:K60, O26:NM, O41:H−, O45:K1 (strain S88/ExPEC), O51:H−, O55:H51, O55:H6, O55:H7, O5:H−, O6, O63:H6, O63:HNM, O6:K15:H31 (strain 536/UPEC), O7:K1(strain IAI39/ExPEC), O8 (strain IAI1), O81 (strain ED1a), O84:H−, O86a:H34, O86a:H40, O90:H8, O91:H21, O9:H4 (strain HS), O9:H51, ONT:H−, ONT:H25, OP50, Orough:H12, Orough:H19, Orough:H34, Orough:H37, Orough:H9, OUT:H12, OUT:H45, OUT:H6, OUT:H7, OUT:HNM, OUT:NM, RN587/1, RS218, 55989/EAEC, B/BL21,B/BL21-DE3, SE11, SMS-3-5/SECEC, UTI89/UPEC, TA004, TA155, TX1999, or Vir68.

In some embodiments, the viable Gram-negative bacteria of the present invention have reduced activity of the functional D-arabinose-5-phosphate (A5P) isomerases (APIs) KdsD and GutQ. The reduced activity of functional APIs KdsD and GutQ may be a result of substantial inactivation of the APIs, for example a chemical agent functioning to substantially inactivate the APIs, a dominant negative protein functioning to substantially inactivate the APIs, an antibody of fragment thereof that binds and functions to substantially inactivate the APIs, or the like. In some embodiments, the reduced activity of functional APIs KdsD and GutQ may be a result of a partial or substantial deletion or a mutation in the genes encoding the APIs (e.g., kdsD, gutQ). The bacteria may include E. coli K-12 TCM15, BL21, BL21(DE3), W3110.

Suppressor Mutations

The viable Gram-negative bacteria of the present invention comprise a suppressor mutation that enables growth despite lacking any TLR4 agonists in the membrane. For example, the viable Gram-negative bacteria may be derived from E. coli K-12 TCM15, which lacks both API genes (thus lacks Kdo) and is not viable unless supplied with exogenous A5P. The viable Gram-negative bacteria may comprise a suppressor mutation that allows the bacteria to be viable despite lacking both API genes (and Kdo). Suppressor mutations may include gain-of-function suppressor mutations as well as loss-of-function suppressor mutations. In some embodiments, the suppressor mutation is a mutation in a gene encoding a transporter or a membrane protein, e.g., the transporter MsbA encoded by msbA or the membrane protein YhjD encoded by yhjD. The suppressor mutation may provide the transporter or membrane protein an increased capacity to transport lipid $IV_A$. The suppressor mutation may include an amino acid substitution, for example a mutation at amino acid position 18, or at position 50, or at position 283, or at position 310, or at position 448 in MsbA or a mutation at amino acid position 134 in YhjD.

In some embodiments, the suppressor mutation results in up-regulated expression of a transporter (e.g., MsbA), increasing the bacterium's capability of transporting lipid $IV_A$. The suppressor mutation is not limited to the aforementioned examples. The bacteria may include E. coli K-12 KPM22, KPM22 L1, KPM22 L11. In some embodiments, the bacteria include E. coli K-12 KPM22 L13, KPM22 L14, KPM22 L15, KPM22 L18, KPM22 L20. In some embodiments, the suppressor alleles of the E. coli msbA gene may be used in distantly related Gram-negative bacterial species (such as Pseudomonas) even though the wild type E. coli msbA gene itself cannot replace the native msbA gene.

Non-Revertable Strains

In wild-type Gram-negative bacteria, the O-acyl transferases LpxL and LpxM add O-linked lipids to Kdo2-lipid $IV_A$ to form a 6-acyl lipid that functions as an agonist of TLR4/MD-2. In the absence of Kdo, the O-acyl transferases LpxL and LpxM fail to use lipid $IV_A$ as a substrate and do not add the O-linked lipids. However, it is possible that mutations in lpxL (encoding LpxL) or lpxM (encoding LpxM) may alter specificity of the enzymes, allowing the transferases to use lipid $IV_A$ as a substrate and thereby generating a 6-acyl lipid that functions as an agonist of TLR4/MD-2. Or, mutations may arise in promoters or regulators of lpxP or pagP, activating expression of these normally absent or very low abundance transferases. Or, mutations may arise in promoters or regulators of lpxL or lpxM, which may activate their overexpression.

To help avoid these situations, the bacteria of the present invention may further comprise a deletion (e.g. partial deletion, substantial deletion, etc.) in one or more of the following genes: lpxL, lpxM, pagP, and lpxP. Or, in some embodiments, one or more enzymes (e.g., LpxL, LpxM, PagP, LpxP) are substantially inactivated in the bacterium. In some embodiments, the gene eptA encoding for the lipid A phosphoethanolamine transferase is partially or substantially deleted. In some embodiments, the bacteria is E. coli K-12 KPM279 (KPM22 ΔlpxL::Km$^+$), KPM 280 (KPM22 ΔlpxM::Km$^+$), KPM 288 (KPM22 L1 ΔlpxL::Km$^+$), KPM 290 (KPM22 L11 ΔlpxL::Km$^+$), KPM 296 (KPM22 L11 ΔlpxL), KPM 300 (KPM22 L11 ΔlpxL ΔlpxM::Km$^+$), KPM 303 (KPM22 L11 ΔlpxL ΔlpxM), KPM310 (KPM22 L11 ΔlpxL ΔlpxM ΔpagP::Km$^+$), KPM312 (KPM22 L11 ΔlpxL ΔlpxM ΔpagP), KPM314 (KPM22 L11 ΔlpxL ΔlpxM ΔpagP ΔlpxP::Km$^+$), KPM316 (KPM22 L11 ΔlpxL ΔlpxM ΔpagP ΔlpxP), KPM317 (KPM22 L11 ΔlpxL ΔlpxM ΔpagP ΔlpxP ΔeptA::Km$^+$), or KPM 318 (KPM22 L11 ΔlpxL ΔlpxM ΔpagP ΔlpxP ΔeptA) or further derivatives of these strains.

Laboratory Tools

The present invention also features laboratory tools, reagents, strains (e.g., base strains, donor strains), and the like, derived from the viable Gram-negative bacteria as described. For example, in some embodiments, the bacteria of the present invention are competent to take up extracellular DNA. In some embodiments, the bacteria are electrocompetent. In some embodiments, the bacteria comprise a means of conferring resistance to an antibiotic (e.g., kanamycin, penicillin, neomycin, ampicillin, etc.). In some embodiments, the bacteria comprise a means to express proteins for high-throughput screening on cells. In some embodiments, the bacteria comprise a means to express recombinant proteins for research and/or therapeutic and/or diagnostic use.

The bacteria may comprise at least one additional suppressor mutation that enables growth above 37 degrees Celsius (e.g., at 42 degrees Celsius). The additional suppressor mutations may for example stabilize the outer membrane of the bacteria or enhance transport of a toxic precursor away from the inner membrane. In some embodiments, bacteria can grow exponentially above 37 degrees Celsius, for example at about 38 degrees Celsius, at about 39 degrees Celsius, at about 40 degrees Celsius, at about 41 degrees Celsius, at about 42 degrees Celsius.

In some embodiments, the bacteria exhibit an exponential phase doubling time of less than about 30 minutes at above 37 degrees Celsius. Or, the bacteria may exhibit an exponential phase doubling time of less than 35 minutes or less than 40 minutes or less than about 45 minutes at above 37 degrees Celsius. In some embodiments, the bacteria exhibit an exponential phase doubling time of less than about 30 minutes (or less than about 35 minutes or less than about 40 minutes or less than about 45 minutes) at above 40 degrees Celsius. In some embodiments, the bacteria exhibit an exponential phase doubling time of less than about 30 minutes (or less than about 35 minutes or less than about 40 minutes or less than about 45 minutes) at 42 degrees Celsius. In some embodiments, the bacterial strain is E. coli K-12 KPM296-6.

In some embodiments, additional suppressor mutations may alter (e.g., enhance) the bacteria's ability to grow in various salt concentrations. In some embodiments, the viable gram-negative bacteria are viable in a salt (NaCl) concentration between about 0.1 M and 0.9 M.

Donor strains may provide the ability to rapidly construct new variant strains. The donor strains may comprise one or more of the aforementioned gene modifications, for example partial or substantial deletions in one of the following genes: lpxL, lpxM, lpxP, pagP, eptA, kdsD, gutQ, etc. Each donor deletion construct has a selectable marker gene cassette replacing the deleted DNA sequence, and the cassette is flanked by site-specific deletion sites in such an orientation and arrangement that they may be used subsequently to delete the selectable marker gene cassette when the corresponding recombinase is transiently or temporarily introduced into the strain.

In some embodiments, the bacteria further comprise an F plasmid, an F' plasmid, or genes encoding for F pilus production. In some embodiments, the bacteria can propagate bacteriophages fd, M13, or bacteriophages related to fd or M13. In some embodiments a gene encoding for a DNA restriction enzyme or a DNA methylation enzyme is mutated or deleted. This may allow for enhanced transformation and/or cloning of unmodified DNA or PCR-amplified DNA. In some embodiments a gene encoding for RecA and/or a gene encoding EndA is mutated, partially deleted, or substantially deleted. Such inactivation or deletion of recA results in a host that predominantly produces monomeric plasmid DNAs following transformation with a plasmid. Inactivation of endA leads to increased yields of supercoiled DNA of a plasmid introduced into such a strain.

The present invention also features an outer membrane of a Gram-negative bacterium that substantially lacks a ligand that is an agonist of a TLR4/MD2 receptor.

Bacteria of the present invention may be used as donor strains. In some embodiments, the donor strains may comprise an outer membrane that substantially lacks a ligand that acts as an agonist of TLR4/MD2. In some embodiments, the donor strains comprise a DNA cassette comprising a gene having an open reading frame deletion. For example, the gene may be selected from the group consisting of lpxL, lpxM, pagP, lpxP, and eptA. The DNA cassette may further comprise a means of conferring resistance to an antibiotic and/or a recombinase component.

The bacteria of the present invention may retain "scar" DNA sequences at the site(s) of the engineered gene deletions, particularly in one or more of the genes selected from the group consisting of kdsD, gutQ, lpxL, lpxM, pagP, lpxP, and eptA. The "scar" is produced upon deletion of the selectable cassette by site-specific recombination. The recombinase may be one selected from the group consisting of FLP, Cre, Int/Xis, Hin, Gin, or the like. The scar produced may be active for subsequent recombination by the same recombinase, or alternatively the scar may be inactive for further recombination events by the same recombinase. Deletion of the selectable cassette DNA results in a strain that may be used again as a recipient for subsequent transfer of a further gene deletion using a similar selectable cassette, thereby facilitating the construction of multiple gene deletions in a single strain.

Methods

The present invention also features methods of selecting a Gram-negative bacterium substantially lacking a ligand that acts as an agonist of TLR4/MD2, wherein the bacterium is capable of exponential growth at a temperature above 40 degrees Celsius. In some embodiments, the method comprises growing the bacteria that substantially lack the ligand that acts as an agonist of the TLR4/MD2 receptor (e.g., lipid A, 6-acyl lipid, etc.) and has a suppressor mutation that allows growth between about 30 to 40 degrees Celsius. The bacteria can then be plated on a suitable nutrient medium and incubated at 42 degrees Celsius. Single colonies that appear under such conditions represent the bacterium substantially lacking the ligand that acts as an agonist of TLR4/MD2 and capable of exponential growth at 42 degrees Celsius.

The present invention also features methods of constructing bacteria substantially lacking a gene selected from the group consisting of lpxL, lpxM, pagP, lpxP, and eptA. The method comprises obtaining a viable Gram-negative bacterium comprising (i) an outer membrane that substantially lacks a ligand that acts as an agonist of TLR4/MD2 and (ii) a DNA cassette comprising a modified gene, the modified gene being a modified target gene having an open reading frame deletion, the DNA cassette further comprising a means of conferring resistance to an antibiotic and further being flanked by appropriate target sites for a site-specific recombinase. The method further comprises subjecting the bacterium to P1 vir transduction and replacing the target gene with the modified resistance cassette gene via homologous recombination. Subsequently, a site-directed recombinase enzyme or DNA encoding the enzyme is introduced into the cells and this enzyme acts on the corresponding recognition sites flanking the cassette to catalyze recombination, leaving a scar sequence only in the chromosome (see Example 3 below). Alternatively, the gene deletion cassette described above may be introduced into the chromosome of the strain directly using a PCR-amplified linear form of the cassette via the "Red-Gam" homologous recombination method (see BMC Molecular Biology 2008, 9:20). As above, the resistance gene is then subsequently deleted using a site-specific recombination step, again leaving a "scar" sequence. P1vir transduction, Red-Gam recombination using linear DNA, and site-directed recombination are all techniques well known to one of ordinary skill in the art.

Bacteria, for example Gram-negative bacteria such as E. coli, are commonly used as expression systems for amplifying DNA or expressing proteins of interest. In some cases, the harvested DNA or protein obtained from the bacteria may be contaminated with components of the bacteria, for example ligands that act as agonists of TLR4/MD-2 (e.g., lipid A, LPS). The contamination can have deleterious effects on further experiments and procedures, such as transient transfection of mammalian host cell lines, treatment of cultured mammalian cells that serve as reporter lines in cell-based screening assay.

The present invention also features methods of producing DNA samples substantially free of a ligand that acts as an agonist of TLR4/MD-2. The method may comprise obtaining Gram-negative bacteria comprising an outer membrane that substantially lacks the ligand that acts as an agonist of TLR4/MD-2. The bacteria are generally competent to take up extracellular DNA. A DNA vector can be introduced to the bacteria via standard methods well known to one of ordinary skill in the art. The bacteria function to amplify the DNA vector, and the bacteria can be grown in appropriate media. The amplified DNA sample can be harvested from the bacteria via a standard DNA isolation protocol well known to one of ordinary skill in the art. Because the bacteria used for amplification of the DNA substantially lacks the ligand that acts as an agonist of TLR4/MD-2, the DNA sample also substantially lacks of the ligand. DNA isolated from these bacteria is of particular use for transient transfection of mammalian cells for expression of proteins encoded by the plasmid. LPS from the normal $E.\ coli$ employed as plasmid hosts can adversely affect the productivity and yield of protein from transient transfection procedures.

The present invention also features methods of producing protein samples substantially free of a ligand that acts as an agonist of TLR4/MD2. The method may comprise obtaining Gram-negative bacteria comprising an outer membrane that substantially lacks the ligand that acts as an agonist of TLR4/MD2 (the bacteria are competent to take up extracellular DNA) and introducing a DNA vector expression construct to the bacteria via standard protocols well known to one of ordinary skill in the art. The DNA vector expression construct comprises both a gene encoding a protein of interest expressed from a functional promoter and a selectable marker gene. In some embodiments, the bacteria comprise mutations in or deletions of at least one of the following genes: lolA, lolB or lpp.

The bacteria transformed with the DNA vector expression construct can then be grown (e.g., via standard methods) so as to allow the bacteria to express the protein of interest. In some embodiments, the bacteria are induced to express the protein of interest. The protein of interest can then be harvested from the bacteria via standard methods. In some embodiments, the bacteria are removed from the culture medium to leave the protein of interest behind in the medium. Because the bacteria used for protein expression lack the ligand that acts as an agonist of TLR4/MD-2, the protein sample also substantially lacks of the ligand.

Libraries are extremely useful tools for screening various protein variants. The present invention also features a library of bacteria, the bacteria being substantially free of a ligand that acts as an agonist of TLR4/MD2. The library of bacteria may express a series of variants of a protein. In some embodiments, the library of bacteria is used to screen the protein variants for activity in a mammalian cell based assay, however the present invention is not limited to mammalian cell based assays. Members of the library may be generated via phage display, via mutagenesis of a plasmid vector expressing a prototype member of the library, or via other standard methods.

Various reagents, strains, and the like may be provided (or combined with other reagents, strains, and the like) in the form of a kit. For example, the kit may comprise a viable Gram-negative bacterium having an outer membrane substantially free of a ligand that acts as an agonist of TLR4/MD2, wherein the bacterium is competent to take up extracellular DNA.

EXAMPLES

The examples provided below are merely examples to further clarify the present invention, and do not limit the scope of the invention in any way.

Example 1

Determination of Growth Rates

The following examples describe measurements of growth rates of various strains according to the present invention. The present invention is not limited to the following examples. Growth rates of strains can be determined by monitoring the cell densities at 600 nm of exponentially growing cultures. Fresh overnight cultures can be diluted 1:50 in pre-warmed media to continue the growth of the bacteria to the mid-exponential growth phase ($OD_{600}$ of 0.5 to 0.6). Cultures can then be diluted again to an $OD_{600}$ of about 0.005 in pre-warmed media to keep the cells growing exponentially for determination of generation times. Media may comprise Luria-Bertani (LB) media, and may further comprise 10 g/L NaCl. As shown in FIG. 1, KPM22 L1, KPM22 L11, KPM22 L13, KPM22 L18, and KPM22 L20 were grown at 37 degrees Celsius. KPM22 L1, KPM22 L11, and KPM22 L18 all had generation times between about 36 to 44 minutes.

Figure 2:
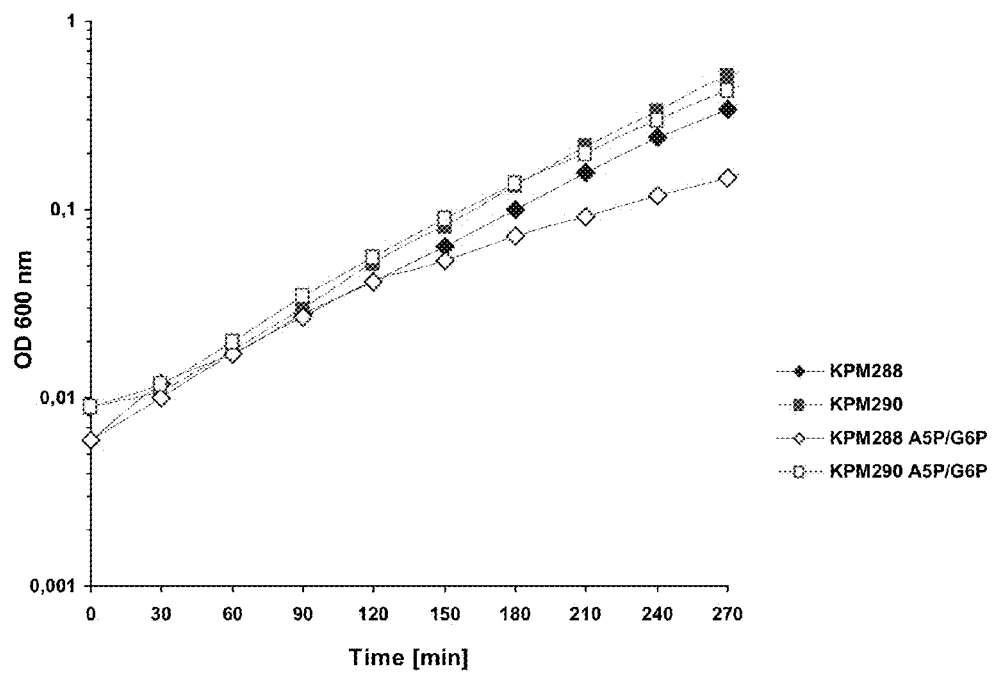
FIG. 2 shows growth curves of E. coli strain KPM288 (KPM22 L1 ΔlpxL::Km$^+$) and strain KPM290 (KPM22 L11 ΔlpxL::Km$^+$) in either Luria-Bertani (LB) media at 37° C. or in LB media supplemented with 15 μM D-arabinose 5-phosphate (A5P) and 10 μM D-glucose 6-phosphate (G6P) at 37° C. Generation times in LB media were calculated to be as follows: KPM288 45 min, KPM290 43 min. Results from growth in LB media supplemented with A5P and G6P were as follows: KPM288 ceased to grow exponentially after 2-3 generations, KPM290 46 min.

As shown in FIG. 2, $E.\ coli$ strain KPM288 (KPM22 L1 ΔlpxL::Km$^+$) and strain KPM290 (KPM22 L11 ΔlpxL::Km$^+$) were grown in either Luria-Bertani (LB) media at 37 degrees Celsius or in LB media supplemented with 15 μM D-arabinose 5-phosphate (A5P) and 10 μM D-glucose 6-phosphate (G6P) at 37° C. Generation times in LB media were calculated to be as follows: KPM288 45 min, KPM290 43 min. Results from growth in LB media supplemented with A5P and G6P were as follows: KPM288 ceased to grow exponentially after 2-3 generations, KPM290 46 min.

Figure 3:
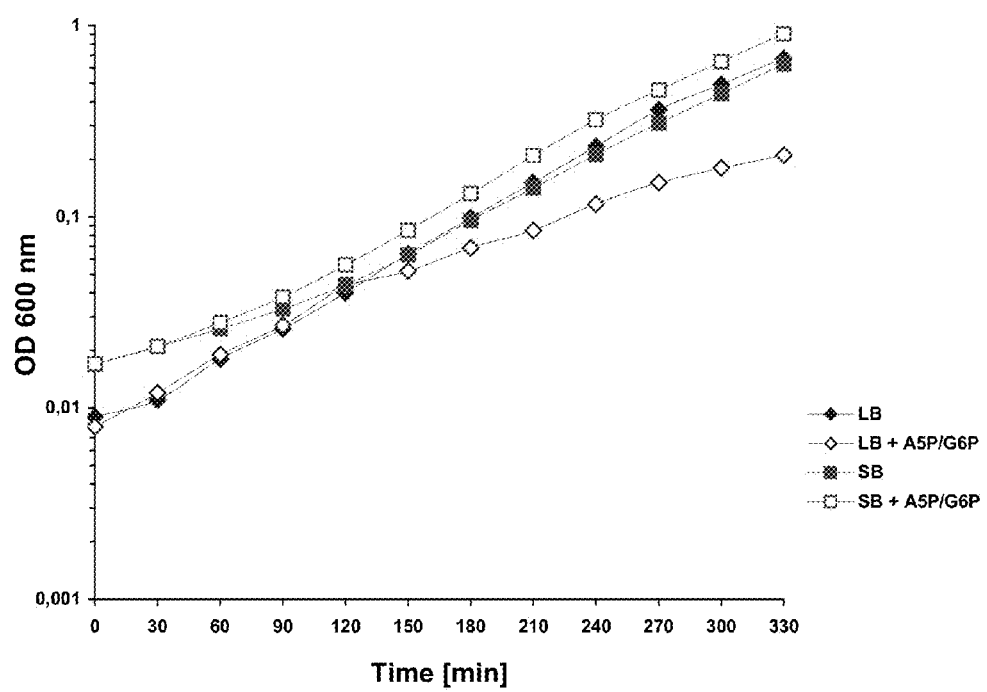
FIG. 3 shows growth curves of E. coli strain KPM303 (KPM22 L11 ΔlpxL ΔlpxM) at 37° C. in either LB media, LB media supplemented with 15 μM A5P and 10 μM G6P, Super Broth (SB) media (containing 10 g/L NaCl), or SB media (containing 10 g/L NaCl) supplemented with 15 μM A5P and 10 μM G6P. SB media did not improve the growth rate of KPM303 as compared to LB media. However, in contrast to the growth in LB medium supplemented with A5P and G6P, KPM303 continued to grow exponentially after 2-3 generations when cultivated in SB supplemented with A5P and G6P.

As shown in FIG. 3, $E.\ coli$ strain KPM303 (KPM22 L11 ΔlpxL ΔlpxM) was grown at 37° C. in either LB media, LB media supplemented with 15 μM A5P and 10 μM G6P, Super Broth (SB) media (containing 10 g/L NaCl), or SB media (containing 10 g/L NaCl) supplemented with 15 μM A5P and 10 μM G6P. SB media did not improve the growth rate of KPM303 as compared to LB media. However, in contrast to the growth in LB medium supplemented with A5P and G6P, KPM303 continued to grow exponentially after 2-3 generations when cultivated in SB supplemented with A5P and G6P.

Figure 4:
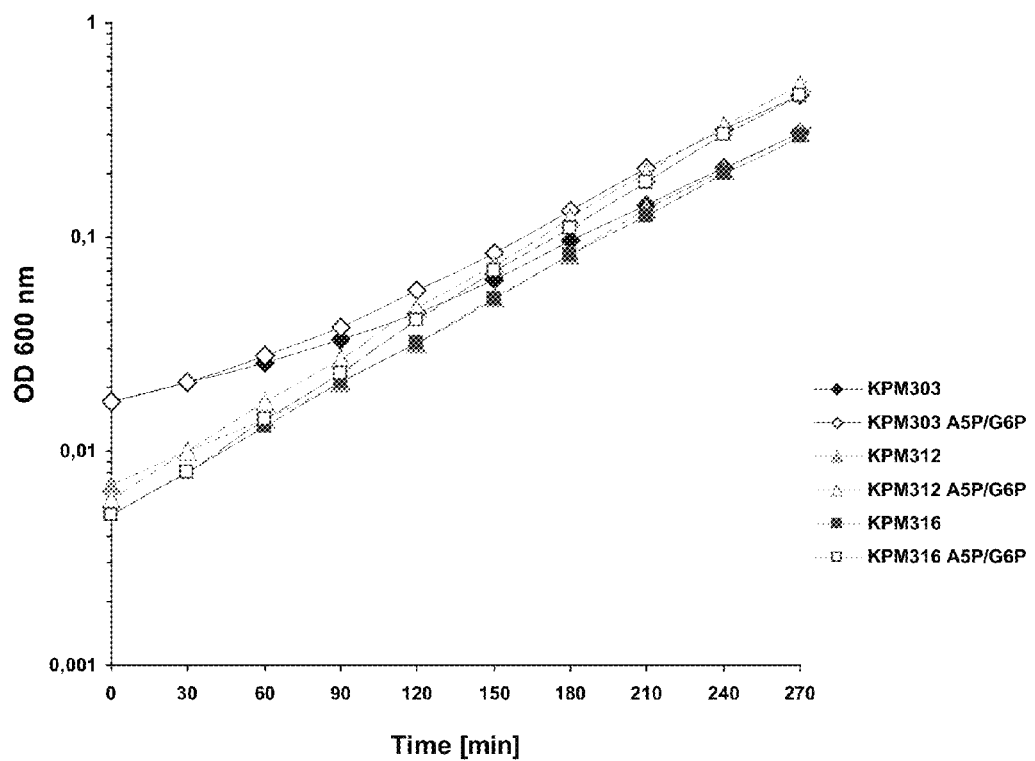
FIG. 4 shows growth curves of E. coli strains KPM303 (KPM22 L11 ΔlpxL ΔlpxM), KPM312 (KPM22 L11 ΔlpxL ΔlpxM ΔpagP), and KPM316 (KPM22 L11 ΔlpxL ΔlpxM ΔpagP ΔlpxP) at 37° C. in either SB media or SB supplemented with 15 μM A5P and 10 μM G6P. Generation times in SB media were as follows: KPM303 54 min, KPM312 50 min, KPM316 46 min. Generation times in SB media supplemented with A5P and G6P were as follows: KPM303 39 min, KPM312 42 min, KPM316 42 min.

As shown in FIG. 4, $E.\ coli$ strains KPM303 (KPM22 L11 ΔlpxL ΔlpxM), KPM312 (KPM22 L11 ΔlpxL ΔlpxM ΔpagP), and KPM316 (KPM22 L11 ΔlpxL ΔlpxM ΔpagP ΔlpxP) were grown at 37° C. in either SB media or SB supplemented with 15 μM A5P and 10 μM G6P. Generation times in SB media were as follows: KPM303 54 min, KPM312 50 min, KPM316 46 min. Generation times in SB media supplemented with A5P and G6P were as follows: KPM303 39 min, KPM312 42 min, KPM316 42 min.

Figure 5:
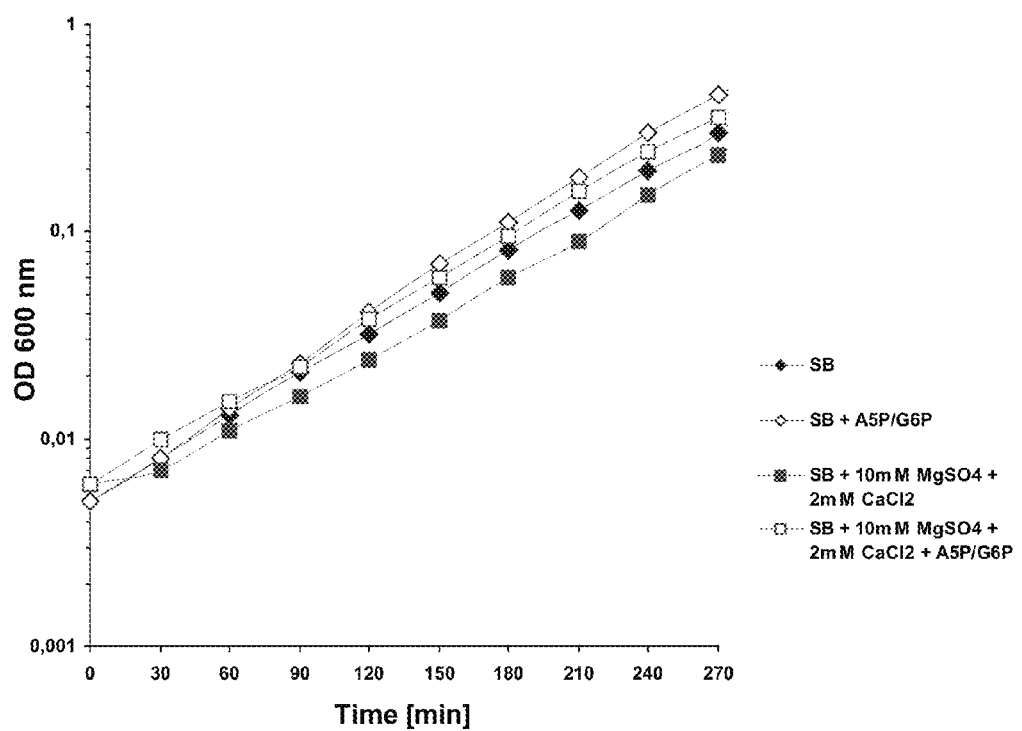
FIG. 5 shows growth curves of E. coli strain KPM316 at 37° C. in either SB medium supplemented with 10 mM MgSO$_4$ and 2 mM CaCl$_2$ or SB medium supplemented with 10 mM MgSO$_4$, 2 mM CaCl$_2$, 15 μM A5P, and 10 μM G6P. KPM316 had a generation time of 51 min in SB with 10 mM MgSO$_4$ and 2 mM CaCl$_2$. KPM316 had a generation time of 46 minutes in SB with 10 mM MgSO$_4$, 2 mM CaCl$_2$, 15 μM A5P, and 10 μM G6P.

As shown in FIG. 5, $E.\ coli$ strain KPM316 was grown at 37° C. in either SB medium supplemented with 10 mM $MgSO_4$ and 2 mM $CaCl_2$ or SB medium supplemented with 10 mM $MgSO_4$, 2 mM $CaCl_2$, 15 μM A5P, and 10 μM G6P. KPM316 had a generation time of 51 min in SB with 10 mM MgSO$_4$ and 2 mM CaCl$_2$. KPM316 had a generation time of 46 minutes in SB with 10 mM MgSO$_4$, 2 mM CaCl$_2$, 15 μM A5P, and 10 μM G6P.

Figure 6:
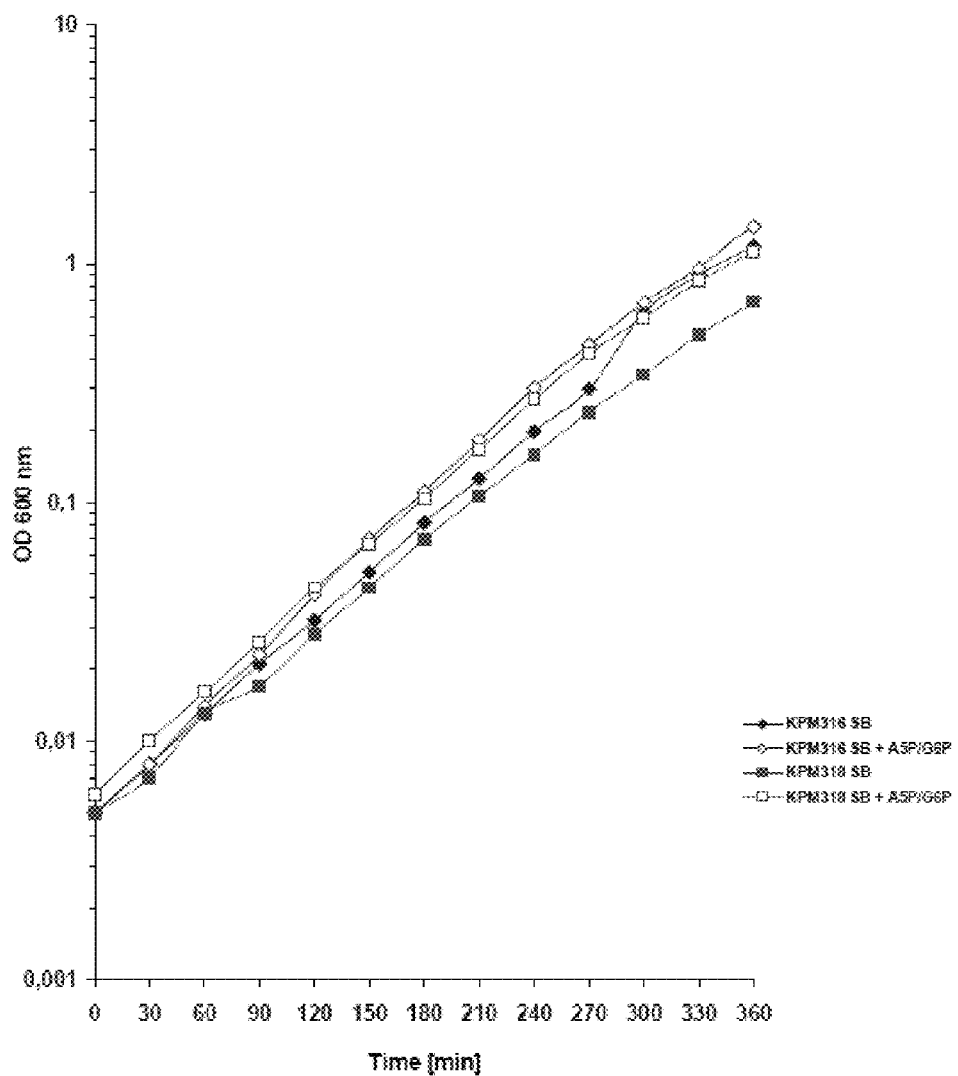
FIG. 6 shows growth curves of E. coli strains KPM316 and KPM318 grown in either SB or in SB supplemented with 15 μM ASP, and 10 μM G6P at 37° C. The doubling times are very similar in the range 39-44 min.

As shown in FIG. 6, *E. coli* strains KPM316 and KPM318 were grown at 37° C. in either SB medium or SB medium supplemented with 15 μM A5P, and 10 μM G6P. KPM316 and KPM318 showed generation times of 39-44 min in these media.

Example 2

Generation of Temperature-Resistant Strains

The following example describes generation of a temperature-resistant derivative of KPM296. The present invention is not limited to the following example. Fresh overnight cultures of KPM296 grown in LB medium at 37° C. can be plated on LB agar plates and incubated at 42° C. Incubation at 42° C. can be continued for several days, for example four to five days. Clones with colony-forming ability at 42° C. may appear (representing 42° C.-resistant derivatives of KPM296). The 42° C.-resistant strains can be confirmed by overnight growth on LB agar plates at 42° C. KPM296-6 is a 42° C.-resistant derivative of KPM296.

Figure 7:
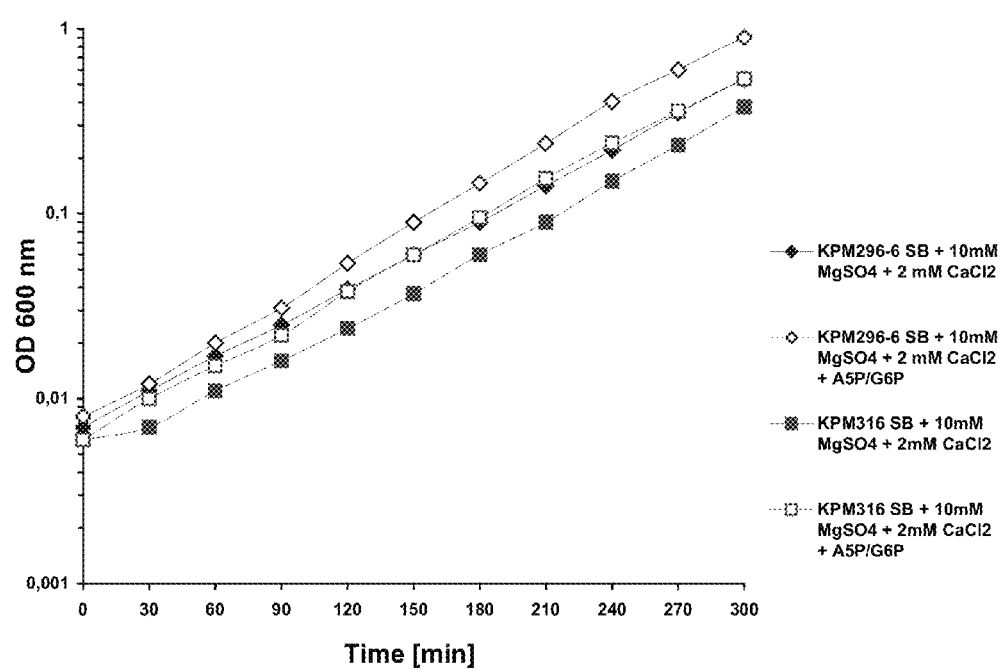
FIG. 7 shows growth curves of E. coli strains KPM296-6 and KPM316 at 37° C. in either SB medium supplemented with 10 mM MgSO$_4$ and 2 mM CaCl$_2$ or SB medium supplemented with 10 mM MgSO$_4$, 2 mM CaCl$_2$, 15 μM ASP, and 10 μM G6P. The growth rate of KPM296-6 in SB medium with 10 mM MgSO$_4$ and 2 mM CaCl$_2$ was 48 min. In SB with 10 mM MgSO$_4$, 2 mM CaCl$_2$, 15 μM ASP, and 10 μM G6P the growth rate of KPM296-6 was 42 min.

As shown in FIG. 7, *E. coli* strains KPM296-6 and KPM316 (KPM22 L11 ΔlpxL ΔlpxM ΔpagP ΔlpxP) were grown at 37° C. in either SB with 10 mM MgSO$_4$ and 2 mM CaCl$_2$, or in SB with 10 mM MgSO$_4$, 2 mM CaCl$_2$, 15 μM A5P, and 10 μM G6P. The growth rate of KPM296-6 in SB medium with 10 mM MgSO$_4$ and 2 mM CaCl$_2$ was 48 min. In SB with 10 mM MgSO$_4$, 2 mM CaCl$_2$, 15 μM A5P, and 10 μM G6P the growth rate of KPM296-6 was 42 min.

Figure 8:
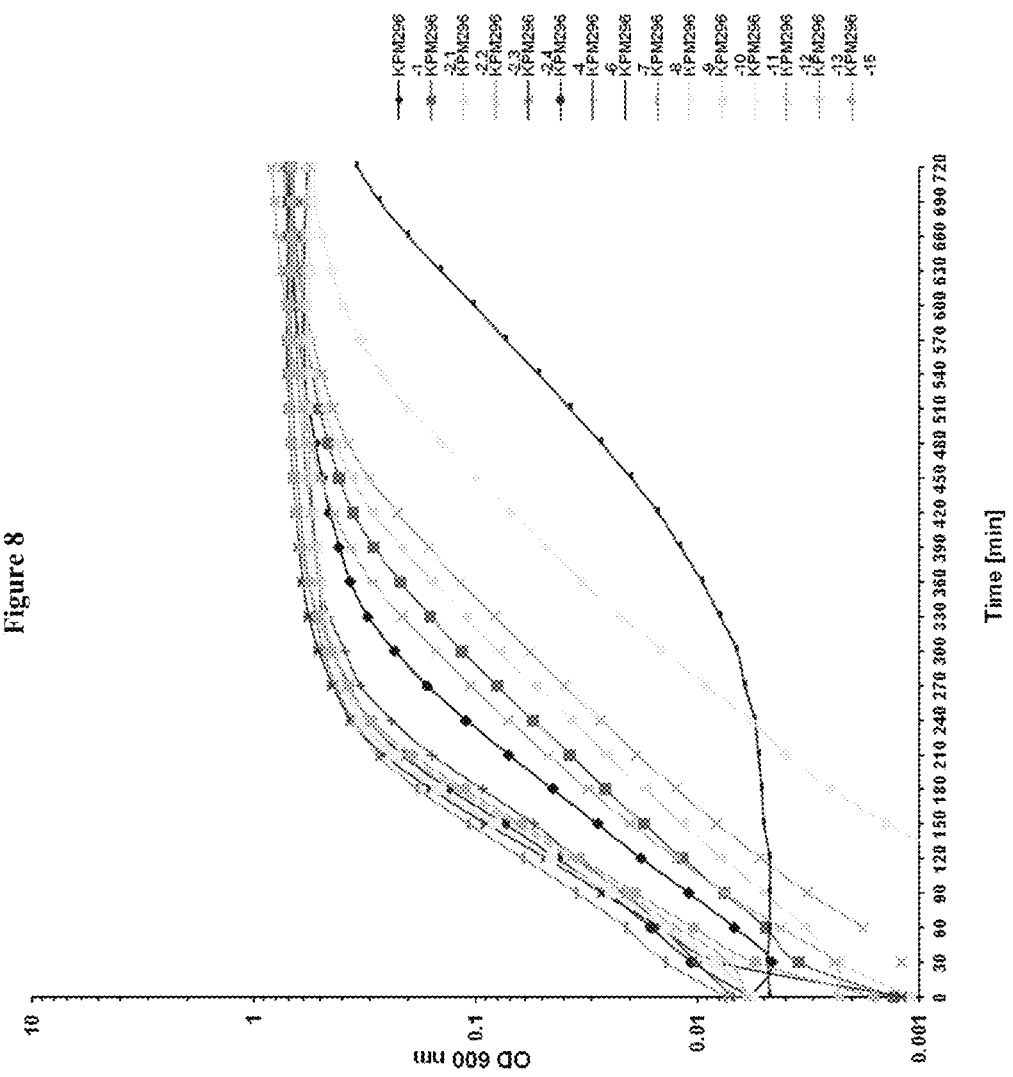
FIG. 8 Growth curves of a series of independent isolates selected from KPM296 at 42° C. Growth was in SB medium at 42° C. Individual isolates are numbered in the inset and keyed to the symbols used to represent their growth curve. Considerable variation in generation time is seen, but each shows exponential growth, FIG. 9 Analysis of PCR products produced by primers flanking each gene to confirm deletions of O-acyl transferase genes and deletion of eptA gene in KPM318. The parental strain BW30270 is used as a control beside KPM318 for each gene analysed. Template DNAs and the gene for which the particular PCR primer pairs were designed are indicated. It can be seen in each case that the parental strain BW30270 gives rise to a larger PCR product than that seen for KPM318. Only the scar sequence remains in the place of the whole gene in KPM318.

As shown in FIG. 8, a series of *E. coli* strains isolated independently from parallel selections at 42° C. from KPM296 were grown at in SB medium at 42° C. Virtually every isolate tested, including KPM296-6, exhibits exponential growth at 42° C., with a wide variation in doubling times. The parental strain, KPM296, was unable to grow at all in LB or in SB medium at 42° C.

KPM316 and KPM318 have also been successfully used to select a series of independent isolates able to grow at 42° C. by this method.

Example 3

Strain Construction

The following example describes construction of various aforementioned strains. The present invention is not limited to these examples. Kanamycin resistance cassettes targeting the lpxL, lpxM, pagP, lpxP, and/or eptA genes can be generated in donor strains using the phage λRed recombinase procedure, and then transferred to a KPM strain by P1 vir transduction. Excision of the kanamycin resistance gene can be carried out in the presence of the FLP recombinase, and the temperature-sensitive helper plasmid pCP20 can be removed. P1 vir transduction and other such techniques are well known to one of ordinary skill in the art.

For example, the ΔlpxL:Km$^+$ cassette can be generated in KPM22 to yield strain KPM279 (KPM22 ΔlpxL:Km$^+$). KPM279 can be used as a donor for transfer of the ΔlpxL::Km$^+$ cassette to KPM22 L1 via P1 vir transduction to yield strain KPM288 (KPM22 L1 ΔlpxL:Km$^+$) or to KPM22 L11 via P1 vir transduction to yield strain KPM290 (KPM22 L1 ΔlpxL:Km$^+$).

Further, strain KPM316 (KPM22 L11 ΔlpxL ΔlpxM ΔpagP ΔlpxP) can be obtained via successive deletions of the acyl transferases (in the following order) using KPM280 (KPM22 ΔlpxM::Km$^+$), BW30270 ΔlpxP::Km$^+$, and BW30270 ΔpagP::Km$^+$ as donor strains of the targeting cassettes, respectively: KPM 290 (KPM22 L11 ΔlpxL:Km$^+$)>KPM 296 (KPM22 L11 ΔlpxL)>KPM 300 (KPM22 L11 ΔlpxL ΔlpxM::Km$^+$)>KPM 303 (KPM22 L11 ΔlpxL ΔlpxM)>KPM310 (KPM22 L11 ΔlpxL ΔlpxM ΔpagP::Km$^+$)>KPM312 (KPM22 L11 ΔlpxL ΔlpxM ΔpagP)>KPM314 (KPM22 L11 ΔlpxL ΔlpxM ΔpagP ΔlpxP::Km$^+$)>KPM316 (KPM22 L11 ΔlpxL ΔlpxM ΔpagP ΔlpxP).

Figure 9:
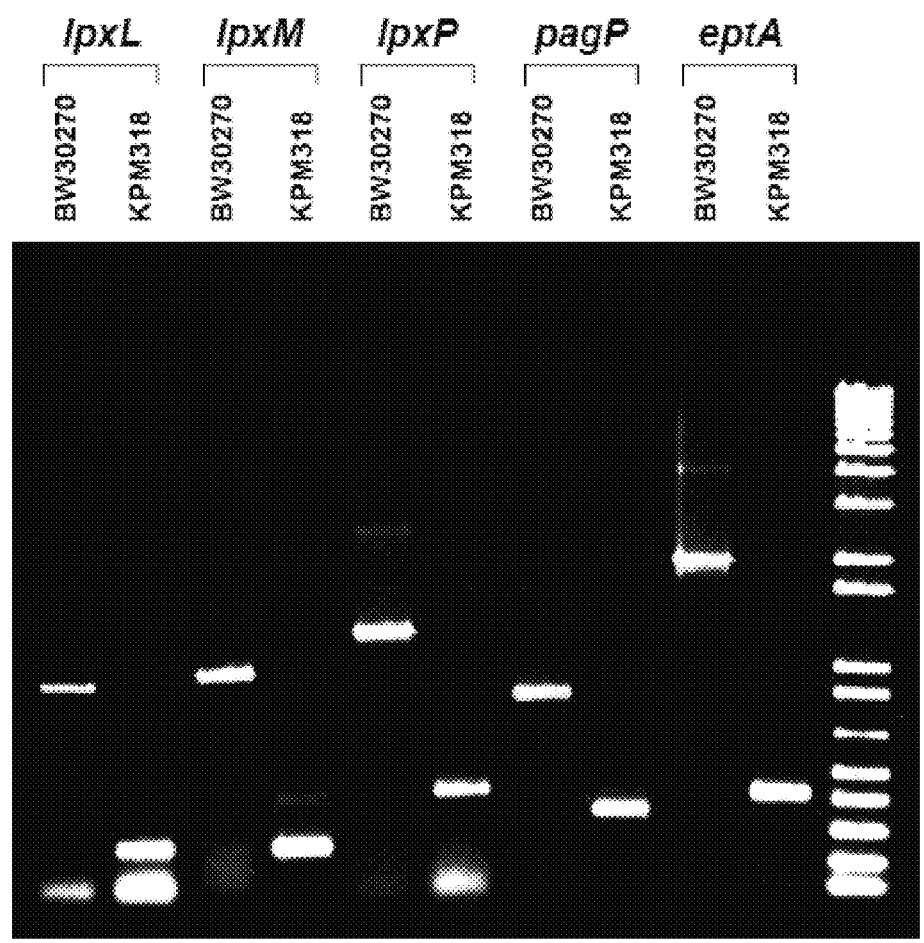

KPM318 was derived from KPM316 by P1 vir transduction of the ΔeptA::Km$^+$ created by the λRed recombinase procedure in BW30270ΔeptA::Km$^+$ to give KPM317 (KPM316 ΔeptA::Km$^+$) which was then cured of the Km cassette by transient expression of FLP recombinase. PCR amplification using primers that flank each deletion were used to confirm the deletions against control DNA from the parental BW30270 (FIG. 9). In each case the parental strain shows a larger PCR product with the primers that flank the gene deleted in KPM318.

Example 4

Other Reagents and Methods

The following example describes other reagents and methods that may be used in accordance with the present invention. The present invention is not limited to these examples.

The presence of endotoxin (e.g., LPS) can be detected via standard assays. For example, HEK-Blue™ LPS Detection Kits (Invivogen, San Diego, Calif.) may be used. In this assay, HEK-Blue™—4 cells are extremely sensitive to LPS (lipid A), and can be used to detect concentrations of LPS (lipid A) as low as 0.3 ng/mL. The assay can be followed according to the manufacturer's protocol.

Figure 10A:
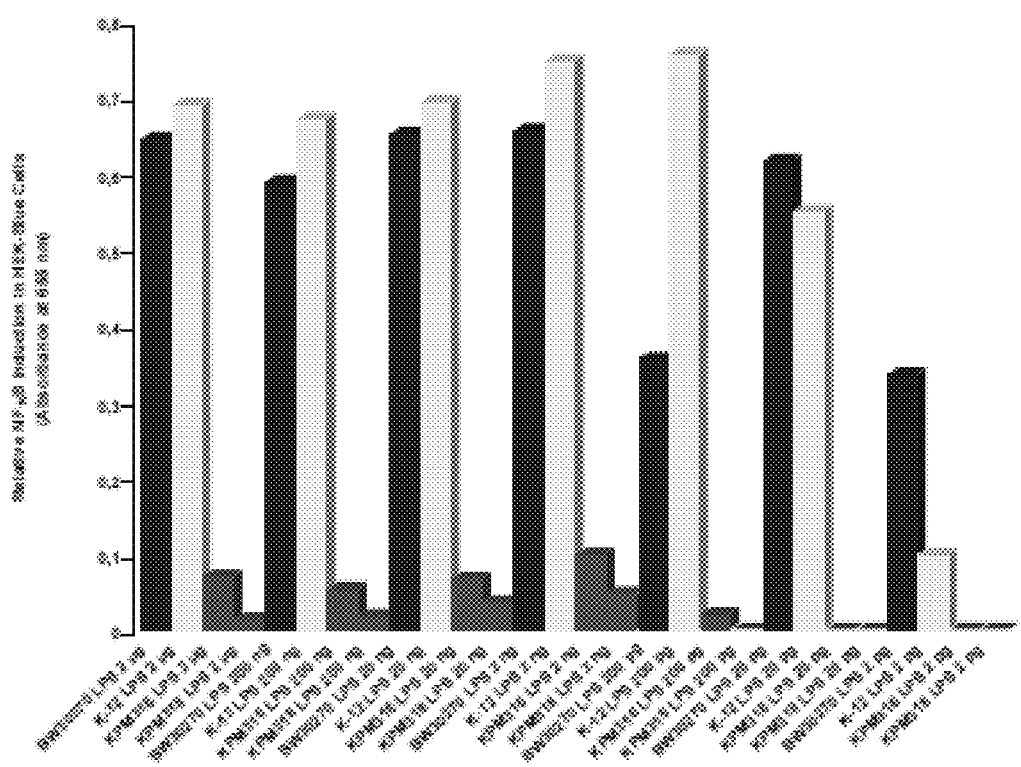
FIGS. 10A and 10B HEK-Blue™ Assays of strains BW30270, KPM316 and KPM318, each grown in LB medium at 37° C. (A) Outer membrane preparations of strains, and (B) whole cells. Numbers of cells added to each well (as cfu—colony forming units) or mass of outer membrane preparation (from 2 microgramms down to 2 picogramms) are indicated. Reference LPS from *E. coli* K-12 supplied with the assay kit was run in parallel with all experiments and is shown for comparison with the outer membrane data with which it is most directly comparable on a mass-to-mass basis.
Figure 10B:
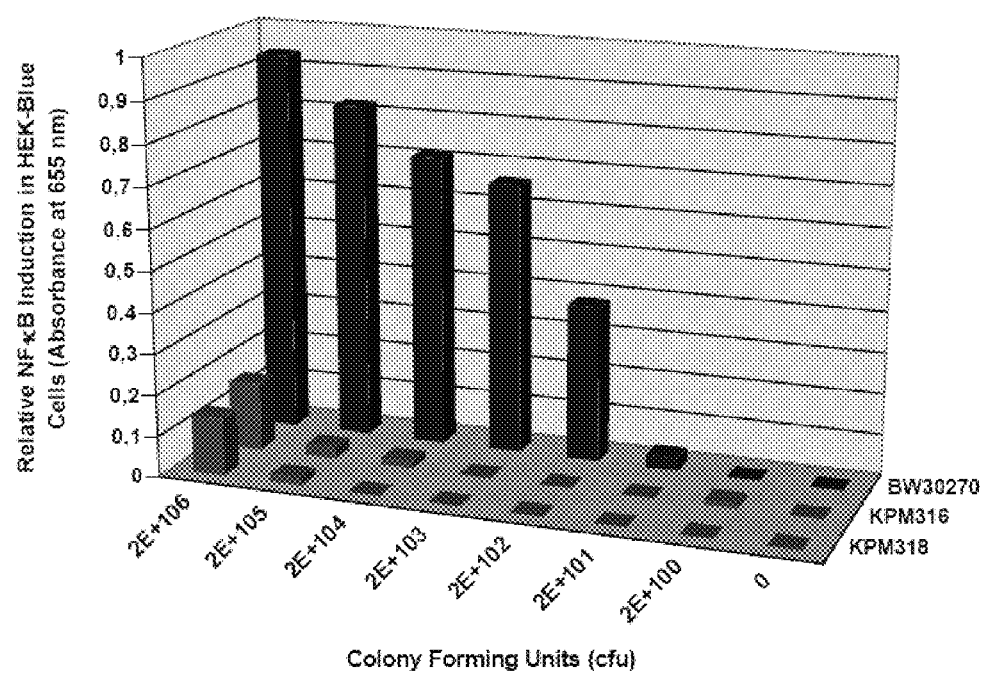

Whole cells and also outer membrane extracts of cells were tested in the HEK-Blue™ LPS Detection Kit. Control wild type cells and outer membranes were prepared from the parent BW30270, and these were tested with samples of cells and extracts from KPM316 and KPM318. The results, shown in FIG. 10, demonstrate that the HEK-Blue™ LPS assay is extremely sensitive to LPS endotoxin, responding to as little as 2 pg of LPS. Signals in any of the samples prepared from KPM316 or KPM318 were at essentially background levels, even at 20 micrograms of outer membrane added to an assay, 9 orders of magnitude less potent for TLR4/MD2 signalling. Whole cells of KPM316 or KPM318 were also unable to elicit a significant signal at the highest levels tested, in contrast to the whole cells of BW30270, which gave significant response at levels 4 orders of magnitude lower.

Analysis of the ESI-Mass spectra of the outer membrane extracts of KPM316 showed the expected prominent masses for lipid IV$_A$ and lipid IV$_A$-phosphoethanolamine (FIG. 11 panel A). ESI-MS of KPM318 outer membranes showed only lipid IV$_A$ (FIG. 10 panel A), as expected since the phosphoethanolamine transferase has been deleted from this strain.

P1 vir transduction is a standard method used to move genes/alleles from a donor strain to a recipient strain via P1 vir, a mutant bacteriophage that enters the lytic phase upon infection. P1 (P1 vir) can package approximately 90 kb of DNA, so it is generally used with a selectable marker. To perform such experiments, donor strains (and recipient strains) are cultured. P1 vir can then be added to the donor strain culture and monitored until the culture has completely lysed. Lysate is then harvested and added to the culture of recipient cells. Following incubation of the recipient cells with the lysate, the recipient cells are plated on selective media to select for colonies with the selectable marker (and thus the gene of interest).

The complete sequence of the *E. coli* (K-12) MG1655 strain is provided in Blattner F R et al. (Science. 1997 Sep. 5; 277(5331):1453-62) and Riley M et al. (Nucleic Acids Res. 2006 Jan. 5; 34(1):1-9. Print 2006). The generation of the KPM316 strain is outlined in FIG. 12. msbA52 replaces the wild type allele of msbA, wherein a C at 965895 is replaced by a T, resulting in a Serine instead of Proline at amino acid 18 in the MsbA protein (FIG. 12*a*). The following were deleted from the parental strain: ΔgutQ (FIG. 12*b*), ΔkdsD (FIG. 12*c*), ΔlpxL (FIG. 12*d*), ΔlpxM (FIG. 12*e*), ΔpagP (FIG. 12*f*), and ΔlpxP (FIG. 12*g*). The KPM316 sequence was compared to that of the wild-type strain MG 1655 (Table 21). The functions of these mutations are unknown.

Figure 14:
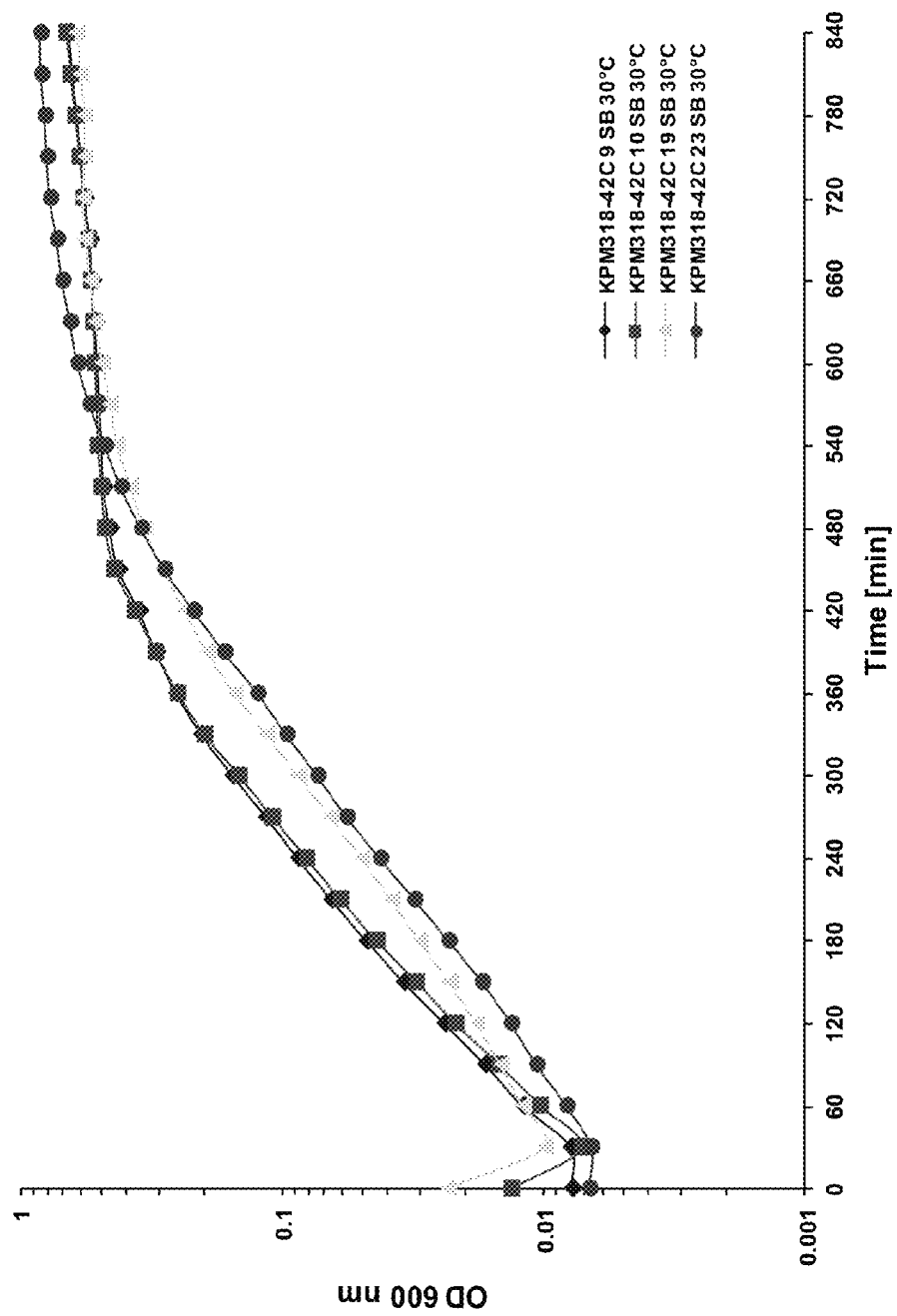
FIG. 14 The growth of the four KPM-318 temperature-resistant derivatives, KPM334, KPM335, KPM336, and KPM337 grown in SB medium at 30° C. were assessed.

The generation of the KPM318 strain is outlined in FIG. 14. msbA52 replaces the wild type allele of msbA, wherein a C at 965895 is replaced by a T, resulting in a Serine instead of Proline at amino acid 18 in the MsbA protein (FIG. 14*a*). The following were deleted from the parental strain: ΔgutQ (FIG. 14*b*), ΔkdsD (FIG. 14*c*), ΔlpxL (FIG. 14*d*), ΔlpxM (FIG. 14*e*), ΔpagP (FIG. 14*f*), ΔlpxP (FIG. 14*g*), and ΔeptA (FIG. 14*f*). Examples of generated strains are provided in Table 1.

The KPM318 and BW30270 strains were sequenced at the Scripps Core DNA sequencing facility using an Illumina DNA sequencer. The sequences were generated using paired end reads of 40 or 60 bases. DNA samples were prepared from each strain and used to generate end-tagged libraries. Up to six libraries were run per lane, along with a reference lane. The other lanes were used for additional unrelated DNA reads, which served as further internal controls. Single nucleotide polymorphisms (SNPs) refer to all single base changes defined as being 100% mutant by the Scripps analysis programs when compared to the reference genome, the Blattner's MG1655 strain. Deletion/insertion polymorphisms (DIPs) refer to all the deletions or insertions (up to 6 bp) defined by the Scripps analysis programs, again using MG1655 as the reference. Only those detected at 100% of reads are provided. Whole gene deletions were independently confirmed by separate sequence alignments. The KPM318 sequence was compared to that of the wild-type strain BW30270 (Table 22). Sequencing identified the msbA-P18S suppressor allele, which was previously established to exist in the original KPM strain (FIG. 13 and Table 22). All known changes introduced by strain engineering were determined to be present at 100% frequency. This was true for all engineered deletions and point mutations.

Figure 15:
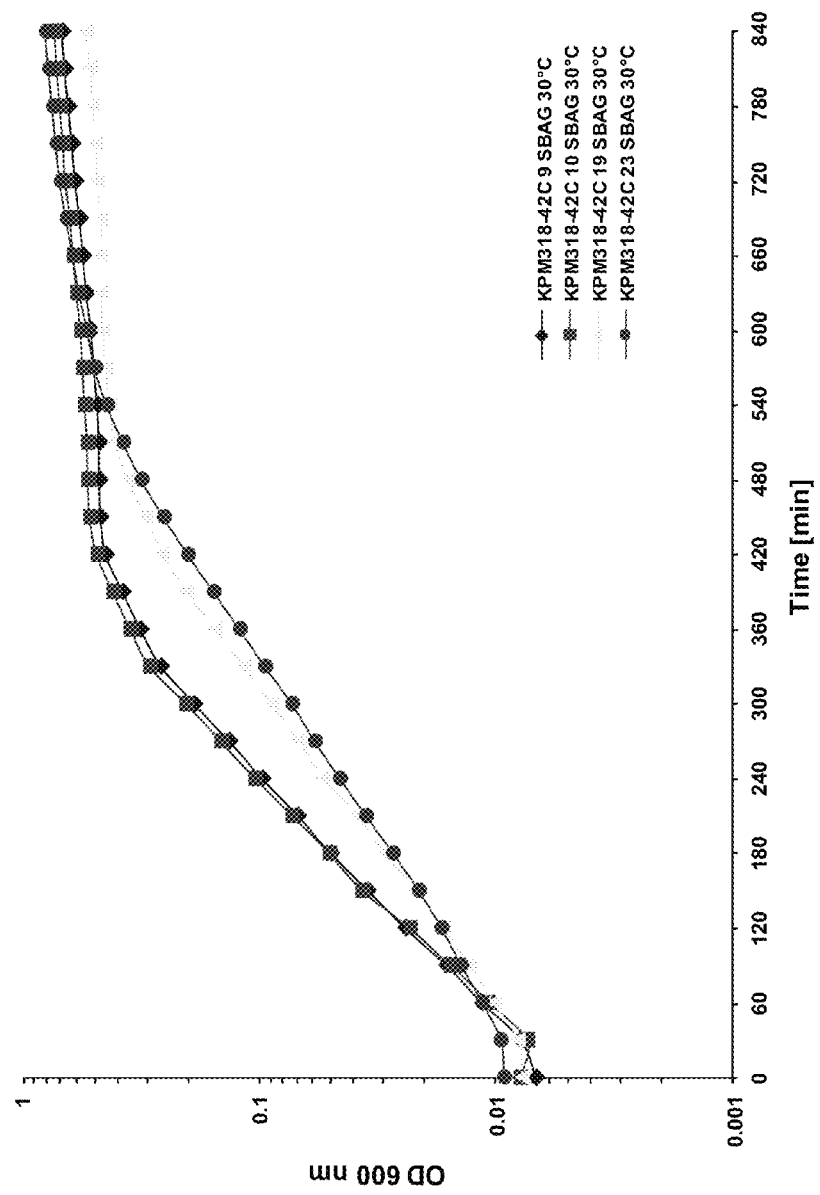
FIG. 15 The growth of the four KPM-318 temperature-resistant derivatives, KPM334, KPM335, KPM336, and KPM337 grown in SB medium supplemented with A5P/G6P at 30° C. were assessed.
Figure 16:
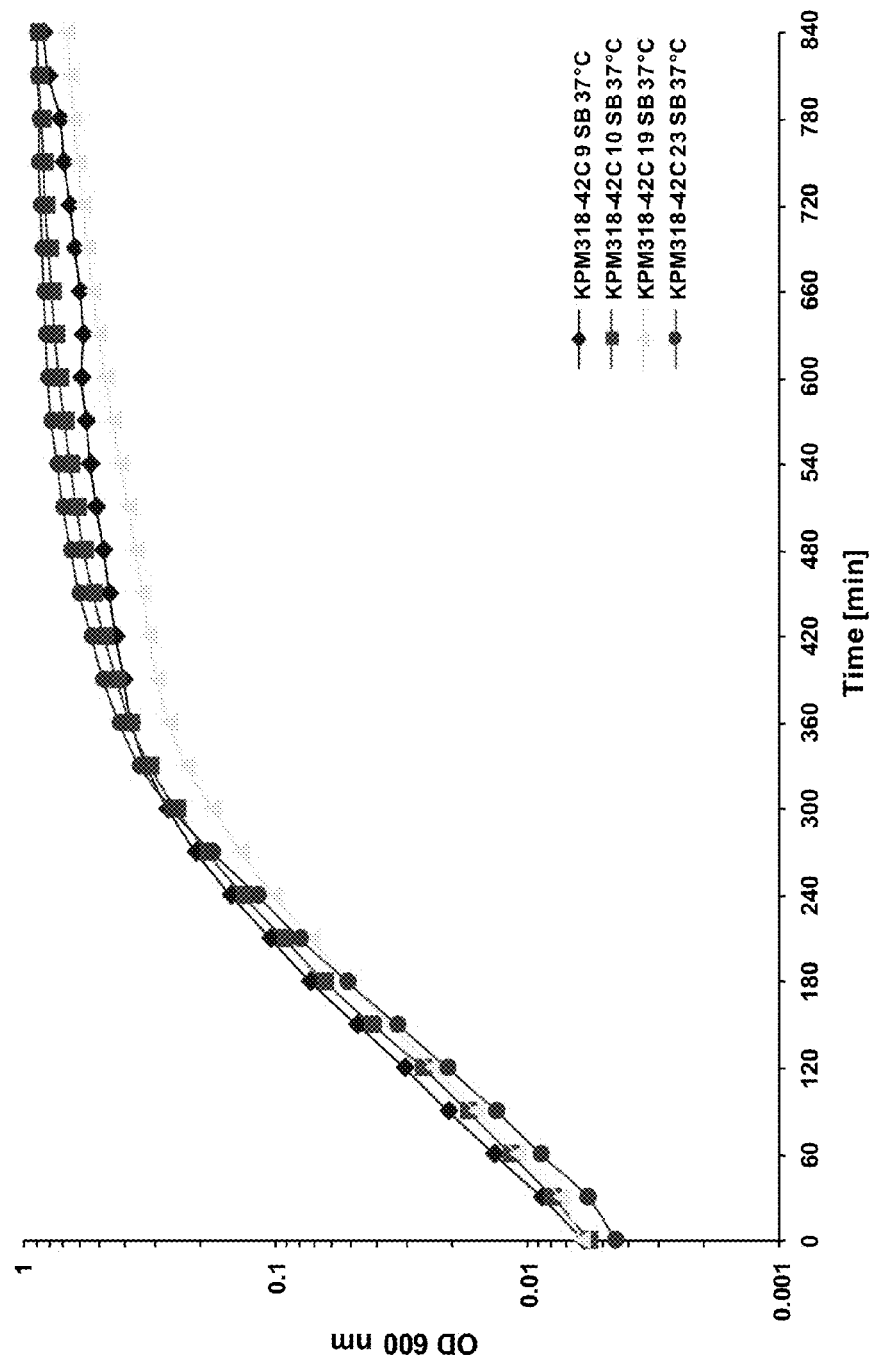
FIG. 16 The growth of the four KPM-318 temperature-resistant derivatives, KPM334, KPM335, KPM336, and KPM337 grown in SB medium at 37° C. were assessed.
Figure 17:
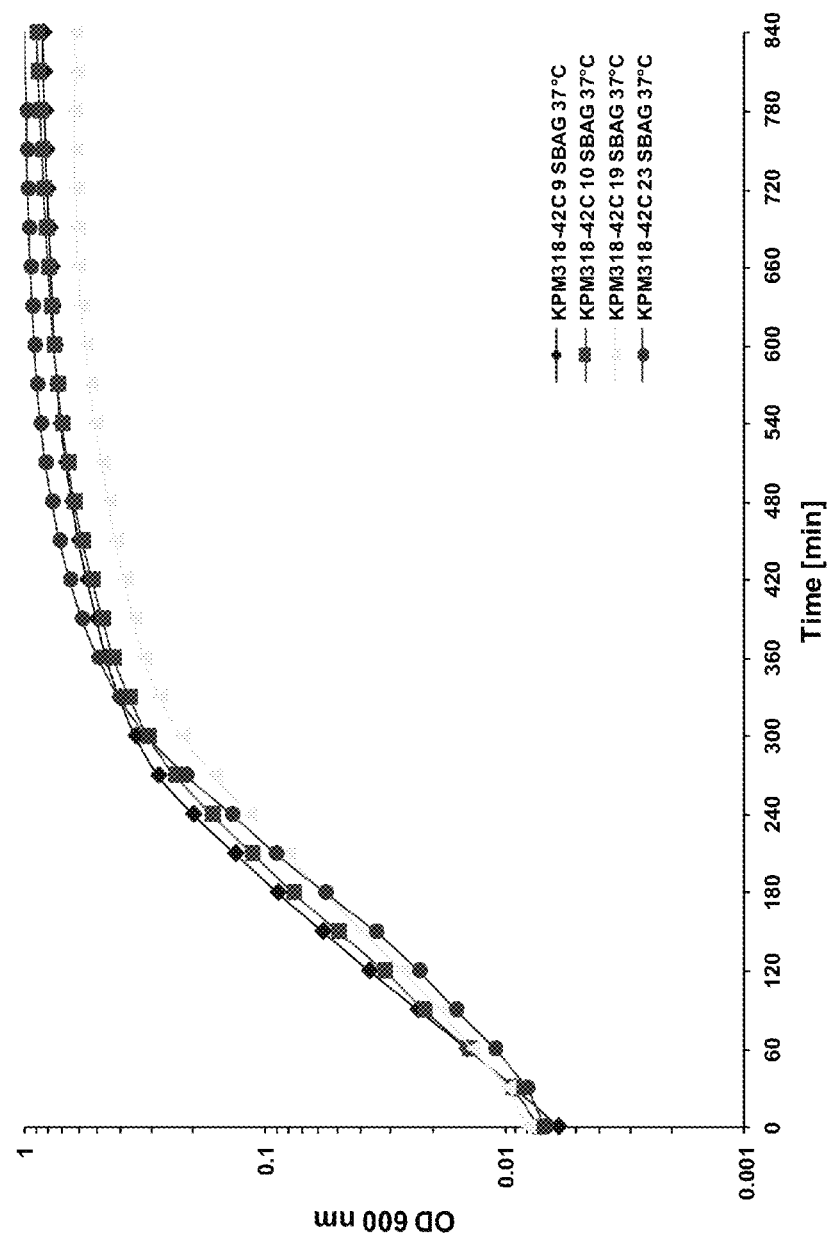
FIG. 17 The growth of the four KPM-318 temperature-resistant derivatives, KPM334, KPM335, KPM336, and KPM337 grown in SB medium supplemented with A5P/G6P at 37° C. were assessed.
Figure 18:
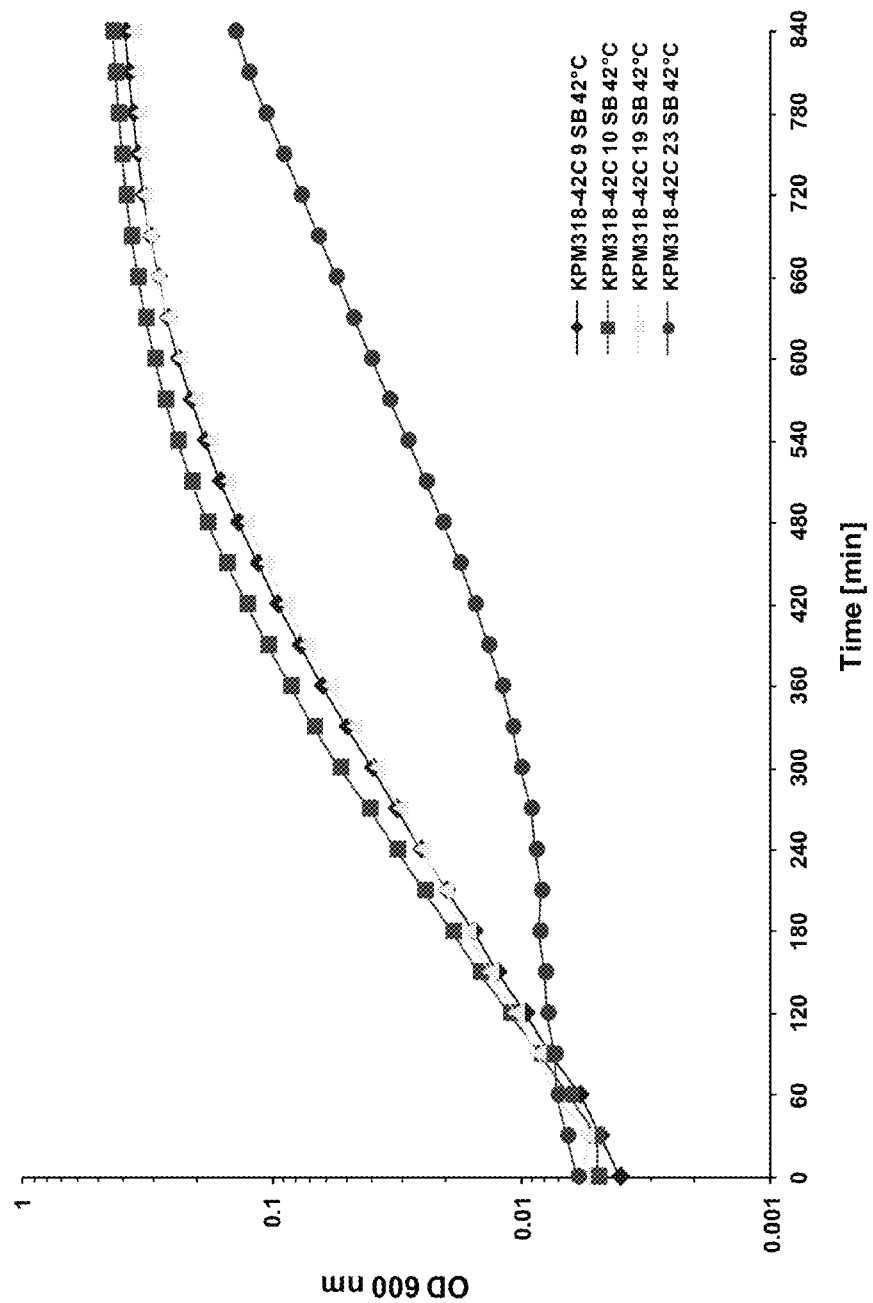
FIG. 18 The growth of the four KPM-318 temperature-resistant derivatives, KPM334, KPM335, KPM336, and KPM337 grown in SB medium at 42° C. were assessed.
Figure 19:
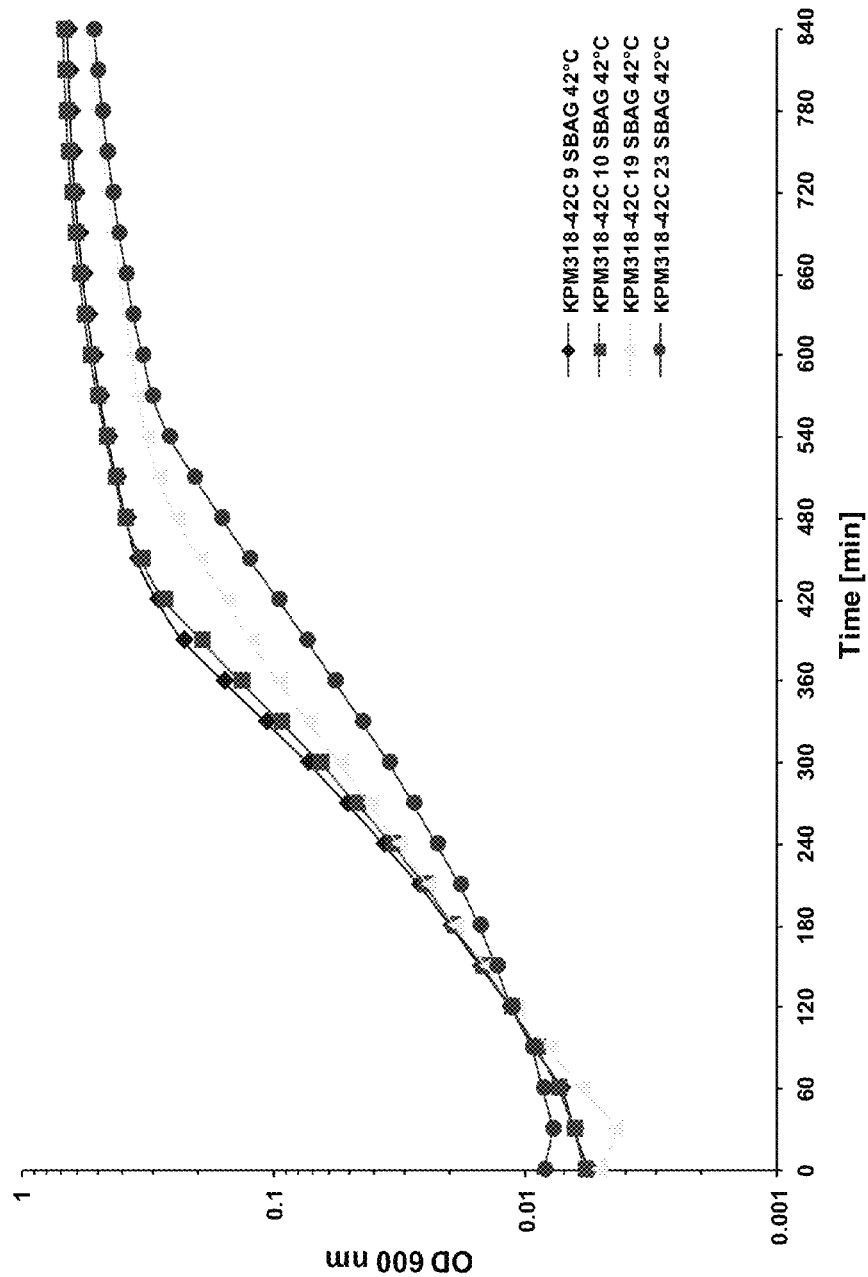
FIG. 19 The growth of the four KPM-318 temperature-resistant derivatives, KPM334, KPM335, KPM336, and KPM337 grown in SB medium supplemented with A5P/G6P at 42° C. were assessed.

Temperature-resistant derivatives of KPM318 were isolated in an attempt to identify more robust strains. Overnight cultures of KPM318 grown in LB medium at 37° C. were plated onto LB-agar plates and incubated at 42° C. Only after continued incubation of the plates at 42° C. for four to five days, a number of clones were obtained that regained their colony-forming ability at the elevated temperature. The 42° C.-resistant phenotype of randomly selected clones was confirmed by overnight growth on LB-agar plates at 42° C. A series of independent, nonclonal 42° C.-resistant derivatives of KPM318 were identified. Among a total of 24 temperature-resistant KPM318 derivatives, the strains KPM318-9 (KPM334), KPM318-10 (KPM335), KPM318-19 (KPM336) and KPM318-23 (KPM337) displayed the best growth characteristics, being capable of exponentially growing at temperatures of 30° C., 37° C. and 42° C. in either SB medium (FIGS. 14, 16, and 18) or under conditions of restored LPS biosynthesis in SB medium supplemented with 15 µM D-arabinose 5-phosphate (A5P) and 10 µM D-glucose 6-phosphate (G6P) (FIGS. 15, 17, and 19). Therefore, these temperature-resistant strains exhibit robust growth characteristics over a range of temperatures.

The KPM318-9 (KPM334), KPM318-10 (KPM335), KPM318-19 (KPM336) and KPM318-23 (KPM337) strains were sequenced at the Scripps Core DNA sequencing facility using an Illumina DNA sequencer (Table 23). Specific mutations were identified that may account for the viability of the strains at 42° C. Strains KPM318-9 (KPM334) and KPM318-10 (KPM335) express a frr-D61Y mutation that alters a ribosomal recycling factor (Tables 23A and 23B). The KPM318-19 (KPM336) strain has a frameshift mutation in efp, which encodes elongation factor P (Table 23C). The KPM318-23 (KPM337) strain has a deletion of P146 and L147 in dcd, which encodes the deoxycytidine deaminase gene (Table 23D). The specific functions of these mutations are unknown.

Figure 20:
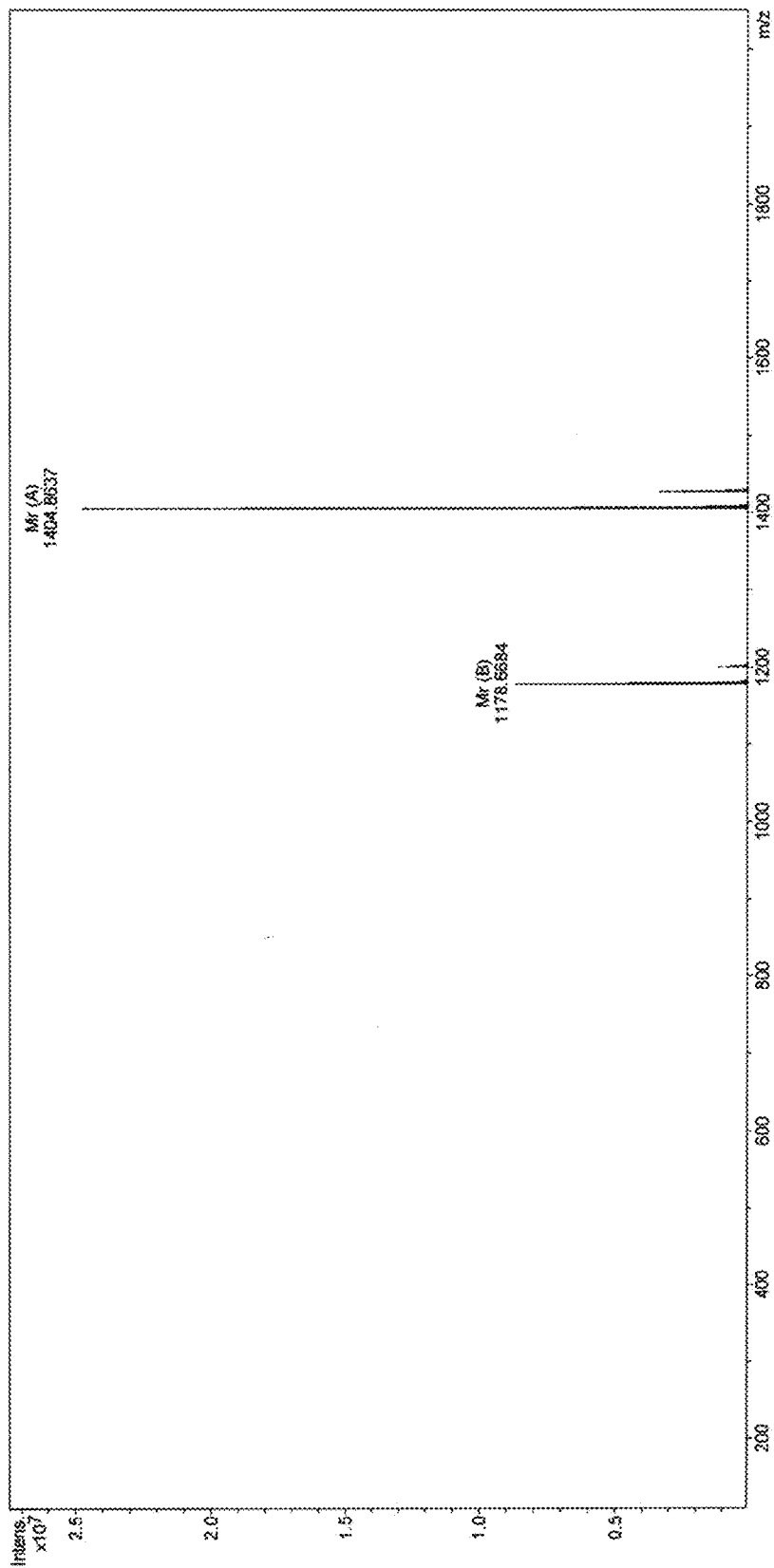
FIG. 20 ESI FT-ICR mass spectrum in negative ion mode of lipid $IV_A$ (1404.86 u) isolated from *E. coli* KPM337 grown at 42° C. in LB medium. Mass numbers given refer to the monoisotopic masses of neutral molecules. The peak corresponding to triacylated lipid A (1178.67 u) is likely an artefact produced during lipid $IV_A$ isolation and/or ionization as it is not consistent with a known pathway intermediate.
Figure 21:
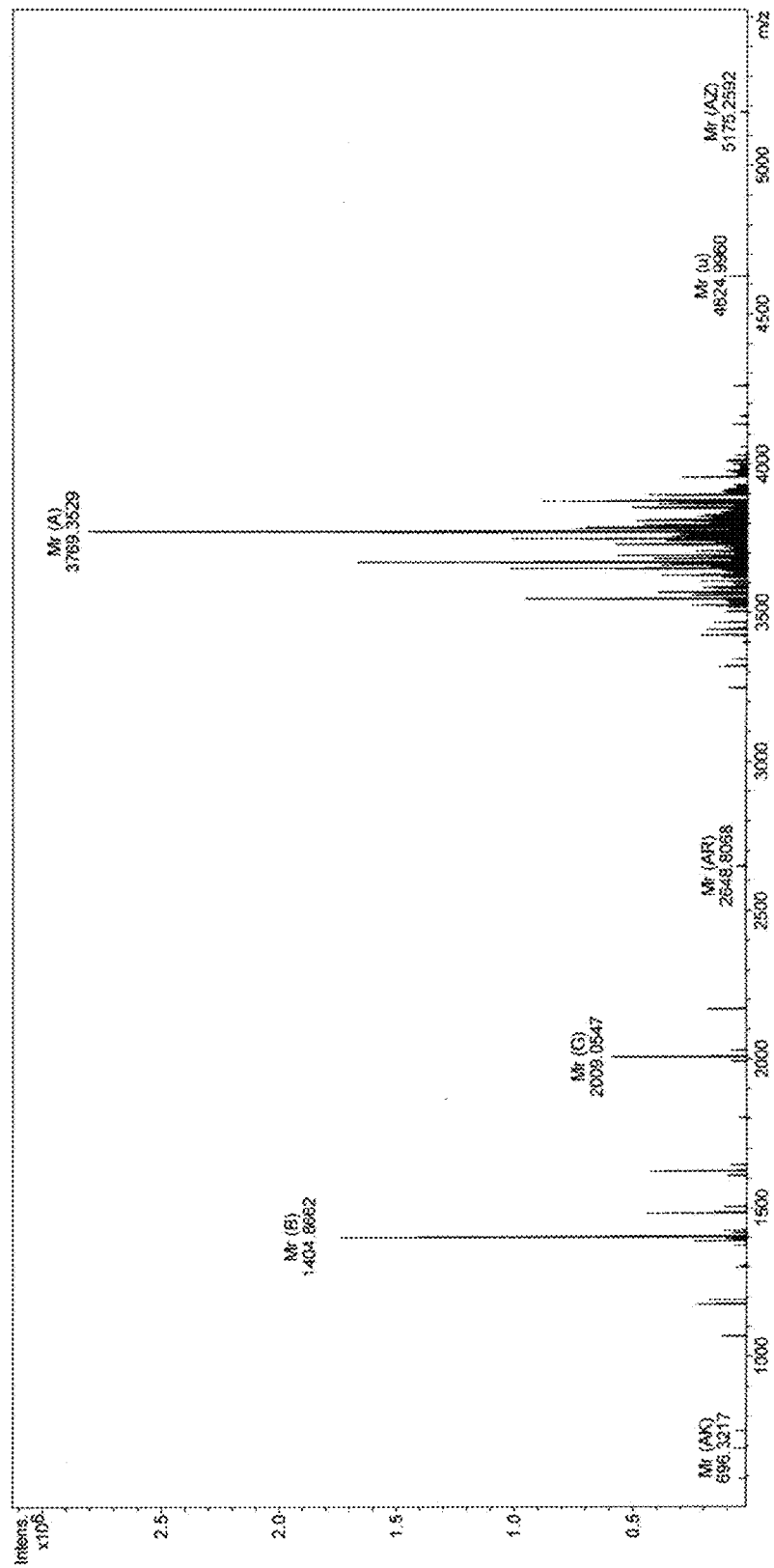
FIG. 21 ESI FT-ICR mass spectrum in negative ion mode of LPS isolated from *E. coli* KPM334 grown at 42° C. in LB medium supplemented with A5P/G6P. Mass numbers given refer to the monoisotopic masses of neutral molecules.
Figure 22:
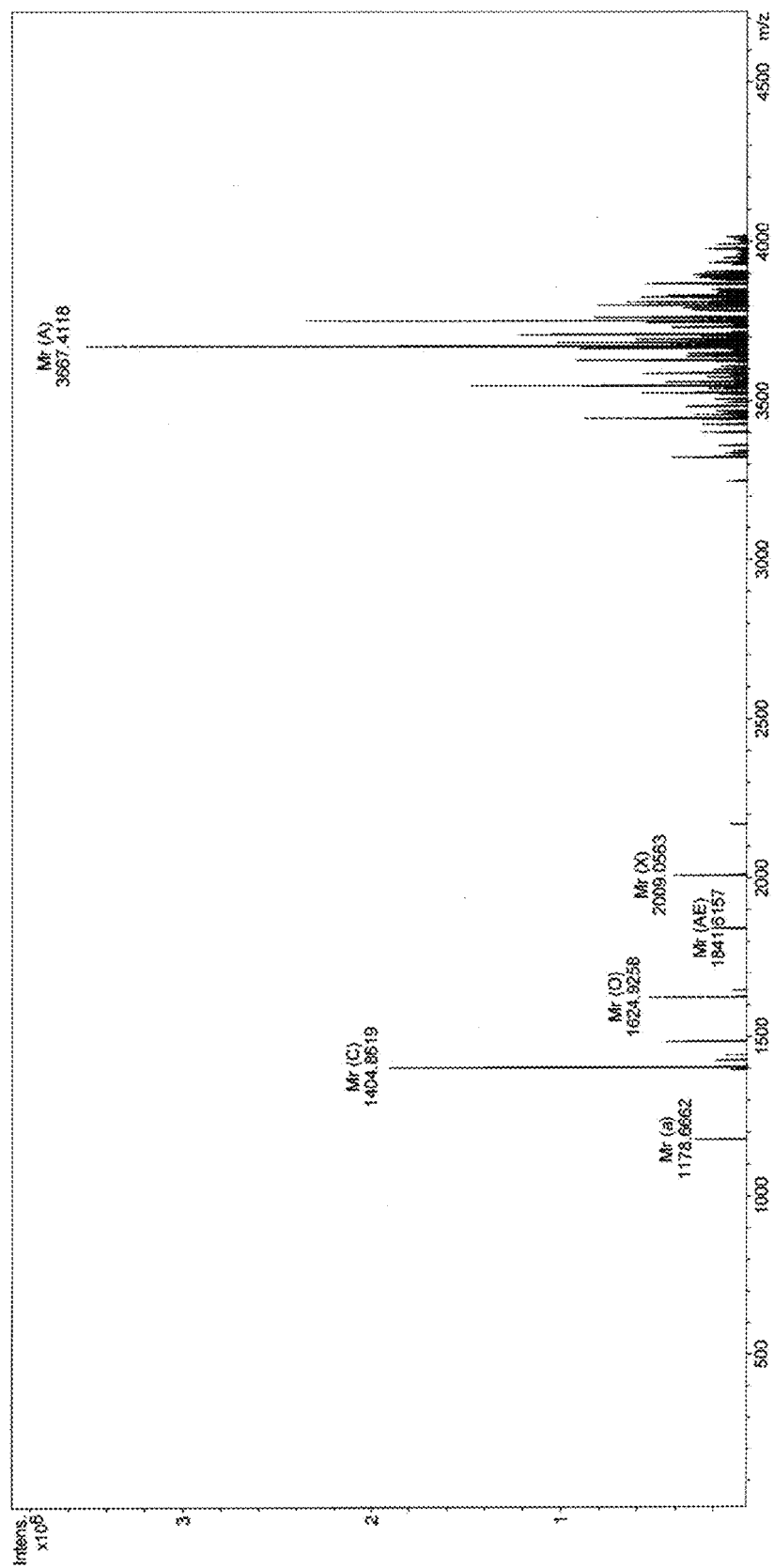
FIG. 22 ESI FT-ICR mass spectrum in negative ion mode of LPS isolated from *E. coli* KPM335 grown at 42° C. in LB medium supplemented with A5P/G6P. Mass numbers given refer to the monoisotopic masses of neutral molecules.
Figure 23:
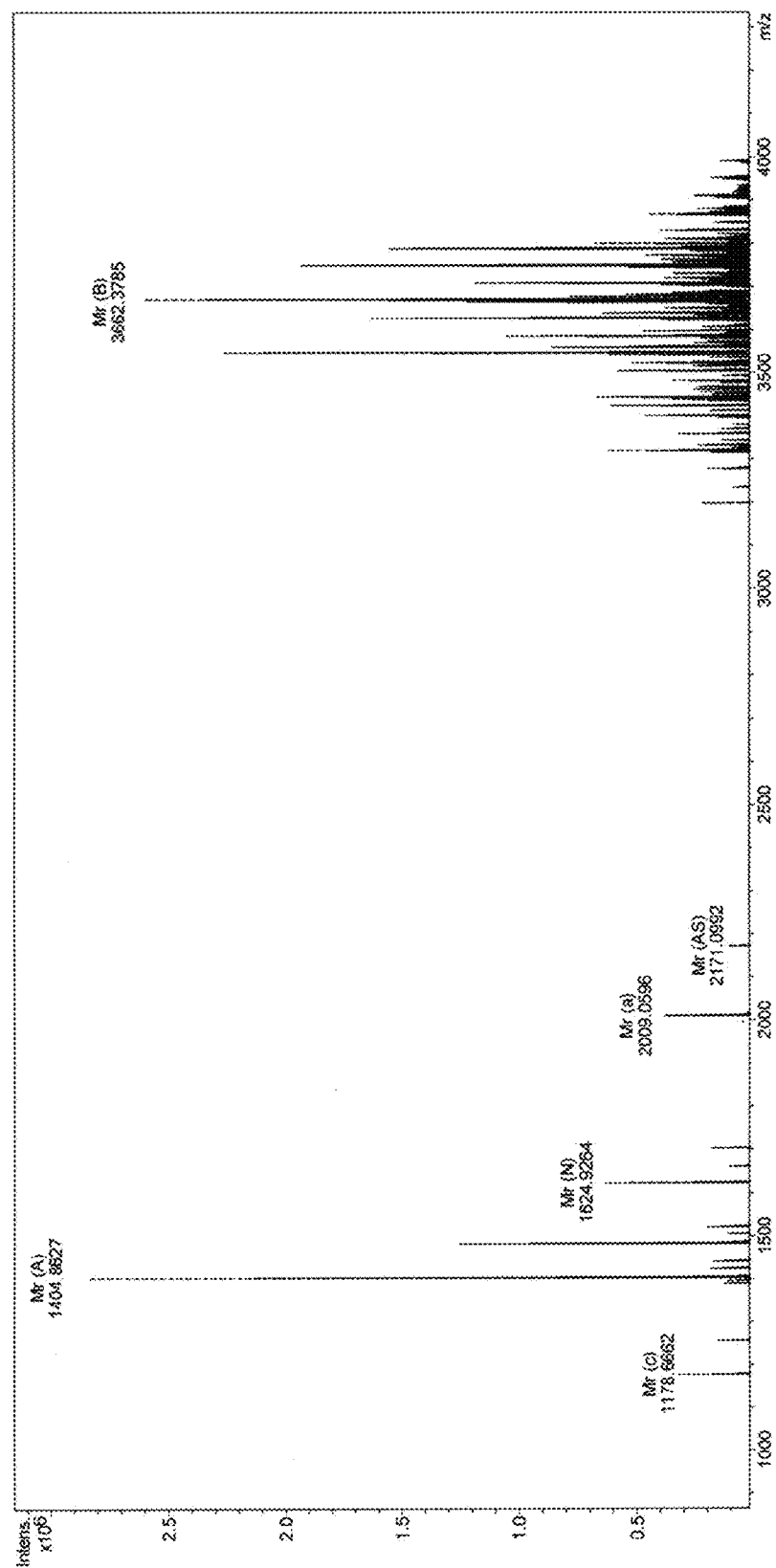
FIG. 23 ESI FT-ICR mass spectrum in negative ion mode of LPS isolated from *E. coli* KPM337 grown at 42° C. in LB medium supplemented with A5P/G6P. Mass numbers given refer to the monoisotopic masses of neutral molecules.
Figure 24:
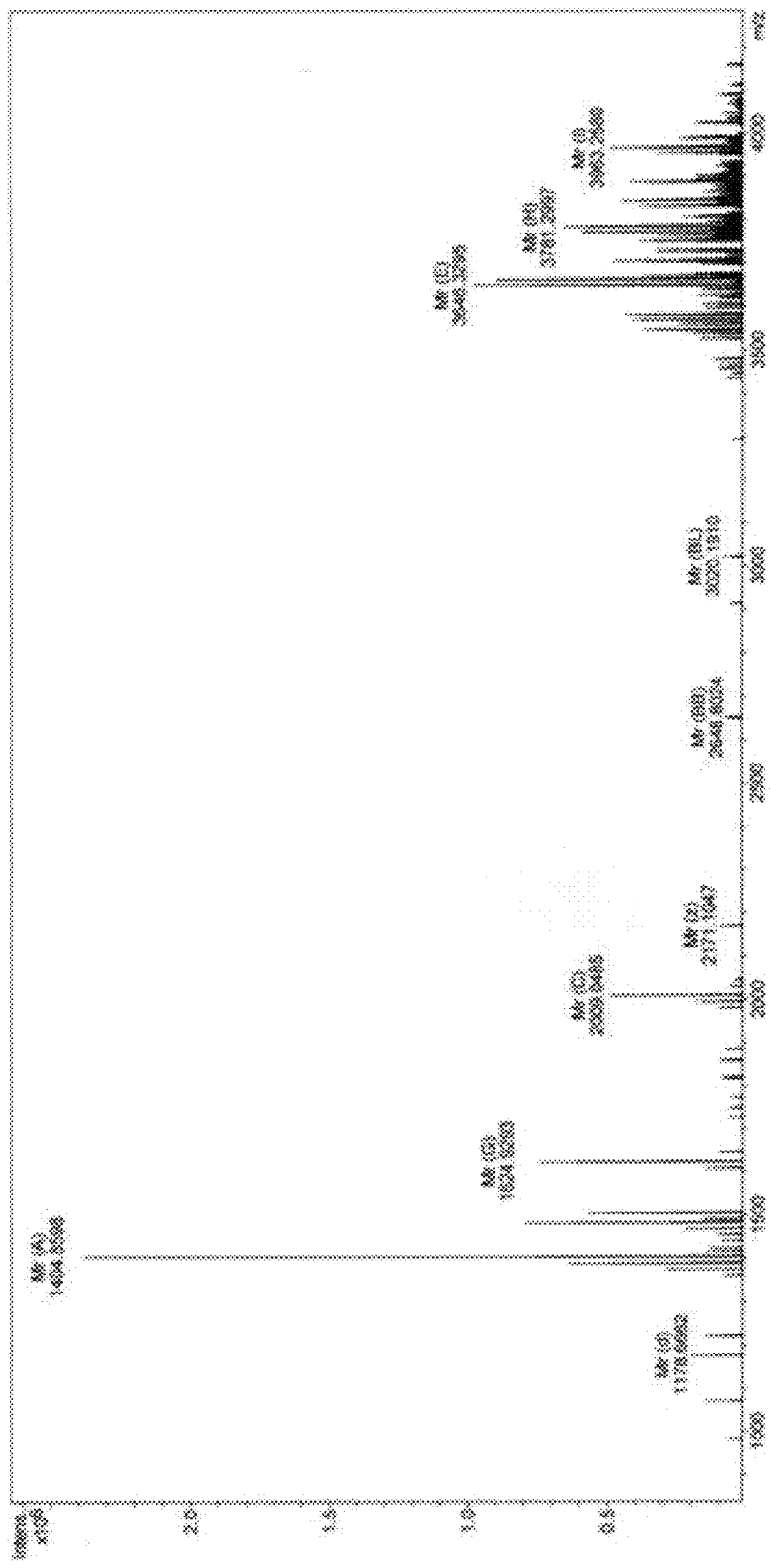
FIG. 24 ESI FT-ICR mass spectrum in negative ion mode of LPS isolated from *E. coli* KPM318 grown at 37° C. in LB medium supplemented with A5P/G6P (control). Mass numbers given refer to the monoisotopic masses of neutral molecules. Peak assignments are listed in Table 1.

The LPS/lipid $IV_A$ composition of the KPM318-9, KPM318-10, KPM318-19 and KPM318-23 strains was analyzed. The cultures (2.5 L each) were grown at 42° C. to stationary phase in either LB medium or LB medium supplemented with A5P/G6P. The LPS/lipid $IV_A$ was extracted from the dried biomass of each strain using either the original phenol-chloroform-light petroleum (PCP) procedure for those strains grown in LB medium with A5P/G6P or a modified PCP protocol for strains grown in LB-only medium. Then the extracts were subjected to ESI FT-ICR mass spectrometry. The KPM318-23 (KPM337) strain grown in LB medium predominantly expresses lipid $IV_A$ (peak at 1404.86 u) at 42° C. (FIG. 20). When the 42° C.-resistant KPM318 derivatives were grown in LB medium supplemented with A5P/G6P, biosynthesis of the *E. coli* K-12 core oligosaccharide was restored. There was expression of a similar mixture of different glycoforms in all strains, albeit attached to the tetraacylated precursor lipid $IV_A$ (FIGS. 21-23). LPS isolated from the parental strain KPM318 grown at 37° C. in LB medium supplemented with A5P/G6P was used as a control for all these experiments (FIG. 24). A number of the molecular masses of the different glycoforms expressed by KPM318 could be assigned and are provided in Table 2. Taken together, the overall LPS/lipid $IV_A$ composition of the 42° C.-resistant derivatives of KPM318 did not show any peculiarities with respect to the typical heterogeneous oligosaccharide composition of the K-12 core. All outer membrane preparations of these strains showed no lipid A; they only contained lipid $IV_A$.

Figure 25:
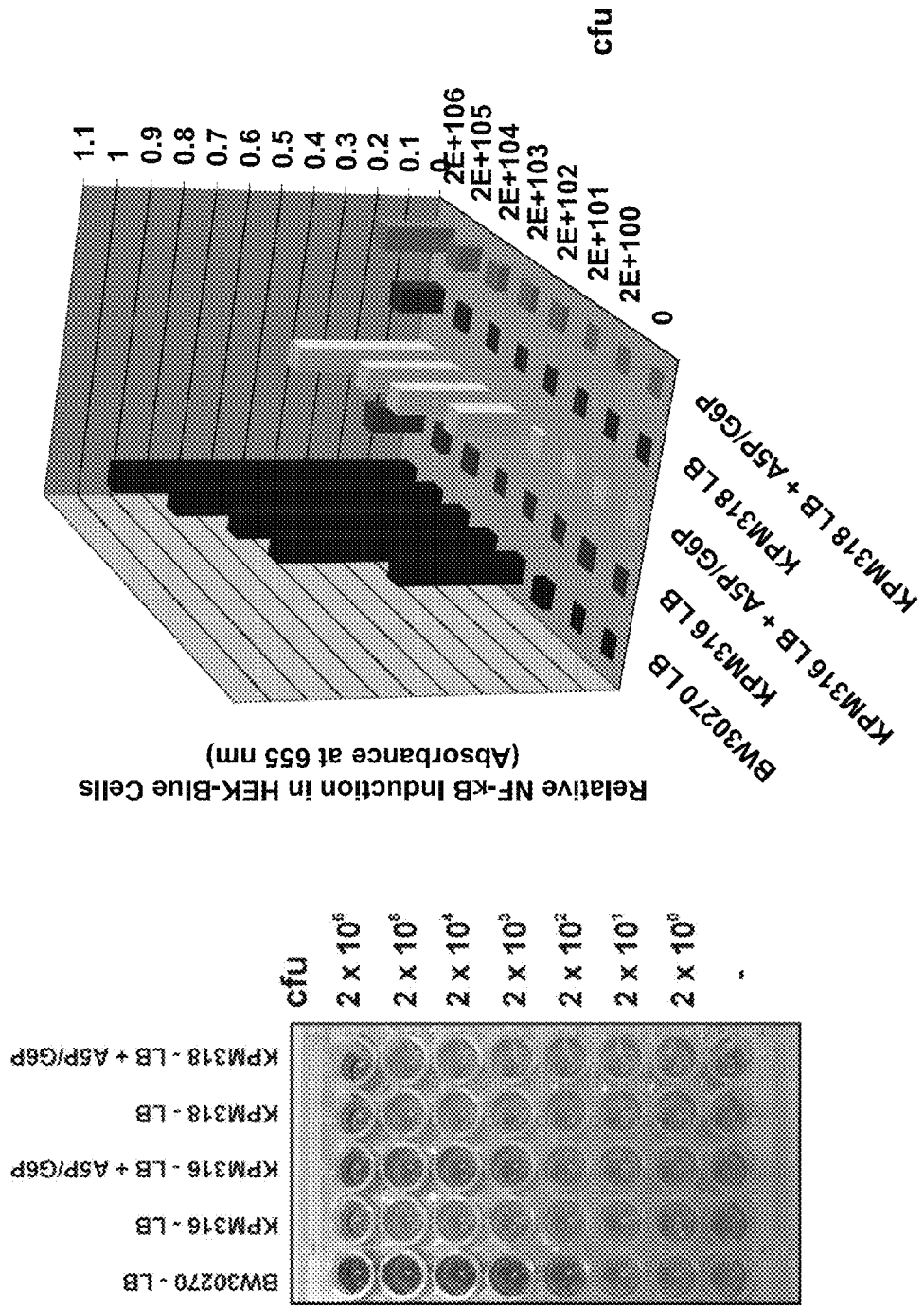
FIG. 25 Detection of LPS in bacterial cell suspensions of KPM316 and KPM318 grown at 37° C. in either LB medium or LB medium supplemented with A5P/G6P. The *E. coli* K-12 wild-type strain BW30270 was used as a control.
Figure 26:
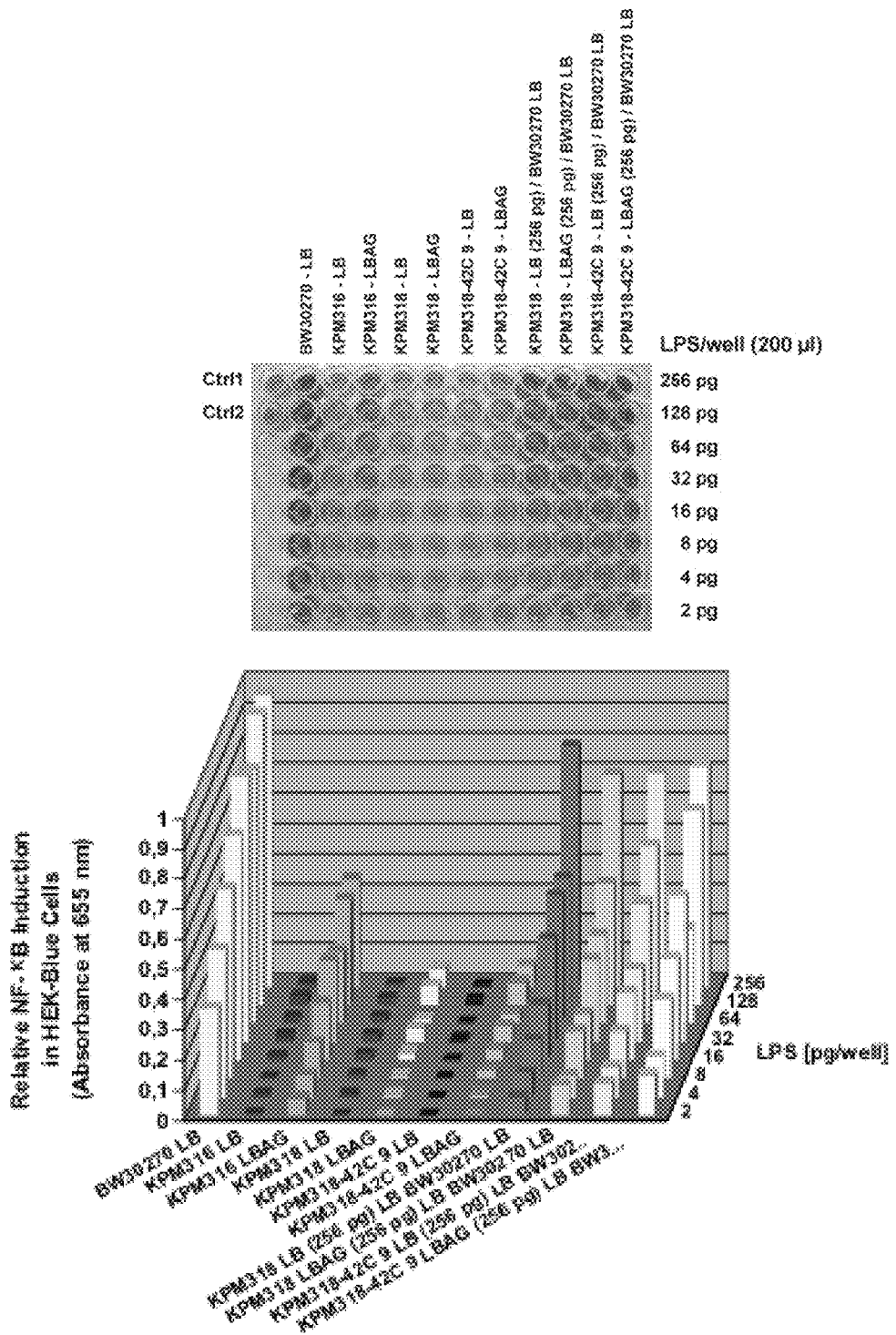
FIG. 26 Relative NF-κB induction in HEK-Blue cells caused by LPS/lipid $IV_A$ isolates from *E. coli* strains BW30270, KPM316, KPM318 and KPM334.

The biological activity of both the bacterial cells and the LPS/lipid $IV_A$ isolated from various KPM strains grown in either LB/SB medium or LB/SB medium supplemented with A5P/G6P was examined using the HEK-Blue LPS detection assay (InvivoGen). For preparation of bacterial cells for this detection assay, 1 ml of an overnight culture of each strain was sedimented by centrifugation and washed in Dulbecco's phosphate buffered saline (DPBS). To kill the bacterial cells, the pellet was subsequently resuspended in 1 ml of a 10× conc. penicillin-streptomycin (Pen-Strep) in DPBS solution. The mixture was incubated at room temperature for 2 hr and stored at 4° C. overnight. At the same time, serial dilutions of the overnight cultures were prepared for calculation of cell number (cfu/ml) of the overnight cultures/Pen-Strep killed cells. The Pen-Strep suspensions of the strains were diluted to $10^8$ cfu/ml in 10× conc. Pen-Strep in DPBS solution, and serial dilutions of the suspensions were then prepared in 10× conc. Pen-Strep in DPBS solution to yield bacterial cell suspensions of $10^7$, $10^6$, $10^5$, $10^4$, $10^3$, $10^2$ and $10^1$ cfu/ml. A typical HEK-Blue LPS detection assay using serial dilutions of bacterial cell suspensions from strains BW30270, KPM316 and KPM318 is shown in FIG. 25. There is little to no LPS activity in the bacterial cell suspensions from the KPM316 and KPM318 strains grown in LB medium, as compared to the control strain BW30270. There is a slight increase in activity for the KPM316 and KPM318 strains grown in media supplemented with A5P/G6P. There is little to no NFκB activation induced by serial dilutions of the LPS/lipid $IV_A$ samples isolated from the KPM316 and KPM318 strains (FIG. 26).

The biological activity of the LPS/lipid $IV_A$ isolated from the temperature-resistant strain KPM318-9 (KPM334) grown at 42° C. in LB-only medium and LB medium supplemented with A5P/G6P was compared with the ability of LPS/lipid $IV_A$ samples from BW30270, KPM316 and KPM318 to induce NFκB activation in HEK-Blue cells. Strain BW30270 was grown at 37° C. in LB medium, whereas strains KPM316 and KPM318 were cultivated at 37° C. in either LB medium or LB medium containing A5P/G6P. To examine the potential antagonistic activity of KPM318-9 (KPM334), constant amounts of the LPS/lipid $IV_A$ isolated from KPM318-9 (KPM334) (256 pg) were mixed with decreasing amounts of BW30270-derived LPS. The LPS/lipid $IV_A$ from LPM318-9 (KPM334) is a potent antagonist of LPS activity as demonstrated by the ability of BW30270 to compete with this antagonist when it is present at high concentrations (FIG. 26, lanes 9-12).

Figure 27:
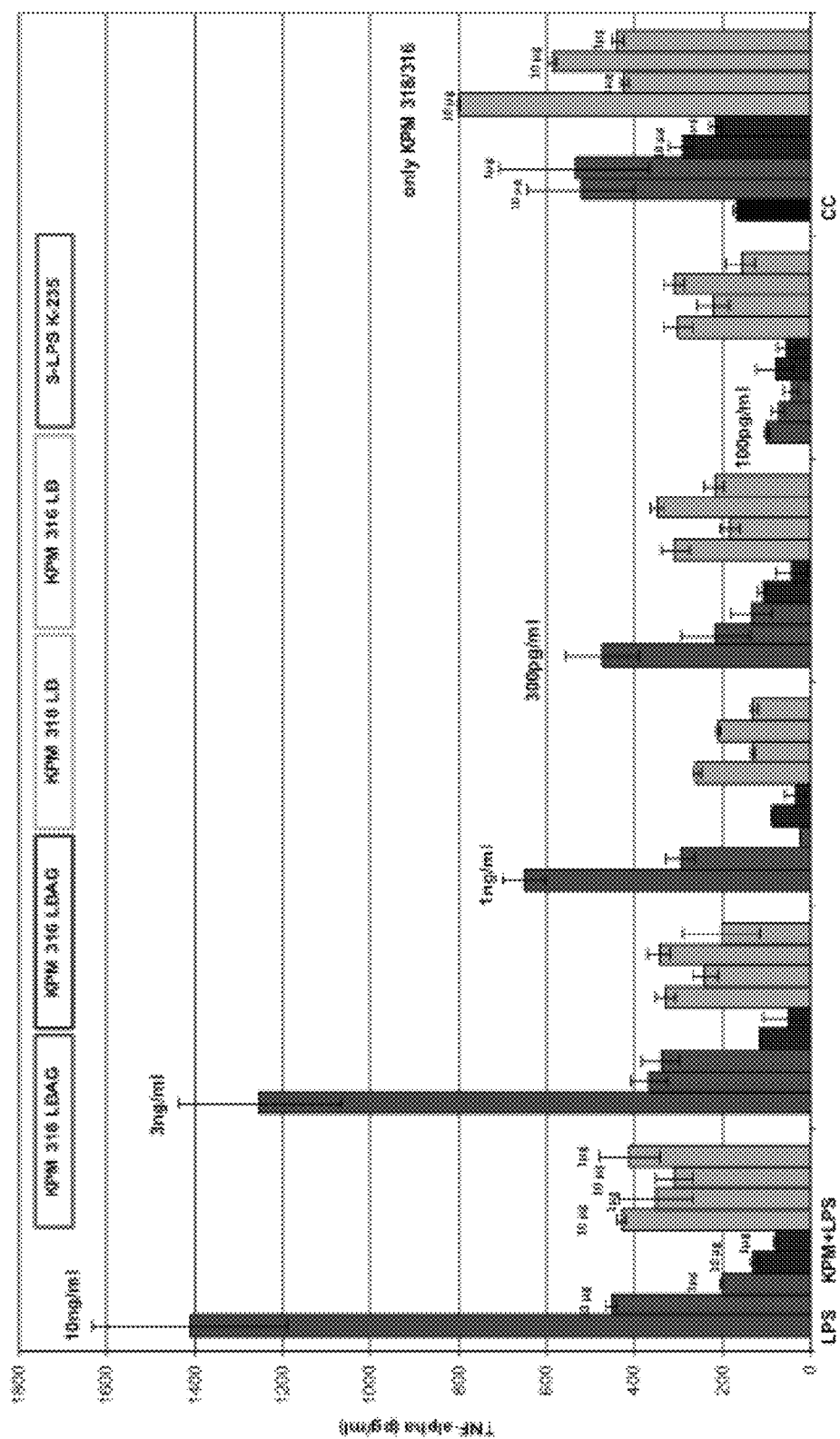
FIG. 27 Human TNF-alpha ELISA to determine the antagonistic activity of LPS/lipid $IV_A$ samples isolated from *E. coli* strains KPM316 and KPM318. For details, see the protocol in the text.
Figure 28:
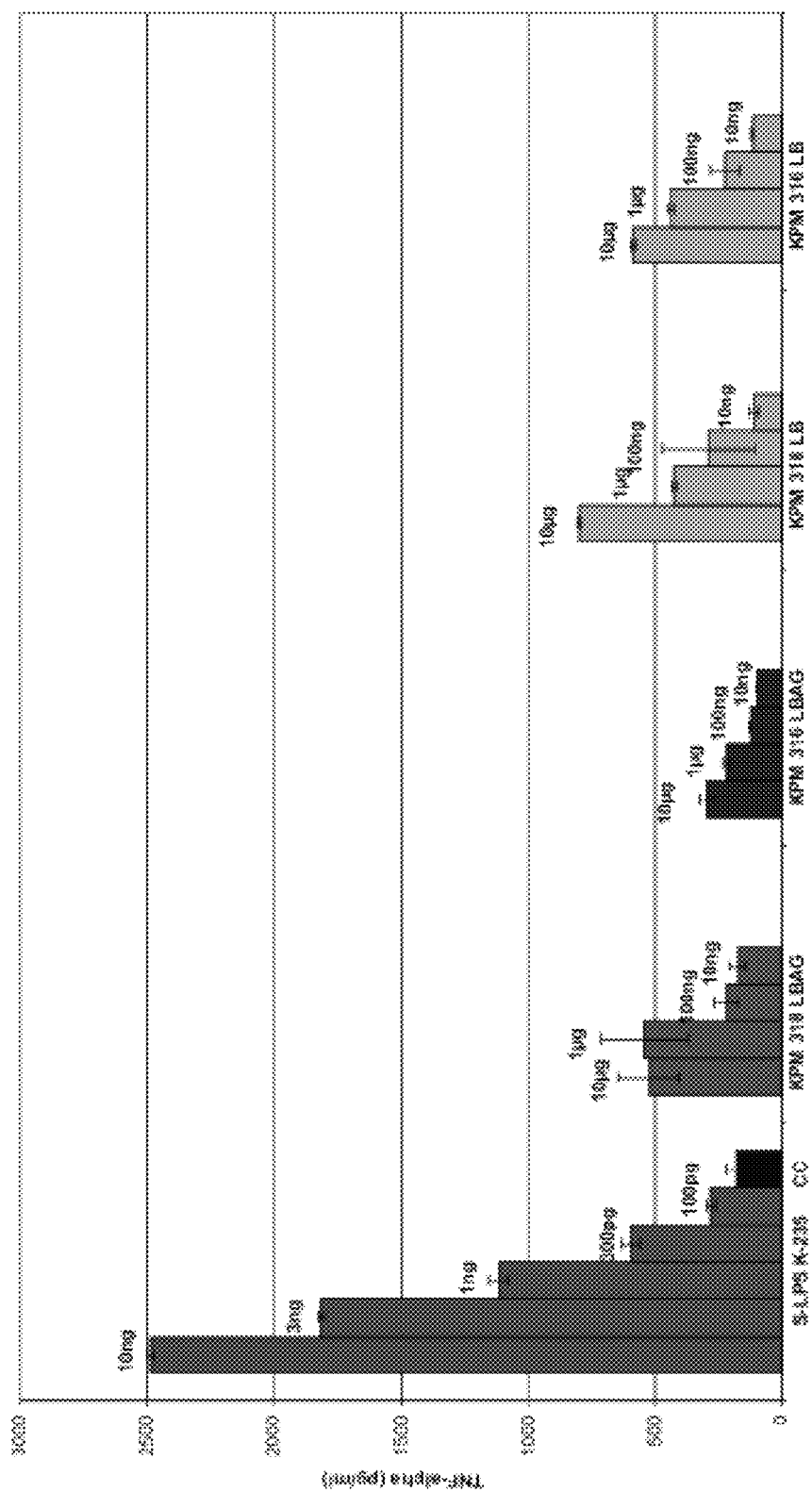
FIG. 28 TNF-alpha release in human macrophages caused by LPS/lipid $IV_A$ samples from *E. coli* strains KPM316 and KPM318 in medium containing 4% AB-serum. The S-LPS of *E. coli* K-235 was used as a control.
Figure 29:
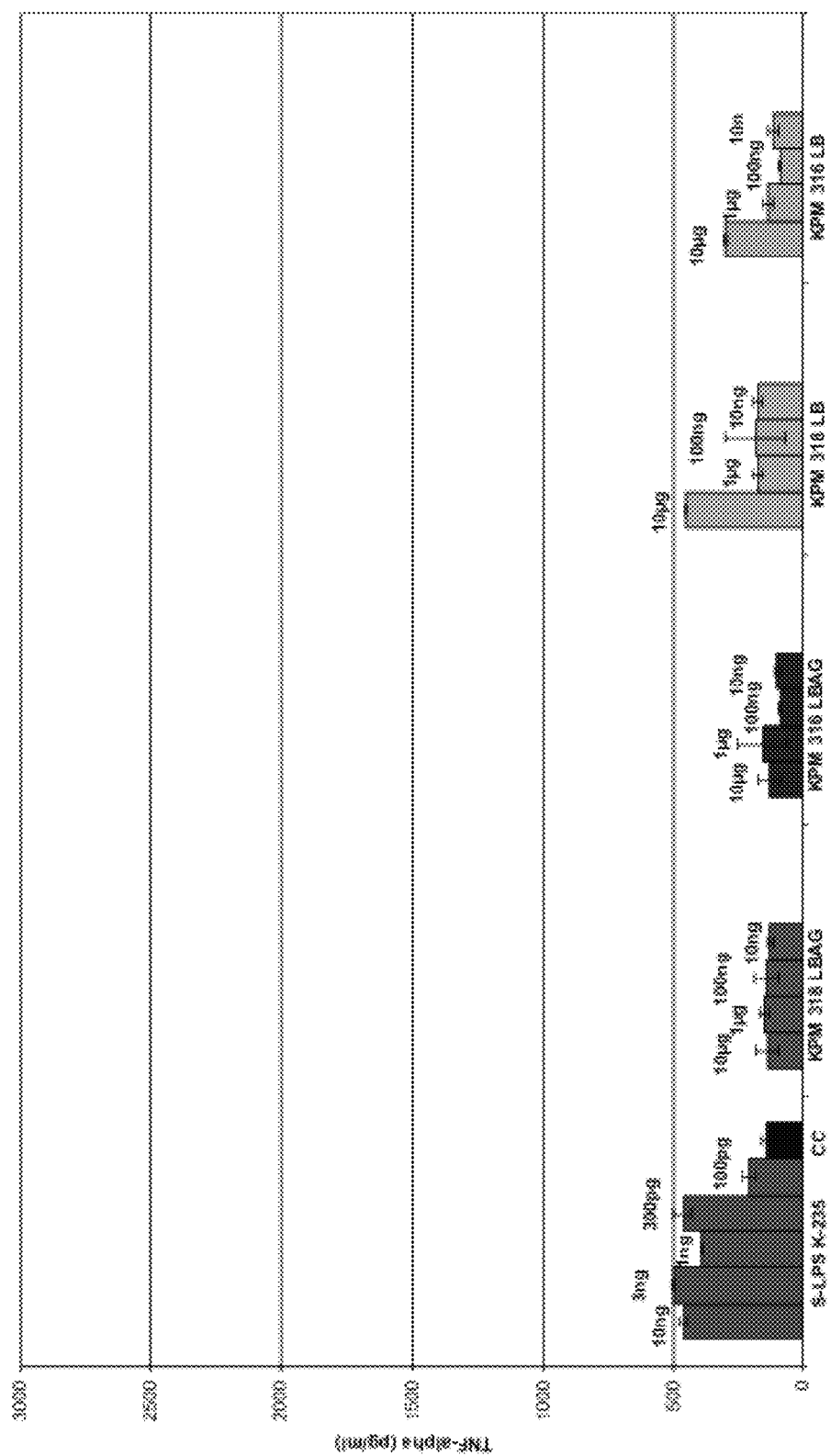
FIG. 29 TNF-alpha release in human macrophages caused by LPS/lipid $IV_A$ samples from *E. coli* strains KPM316 and KPM318 in serum-free medium. The S-LPS of *E. coli* K-235 was used as a control.

A human TNF-alpha ELISA was performed with LPS/lipid $IV_A$ samples isolated from the KPM316 and KPM318 strains grown at 37° C. in either LB medium or LB medium containing A5P/G6P (FIGS. 27-29). The S-LPS isolated from E. coli K-235 was used as a positive control. The blood was separated using Biocoll (density: 1.077 g/mL). Mononuclear cells (MNCs) were isolated and washed twice in Hanks and once in VLE RPMI. The monocytes were differentiated into macrophages by incubating them in Teflon bags with M-CSF. The macrophages were harvested after 7 days. The number of cells was determined. Macrophages were seeded into flat-bottom 96 well plates at 1×$10^5$ cells/well in VLE RPMI+100 U penicillin+100 µg/ml streptomycin+2 mM L-glutamine+4% AB-serum (and free of serum). The LPS/lipid $IV_A$ samples were isolated from KPM316 and KPM318 strains and preincubated at 37° C. and 5% $CO_2$ for 30 min. S-LPS K-235 was added to the samples for 4 hr. Supernatants were removed and stored overnight at 4° C. An ELISA was performed to assess TNF-alpha activity (BD Biosciences #555212). Serial dilutions of the LPS samples in VLE RPMI without AB-serum were prepared. KPM318 LPS LB, KPM316 LPS LB, KPM 318 LPS LBAG, and KPM 316 LPS LBAG were prepared at_1 mg/ml in 20 mM HEPES, pH 7.0. Then serial dilutions from 100 µg/mL to 1 ng/mL were prepared. The plates were coated with capture antibody, which was diluted 1:250 in coating buffer (PBS). The plate was agitated overnight and then washed three times with wash buffer. The plate was blocked with 180 µl assay diluent/well and agitated at room temperature for 1 hr. The plate was washed three times with wash buffer.

Samples were diluted in assay diluent and serial dilutions of the standard were prepared as follows:
1:212=500 µg/ml
1:2=250 µg/ml
1:2=125 µg/ml
1:2=62.5 µg/ml
1:2=31.25 µg/ml
1:2=15.6 µg/ml
1:2=7.8 µg/ml
1:2=3.9 µg/ml The plates were agitated with standard, samples and blank at room temperature for 2 hr. The plate was washed three times with wash buffer. The detector solution and detection antibody (biotinylated anti-human TNF-alpha) were added to the plate at 1:1000. The enzyme reagent (streptavidin-horseradish peroxidase conjugate) was added at 1:250. The plate was agitated at room temperature for 1 hr and then washed three times with wash buffer. The plate was agitated in the dark with TMB (1:20) in substrate buffer. The plate was incubated for a minimum of 30 min until the wells turned blue. The reaction was stopped with 50 µl/well $H_2SO_4$. The absorbance was measured at 450 nm. The LPS/lipid $IV_A$ isolated from the positive control K-235 potently increased TNF-alpha activity at all concentrations tested (FIG. 27). The LPS/lipid $IV_A$ from the KPM316 and KPM318 strains was able to inhibit the induction of TNF-alpha by the K-235-derived LPS at all concentrations tested (FIG. 30); therefore, the LPS/lipid $IV_A$ isolated from the KPM316 and KPM318 strains is a potent antagonist of LPS activity. The LPS/lipid $IV_A$ from the KPM316 and KPM318 strains grown in medium containing 4% AB-serum was able to inhibit the release of TNF-alpha from macrophages (FIG. 28). The LPS/lipid $IV_A$ from the KPM316 and KPM318 strains grown in serum free medium was able to inhibit the release of TNF-alpha from macrophages (FIG. 29). Therefore, the LPS/lipid $IV_A$ isolated from the KPM316 and KPM318 strains is a potent inhibitor of TNF-alpha activity.

Figure 30:
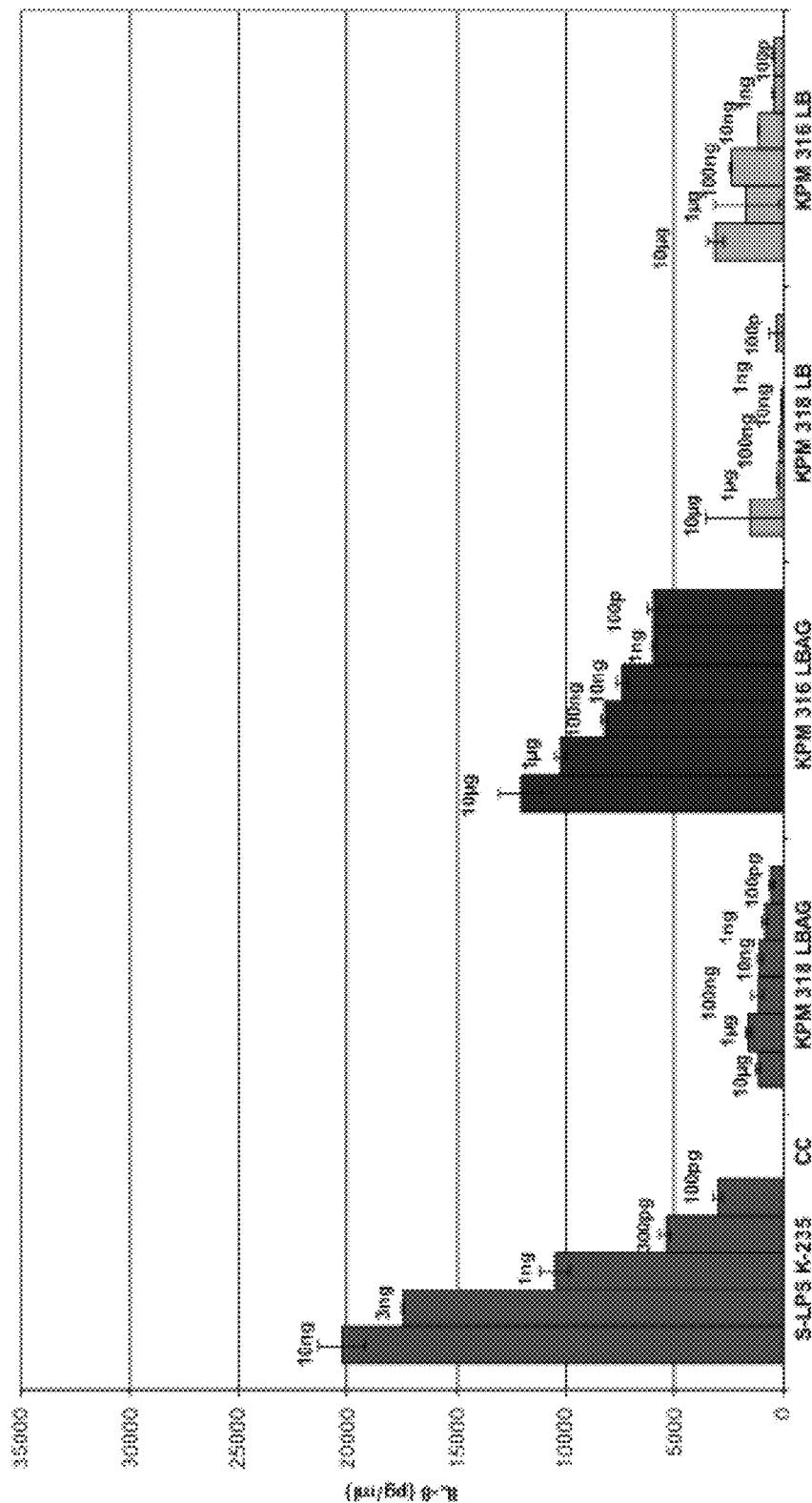
FIG. 30 IL-8 release in HEK293 hTLR4/MD2 #33 cells stimulated with LPS/lipid $IV_A$ samples from *E. coli* strains KPM316 and KPM318. The S-LPS of *E. coli* K-235 was used as a control.
Figure 31:
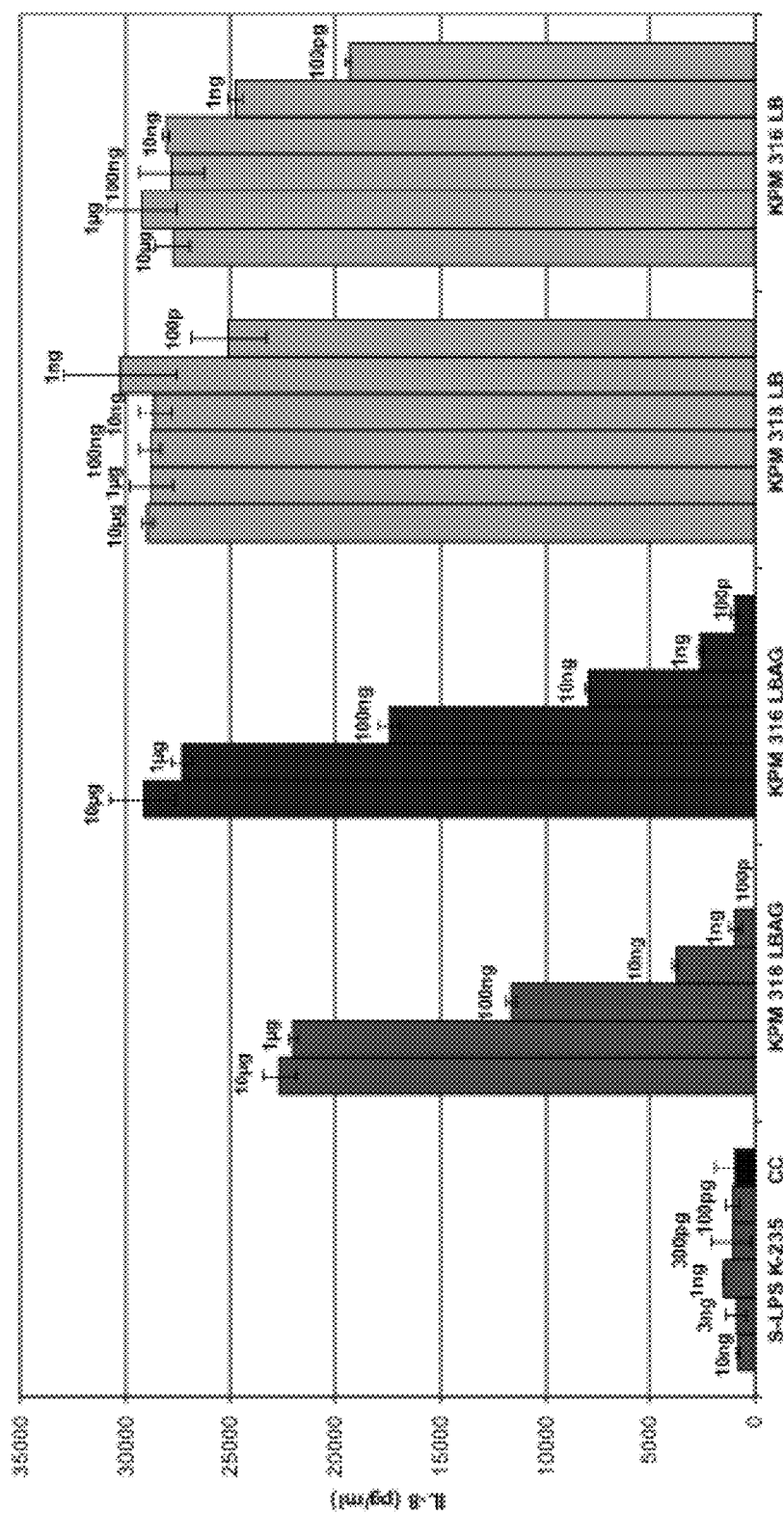
FIG. 31 IL-8 release in HEK293 hTLR2 #2 cells stimulated with LPS/lipid $IV_A$ samples from *E. coli* strains KPM316 and KPM318. The S-LPS of *E. coli* K-235 was used as a control.

LPS is known to exert its inflammatory functions via activation of the TLR4 receptor in human cells. The biological activity of the LPS/lipid $IV_A$ from the KPM316 and KPM318 strains was evaluated by assessing the release of IL-8 from HEK293 hTLR4/MD2 #33 (FIG. 30) and HEK293 hTLR4 #2 cells (FIG. 31). hTLR4/MD2 #33 cells respond to LPS binding, generating a signal, while HEK293 hTLR4 #2 cells respond to peptidoglycan, and not to LPS. Therefore, the latter cell line can be used to assess LPS specificity. S-LPS from the K-235 strain was used as a positive control in these assays. The HEK293 hTLR4/MD2 #33 cell medium was DMEM (Biochrom) supplemented with Pen/Strep/Glu and 10% FCS. There were 50,000 HEK293 hTLR4/MD2 #33 cells/well seeded in the wells. The cells were stimulated in the presence of the LPS/lipid $IV_A$ samples for a period of 24 hr, followed by measurement of human IL-8 release (BD Biosciences #555244). The LPS/lipid $IV_A$ from the KPM316 and KPM318 strains was able to block the release of IL-8 from HEK293 hTLR4/MD2 #33 cells (FIG. 30). The LPS/lipid $IV_A$ extracts from the strains were crude extracts as they were able to promote the release of IL-8 from HEK293 hTLR2 #2 cells (FIG. 31). TLR2 is a receptor for peptidoglycan, another bacterial component that can cause cytokine signalling. The abundance of free peptidoglycan is typically far lower than the levels of LPS, so it is usually a minor component. Here it is used to demonstrate that the extracts do indeed contain material derived from the outer membrane-periplasm of the cells, since this is where peptidoglycan is located. The HEK cells overexpressing TLR4/MD2 (cell line #33) responded to LPS binding, i.e., released IL-8 (FIG. 33), while the HEK cells overexpressing TLR2 (cell line #2), which respond to peptidoglycan, do not respond to LPS (FIG. 31). Therefore, this control confirms that something from the outer membrane extracts was indeed added to the assays in both cases.

The ability of the KPM318-9 (KPM334), KPM318-10 (KPM335), KPM318-19 (KPM336) and KPM318-23

(KPM337) strains to overexpress heterologous genes was assessed. The MalE-LacZα fusion protein was used as a model protein to investigate the capability of these strains to express cytoplasmic and periplasmic variants of the MalE protein in large quantities under standard growth and induction conditions. The BW30270, KPM318, KPM318-9, KPM318-10, KPM318-19 and KPM318-23 strains were transformed each with plasmids pMAL-c2 and pMAL-p2 for cytoplasmic (FIG. 32, upper panel) and periplasmic MalE-LacZα (FIG. 32, lower panel) expression, respectively. The following strains were obtained:

BW30270/pMAL-c2 (control)
KPM318/pMAL-c2
KPM318-9/pMAL-c2
KPM318-10/pMAL-c2
KPM318-19/pMAL-c2
BW30270/pMAL-p2 (control)
KPM318/pMAL-p2
KPM318-9/pMAL-p2
KPM318-10/pMAL-p2
KPM318-19/pMAL-p2
KPM318-23/pMAL-p2

To induce expression of MalE-LacZα, isopropyl-β-D-thiogalactoside (IPTG) was added to a final concentration of 0.4 mM when the cultures reached the mid-exponential growth phase at an $OD_{600}$ of approximately 0.6. For strains carrying the plasmid pMAL-c2, the cells were harvested prior to induction (uninduced), 3 hr after induction, as well as after overnight induction. For strains with plasmid pMAL-p2, samples were taken from uninduced cells and after induction times of 3 hr, 6 hr, 12 hr, and 24 hr. The ability to secrete the MalE-LacZα protein into the medium was additionally examined for strains carrying the pMAL-p2 plasmid, with pMAL-c2 strains used as controls. Protein extracts were prepared using the BugBuster reagent according to the manufacturer's recommendations (Novagen). Western blot analyses using a monoclonal antibody against MalE (NEB) were performed to detect MalE-LacZα expression.

The expression levels of MalE-LacZα were highest at 3 hr post-induction in pMAL-c2 strains, and at 3 hr and 6 hr post-induction in pMAL-p2 strains (FIGS. 33-39). Expression of MalE-LacZα was consistently highest in strains KPM318, KPM318-9 (KPM334) and KPM318-10 (KPM335), showing almost identical expression levels to the BW30270 wild-type controls (FIGS. 33-39). As expected, both Coomassie-blue stained polyacrylamide gels and immunoblots did not detect MalE-LacZα in the culture media of strains carrying the plasmid pMAL-c2 for cytoplasmic expression of the protein (FIGS. 33-39). In contrast, the abundance of the MalE-LacZα protein in the culture media of pMAL-p2 strains apparently increased with increasing duration of IPTG induction. This did not only apply to all KPM mutants, but also to the BW30270 wild-type strain (FIGS. 33-39). It is unknown whether the presence of MalE-LacZα in the culture medium is a result of secretion of the protein as a result of a compromised outer membrane in the KPM strains or simply cell lysis due to periplasmic overexpression of the protein under the experimental conditions used in this study. MBP is known to be highly expressed in *E. coli*. The KPM18 temperature-resistant derivatives exhibited similar levels of protein expression to the wild-type control strain BW30270. These strains secrete or leak MBP more readily than the wild-type strain, which allows the collection of protein in the absence of cell lysis.

Figure 40:
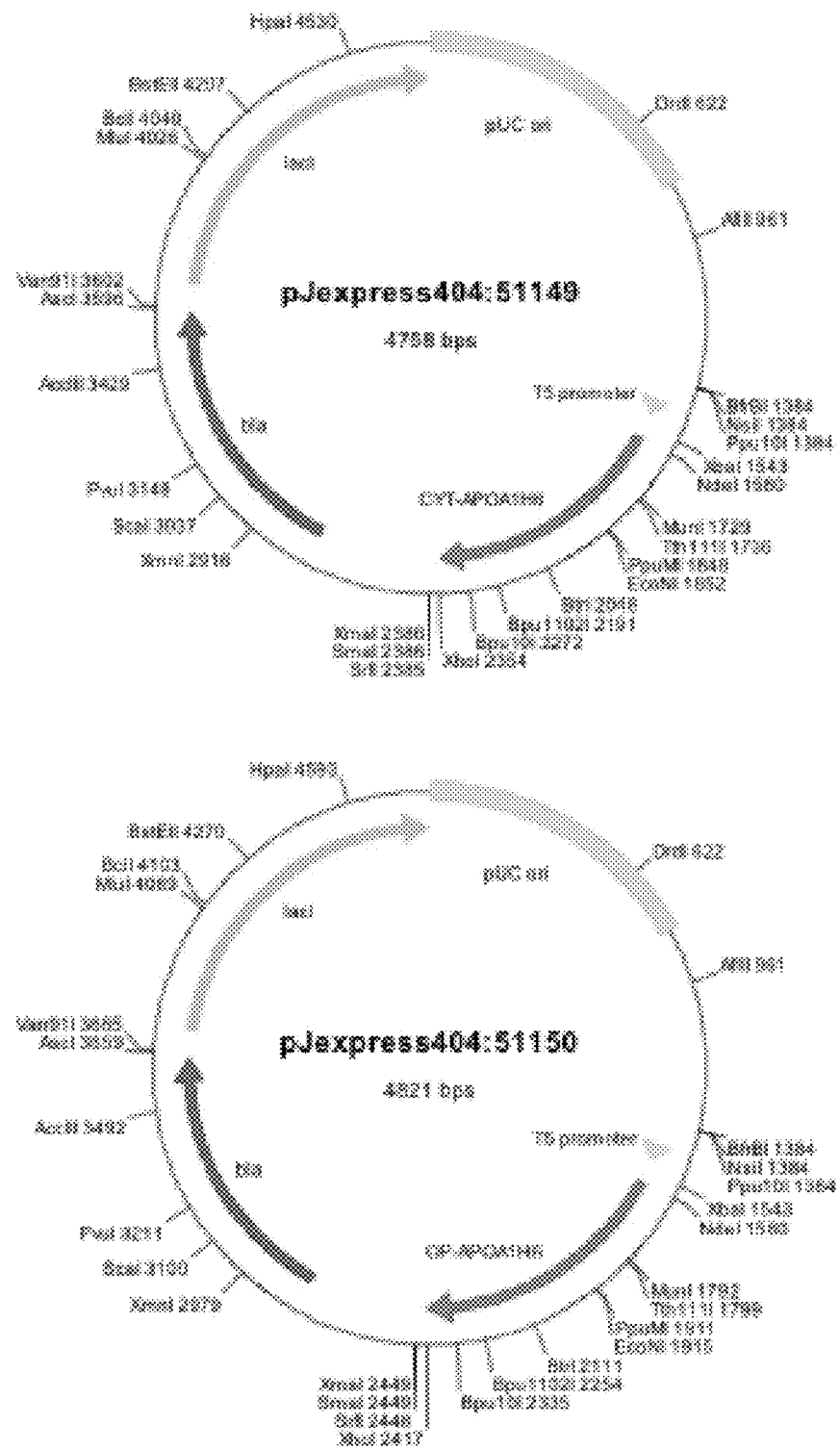
FIG. 40 Maps of plasmids pJexpress404:51149 and pJexpress404:51150 for cytoplasmic (upper panel) and periplasmic ApoA1 expression (lower panel).
Figure 41:
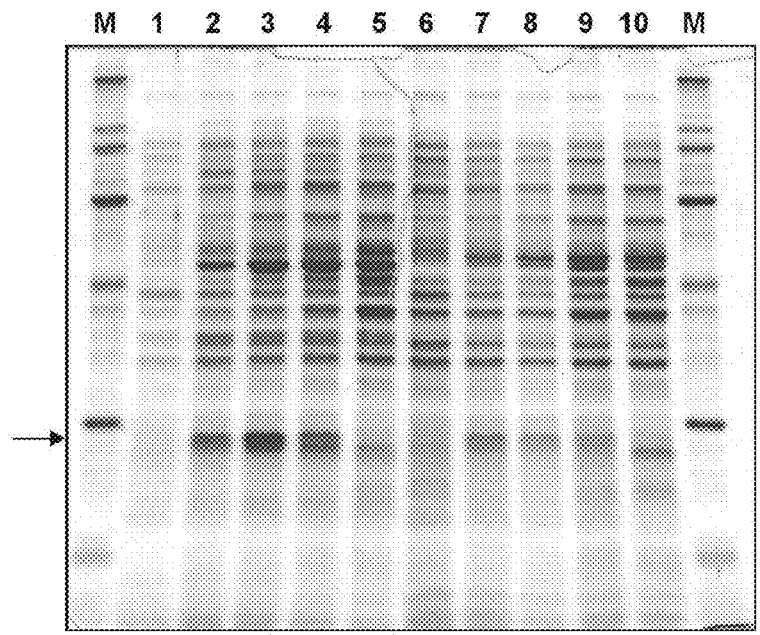
FIG. 41 SDS-PAGE analysis of protein extracts (6 μg each) prepared from strains BW30270/pJexpress404:51149 and KPM318/pJexpress404:51149. The protein extracts were obtained from uninduced cells and cells after induction times of 3 hr, 6 hr, 12 hr and 24 hr. The samples were resolved using 12% polyacrylamide gels and stained with Coomassie blue. Molecular mass protein markers (Broad Range—Bio-Rad) were run in lanes M. The arrow indicates the ApoA1 protein.
Figure 42:
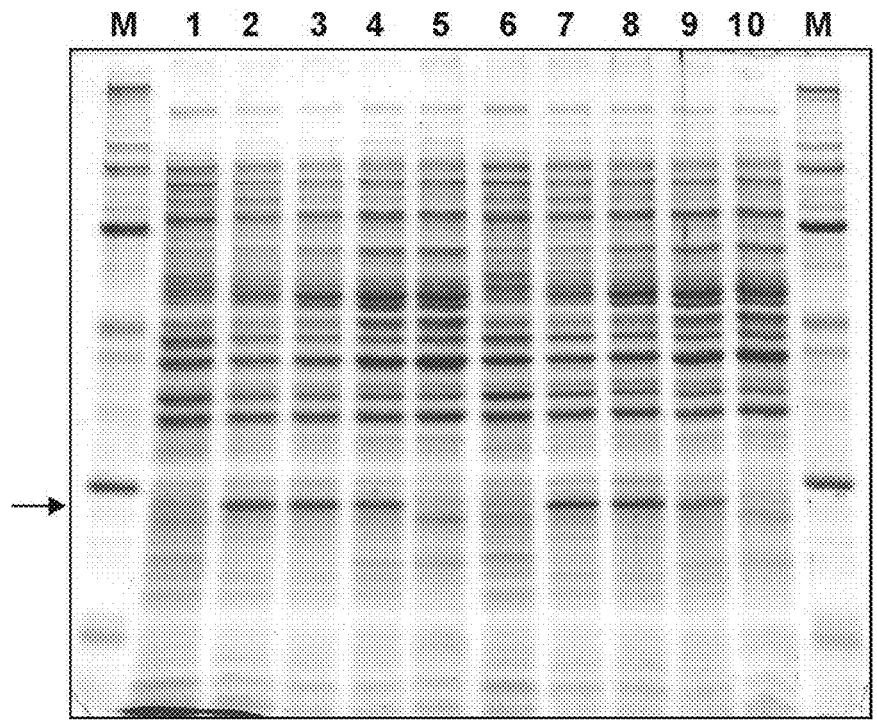
FIG. 42 SDS-PAGE analysis of protein extracts (6 μg each) prepared from strains KPM334/pJexpress404:51149 and KPM335/pJexpress404:51149. The protein extracts were obtained from uninduced cells and cells after induction times of 3 hr, 6 hr, 12 hr and 24 hr. The samples were resolved using 12% polyacrylamide gels and stained with Coomassie blue. Molecular mass protein markers (Broad Range—Bio-Rad) were run in lanes M. The arrow indicates the ApoA1 protein.
Figure 43:
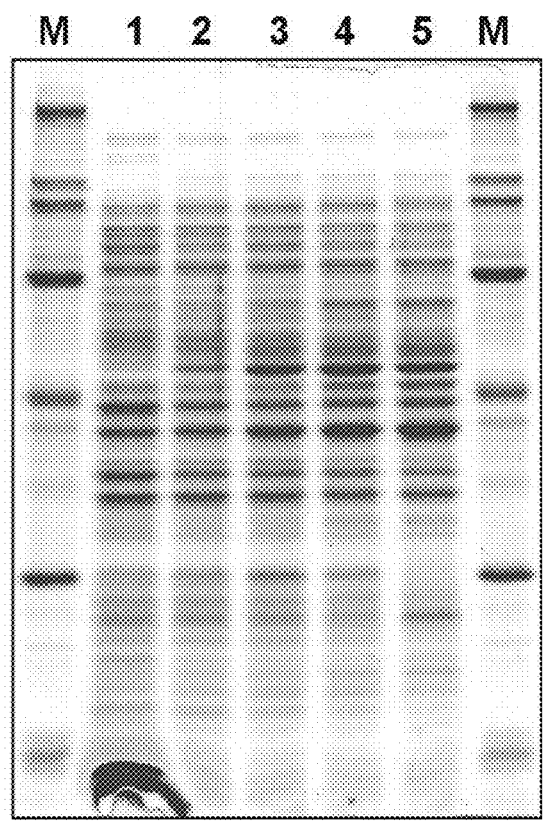
FIG. 43 SDS-PAGE analysis of protein extracts (6 μg each) prepared from strain KPM336/pJexpress404:51149. The protein extracts were obtained from uninduced cells and cells after induction times of 3 hr, 6 hr, 12 hr and 24 hr. The samples were resolved using 12% polyacrylamide gels and stained with Coomassie blue. Molecular mass protein markers (Broad Range—Bio-Rad) were run in lanes M.

The ability of KPM318 and its temperature-resistant derivatives to produce the human ApoA1 protein was investigated. The apoA1 gene optimized for codon usage of *E. coli* was synthesized and cloned under the control of the Tn5 promoter in pJexpress404 by the company DNA 2.0. For periplasmic expression of ApoA1, the gene was fused to the leader sequence of ompA for the major outer membrane protein A of *E. coli*. In addition, both the cytoplasmic and the periplasmic version of the apoA1 gene were C-terminally fused to a 6×His:tag-coding sequence. The strains were transformed with pJexpress404:51149 and pJexpress404:51150 for cytoplasmic (FIG. 40, upper panel) and periplasmic ApoA1 (FIG. 40, lower panel) expression, respectively. Despite several attempts, the strain KPM318-23 (KPM337) could not be transformed with the pJexpress404:51149 and pJexpress404:51150 expression vectors. The following strains were obtained:

1. BW30270/pJexpress404:51149 (control)
2. KPM318/pJexpress404:51149
3. KPM318-9 (KPM334)/pJexpress404:51149
4. KPM318-10 (KPM335)/pJexpress404:51149
5. KPM318-19 (KPM336)/pJexpress404:51149
6. BW30270/pJexpress404:51150 (control)
7. KPM318/pJexpress404:51150
8. KPM318-9 (KPM334)/pJexpress404:51150
9. KPM318-10 (KPM335)/pJexpress404:51150
10. KPM318-19 (KPM336)/pJexpress404:51150

The cultures were grown overnight at 37° C. in 5 ml of SB medium containing 100 µg/ml ampicillin. The overnight cultures (1:50) were diluted in 40 ml of pre-warmed SB medium containing 100 µg/ml ampicillin. The cultures were grown at 37° C. and agitated at 250 rpm to an $OD_{600}$ of approximately 0.6. The cell number (cfu/ml) for each strain was determined (Table 3). The uninduced cultures were centrifuged for 10 min at 6,000 rpm (4° C.). A 1 ml aliquot of each pJexpress404:51150-culture supernatant was obtained for further analysis. The 1-ml culture supernatants and cell pellets were frozen and stored at −80° C. IPTG was added to the cultures (at a final concentration of 0.4 mM). The cells were incubated at 37° C. and agitated at 250 rpm for 3 hr. The cell number (cfu/ml) for each strain (Table 4) was evaluated. After the 3 hr induction, 5 ml of each culture was removed:

1. BW30270/pJexpress404:51149—induced (3 hr)
2. KPM318/pJexpress404:51149—induced (3 hr)
3. KPM318-42C 9 (KPM334)/pJexpress404:51149—induced (3 hr)
4. KPM318-42C 10 (KPM335)/pJexpress404:51149—induced (3 hr)
5. KPM318-42C 19 (KPM336)/pJexpress404:51149—induced (3 hr)
6. BW30270/pJexpress404:51150—induced (3 hr)
7. KPM318/pJexpress404:51150—induced (3 hr)
8. KPM318-42C 9 (KPM334)/pJexpress404:51150—induced (3 hr)
9. KPM318-42C 10 (KPM335)/pJexpress404:51150—induced (3 hr)
10. KPM318-42C 19 (KPM336)/pJexpress404:51150—induced (3 hr)

The induced cultures were centrifuged for 10 min at 6,000 rpm (4° C.). A 1 ml aliquot of each pJexpress404:51150-culture supernatant was obtained for further analysis. The 1-ml culture supernatants and cell pellets were stored at −80° C. The induction was continued at 37° C. and 250 rpm. The cell number (cfu/ml) for each culture was determined strain after 6 hr of induction (Table 5). A 3 ml aliquot of each culture was removed after 6 hr of induction:

1. BW30270/pJexpress404:51149—induced (6 hr)
2. KPM318/pJexpress404:51149—induced (6 hr)

3. KPM318-42C 9 (KPM334)/pJexpress404:51149—induced (6 hr)
4. KPM318-42C 10 (KPM335)/pJexpress404:51149—induced (6 hr)
5. KPM318-42C 19 (KPM336)/pJexpress404:51149—induced (6 hr)
6. BW30270/pJexpress404:51150—induced (6 hr)
7. KPM318/pJexpress404:51150—induced (6 hr)
8. KPM318-42C 9 (KPM334)/pJexpress404:51150—induced (6 hr)
9. KPM318-42C 10 (KPM335)/pJexpress404:51150-induced (6 hr)
10. KPM318-42C 19 (KPM336)/pJexpress404:51150—induced (6 hr)

The induced cultures were centrifuged for 10 min at 6,000 rpm (4° C.) There was a 1 ml aliquot of each pJexpress404:51150 culture supernatant removed for further analysis. The 1-ml culture supernatants and cell pellets were frozen and stored at −80° C. The induction was continued at 37° C. and 250 rpm. The cell number (cfu/ml) was determined for each strain after 12 hr of induction (Table 6). A 2 ml aliquot of each culture was removed after the 12 hr induction:

1. BW30270/pJexpress404:51149—induced (12 hr)
2. KPM318/pJexpress404:51149—induced (12 hr)
3. KPM318-42C 9 (KPM334)/pJexpress404:51149—induced (12 hr)
4. KPM318-42C 10 (KPM335)/pJexpress404:51149—induced (12 hr)
5. KPM318-42C 19 (KPM336)/pJexpress404:51149—induced (12 hr)
6. BW30270/pJexpress404:51150—induced (12 hr)
7. KPM318/pJexpress404:51150—induced (12 hr)
8. KPM318-42C 9 (KPM334)/pJexpress404:51150—induced (12 hr)
9. KPM318-42C 10 (KPM335)/pJexpress404:51150-induced (12 hr)
10. KPM318-42C 19 (KPM336)/pJexpress404:51150—induced (12 hr)

The induced cultures were centrifuged for 10 min at 6,000 rpm (4° C.). There was 1 ml of each pJexpress404:51150-culture supernatant obtained for further analysis. The 1-ml culture supernatants and cell pellets were frozen and stored at −80° C. The induction was continued at 37° C. and 250 rpm. The cell number (cfu/ml) for each strain was determined after 24 hr of induction (Table 7). There was 1 ml of each culture removed after the 24 hr induction:

1. BW30270/pJexpress404:51149—induced (24 hr)
2. KPM318/pJexpress404:51149—induced (24 hr)
3. KPM318-42C 9 (KPM334)/pJexpress404:51149—induced (24 hr)
4. KPM318-42C 10 (KPM335)/pJexpress404:51149—induced (24 hr)
5. KPM318-42C 19 (KPM336)/pJexpress404:51149—induced (24 hr)
6. BW30270/pJexpress404:51150—induced (24 hr)
7. KPM318/pJexpress404:51150—induced (24 hr)
8. KPM318-42C 9 (KPM334)/pJexpress404:51150—induced (24 hr)
9. KPM318-42C 10 (KPM335)/pJexpress404:51150—induced (24 hr)
10. KPM318-42C 19 (KPM336)/pJexpress404:51150—induced (24 hr)

The cultures were induced for 10 min at 6,000 rpm (4° C.). The pJexpress404:51150-culture supernatants were obtained for further analysis. The 1-ml culture supernatants and cell pellets were frozen and stored at −80° C. The uninduced and induced cells were thawed and all cell pellets were resuspended in 300 µl of 1×BugBuster. There was 3 µl of 20 mg/ml lysozyme solution added to the samples and 0.5 µl of Benzonase. The samples were incubated at room temperature for 20 min with shaking. The samples were centrifuged at 14,000 rpm for 20 min (4° C.). The 1×Bug Buster contains:

1 ml 10× conc. BugBuster
200 µl 1 M Tris-HCl, pH 7.5 (20 mM Tris-HCl, pH 7.5)
3.5 µl 2-mercaptoEtOH (5 mM 2-mercaptoEtOH)

Figure 44:
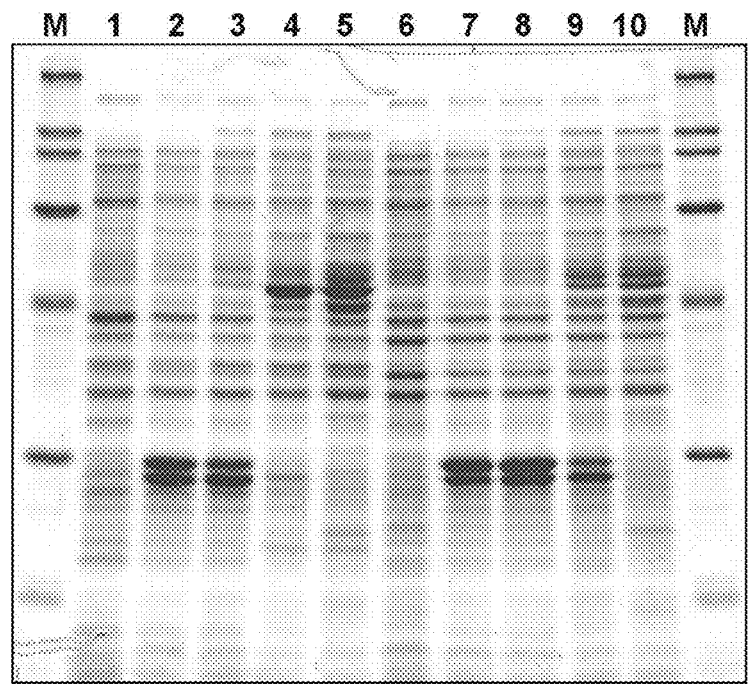
FIG. 44 SDS-PAGE analysis of protein extracts (6 μg each) prepared from strains BW30270/pJexpress404:51150 and KPM318/pJexpress404:51150. The protein extracts were obtained from uninduced cells and cells after induction times of 3 hr, 6 hr, 12 hr and 24 hr. The samples were resolved using 12% polyacrylamide gels and stained with Coomassie blue. Molecular mass protein markers (Broad Range—Bio-Rad) were run in lanes M.
Figure 45:
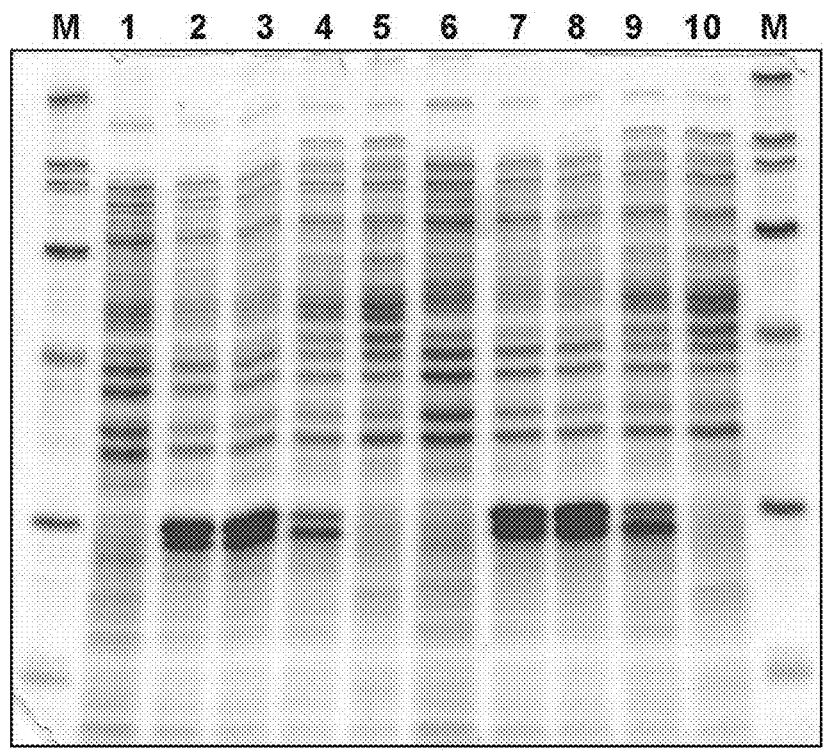
FIG. 45 SDS-PAGE analysis of protein extracts (6 μg each) prepared from strains KPM334/pJexpress404:51150 and KPM335/pJexpress404:51150. The protein extracts were obtained from uninduced cells and cells after induction times of 3 hr, 6 hr, 12 hr and 24 hr. The samples were resolved using 12% polyacrylamide gels and stained with Coomassie blue. Molecular mass protein markers (Broad Range—Bio-Rad) were run in lanes M.
Figure 46:
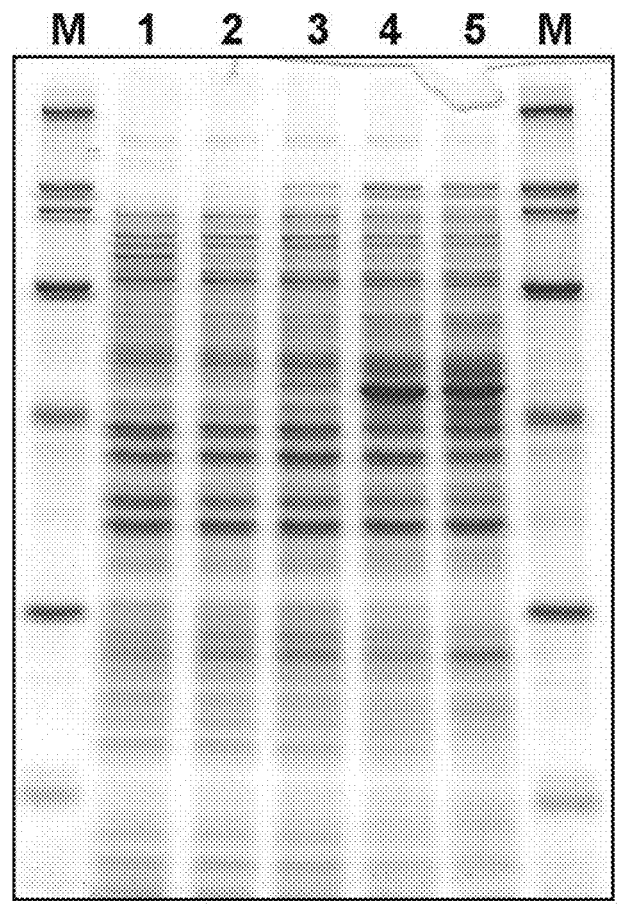
FIG. 46 SDS-PAGE analysis of protein extracts (6 μg each) prepared from strain KPM336/pJexpress404:51150. The protein extracts were obtained from uninduced cells and cells after induction times of 3 hr, 6 hr, 12 hr and 24 hr. The samples were resolved using 12% polyacrylamide gels and stained with Coomassie blue. Molecular mass protein markers (Broad Range—Bio-Rad) were run in lanes M.
Figure 47:
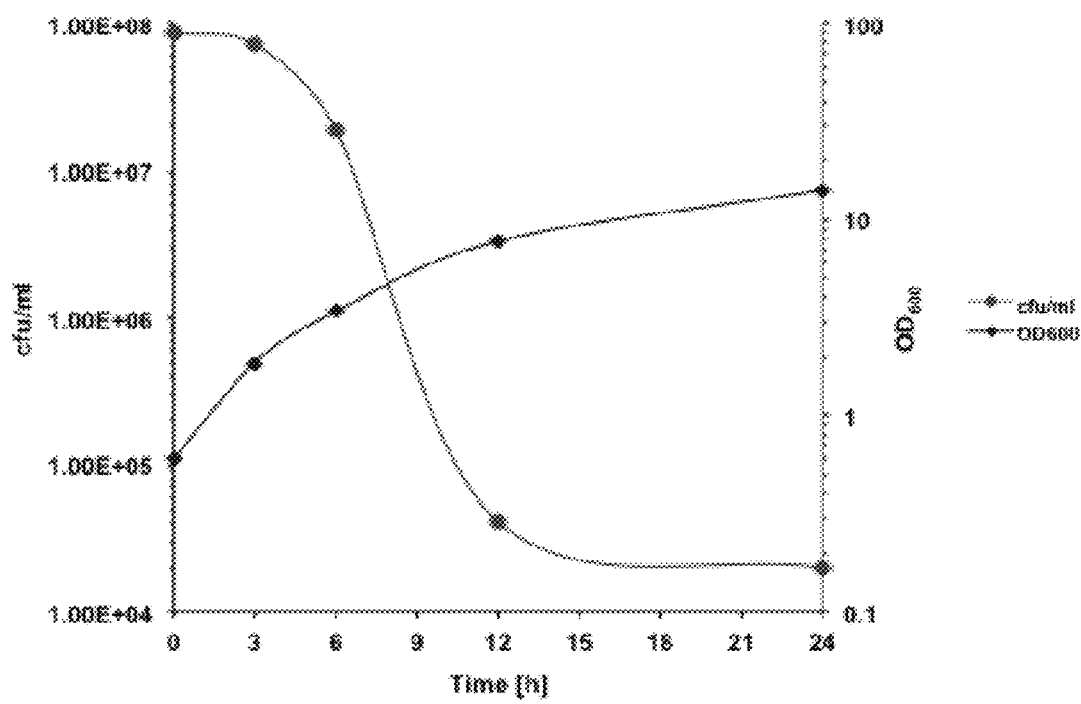
FIG. 47 The optical cell density ($OD_{600}$) vs. number of viable cells (cfu/ml) of strain KPM335/pJexpress404:51150 was evaluated during the period of induced ApoA1 expression.

Both the cytoplasmic and the periplasmic version of the human ApoA1 protein, as analyzed by 12% SDS-PAGE, were expressed in *E. coli* strains BW30270, KPM318, KPM318-9 (KPM334) and KPM318-10 (KPM335), but not in KPM318-19 (KPM336) (FIGS. 41-46). The apparent relative molecular mass of the 29-kDa band was in accordance with the calculated mass of the protein (29.4 kDa) fused to the C-terminal histidine tag. Strikingly, periplasmically expressed ApoA1 migrated as two bands with apparent relative molecular masses of 29 kDa and 31 kDa, the latter being consistent with the calculated mass of unprocessed ApoA1 of 31.4 kDa (FIGS. 44 and 45). It has been previously shown that ApoA1 is expressed in the cytoplasm of *E. coli* as a mixture of soluble and insoluble protein, which suggests that the supposed unprocessed form of ApoA1 constitutes the insoluble fraction of the protein that is not accessible to transport to its final destination in the periplasm and processing. However, we currently cannot rule out the possibility that the appearance of the slower migrating band is a result of sample preparation at 95° C. for 2 min prior to SDS-PAGE. In any case, the results indicate that the expression rate of ApoA1 in the KPM strains was at least as high as in BW30270, showing a steady level for at least 6 hr.

Figure 48:
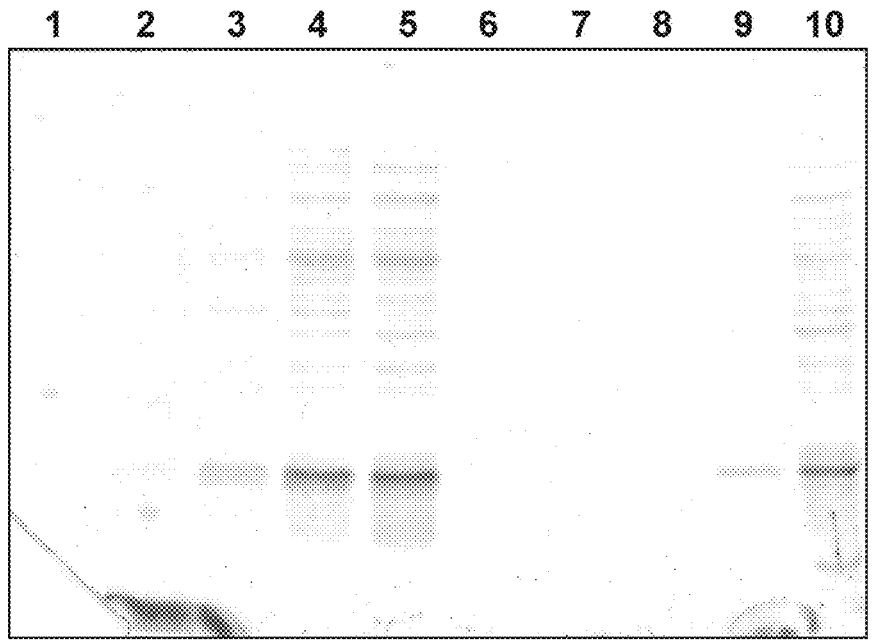
FIG. 48 SDS-PAGE analysis of culture media from strains BW30270/pJexpress404:51150 and KPM318/pJexpress404:51150. The culture media were obtained from uninduced cells and cells after induction times of 3 hr, 6 hr, 12 hr and 24 hr. The samples were resolved using 12% polyacrylamide gels and stained with Coomassie blue. For the amounts of samples loaded, see Tables 7-11.
Figure 49:
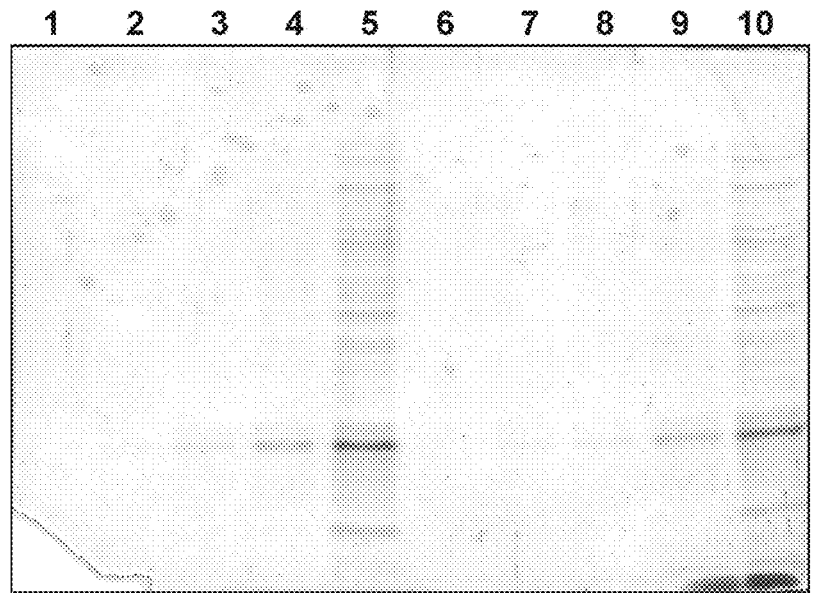
FIG. 49 SDS-PAGE analysis of culture media from strains KPM334/pJexpress404:51150 and KPM335/pJexpress404:51150. The culture media were obtained from uninduced cells and cells after induction times of 3 hr, 6 hr, 12 hr and 24 hr. The samples were resolved using 12% polyacrylamide gels and stained with Coomassie blue. For the amounts of samples loaded, see Tables 7-11.
Figure 50:
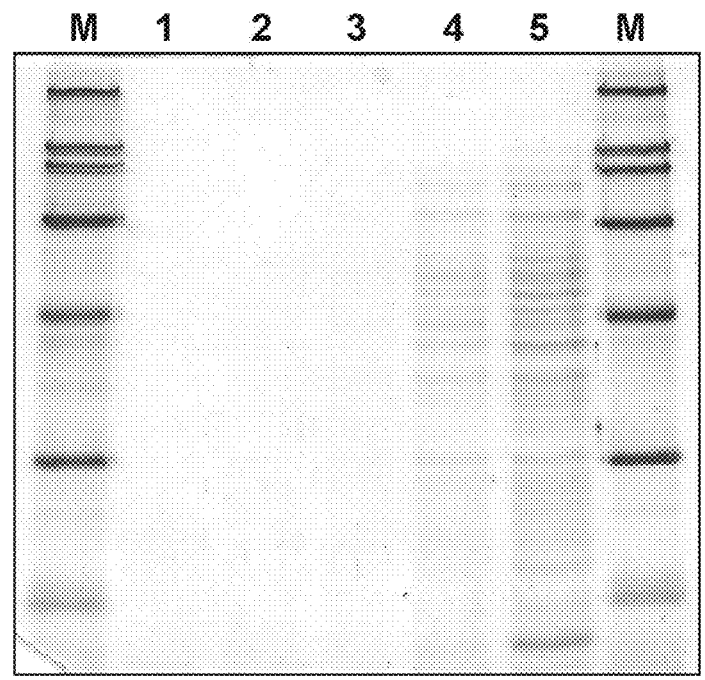
FIG. 50 SDS-PAGE analysis of culture media of KPM336/pJexpress404:51150. The culture media were obtained from uninduced cells and cells after induction times of 3 hr, 6 hr, 12 hr and 24 hr. The samples were resolved using 12% polyacrylamide gels and stained with Coomassie blue. For the amounts of samples loaded, see Tables 7-11. Molecular mass protein markers (Broad Range—Bio-Rad) were run in lanes M.
Figure 51:
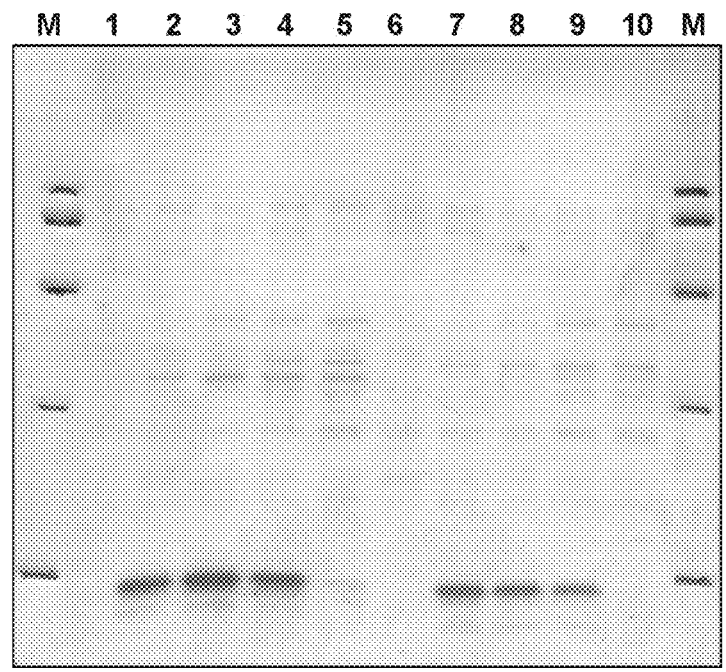
FIG. 51 Immunoblot analysis of protein extracts (3 μg each) of strains BW30270/pJexpress404:51149 and KPM318/pJexpress404:51149. The protein extracts were prepared from uninduced cells and cells after induction times of 3 hr, 6 hr, 12 hr and 24 hr. The samples were resolved using 10% polyacrylamide gels, followed by blotting and probing of the membranes with Penta-His antibody and alkaline phosphatase-conjugated goat anti-mouse IgG (H+L) antibodies, and developed in the presence of NBT and BCIP substrate. Molecular mass protein markers (Broad Range—Bio-Rad) were run in lanes M and labelled after blotting.
Figure 52:
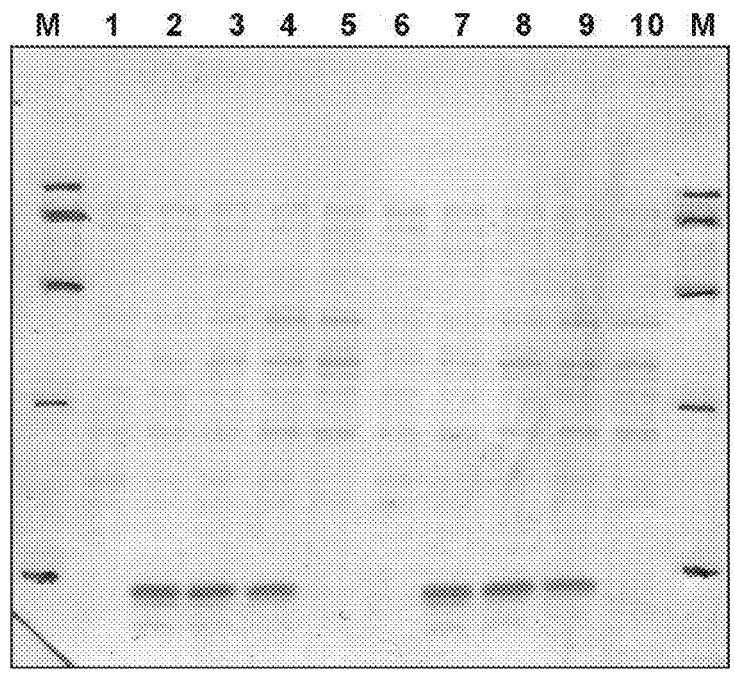
FIG. 52 Immunoblot analysis of protein extracts (3 μg each) of strains KPM334/pJexpress404:51149 and KPM335/pJexpress404:51149. The protein extracts were prepared from uninduced cells and cells after induction times of 3 hr, 6 hr, 12 hr and 24 hr. The samples were resolved using 10% polyacrylamide gels, followed by blotting and probing of the membranes with Penta-His antibody and alkaline phosphatase-conjugated goat anti-mouse IgG (H+L) antibodies, and developed in the presence of NBT and BCIP substrate. Molecular mass protein markers (Broad Range—Bio-Rad) were run in lanes M and labelled after blotting.
Figure 53:
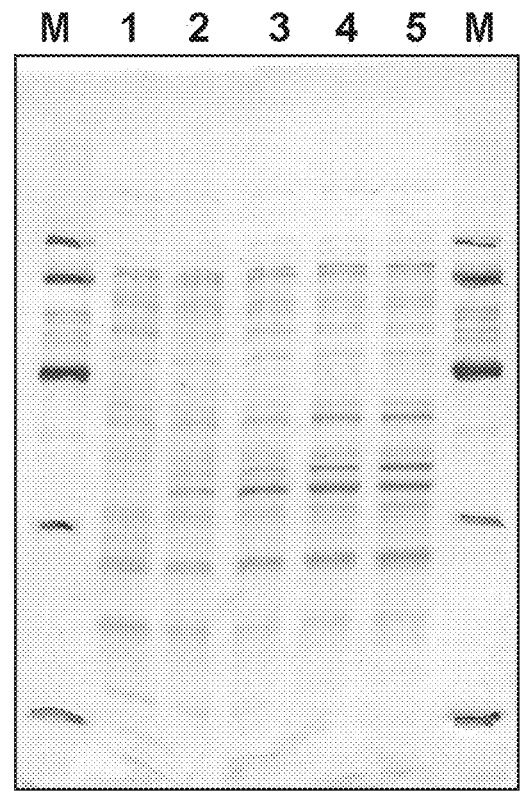
FIG. 53 Immunoblot analysis of protein extracts (3 μg each) of KPM336/pJexpress404:51149. The protein extracts were prepared from uninduced cells and cells after induction times of 3 hr, 6 hr, 12 hr and 24 hr. The samples were resolved using 10% polyacrylamide gels, followed by blotting and probing of the membranes with Penta-His antibody and alkaline phosphatase-conjugated goat anti-mouse IgG (H+L) antibodies, and developed in the presence of NBT and BCIP substrate. Molecular mass protein markers (Broad Range—Bio-Rad) were run in lanes M and labelled after blotting.
Figure 54:
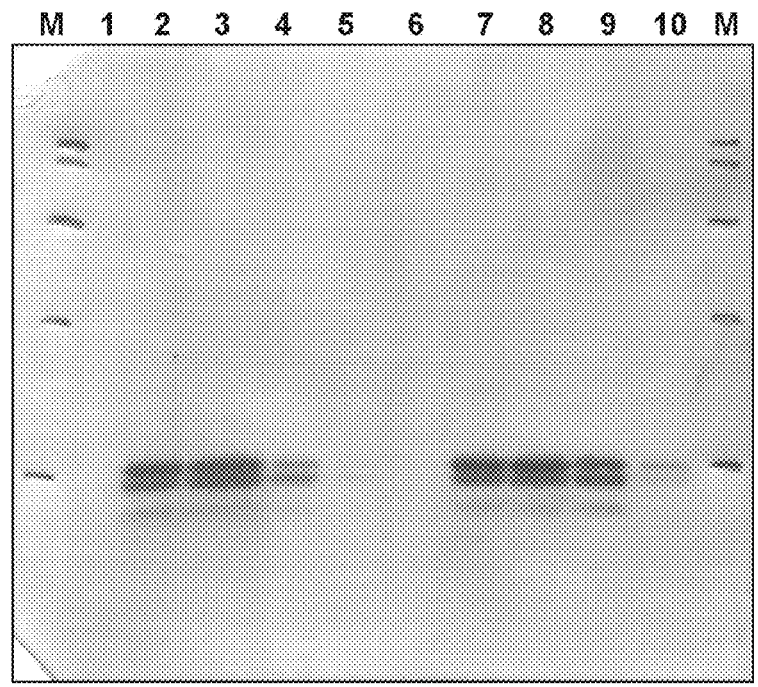
FIG. 54 Immunoblot analysis of protein extracts (3 μg each) of strains BW30270/pJexpress404:51150 and KPM318/pJexpress404:51150. The protein extracts were prepared from uninduced cells and cells after induction times of 3 hr, 6 hr, 12 hr and 24 hr. The samples were resolved using 12% polyacrylamide gels, followed by blotting and probing of the membranes with Penta-His antibody and alkaline phosphatase-conjugated goat anti-mouse IgG (H+L) antibodies, and developed in the presence of NBT and BCIP substrate. Molecular mass protein markers (Broad Range—Bio-Rad) were run in lanes M and labelled after blotting.
Figure 55:
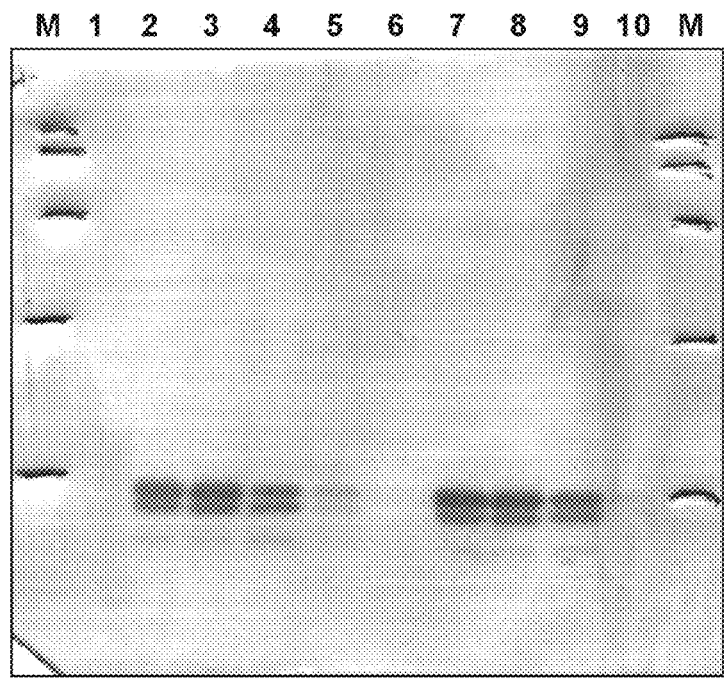
FIG. 55 Immunoblot analysis of protein extracts (3 μg each) of strains KPM334/pJexpress404:51150 and KPM335/pJexpress404:51150. The protein extracts were prepared from uninduced cells and cells after induction times of 3 hr, 6 hr, 12 hr and 24 hr. The samples were resolved using 12% polyacrylamide gels, followed by blotting and probing of the membranes with Penta-His antibody and alkaline phosphatase-conjugated goat anti-mouse IgG (H+L) antibodies, and developed in the presence of NBT and BCIP substrate. Molecular mass protein markers (Broad Range—Bio-Rad) were run in lanes M and labelled after blotting.
Figure 56:
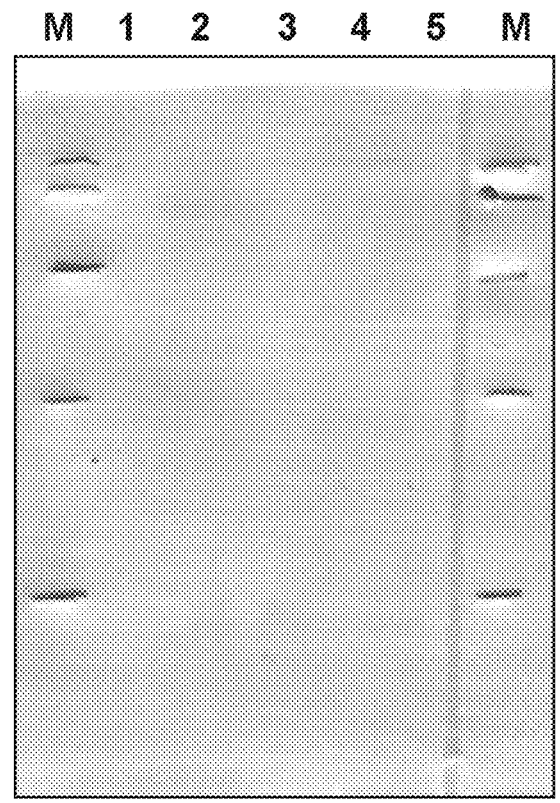
FIG. 56 Immunoblot analysis of protein extracts (3 μg each) of KPM336/pJexpress404:51150. The protein extracts were prepared from uninduced cells and cells after induction times of 3 hr, 6 hr, 12 hr and 24 h. The samples were resolved using 12% polyacrylamide gels, followed by blotting and probing of the membranes with Penta-His antibody and alkaline phosphatase-conjugated goat anti-mouse IgG (H+L) antibodies, and developed in the presence of NBT and BCIP substrate. Molecular mass protein markers (Broad Range—Bio-Rad) were run in lanes M and labelled after blotting.
Figure 57:
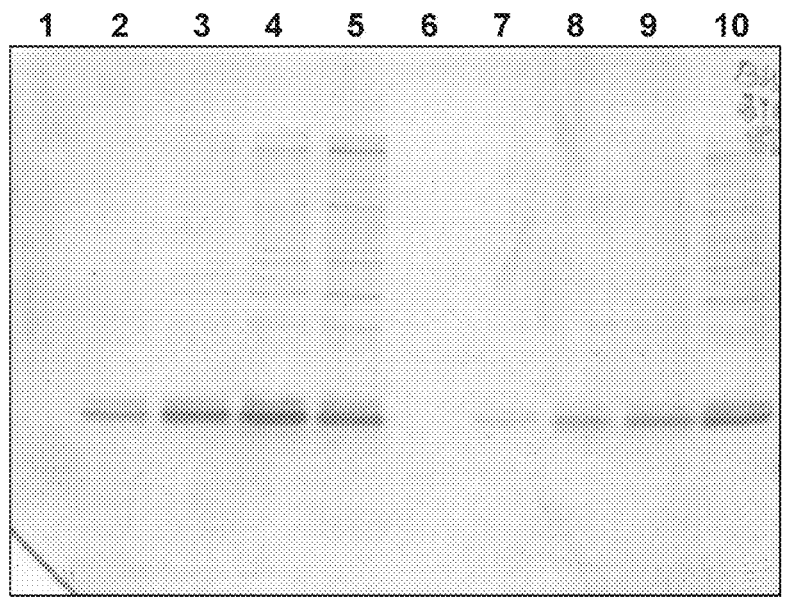
FIG. 57 Immunoblot analysis of culture media from strains BW30270/pJexpress404:51150 and KPM318/pJexpress404:51150. The culture media were obtained from uninduced cells and cells after induction times of 3 hr, 6 hr, 12 hr and 24 hr. The samples were resolved using 12% polyacrylamide gels, followed by blotting and probing of the membranes with Penta-His antibody and alkaline phosphatase-conjugated goat anti-mouse IgG (H+L) antibodies, and developed overnight in the presence of NBT and BCIP substrate. For the amounts of samples loaded, see Tables 7-11.
Figure 58:
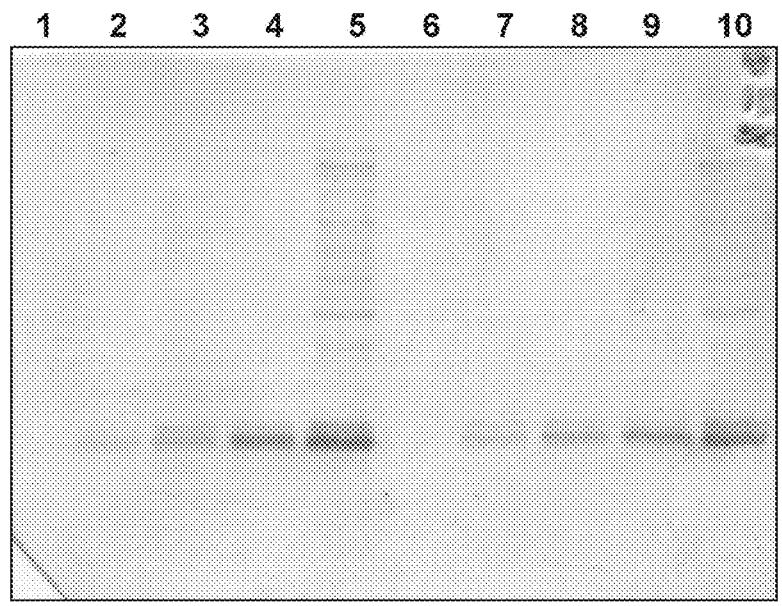
FIG. 58 Immunoblot analysis of culture media from strains KPM334/pJexpress404:51150 and KPM335/pJexpress404:51150. The culture media were obtained from uninduced cells and cells after induction times of 3 hr, 6 hr, 12 hr and 24 hr. The samples were resolved using 12% polyacrylamide gels, followed by blotting and probing of the membranes with Penta-His antibody and alkaline phosphatase-conjugated goat anti-mouse IgG (H+L) antibodies, and developed overnight in the presence of NBT and BCIP substrate. For the amounts of samples loaded, see Tables 7-11.
Figure 59:
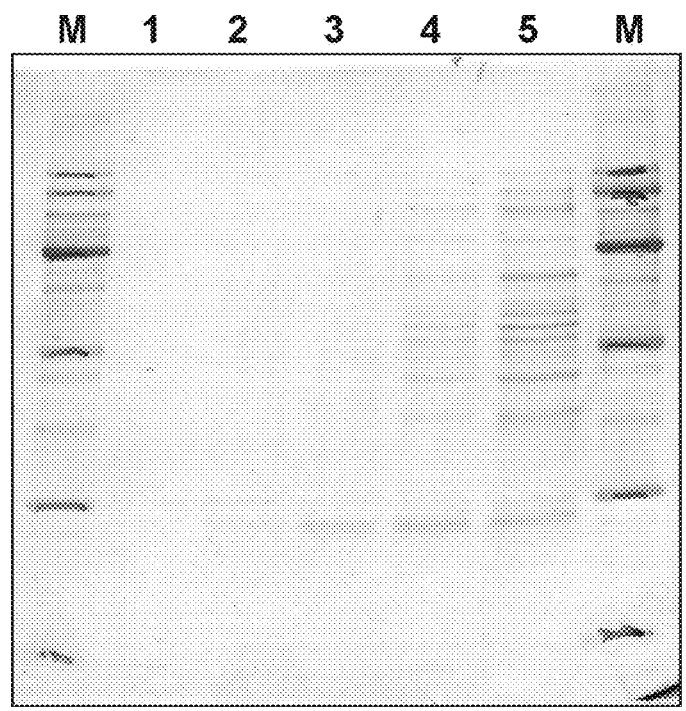
FIG. 59 Immunoblot analysis of culture media of KPM336/pJexpress404:51150. The culture media were obtained from uninduced cells and cells after induction times of 3 hr, 6 hr, 12 hr and 24 hr. The samples were resolved using 12% polyacrylamide gels, followed by blotting and probing of the membranes with Penta-His antibody and alkaline phosphatase-conjugated goat anti-mouse IgG (H+L) antibodies, and developed overnight in the presence of NBT and BCIP substrate. For the amounts of samples loaded, see Tables 7-11.

In contrast to the experiments performed with MalE-LacZα, the volume of the culture media for SDS-PAGE analyses was adjusted in relation to the optical density ($OD_{600}$) of pJexpress404:51150-carrying cells so that the amount of the culture supernatant loaded onto the polyacrylamide gel came from one and the same $OD_{600}$ value (Tables 8-12). Remarkably enough and as presented for strain KPM318-10 (KPM335)/pJexpress404:51150 in FIG. 50, the optical cell densities of all temperature-resistant strains increased while the number of viable cells decreased over the entire period of IPTG induction (Tables 3-7). As shown in FIGS. 48-50, the strains carrying the pJexpress404:51150 µlasmid were not capable of secreting ApoA1 into the culture medium. The weakly Coomassie-stained bands rather resembled the protein banding pattern of the cell extracts and, thus, most likely originated from cell lysis. By using immunoblots with a Penta-His antibody (QIAGEN), we could corroborate all findings of SDS-PAGE analyses (FIGS. 51-59). Taken together, our data suggests that the 42° C.-resistant KPM318 derivatives KPM318-9 (KPM334) and KPM318-10 (KPM335) are suitable hosts for protein expression. Optimization of the conditions for bacterial growth, induction and sample preparation should further improve the expression rate and yield of the proteins of interest.

The DNA transformation ability of the cells was assessed. For preparation of electrocompetent cells, the cultures were grown to mid-exponential growth phase ($OD_{600}$=0.5-0.7) at 37° C. with vigorous shaking (220 rpm). The cells were subsequently washed three times with ice-cold water and twice with ice-cold 10% glycerol. Finally, the cell sediments were resuspended in a small volume of ice-cold 10% glycerol, and 50-µl aliquots were prepared for storage at −80° C. First, we examined the influence of restored K-12 core oligosaccharide biosynthesis on the transformation of KPM318 with pMAL-c2. Strain BW30270 was grown in LB medium as a control, whereas KPM318 was cultivated in LB medium and LB medium containing A5P/G6P. The cells were harvested for preparation of electrocompetent cells when strains BW30270, KPM318 (LB) and KPM318 (LB A5P/G6P) reached an optical density ($OD_{600}$) of 0.621, 0.613, and 0.519, respectively. In order to use one and the same number of electrocompetent cells for transformation, we determined the colony forming units per milliliter of the competent cells of each strain (Table 13).

Figure 32:
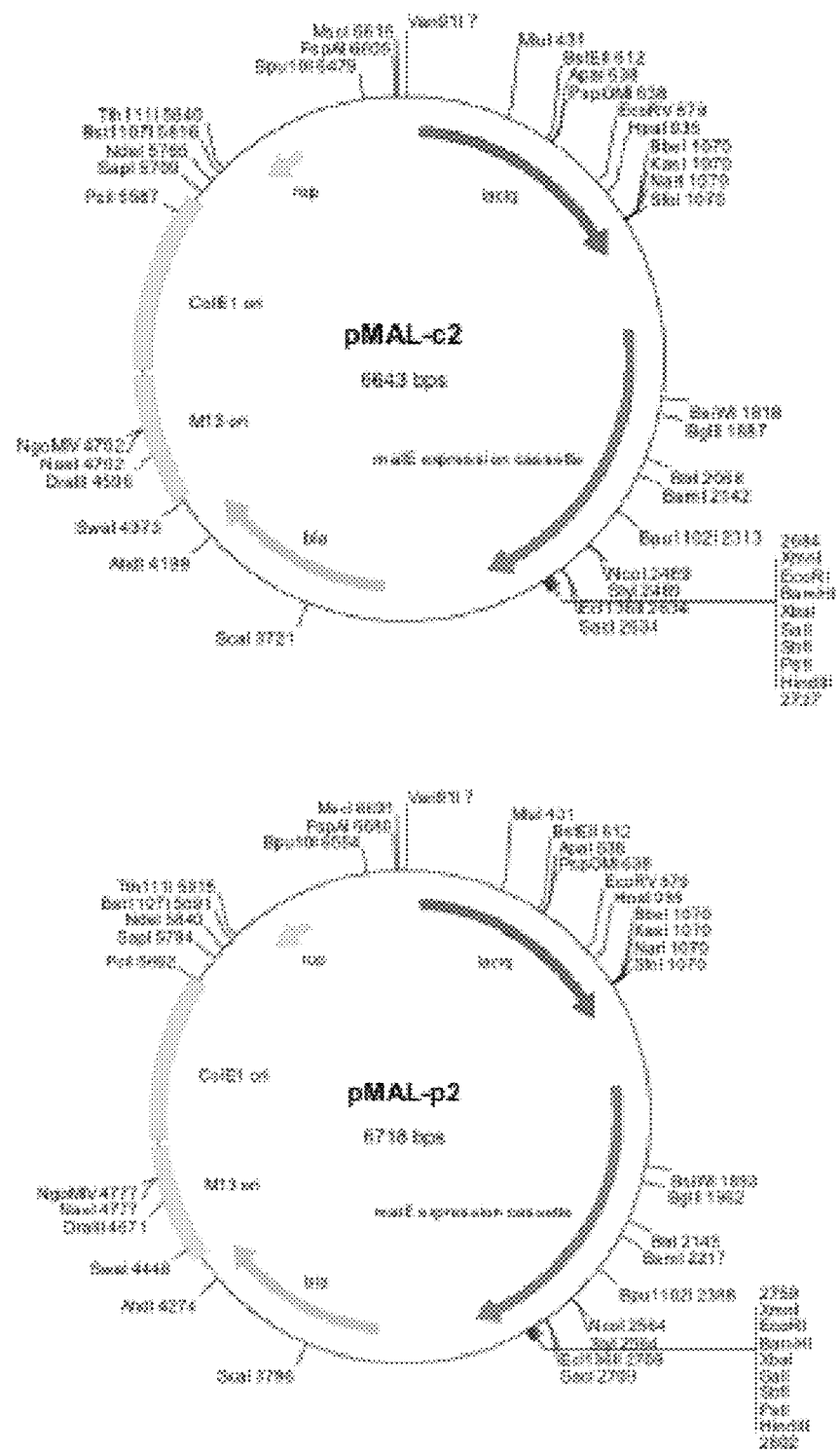
FIG. 32 Maps of plasmids pMAL-c2 and pMAL-p2 for cytoplasmic (upper panel) and periplasmic MalE-LacZα expression (lower panel).
Figure 37:
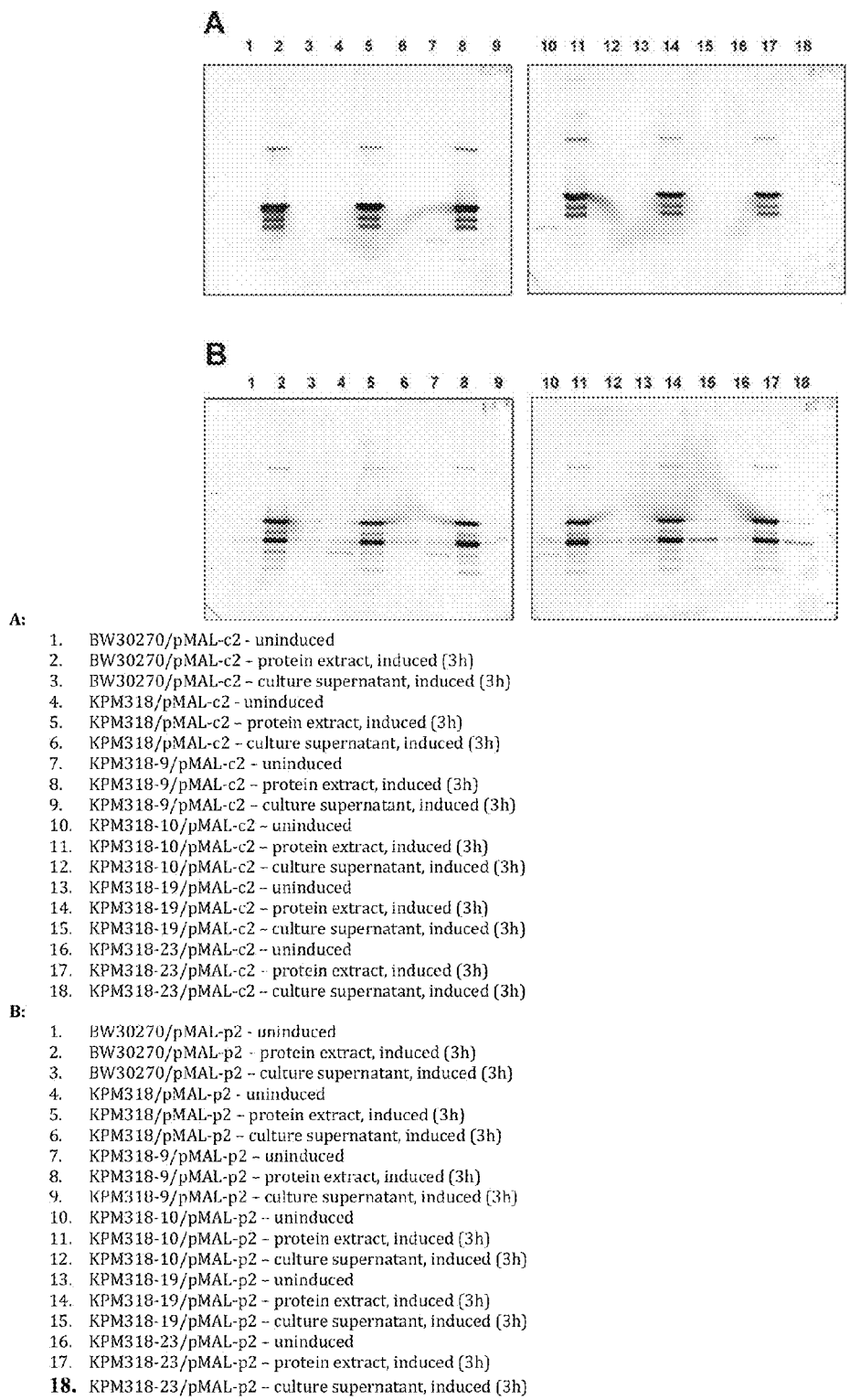
FIG. 37 Immunoblot analysis of protein extracts (8 μg each) and culture media (2.5 μl each). The protein extracts were prepared from uninduced cells and cells after an induction time of 3 hr. The culture media were from cells grown under conditions of IPTG induction for 3 hr. The samples were resolved using 10% polyacrylamide gels, followed by blotting and probing of the membranes with anti-MalE and alkaline phosphatase-conjugated goat anti-mouse IgG (H+L) antibodies, and developed in the presence of NBT and BCIP substrate.
Figure 38:
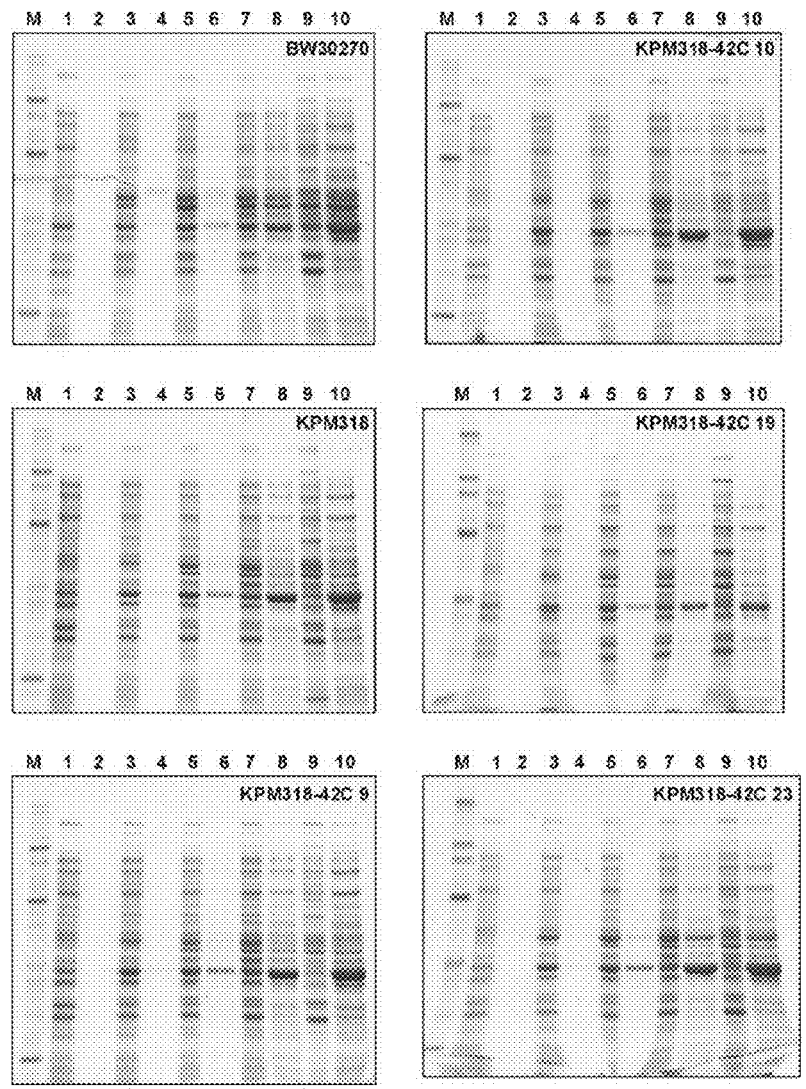
FIG. 38 SDS-PAGE analysis of protein extracts (6 μg each) and culture media (8 μl each) of pMAL-p2 strains. The protein extracts were prepared from uninduced cells and cells after induction times of 3 hr, 6 hr, 12 hr and 24 hr. The culture media were from cells after 3 hr, 6 hr, 12 hr and 24 hr of induction. The samples were resolved using 10% polyacrylamide gels and stained with Coomassie blue. Molecular mass protein markers (Broad Range—Bio-Rad) were run in lanes M.
Figure 39:
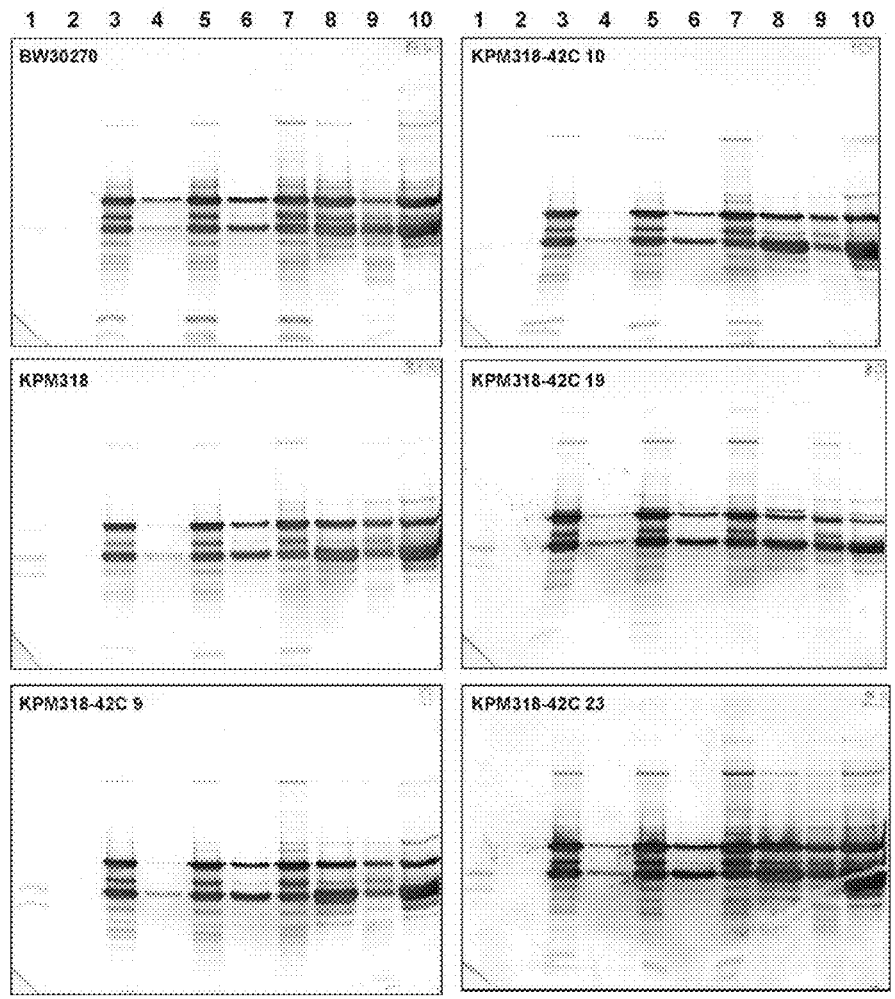
FIG. 39 Immunoblot analysis of protein extracts (6 μg each) and culture media (10 μl each) of pMAL-p2 strains. The protein extracts were prepared from uninduced cells and cells after induction times of 3 h, 6 h, 12 h and 24 h. The culture media were from cells after 3 h, 6 h, 12 h and 24 h of induction. The samples were resolved using 10% polyacrylamide gels, followed by blotting and probing of the membranes with anti-MalE and alkaline phosphatase-conjugated goat anti-mouse IgG (H+L) antibodies, and developed in the presence of NBT and BCIP substrate.

The electrocompetent cells of KPM318 (LB) and KPM318 (LB A5P/G6P) were diluted to $7.3 \times 10^8$ cfu/ml with ice-cold 10% glycerol ($3.65 \times 10^7$ cfu/50 μl) and transformed each with 25 ng of plasmid pMAL-c2 (FIG. 32). The transformation mixtures were serially diluted, plated onto LB agar plates containing 100 μg/ml ampicillin and incubated at 37° C. The results in Table 14 demonstrate that strains BW30270, KPM318 (LB) and KPM318 (LB A5P/G6P) were transformed with similar efficiencies. The data further shows that KPM318 predominantly expressing lipid $IV_A$ in the outer membrane when grown in LB-only medium (FIG. 11) was not transformed with higher efficiency than BW30270 or KPM318 under conditions of restored core oligosaccharide biosynthesis.

Figure 60:
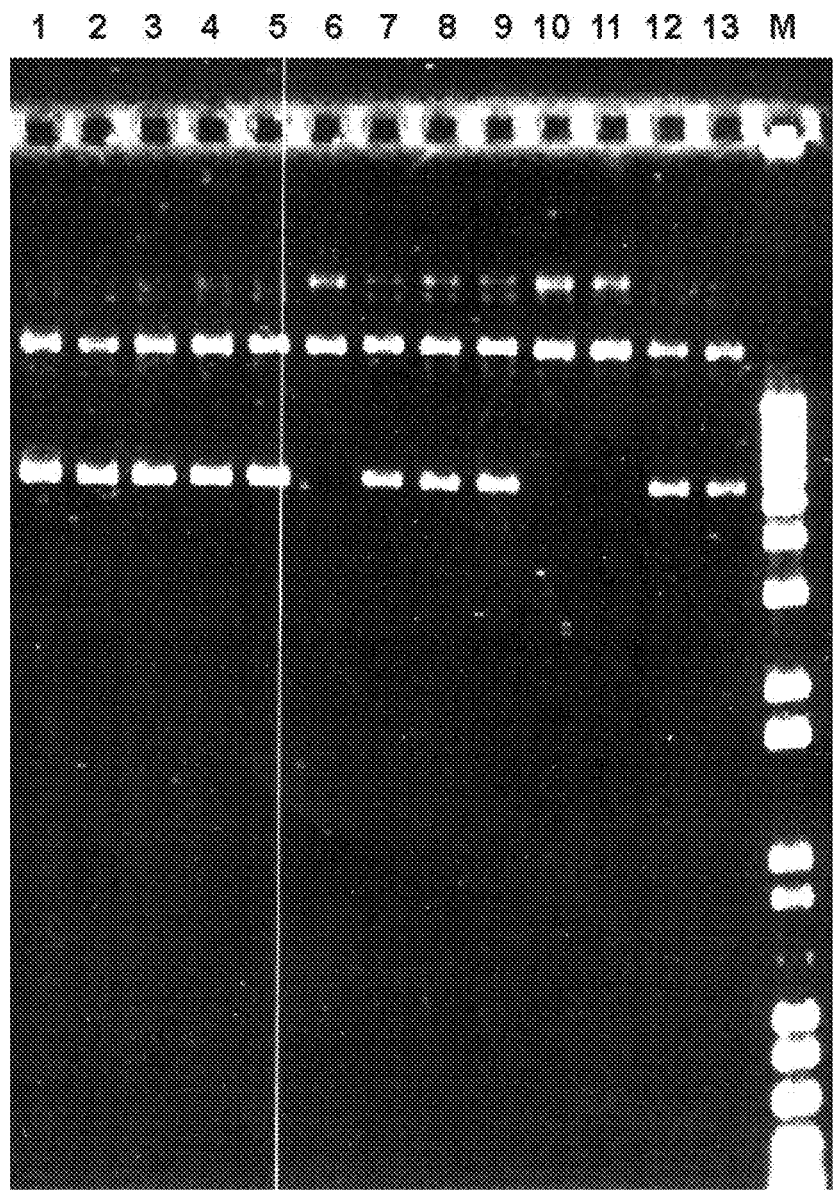
FIG. 60 Agarose gel electrophoresis of pMAL-c2 μlasmids isolated from four randomly selected transformants of E. coli strains BW30270/pMAL-c2, KPM318 (LB)/pMAL-c2, and KPM318 (LB A5P/G6P)/pMAL-c2. The samples were subjected to electrophoresis on a 0.8% agarose gel in TBE buffer. Lane 1, pMAL-c2 control; lane 2, BW30270/pMAL-c2 (1); lane 3, BW30270/pMAL-c2 (2); lane 4, BW30270/pMAL-c2 (3); lane 5, BW30270/pMAL-c2 (4); lane 6, KPM318 (LB)/pMAL-c2 (1); lane 7, KPM318 (LB)/pMAL-c2 (2); lane 8, KPM318 (LB)/pMAL-c2 (3); lane 9, KPM318 (LB)/pMAL-c2 (4); lane 10, KPM318 (LB A5P/G6P)/pMAL-c2 (1); lane 11, KPM318 (LB A5P/G6P)/pMAL-c2 (2); lane 12, KPM318 (LB A5P/G6P)/pMAL-c2 (3); lane 13, KPM318 (LB A5P/G6P)/pMAL-c2 (4); lane M, 1-kb Plus DNA Ladder (Invitrogen).

The plasmid pMAL-c2 from four randomly selected transformants of each strain was isolated from 5-ml overnight cultures grown in LB medium containing 100 μg/ml ampicillin at 37° C. and 200 rpm. The plasmids were isolated using the Wizard Plus Minipreps DNA Purification System (Promega). Samples of 1 μl were subsequently run on a 0.8% agarose gel in TBE buffer (FIG. 60). The electrophoresis results indicated that the yield of plasmid pMAL-c2 was apparently almost identical for *E. coli* strains BW30270/pMAL-c2, KPM318 (LB)/pMAL-c2, and KPM318 (LB A5P/G6P)/pMAL-c2.

As a next step, the 42° C.-resistant KPM318 derivatives KPM318-9 (KPM334), KPM318-10 (KPM335), KPM318-19 (KPM336) and KPM318-23 (KPM337) were transformed each with plasmids pMAL-c2 and pMAL-p2 (FIG. 32). The cells were grown in SB medium at 37° C. and harvested for preparation of electrocompetent cells when KPM318-9 (KPM334), KPM318-10 (KPM335), KPM318-19 (KPM336) and KPM318-23 (KPM337) reached an optical density ($OD_{600}$) of 0.618, 0.596, 0.491, and 0.702, respectively. The electrocompetent cells were transformed each with 25 ng pMAL-c2 and 25 ng pMAL-p2. Serial dilutions of the transformation mixtures were then plated onto LB agar plates with 100 μg/ml ampicillin and incubated at 37° C. The transformation efficiencies for the 42° C.-resistant KPM318 strains are summarized in Table 15. While strains KPM318-9 (KPM334), KPM318-10 (KPM335) and KPM318-19 (KPM336) were transformed with high efficiency, the capability of KPM318-23 (KPM337) to uptake plasmids pMAL-c2 and pMAL-p2 was only marginal. In fact, the latter result was consistent with the failure to transform KPM318-23 (KPM337) with plasmids pJexpress404:51149 and pJexpress404:51150.

Figure 61:
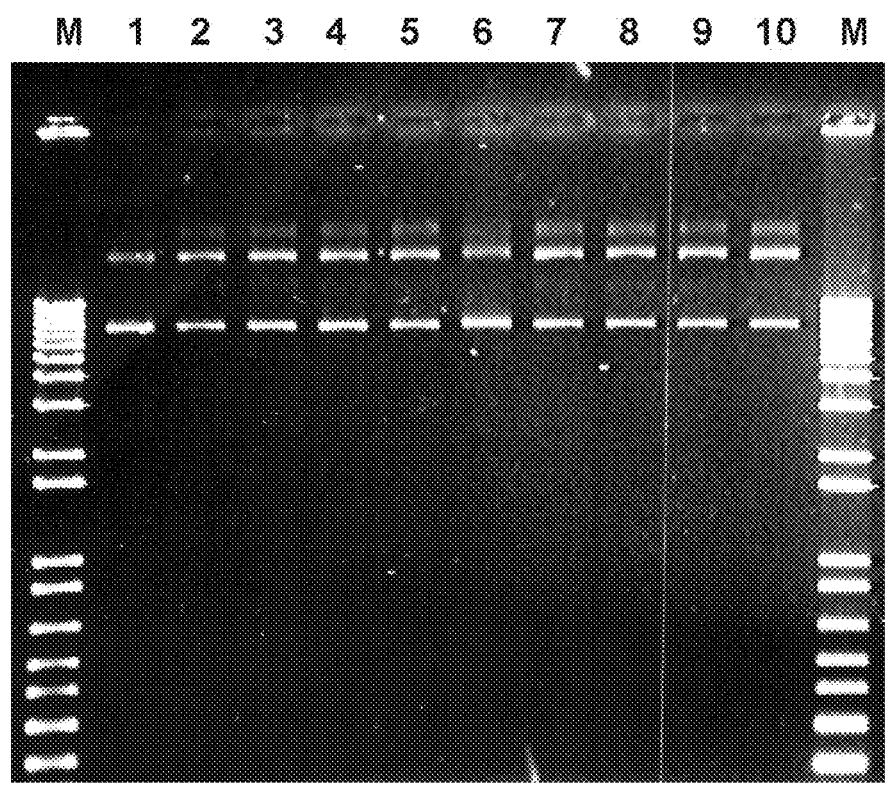
FIG. 61 Agarose gel electrophoresis of pMAL-c2 and pMAL-p2 plasmids isolated from two randomly selected transformants of E. coli strains KPM334/pMAL-c2, KPM334/pMAL-p2, KPM335/pMAL-c2, and KPM335/pMAL-p2. Lane 1, pMAL-c2 control; lane 2, KPM334/pMAL-c2 (1); lane 3, KPM334/pMAL-c2 (2); lane 4, KPM335/pMAL-c2 (1); lane 5, KPM335/pMAL-c2 (2); lane 6, pMAL-p2 control; lane 7, KPM334/pMAL-p2 (1); lane 8, KPM334/pMAL-p2 (2); lane 9, KPM335/pMAL-p2 (1); lane 10, KPM335/pMAL-p2 (2); lanes M, 1-kb Plus DNA Ladder (Invitrogen).
Figure 62:
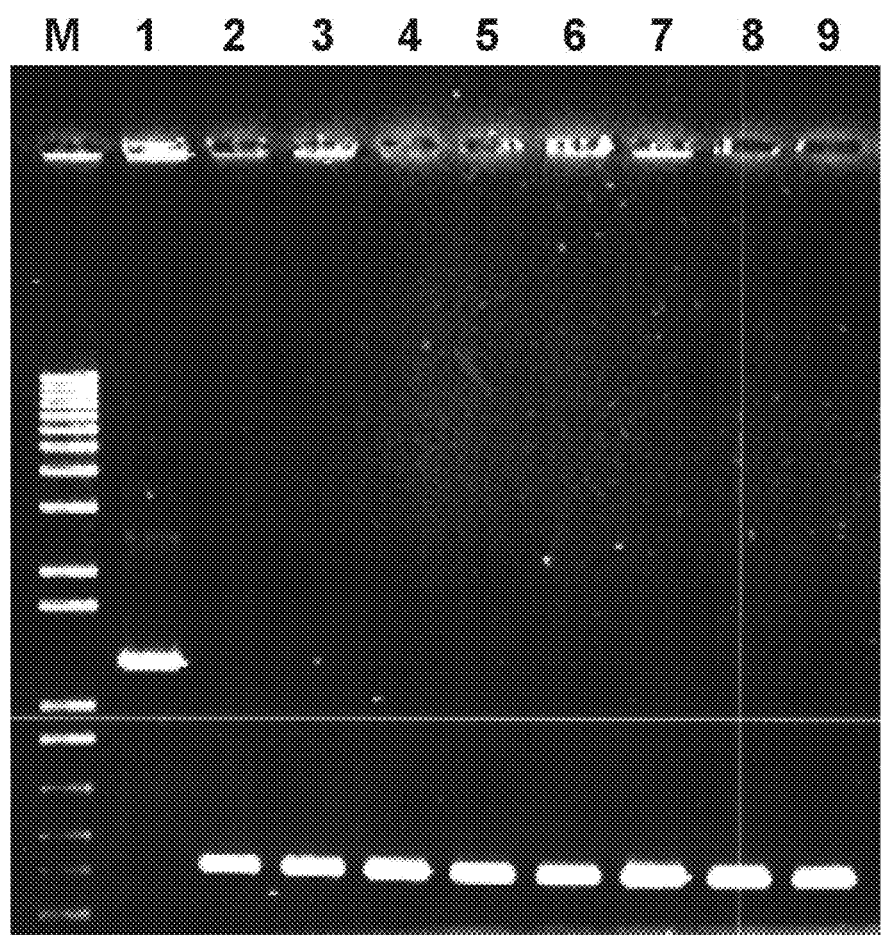
FIG. 62 Agarose gel electrophoresis of PCR products obtained by using the primer pair 5EClpxPctrl/3EClpxPctrl to distinguish between the presence of the lpxP wild-type gene and the ΔlpxP knockout mutation in KPM strains. The biomasses of a potential BW30270 (F'121 Tn10) strain (lane 1) and eight tetracycline-resistant KPM318 (F'121 Tn10) transconjugants (lanes 2-9) were used as templates. The 1-kb Plus DNA Ladder (Invitrogen) is shown in lane M.

The plasmids pMAL-c2 and pMAL-p2 were isolated from 5-ml overnight cultures of two randomly selected transformants of KPM318-9 (KPM334)/pMAL-c2, KPM318-9 (KPM334)/pMAL-p2, KPM318-10 (KPM335)/pMAL-c2, and KPM318-10 (KPM335)/pMAL-p2, using the Wizard Plus Minipreps DNA Purification System according to the manufacturer's recommendations (Promega). The samples (1 μl each) were run on a 0.8% agarose gel in TBE buffer (FIG. 61). Finally, the yields of the isolated plasmids were determined for those strains that were subsequently used for the protein expression studies described above (Table 16). Taken together, both the high transformation efficiency and the acceptable yield of plasmid DNA obtained from a standard miniprep culture suggests that KPM318-9 (KPM334) and KPM318-10 (KPM335) are suitable "base strains" for the development of plasmid DNA production strains.

Figure 65:
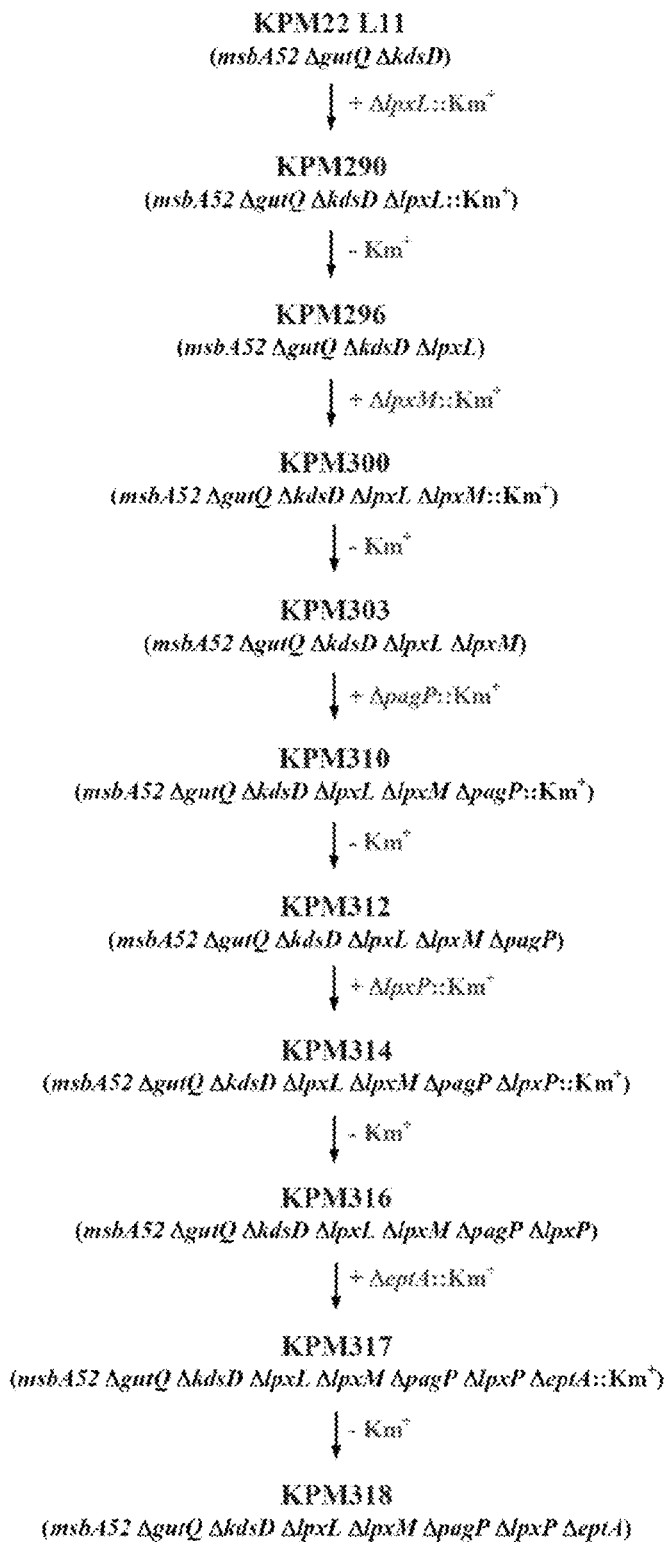
FIG. 65-67 show the construction path for each E. coli strain.
Figure 66:
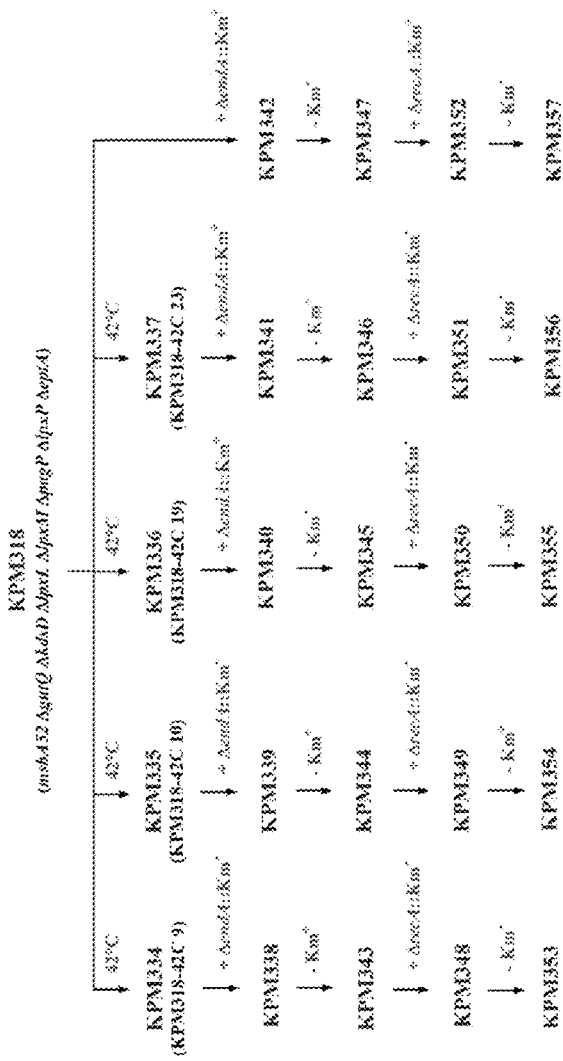
Figure 67:
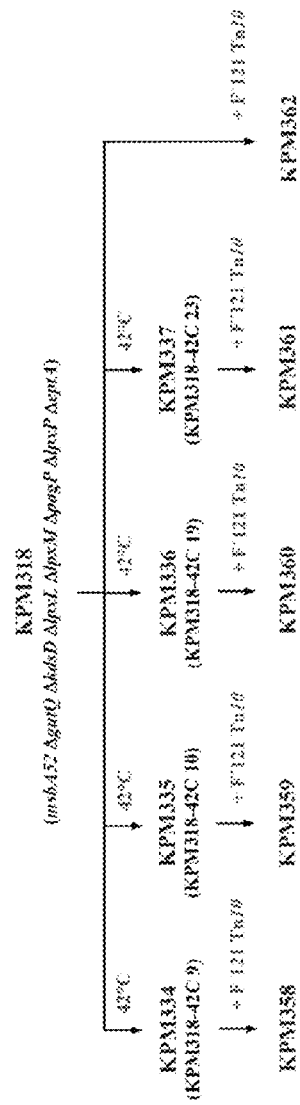

To develop a KPM "base strain" dedicated to screening proteins derived from phage display libraries, the strain should have an F' plasmid to permit infection with M13 phage. We have used the *E. coli* JC19022 (F'121 Tn10) as a donor strain to transfer the F'121 Tn10 μlasmid to BW30270, KPM318, KPM318-9 (KPM334), KPM318-10 (KPM335), KPM318-19 (KPM336), and KPM318-23 (KPM337) by a tube mating protocol. The cultures were grown overnight in 5 ml of medium at 37° C. with vigorous shaking (220 rpm). LB medium containing 10 μg/ml tetracycline was used for JC19022 (F'121 Tn10), LB medium for BW30270, and LB medium supplemented with A5P/G6P was used for KPM318 and its temperature-resistant derivatives. The following dilutions of the overnight cultures were set-up using the same media as used for overnight growth:
Donor: 25 μl 5 ml
50 μl 5 ml
100 μl 5 ml
200 μl 5 ml
Recipients: 25 μl 5 ml
50 μl 5 ml
100 μl 5 ml
200 μl 5 ml The samples were vigorously (220 rpm) shaken at 37° C. for approximately 2 to 3 hr. The optical density ($OD_{600}$) of the suspensions (1 ml) was recorded. The optimal $OD_{600}$ range is 0.08 to 0.2; the dilution with the $OD_{600}$ closest to 0.1 should be used if there are options available (this is true for the donor and recipient cultures). In order to remove the tetracycline from the medium of the donor strain, the culture should be centrifuged, and the cell pellet should be resuspended in 4 ml LB medium. A 1:1 ratio of donor:recipient is used for the transfer. The dilution of the donor dilution is determined and multiplied by 500. This value is divided by the $OD_{600}$ of the recipient to obtain the amount of the recipient in μl to add to 500 μl of the donor. The donor culture (500 μl) is incubated with the appropriate amounts of the recipient cultures (Tables 17 and 18). The mating cultures are incubated at 37° C. for 2 hr without agitation. The cultures are then incubated for another 2 hr at 37° C. and agitated at 220 rpm. The samples are vigorously vortexed to disrupt the mating pairs. Dilutions at $10^{-1}$, $10^{-2}$, $10^{-3}$, and $10^{-4}$ in PBS (pre-warmed to room temperature) for each mating were prepared, and 100 μl of each undiluted and diluted mating culture was added to M9 agar plates containing 1 μg/ml thiamine and 10 μg/ml tetracycline. The cultures were incubated at 37° C. The potential transconjugants were streaked onto M9 agar plates containing 1 μg/ml thiamine and 10 μg/ml tetracycline and incubated at 37° C. The tube mating experiments yielded a number of potential transconjugants for all recipient strains. A subset of potential transconjugants was subsequently examined by PCR for the presence of the ΔlpxP knockout mutation to distinguish between false positive clones and tetracycline-resistant KPM strains. As shown in FIG. 65, all tested tetracycline-resistant KPM318 transconjugants contained the ΔlpxP knockout mutation, which indicated the successful transfer of the F'121 Tn10 plasmid to the KPM strain. By using the lpxP PCR, we also could identify several potential F'121

Tn10 transconjugants of KPM318-9 (KPM334), KPM318-10 (KPM335), KPM318-19 (KPM336) and KPM318-23 (KPM337), which contained the required ΔlpxP knockout mutation.

To provide evidence for the presence of the F'121 Tn10 plasmid in KPM318 and its 42° C.-resistant derivatives, as well as to show that the transconjugants are susceptible to M13 infection, the M13KO7 helper phage was used to infect four randomly selected transconjugants of each strain. As M13KO7 contains the origin of replication from P15A and the kanamycin resistance gene from Tn903 both inserted within the M13 origin of replication, the development of kanamycin-resistant clones following infection is an indication for the susceptibility of a given strain to M13KO7. Overnight cultures of E. coli JC19022 (F'121 Tn10) and BW30270 (F'121 Tn10) in LB medium containing 10 µg/ml tetracycline, and KPM318 (F'121 Tn10) and 42° C.-resistant KPM318 (F'121 Tn10) derivatives in LB medium with 10 µg/ml tetracycline and A5P/G6P were set-up. The BW30270 and KPM318 strains were grown in LB medium and LB medium supplemented with A5P/G6P, respectively, as controls. The cultures were vigorously agitated (220 rpm) at 37° C. The following strains and potential transconjugants were grown:

1. BW30270 (control)
2. KPM318 (control)
3. JC19022 (F'121 Tn10) (control)
4. BW30270 (F'121 Tn10)-1
5. BW30270 (F'121 Tn10)-2
6. BW30270 (F'121 Tn10)-3
7. BW30270 (F'121 Tn10)-4
8. KPM318 (F'121 Tn10)-4
9. KPM318 (F'121 Tn10)-6
10. KPM318 (F'121 Tn10)-7
11. KPM318 (F'121 Tn10)-8
12. KPM318-9 (KPM334) (F'121 Tn10)-1
13. KPM318-9 (KPM334) (F'121 Tn10)-2
14. KPM318-9 (KPM334) (F'121 Tn10)-3
15. KPM318-9 KPM334) (F'121 Tn10)-4
16. KPM318-10 (KPM335) (F'121 Tn10)-1
17. KPM318-10 (KPM335) (F'121 Tn10)-3
18. KPM318-10 (KPM335) (F'121 Tn10)-4
19. KPM318-10 (KPM335) (F'121 Tn10)-5
20. KPM318-19 (KPM336) (F'121 Tn10)-3
21. KPM318-19 (KPM336) (F'121 Tn10)-4
22. KPM318-19 (KPM336) (F'121 Tn10)-5
23. KPM318-19 (KPM336) (F'121 Tn10)-6
24. KPM318-23 (KPM337) (F'121 Tn10)-1
25. KPM318-23 (KPM337) (F'121 Tn10)-2
26. KPM318-23 (KPM337) (F'121 Tn10)-3
27. KPM318-23 (KPM337) (F'121 Tn10)-5

The overnight cultures of BW30270 and JC19022 (F'121 Tn10) were grown in 3 ml LB medium (1:100), and KPM318 and the potential transconjugants were cultured in 3 ml of LB medium supplemented with A5P/G6P (1:50). The cultures were grown to an early exponential growth phase at 37° C. with vigorous shaking (280 rpm). A 1 ml aliquot was removed for determination of the $OD_{600}$ of the suspension (Table 19)

The M13KO7 infection experiments resulted in kanamycin resistant colonies for all potential transconjugants of KPM318 and its temperature-resistant derivatives (Table 20). Although the number of kanamycin-resistant colonies significantly varied among the strains, the results suggest that: (i) the conjugative transfer of plasmid F'121 Tn10 to the KPM strains was successful, and (ii) the strains became susceptible to M13 infection. This should provide a fundamental basis for the generation of phage display libraries in temperature-resistant KPM318 derivatives.

Figure 63:
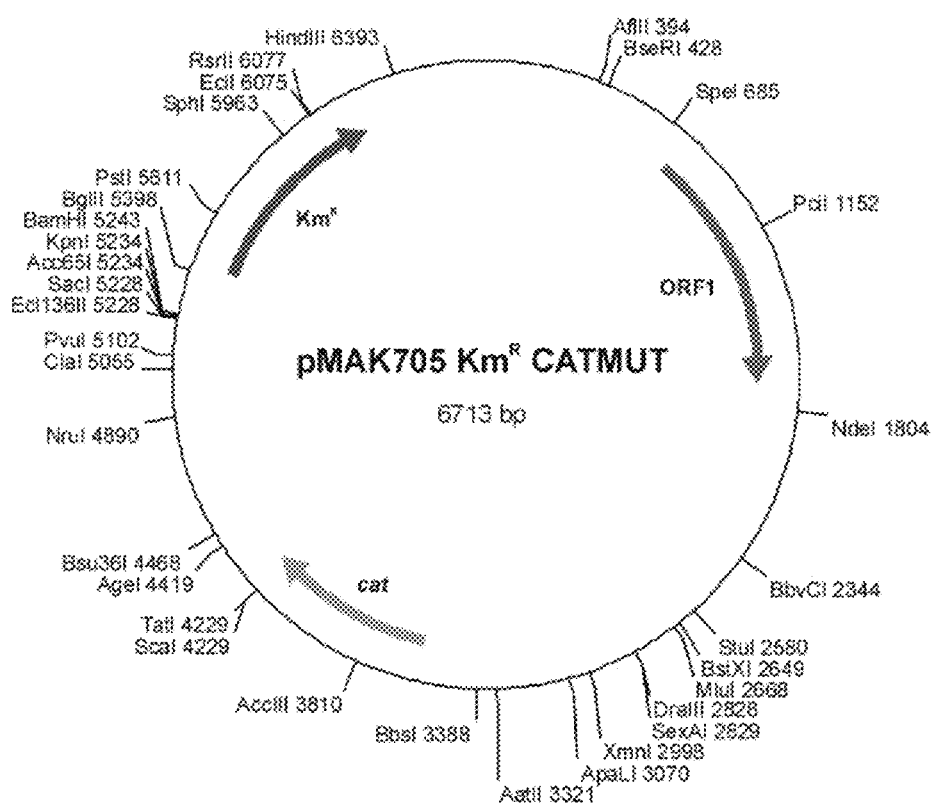
FIG. 63 Map of the helper plasmid pMAK705 $Km^R$ CATMUT.

The supE44 gene from E. coli XL1-Blue was transferred to BW30270, KPM318 and its 42° C.-resistant derivatives. To facilitate selection for supE44 in BW30270, KPM318 and its derivatives, the helper plasmid pMAK705 KmR CATMUT was constructed (FIG. 63). First, the kanamycin resistance gene of plasmid pKD4 was amplified using the primers 5BamHIKmR and 3HindIIIKmR, followed by digestion of the PCR product with BamHI and HindIII. Second, the BamHI/HindIII digested PCR product was cloned into the BamHI/HindIII sites of the temperature-sensitive plasmid pMAK705 to yield pMAK705 $Km^R$. Finally, the codon ACC at position 10 was substituted for a TAG (amber) nonsense codon using primers CATamber and CATwtreverse in site-directed mutagenesis with the Change-IT Mutagenesis System (USB).

5BamHIKmR:
(SEQ ID NO: 1)
ATATGGATCCTTACATGGCGATAGCTAGACTGG;

3HindIIIKmR:
(SEQ ID NO: 2)
ATATAAGCTTGAAGAACTCCAGCATGAGATCC;

CATamber:
(SEQ ID NO: 3)
GAGAAAAAATCACTGGATATACCTAGGTTGATATATCCCAATGGCA;

CATwtreverse:
(SEQ ID NO: 4)
CAGTACTGTTGTAATTCATTAAGCATTCTGCCGACATGGAAGCCATC.

To verify the introduction of the amber nonsense codon into the cat gene, the E. coli strains TOP10 and XL1-Blue were transformed with plasmid pMAK705 $Km^R$ CATMUT. The resulting strains TOP10/pMAK705 $Km^R$ CATMUT and XL1-Blue/pMAK705 $Km^R$ CATMUT were streaked on both LB+30 µg/ml kanamycin and LB+30 µg/ml kanamycin+15 µg/ml chloramphenicol plates (FIG. 64). In contrast to TOP10/pMAK705 $Km^R$ CATMUT carrying the wild-type allele of glnV, strain XL1-Blue/pMAK705 $Km^R$ CATMUT was capable of growing on LB+30 µg/ml kanamycin +15 µg/ml chloramphenicol plates, indicating the suppression of the nonsense mutation by supE44 (FIG. 64).

Example 5

Construction Of the KPM Derived ΔendA ΔrecA Strains

The ΔrecA::$Km^R$ strains KPM348, KPM349, KPM350, KPM351 and KPM352, were each derived from the corresponding ΔendA strains to KPM343, KPM344, KPM345, KPM346 and KPM347. A as used in this example means deletion. The ΔrecA::$Km^R$ targeting cassette was transferred to KPM343, KPM344, KPM345, KPM346 and KPM347 by P1 vir transduction essentially as described for construction of other knockout mutations:

1. The E. coli strain BW26547 carrying the ΔrecA::$Km^R$ mutation was used as a donor for transduction. The strain was obtained from the E. coli Genetic Stock Center.
2. Phage P1 vir was propagated on BW26547 grown at 37° C. in LB medium with 30 µg/ml kanamycin to obtain a ΔrecA::$Km^R$ transducing lysate.
3. For transduction, the ΔendA recipient strains KPM343, KPM344, KPM345, KPM346 and KPM347 were grown at 37° C. in LB medium supplemeted with A5P/G6P.

4. Transduction was performed according to standard protocols, with selection of potential transductants at 37° on LB-agar plates containing 30 µg/ml kanamycin.
5. The distance between recA and gutQ is only about 6 kb (theoretical co-transduction rate: about 82%), so potential kanamycin-resistant transductants were tested by PCR for the presence of both the ΔrecA::Km$^R$ cassette and the deleted gutQ gene in KPM strains.

```
gutQ control primers:
                                   (SEQ ID NO: 13)
5'gutQctrl1-    GTCGATAAGCTGATTACCGACGC (SEQ ID NO: 14)
3'gutQctrl2-    GTGAAACTATTCGTCAGGCACTGG recA control primers:
                                   (SEQ ID NO: 15)
5'recActrl-     CTACTGCGTATGCATTGCAG (SEQ ID NO: 16)
3'recActrl-     TCGTAATCTTCTGCCGTAGC
```

6. As a result, strains KPM348, KPM349, KPM350, KPM351 and KPM352 containing ΔrecA::Km$^R$ and the original ΔgutQ mutation were obtained.
7. The kanamycin resistance gene is removed using transient transformation by pCP20 to obtain strains KPM353, KPM354, KPM355, KPM356, and KPM357.
8. The above recA primers serve for identifying the elimination of the Kan$^R$ insert in the ΔrecA final strains.

Example 6

Growth of BL21 Strains with Suppressor Mutations

The suppressor mutations generated in the *E. coli* K-12 hosts were tested in BL21 strains, in parallel with other mutations that were less effective in the original *E. coli* K-12 background. The mutations tested included: msbA-P18S, msbA-L48F, msbA-P50S, msbA-T283A and msbA-R310S of *E. coli* strains KPM22 L11, KPM22 L14, KPM22 L1, KPM22 L15 and KPM22 L18, respectively. An insert cassette was constructed targeting the lpxL gene of *E. coli* strains BL21 (DE3) msbA L1, BL21 (DE3) msbA L11, BL21 (DE3) msbA L14, BL21 (DE3) msbA L15, and BL21 (DE3) msbA L18.

The ΔlpxL::Km was constructed with the template pKD4 and primer pair H1 P1 lpxL/H2P2 lpxL. The PCR mix (50 µl) included:

| | |
|---|---|
| H$_2$O | 30 µl |
| 10 × Buffer | 5 µl |
| 25 mM MgSO$_4$ | 3 µl (1.5 mM) |
| dNTPs (2 mM each) | 5 µl (0.2 mM each) |
| 5'-Primer (10 µM) | 1 µl |
| 3'-Primer (10 µM) | 1 µl |
| pKD4 | 4 µl (50 ng) |
| KOD Pol. (1 U/µl) | 1 µl (0.02 U/µl) |

The ΔlpxL::Cm was constructed with the template pKD3 and primer pair H1 P1 lpxL/H2P2 lpxL. The PCR mix (50 µl) included:

| | |
|---|---|
| H$_2$O | 32 µl |
| 10 × Buffer | 5 µl |
| 25 mM MgSO$_4$ | 3 µl (1.5 mM) |
| dNTPs (2 mM each) | 5 µl (0.2 mM each) |
| 5'-Primer (10 µM) | 1 µl |
| 3'-Primer (10 µM) | 1 µl |
| pKD3 (50 ng/µl) | 2 µl |
| KOD Pol. (1 U/µl) | 1 µl (0.02 U/µl) |

The PCR conditions were: 95° C. 2 min
  4 cycles: 95° C. 20 sec; 55° C. 10 sec; 70° C. 30 sec;
  30 cycles: 95° C. 20 sec; 70° C. 30 sec; 4° C. ∞

Figure 68C:
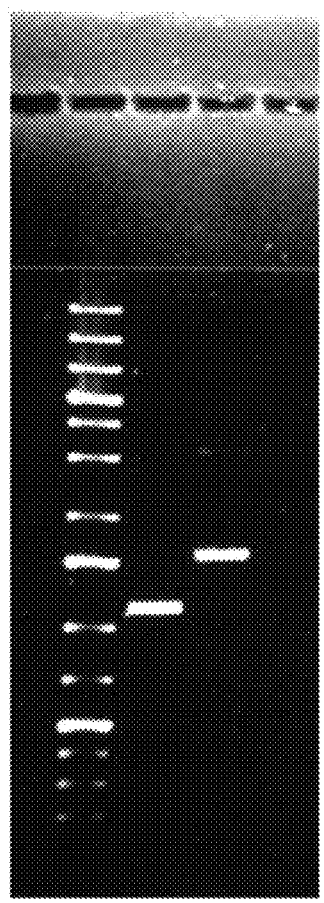
FIG. 68C shows the gel-purified PCR products.

The PCR products were analyzed by agarose gel electrophoresis (0.8% TBE agarose) (FIG. 68A). The PCR products were digested with DpnI: 1 µl of DpnI (20 U/µl) was added to the PCR mix, and the reaction was incubated at 37° C. for 3 h. Gel purification of the PCR products was performed using electrophoresis in 1% TAE low melting point agarose (Invitrogen) (FIG. 68B), followed by gel extraction of the PCR products using the Roche Gel Extraction Kit as recommended by the manufacturer. The gel-purified PCR products were analyzed by agarose gel electrophoresis (0.8% TBE agarose) (FIG. 68C). The ΔlpxL targeting cassettes were concentrated using the DNA Clean & Concentrator TM-5 Kit (Zymo Research) according to the recommendations of the manufacturer; 49 µl of each DNA sample was applied, and each was eluted with 7 µl of nuclease-free water.

Transformation of BL21(DE3) msbA L1/pKD46, BL21 (DE3) msbA L11/pKD46, BL21(DE3) msbA L14/pKD46, BL21(DE3) msbA L15/pKD46, and BL21(DE3) msbA L18/pKD46 with insert cassettes targeting the lpxL. Competent cells of *E. coli* strains BL21(DE3) msbA L1/pKD46, BL21 (DE3) msbA L11/pKD46, BL21(DE3) msbA L14/pKD46, BL21(DE3) msbA L15/pKD46, and BL21(DE3) msbA L18/pKD46 were prepared. Fresh overnight cultures were grown in 5 ml of LB medium containing 100 µg/ml ampicillin (30° C., 220 rpm). The cultures were diluted 1:50 (v/v) in 80 ml pre-warmed LB medium containing 100 µg/ml ampicillin and 10 mM L-arabinose. The cultures were grown to an OD$_{600}$ between 0.3 and 0.4 at 30° C. and 220 rpm. The cultures were placed on ice for 20 min. The cells were pelleted by centrifugation (Beckman JA-14 rotor, 6,000 rpm, 4° C., 20 min). The cells were resuspended in 40 ml H$_2$O (ice-cold, sterile). The cells were pelleted by centrifugation (Beckman JA-14 rotor, 6,000 rpm, 4° C., 20 min). The cells were resuspended in 20 ml H$_2$O (ice-cold, sterile). The cells were pelleted by centrifugation (Beckman JA-14 rotor, 6,000 rpm, 4° C., 20 min). The cells were resuspended in 10 ml H$_2$O (ice-cold, sterile). The cells were pelleted by centrifugation (Beckman JA-14 rotor, 6,000 rpm, 4° C., 20 min). The cells were resuspended in 5 ml 10% glycerol (ice-cold, sterile). The cells were pelleted by centrifugation (Beckman JA-14 rotor, 6,000 rpm, 4° C., 20 min). The cells were resuspended in 100 µl 10% glycerol (ice-cold, sterile). Aliquots (50-µl) were prepared. Competent cells (50 µl) were transformed with 1 µl of each (7×concentrated) insert cassette targeting the lpxL gene: 1. ΔlpxL::Km and 2. ΔlpxL::Cm.

Electroporation was performed, and 1 ml of SOC medium containing 10 mM L-arabinose was added to the transformed cells. The cultures were shaken at 30° C. (220 rpm) for 3 h. The transformed cells were plated on: LB agar plates containing 100 µg/ml ampicillin and 30 µg/ml kanamycin for ΔlpxL::Km or LB agar plates containing 100 µg/ml ampicillin and 15 µg/ml chloramphenicol for ΔlpxL::Cm. The plates were incubated at 30° C. PCRs were performed on kanamycin- and chloramphenicol resistant transformants of *E. coli* strains BL21(DE3) msbA L1/pKD46, BL21(DE3)

msbA L11/pKD46, BL21(DE3) msbA L14/pKD46, BL21 (DE3) msbA L15/pKD46, and BL21(DE3) msbA L18/pKD46 using the primer pair ECOlpxLfwd/ECOlpxLrev. The biomass of the following strains were used as PCR templates:
1. BL21(DE3) (control)
2. BL21(DE3) msbA L11/pKD46 ΔlpxL::Km 1-5, 13, 16
3. BL21(DE3) msbA L11/pKD46 ΔlpxL::Cm 6-12, 14, 15
4. BL21(DE3) msbA L18/pKD46 ΔlpxL::Km 1-13
5. BL21(DE3) msbA L18/pKD46 ΔlpxL::Cm 14-16
6. BL21(DE3) msbA L1/pKD46 ΔlpxL::Km 1-5
7. BL21(DE3) msbA L1/pKD46 ΔlpxL::Cm 6
8. BL21(DE3) msbA L14/pKD46 ΔlpxL::Km 1-6
9. BL21(DE3) msbA L14/pKD46 ΔlpxL::Cm 7-9
10. BL21(DE3) msbA L15/pKD46 ΔlpxL::Km 1-3
11. BL21(DE3) msbA L15/pKD46 ΔlpxL::Cm 4-16

The PCR mix is (20 µl per reaction):
H$_2$O: 14.15 µl
10× Buffer: 2 µl
ECOlpxLfwd (10 µM): 1 µl
ECOlpxLrev (10 µM): 1 µl
dATP (10 mM): 0.4 µl
dCTP (10 mM): 0.4 µl
dGTP (10 mM): 0.4 µl
dTTP (10 mM): 0.4 µl
Taq (10 U): 0.25 µl The PCR conditions are:
95° C. 2 min
4 cycles:
95° C. 20 sec
45° C. 30 sec
72° C. 1 min 30 sec
36 cycles:
95° C. 20 sec
65° C. 30 sec
72° C. 1 min 30 sec
4° C.

The PCR products are analyzed by agarose gel electrophoresis (0.8% TBE agarose) using 1-µl samples. The results are shown in FIGS. 69, 70, 71 and 72.

pKD46 was removed from the following *E. coli* strains:
BL21(DE3) msbA L11/pKD46 ΔlpxL::Km 1
BL21(DE3) msbA L11/pKD46 ΔlpxL::Km 2
BL21(DE3) msbA L18/pKD46 ΔlpxL::Cm 14
BL21(DE3) msbA L18/pKD46 ΔlpxL::Cm 15
BL21(DE3) msbA L1/pKD46 ΔlpxL::Cm 6
BL21(DE3) msbA L14/pKD46 ΔlpxL::Km 5
BL21(DE3) msbA L14/pKD46 ΔlpxL::Cm 7
BL21(DE3) msbA L15/pKD46 ΔlpxL::Km 1
BL21(DE3) msbA L15/pKD46 ΔlpxL::Km 3

The strains BL21(DE3) msbA L11/pKD46 ΔlpxL:Km-1, BL21(DE3) msbA L11/pKD46 ΔlpxL:Km-2, BL21(DE3) msbA L14/pKD46 ΔlpxL:Km-5, BL21(DE3) msbA L15/pKD46 ΔlpxL::Km-1 and BL21(DE3) msbA L15/pKD46 ΔlpxL::Km-3 at 37° C. (220 rpm) were grown overnight in LB medium containing 30 µg/ml kanamycin. The strains BL21(DE3) msbA L18/pKD46 ΔlpxL:Cm-14, BL21(DE3) msbA L18/pKD46 ΔlpxL:Cm-15, BL21(DE3) msbA L1/pKD46 ΔlpxL::Cm-6 and BL21(DE3) msbA L14/pKD46 ΔlpxL::Cm-7 at 37° C. (220 rpm) were grown overnight in LB medium containing 15 µg/ml chloramphenicol. Serial dilutions of the cultures in LB medium were prepared to obtain single colonies (10^4-10^6). There was 100 µl of each dilution plated on LB agar plates containing 30 µg/ml kanamycin or LB agar plates containing 15 µg/ml chloramphenicol. The plates were incubated at 37° C. Each single colony (8 per strain) was streaked on both LB agar plates+30 µg/ml kanamycin/LB agar plates+15 µg/ml chloramphenicol and LB agar plates+30 µg/ml kanamycin+100 µg/ml ampicillin/LB agar plates+15 µg/ml chloramphenicol+100 µg/ml ampicillin. The plates were incubated at 30° C. The growth was checked on LB agar plates+30 µg/ml kanamycin/LB agar plates+15 µg/ml chloramphenicol but not on LB agar plates+30 µg/ml kanamycin+100 µg/ml ampicillin/LB agar plates+15 µg/ml chloramphenicol+100 µg/ml ampicillin.

Insert cassettes targeting the lpxL gene from *E. coli* strains BL21(DE3) msbA L1 ΔlpxL::Cm 6, BL21(DE3) msbA L11 ΔlpxL::Km 1, BL21(DE3) msbA L14 ΔldpxL::Km 5, BL21(DE3) msbA L15 ΔlpxL::Km 3 and BL21(DE3) msbA L18 ΔlpxL::Cm 15 were removed. Competent cells of *E. coli* strains BL21(DE3) msbA L1 ΔlpxL::Cm 6, BL21(DE3) msbA L11 ΔlpxL::Km 1, BL21(DE3) msbA L14 ΔlpxL::Km 5, BL21(DE3) msbA L15 ΔlpxL::Km 3, BL21(DE3) msbA L18 ΔlpxL::Cm 15 were prepared. Fresh overnight cultures of BL21(DE3) msbA L1 ΔlpxL::Cm 6 and BL21(DE3) msbA L18 ΔlpxL::Cm 15 were grown in 5 ml LB medium containing 15 µg/ml chloramphenicol (37° C., 220 rpm). Fresh overnight cultures of *E. coli* strains BL21(DE3) msbA L11 ΔlpxL::Km 1, BL21(DE3) msbA L14 ΔlpxL::Km 5 and BL21(DE3) msbA L15 ΔlpxL::Km 3 were grown in 5 ml LB medium containing 30 µg/ml kanamycin (37° C., 220 rpm). The cultures were diluted 1:50 in 80 ml pre-warmed LB medium+30 µg/ml kanamycin or LB medium+15 µg/ml chloramphenicol. The cultures were grown to OD$_{600}$~0.3-0.4 at 37° C. and 220 rpm. The cultures were placed on ice for 20 min and pelleted by centrifugation (Beckman JA-14 rotor, 6,000 rpm, 4° C., 20 min). The cells were resuspended in 40 ml H$_2$O (ice-cold, sterile). The cells were pelleted by centrifugation (Beckman JA-14 rotor, 6,000 rpm, 4° C., 20 min). The cells were resuspended in 25 ml H$_2$O (ice-cold, sterile). The cells were pelleted by centrifugation (Beckman JA-14 rotor, 6,000 rpm, 4° C., 20 min). The cells were resuspended in 10 ml H$_2$O (ice-cold, sterile). The cells were pelleted by centrifugation (Beckman JA-14 rotor, 6,000 rpm, 4° C., 20 min). The cells were resuspended in 5 ml 10% glycerol (ice-cold, sterile). The cells were pelleted by centrifugation (Beckman JA-14 rotor, 6,000 rpm, 4° C., 20 min). The cells were centrifuged in 100 µl 10% glycerol (ice-cold, sterile). The cells were placed on ice and 50 µl aliquots were prepared. 5 µl of pCP20 was added to 50 µl of competent cells. The cells were incubated on ice for 1 min, and the mixture was transferred to a 2-mm electroporation cuvette (Bio-Rad). The samples were electroporated using a Gene Pulser apparatus (Bio-Rad) with the following settings: 26 pFD, 200 Ω, 2.5 kV. 1 ml of SOC medium was added to the transformed cells, and the solution was transferred to a new tube. The samples were shaken at 30° C. and 220 rpm for 1 h. Serial dilutions of the cultures in LB medium were prepared to obtain single colonies (10^0-10^-2). There was 100 µl of each dilution plated on LB agar plates containing 100 µg/ml ampicillin. The plates were incubated at 30° C. Eight colonies of BL21(DE3) msbA L11 ΔlpxL::Km 1 (pCP20), BL21(DE3) msbA L14 ΔlpxL::Km 5 (pCP20), BL21(DE3) msbA L15 ΔlpxL::Km 3 (pCP20) on both LB agar plates+100 µg/ml ampicillin and LB agar plates+30 µg/ml kanamycin+100 µg/ml ampicillin were streaked. Eight colonies of BL21(DE3) msbA L1 ΔlpxL::Cm 6 (pCP20) and BL21(DE3) msbA L18 ΔlpxL::Cm 15 (pCP20) on LB agar plates+100 µg/ml ampicillin were streaked. The plates were incubated at 30° C. The growth was assessed on LB agar plates+100 µg/ml ampicillin but not on LB agar plates+30 µg/ml kanamycin+100 µg/ml ampicillin. All tested clones grew on LB agar plates+100

μg/ml ampicillin but not on LB agar plates+30 μg/ml kanamycin+100 μg/ml ampicillin. Two transformants of each strain BL21(DE3) msbA L1 ΔlpxL(Cm⁻)/pCP20, BL21(DE3) msbA L11 ΔlpxL(Km⁻)/pCP20, BL21(DE3) msbA L14 ΔlpxL(Km⁻)/pCP20, BL21(DE3) msbA L15 ΔlpxL(Km⁻)/pCP20, BL21(DE3) msbA L18 ΔlpxL(Cm⁻)/pCP20 were chosen for verification of the kanamycin/chloramphenicol resistance cassette loss by PCR.

The loss of the kanamycin/chloramphenicol resistance cassette was verified in E. coli strains BL21(DE3) msbA L1 ΔlpxL(Cm⁻)/pCP20, BL21(DE3) msbA L11 ΔlpxL(Km⁻)/pCP20, BL21(DE3) msbA L14 ΔlpxL(Km⁻)/pCP20, BL21(DE3) msbA L15 ΔlpxL(Km⁻)/pCP20 and BL21(DE3) msbA L18 ΔlpxL(Cm⁻)/pCP20.

PCRs were performed on ampicillin resistant transformants of E. coli strains BL21(DE3) msbA L1 ΔlpxL(Cm⁻)/pCP20, BL21(DE3) msbA L11 ΔlpxL(Km⁻)/pCP20, BL21(DE3) msbA L14 ΔlpxL(Km⁻)/pCP20, BL21(DE3) msbA L15 ΔlpxL(Km⁻)/pCP20 and BL21(DE3) msbA L18 ΔlpxL(Cm⁻)/pCP20 using the primer pair EClpxLfwd/EClpxLrev. Biomass of the following strains were used as templates:
1. BL21(DE3)/pKD46 (control 1)
2. BL21(DE3) msbA L1 ΔlpxL::Cm 6 (control 2)
3. BL21(DE3) msbA L1 ΔlpxL(Cm⁻)/pCP20 1
4. BL21(DE3) msbA L11 ΔlpxL::Km 1 (control 3)
5. BL21(DE3) msbA L11 ΔlpxL(Km⁻)/pCP20 1
6. BL21(DE3) msbA L11 ΔlpxL(Km⁻)/pCP20 6
7. BL21(DE3) msbA L14 ΔlpxL::Km 5 (control 4)
8. BL21(DE3) msbA L14 ΔlpxL(Km⁻)/pCP20 1
9. BL21(DE3) msbA L14 ΔlpxL(Km⁻)/pCP20 2
10. BL21(DE3) msbA L14 ΔlpxL(Km⁻)/pCP20 3
11. BL21(DE3) msbA L14 ΔlpxL(Km⁻)/pCP20 4
12. BL21(DE3) msbA L14 ΔlpxL(Km⁻)/pCP20 5
13. BL21(DE3) msbA L14 ΔlpxL(Km⁻)/pCP20 6
14. BL21(DE3) msbA L15 ΔlpxL::Km 3 (control 5)
15. BL21(DE3) msbA L15 ΔlpxL(Km⁻)/pCP20 2
16. BL21(DE3) msbA L15 ΔlpxL(Km⁻)/pCP20 6
17. BL21(DE3) msbA L18 ΔlpxL::Cm 15 (control 6)
18. BL21(DE3) msbA L18 ΔlpxL(Cm⁻)/pCP20 1
19. BL21(DE3) msbA L18 ΔlpxL(Cm⁻)/pCP20 2

The PCR mix was as follows (20 μl/rxn)
H2O: 14.15 μl
10× Buffer: 2 μl
EClpxLfwd (10 μM): 1 μl
EClpxLrev (10 μM): 1 μl
dATP (10 mM): 0.4 μl
dCTP (10 mM): 0.4 μl
dGTP (10 mM): 0.4 μl
dTTP (10 mM): 0.4 μl
Taq (10 U): 0.25 μl The PCR conditions were as follows:
95° C. 2 min
4 cycles:
95° C. 20 sec
45° C. 30 sec
72° C. 1 min 30 sec
36 cycles:
95° C. 20 sec
65° C. 30 sec
72° C. 1 min 30 sec
4° C.

Figure 73:
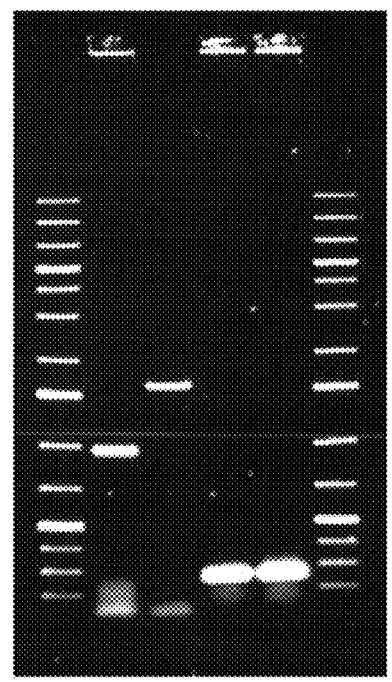
FIG. 73 shows verification of the kanamycin/chloramphenicol resistance cassette loss in E. coli strains BL21(DE3)/pKD46 (control) and BL21(DE3) msbA L11.
Figure 74:
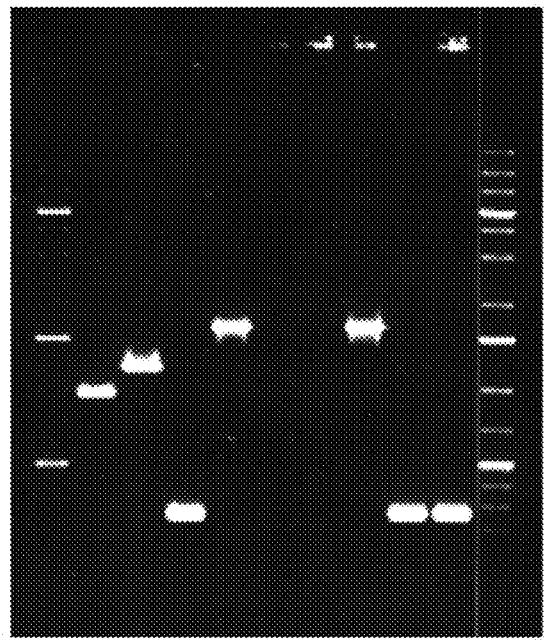
FIG. 74 shows verification of the kanamycin/chloramphenicol resistance cassette loss in E. coli strains BL21(DE3) msbA L11 ΔlpxL(Km-)/pCP20, BL21(DE3) msbA L14 ΔlpxL(Km-)/pCP20, BL21(DE3) and msbA L15 ΔlpxL (Km-).
Figure 75:
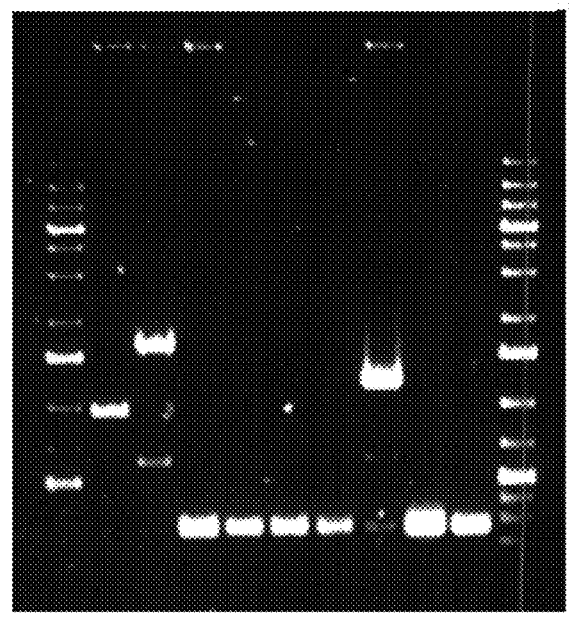
FIG. 75 shows verification of the kanamycin/chloramphenicol resistance cassette loss in E. coli strains BL21(DE3) msbA L14 ΔlpxL(Km-)/pCP20 and BL21(DE3) msbA L18 ΔlpxL(Cm-)/pCP20.

The PCR products were analyzed by agarose gel electrophoresis (0.8% TBE agarose). The results are in FIGS. 73, 74 and 75.

The pCP20 was removed from E. coli strains BL21(DE3) msbA L11 ΔlpxL(Km⁻)/pCP20 1, BL21(DE3) msbA L1 ΔlpxL(Cm⁻)/pCP20 1, BL21(DE3) msbA L15 ΔlpxL(Km⁻)/pCP20 2, BL21(DE3) msbA L14 ΔlpxL(Km⁻)/pCP20 3 and BL21(DE3) msbA L18 ΔlpxL(Cm⁻)/pCP20 1.

The cultures were grown overnight at 37° C. (220 rpm) in LB medium. Serial dilutions of the cultures in LB medium were prepared to obtain single colonies (10^4-10^6). There was 100 μl of each dilution plated on LB agar plates. The plates were incubated at 37° C. Each single colony (8 per strain) was streaked on both LB agar plates and LB agar plates+100 μg/ml ampicillin. The plates were incubated at 30° C. Growth was assessed on LB agar plates but not on LB agar plates+100 μg/ml ampicillin. The following new strains were obtained:
1. E. coli BL21(DE3) msbA-P50S (L1) ΔlpxL
2. E. coli BL21(DE3) msbA-P18S (L11) ΔlpxL
3. E. coli BL21(DE3) msbA-L48F (L14) ΔlpxL
4. E. coli BL21(DE3) msbA-T283A (L15) ΔlpxL
5. E. coli BL21(DE3) msbA-R310S (L18) ΔlpxL The strains did grow on LB agar but not on LB agar+100 μg/ml ampicillin. Thus, the temperature-sensitive plasmid pCP20 was successfully removed.

Figure 76:
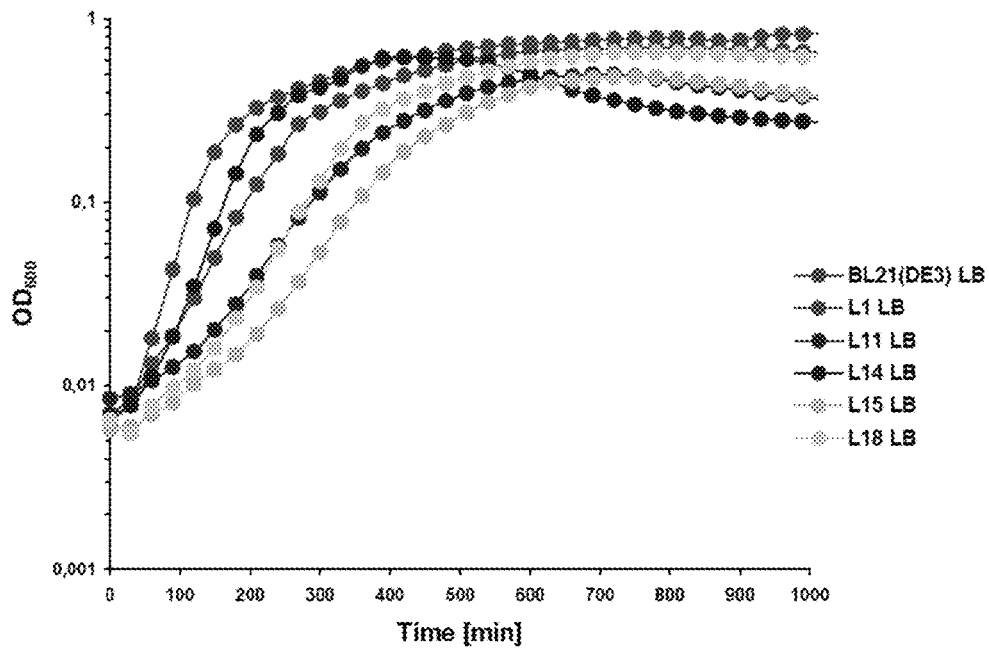
FIG. 76 shows growth of BL21 (DE3) ΔlpxL suppressor strains at 37° C. in LB medium.
Figure 77:
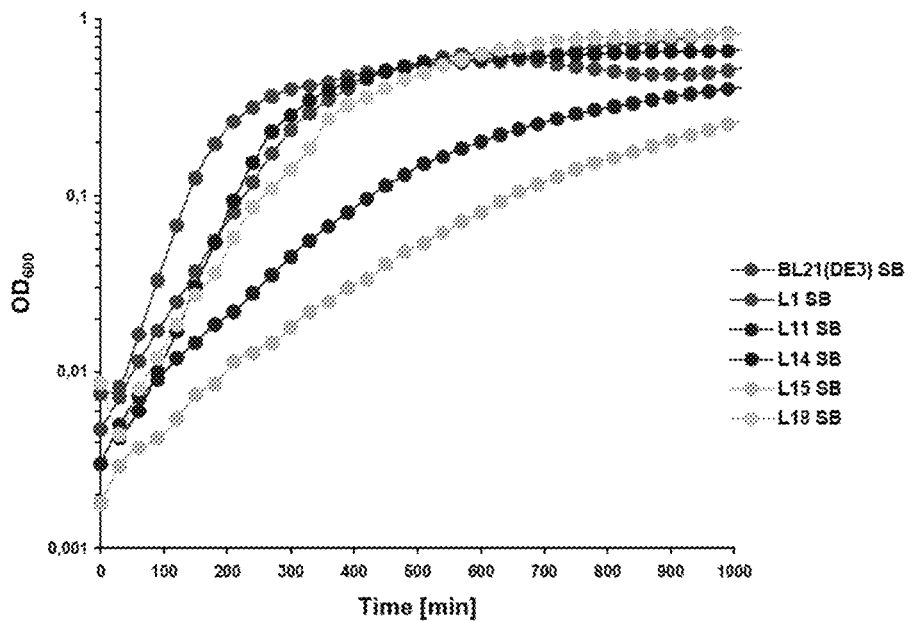
FIG. 77 shows growth of BL21 (DE3) ΔlpxL suppressor strains at 37° C. in SB medium.

The growth of BL21(DE3) msbA suppressor strains lacking the lpxL gene at 37° C. was assessed in SB and LB media. The following strains were assessed:
1. BL21(DE3) (control)
2. BL21(DE3) msbA-P50S (L1) ΔlpxL
3. BL21(DE3) msbA-P18S (L11) ΔlpxL
4. BL21(DE3) msbA-L48F (L14) ΔlpxL
5. BL21(DE3) msbA-T283A (L15) ΔlpxL
6. BL21(DE3) msbA-R310S (L18) ΔlpxL 96-deep-well plates were used to inoculate each strain in 1.5 ml of medium. The cultures were shaken overnight at 37° C. (600 rpm; VWR Microplate Shaker). The overnight cultures were diluted to an $OD_{600}$ of ~0.005 in 200 μl of pre-warmed medium (37° C.). The 96-well plates were shaken at 37° C. in the NanoQuant Infinite 200 Microplate Reader (Tecan) (linear shaking; amplitude=2.5=~99.1 rpm), and the $OD_{600}$ was measured after every half hour. The results are in FIG. 76 and FIG. 77.

Example 7

Construction of kdsD Deficient Strains

An insert cassette was constructed targeting the kdsD gene of E. coli strains BL21(DE3) msbA-P50S (L1) ΔlpxL and BL21(DE3) msbA-L48F (L14) ΔlpxL. The ΔkdsD::Km targeting cassette was constructed with the template pKD4 and primer pair KDF/KDR.

```
KDF primer (kdsD homology region is underlined):
                                        (SEQ ID NO: 17):
GCGATGTTGTACTGGTTATCGCCAATACTCGTTGAATAACTGGAAACGCA

TTGTGTAGGCTGGAGCTGCTTCG

KDR primer (kdsD homology region is underlined):
                                        (SEQ ID NO: 18)
GCGACGCACCTGCTTTGCTCATTGTTGTTTATCCTTGAATCTTTACACTA

CGGATATGAATATCCTCCTTAG
```

The PCR mix (50 μl) included:

| | |
|---|---|
| H₂O | 30 μl |
| 10 × Buffer | 5 μl |
| 25 mM MgSO₄ | 3 μl (1.5 mM) |
| dNTPs (2 mM each) | 5 μl (0.2 mM each) |

| | |
|---|---|
| 5'-Primer (10 µM) | 1 µl (0.2 µM) |
| 3'-Primer (10 µM) | 1 µl (0.2 µM) |
| pKD4 | 4 µl (50 ng) |
| KOD Pol. (1 U/µl) | 1 µl (0.02 U/µl) |

The PCR conditions were:
95° C. 2 min
4 cycles:
95° C. 20 sec
55° C. 10 sec
70° C. 30 sec
36 cycles:
95° C. 20 sec
70° C. 30 sec
4° C. ∞

Figure 78:
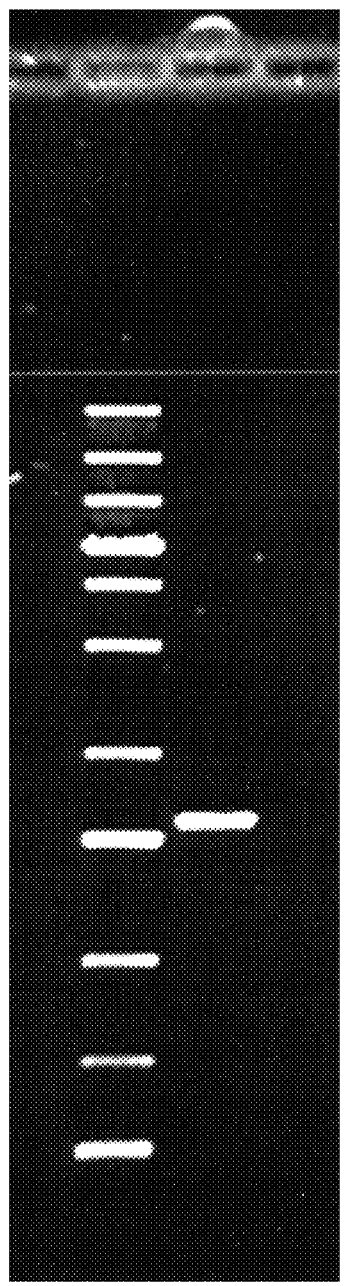
FIG. 78 shows the gel-purified ΔkdsD::Km targeting cassette.

The PCR product was analyzed by agarose gel electrophoresis (0.8% TBE agarose). The PCR product was digested with Dpnl: 1 µl of Dpnl (20 U/µl) was added to the PCR mix, and the reaction was incubated at 37° C. for 3 h. Gel purification of the PCR product was performed using electrophoresis in 1% TAE low melting point agarose (Invitrogen), followed by gel extraction of the PCR product using the Roche Gel Extraction Kit as recommended by the manufacturer. The gel-purified PCR product was analyzed by agarose gel electrophoresis (0.8% TBE agarose) (FIG. 78).

For transformation of BL21(DE3) msbA-P50S (L1) ΔlpxL/pKD46 and BL21(DE3) msbA-L48F (L14) ΔlpxL/pKD46 with the insert cassette targeting the kdsD gene, competent cells of E. coli strains BL21(DE3) msbA-P50S (L1) ΔlpxL/pKD46 and BL21(DE3) msbA-L48F (L14) ΔlpxL/pKD46 were prepared. Fresh overnight cultures were grown in 5 ml of LB medium containing 100 µg/ml ampicillin (30° C., 220 rpm). The cultures were diluted 1:50 (v/v) in 80 ml pre-warmed LB medium containing 100 µg/ml ampicillin and 10 mM L-arabinose. The cultures were grown to an $OD_{600}$ between 0.3 and 0.4 at 30° C. and 220 rpm. The cultures were placed on ice for 20 min. The cells were pelleted by centrifugation (Beckman JA-14 rotor, 6,000 rpm, 4° C., 20 min). The cells were resuspended in 40 ml $H_2O$ (ice-cold, sterile). The cells were pelleted by centrifugation (Beckman JA-14 rotor, 6,000 rpm, 4° C., 20 min). The cells were resuspended in 20 ml $H_2O$ (ice-cold, sterile). The cells were pelleted by centrifugation (Beckman JA-14 rotor, 6,000 rpm, 4° C., 20 min). The cells were resuspended in 10 ml $H_2O$ (ice-cold, sterile). The cells were pelleted by centrifugation (Beckman JA-14 rotor, 6,000 rpm, 4° C., 20 min). The cells were resuspended in 5 ml 10% glycerol (ice-cold, sterile). The cells were pelleted by centrifugation (Beckman JA-14 rotor, 6,000 rpm, 4° C., 20 min). The cells were resuspended in 100 µl 10% glycerol (ice-cold, sterile). Aliquots (50-µl) were prepared. Competent cells (50 µl) were transformed with 3 µl of the insert cassette targeting the kdsD gene.

Electroporation was performed, and 1 ml of SOC medium containing 10 mM L-arabinose was added to the transformed cells. The cultures were shaken at 30° C. (220 rpm) for 3 h. The transformed cells were plated on LB agar plates containing 100 µg/ml ampicillin and 30 µg/ml kanamycin. The plates were incubated at 30° C. PCRs were performed on kanamycin-resistant transformants of E. coli strains BL21 (DE3) msbA-P50S (L1) ΔlpxL/pKD46 and BL21(DE3) msbA-L48F (L14) ΔlpxL/pKD46 using the primer pair ECkdsDctrl1/ECkdsDctrl2.

```
ECkdsDctrl1:
                                          (SEQ ID NO: 19)
GACTACAGCGTGATGTTGCTGG ECkdsDctrl2:
                                          (SEQ ID NO: 20)
TCGACATCGAGGATCAGCAGAC
```

The biomass of the following strains were used as PCR templates:
1. BL21(DE3) msbA L1 ΔlpxL/pKD46 (control 1)
2. BL21(DE3) msbA L1 ΔlpxL (ΔkdsD::Km)/pKD46 1-42
3. BL21(DE3) msbA L14 ΔlpxL/pKD46 (control 2)
4. BL21(DE3) msbA L14 ΔlpxL (ΔkdsD::Km)/pKD46 1-8

The PCR mix was (20 µl per reaction):
$H_2O$: 14.15 µl
10× Buffer: 2 µl
ECkdsDctrl1 (10 µM): 1 µl
ECkdsDctrl2 (10 µM): 1 µl
dATP (10 mM): 0.4 µl
dCTP (10 mM): 0.4 µl
dGTP (10 mM): 0.4 µl
dTTP (10 mM): 0.4 µl
Taq (10 U): 0.25 µl The PCR conditions were:
95° C. 2 min
40 cycles:
95° C. 20 sec
60° C. 30 sec
72° C. 1 min 30 sec
4° C. ∞

Figure 79:
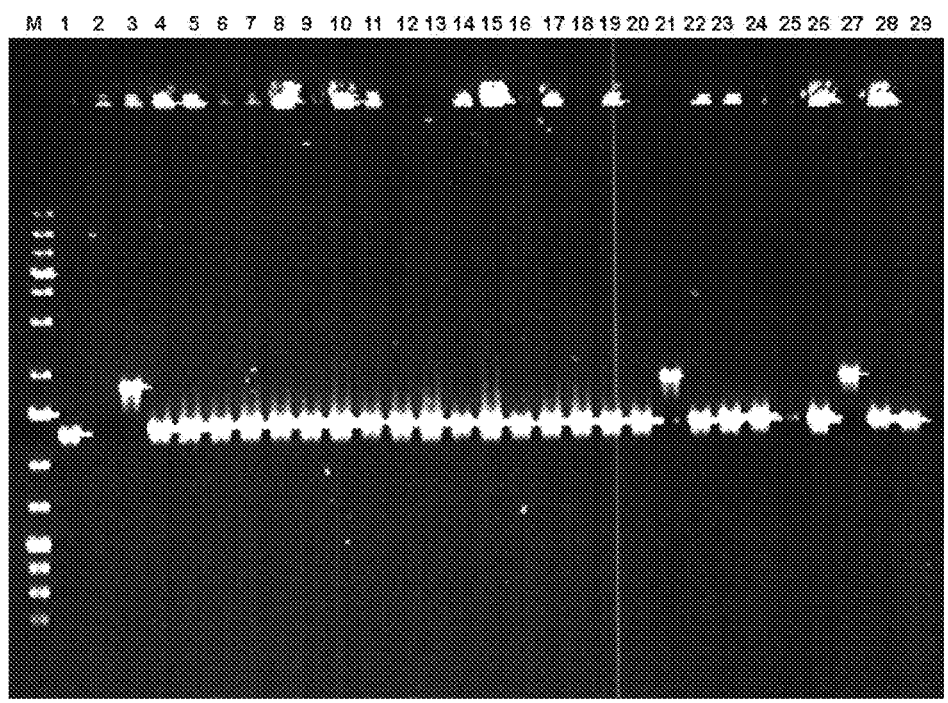
FIG. 79 shows verification of the ΔkdsD mutations in kanamycin-resistant transformants of E. coli strains BL21 (DE3) msbA L1 ΔlpxL (ΔkdsD::Km⁺)/pKD46 and BL21 (DE3) msbA L14 ΔlpxL (ΔkdsD::Km⁺)/pKD46.
Figure 80:
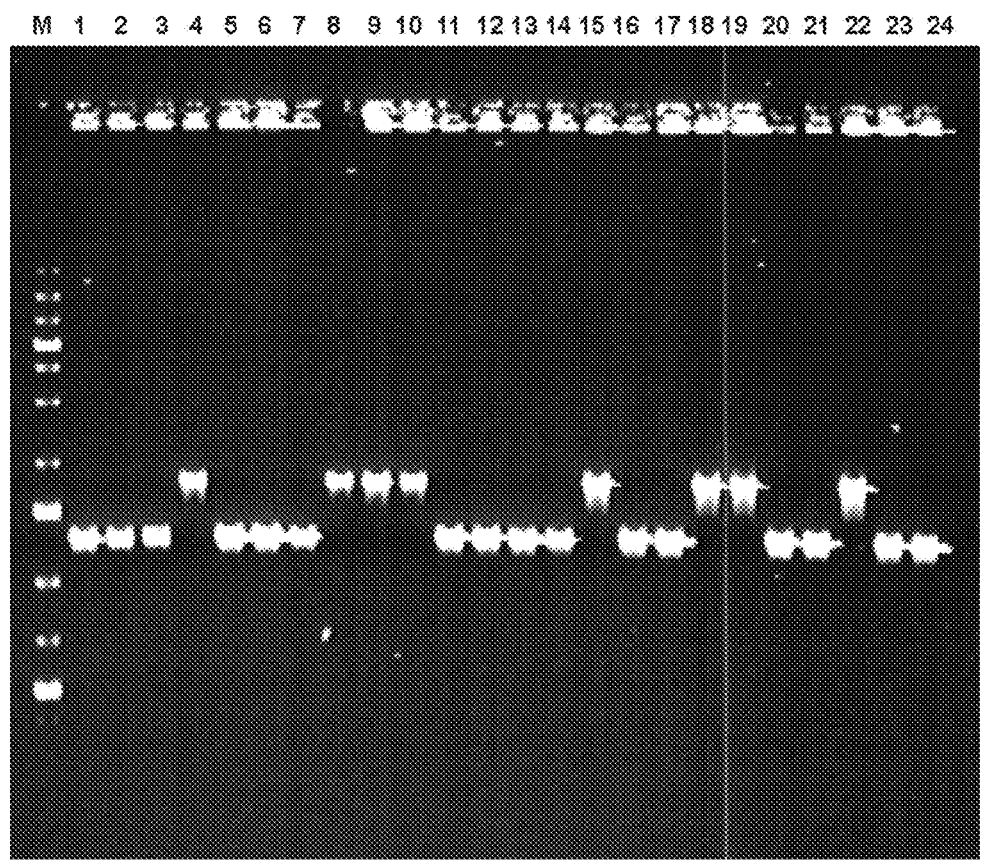
FIG. 80 shows verification of the ΔkdsD mutations in kanamycin-resistant transformants of E. coli strains BL21 (DE3) msbA L1 ΔlpxL (ΔkdsD::Km⁺)/pKD46.

The PCR products were analyzed by agarose gel electrophoresis (0.8% TBE agarose) using 0.5-µl samples. The results are shown in FIGS. 79 and 80.

pKD46 was removed from the following E. coli strains:
1. BL21 (DE3) ΔlpxL msbA L1/pKD46 (ΔkdsD::$Km^+$) 11
2. BL21 (DE3) ΔlpxL msbA L1/pKD46 (ΔkdsD::$Km^+$) 17
3. BL21 (DE3) ΔlpxL msbA L14/pKD46 (ΔkdsD::$Km^+$) 2

The strains BL21 (DE3) ΔlpxL msbA L1/pKD46 (ΔkdsD::$Km^+$) 11, BL21 (DE3) ΔlpxL msbA L1/pKD46 (ΔkdsD::$Km^+$) 17 and BL21 (DE3) ΔlpxL msbA L14/pKD46 (ΔkdsD::$Km^+$) 2 at 37° C. (220 rpm) were grown overnight in LB medium containing 30 µg/ml kanamycin. Serial dilutions of the cultures in LB medium were prepared to obtain single colonies ($10^4$-$10^6$). There was 100 µl of each dilution plated on LB agar plates containing 30 µg/ml kanamycin. The plates were incubated at 37° C. Each single colony (8 per strain) was streaked on both LB agar plates+30 µg/ml kanamycin and LB agar plates+30 µg/ml kanamycin+ 100 µg/ml ampicillin. The plates were incubated at 30° C. The growth was checked on LB agar plates+30 µg/ml kanamycin but not on LB agar plates+30 µg/ml kanamycin+ 100 µg/ml ampicillin.

Insert cassettes targeting the kdsD gene from E. coli strains BL21 (DE3) msbA L1 ΔlpxL ΔkdsD::$Km^+$ 11 and BL21 (DE3) msbA L14 ΔlpxL ΔkdsD::$Km^+$ 2 were removed. Competent cells of E. coli strains BL21 (DE3) msbA L1 ΔlpxL ΔkdsD::$Km^+$ 11 and BL21 (DE3) msbA L14 ΔlpxL ΔkdsD::$Km^+$ 2 were prepared. Fresh overnight cultures of BL21 (DE3) msbA L1 ΔlpxL ΔkdsD::$Km^+$ 11 and BL21 (DE3) msbA L14 ΔlpxL ΔkdsD::$Km^+$ 2 were grown in 5 ml LB medium containing 30 µg/ml kanamycin (37° C., 220 rpm). The cultures were diluted 1:50 in 80 ml pre-warmed LB medium+30 µg/ml kanamycin. The cultures were grown to $OD_{600}$~0.3-0.4 at 37° C. and 220 rpm. The cultures were placed on ice for 20 min and pelleted by centrifugation (Beckman JA-14 rotor, 6,000 rpm, 4° C., 20 min). The cells were resuspended in 40 ml H₂O (ice-cold, sterile). The cells were pelleted by centrifugation (Beckman JA-14 rotor, 6,000 rpm, 4° C., 20 min). The cells were resuspended in 25 ml H₂O (ice-cold, sterile). The cells were pelleted by centrifugation (Beckman JA-14 rotor, 6,000 rpm, 4° C., 20 min). The cells were resuspended in 10 ml H₂O (ice-cold, sterile). The cells were pelleted by centrifugation (Beckman JA-14 rotor, 6,000 rpm, 4° C., 20 min). The cells were resuspended in 5 ml 10% glycerol (ice-cold, sterile). The cells were pelleted by centrifugation (Beckman JA-14 rotor, 6,000 rpm, 4° C., 20 min). The cells were centrifuged in 100 µl 10% glycerol (ice-cold, sterile). The cells were placed on ice and 50-µl aliquots were prepared. 1 µl of pFLP2 [Lee, D. J. et al. (2009) Gene doctoring: a method for recombineering in laboratory and pathogenic *Escherichia coli* strains. *BMC Microbiology* 9: 252] was added to 50 µl of competent cells. The cells were incubated on ice for 1 min, and the mixture was transferred to a 2-mm electroporation cuvette (Bio-Rad). The samples were electroporated using a Gene Pulser apparatus (Bio-Rad) with the following settings: 26 pFD, 200 Ω, 2.5 kV. 1 ml of SOC medium was added to the transformed cells, and the solution was transferred to a new tube. The samples were shaken at 37° C. and 220 rpm for 1 h. Serial dilutions of the cultures in LB medium were prepared to obtain single colonies (10^0-10^-3). There was 100 µl of each dilution plated on LB agar plates containing 100 µg/ml ampicillin. The plates were incubated at 37° C. Eight colonies of BL21 (DE3) msbA L1 ΔlpxL ΔkdsD::Km⁺ 11 (pFLP2) and BL21 (DE3) msbA L14 ΔlpxL ΔkdsD::Km⁺ 2 (pFLP2) were streaked on LB agar plates+100 µg/ml ampicillin and LB agar plates+30 µg/ml kanamycin+100 µg/ml ampicillin. The plates were incubated at 37° C. The growth was assessed on LB agar plates+100 µg/ml ampicillin but not on LB agar plates+30 µg/ml kanamycin+100 µg/ml ampicillin. Some of the tested clones grew on LB agar plates+100 µg/ml ampicillin but not on LB agar plates+30 µg/ml kanamycin+100 µg/ml ampicillin. Seven transformants of BL21(DE3) msbA L1 ΔlpxL ΔkdsD (Km⁻)/pFLP2 and two transformants of BL21(DE3) msbA L14 ΔlpxL ΔkdsD (Km⁻)/pFLP2 were chosen for verification of the kanamycin resistance cassette loss by PCR.

The loss of the kanamycin resistance cassette was verified by PCR on ampicillin resistant transformants using the primer pair ECkdsDctrl1/ECkdsDctrl2. Biomass of the following strains were used as templates:

1. BL21(DE3) msbA L1 ΔlpxL/pKD46 (control 1)
2. BL21(DE3) msbA L1 ΔlpxL ΔkdsD::Km⁺11/pKD46 (control 2)
3. BL21(DE3) msbA L1 ΔlpxL ΔkdsD (Km⁻)/pFLP2 1-6, 8
4. BL21(DE3) msbA L14 ΔlpxL/pKD46 (control 3)
5. BL21(DE3) msbA L14 ΔlpxL ΔkdsD::Km⁺11/pKD46 (control 4)
6. BL21(DE3) msbA L14 ΔlpxL ΔkdsD (Km⁻)/pFLP219, 29

The PCR mix was (20 µl per reaction):

H₂O: 14.15 µl
10× Buffer: 2 µl
ECkdsDctrl1 (10 µM): 1 µl
ECkdsDctrl2 (10 µM): 1 µl
dATP (10 mM): 0.4 µl
dCTP (10 mM): 0.4 µl
dGTP (10 mM): 0.4 µl
dTTP (10 mM): 0.4 µl
Taq (10 U): 0.25 µl The PCR conditions were:
95° C. 2 min
40 cycles:
95° C. 20 sec
60° C. 30 sec
72° C. 1 min 30 sec
4° C. ∞

Figure 81:
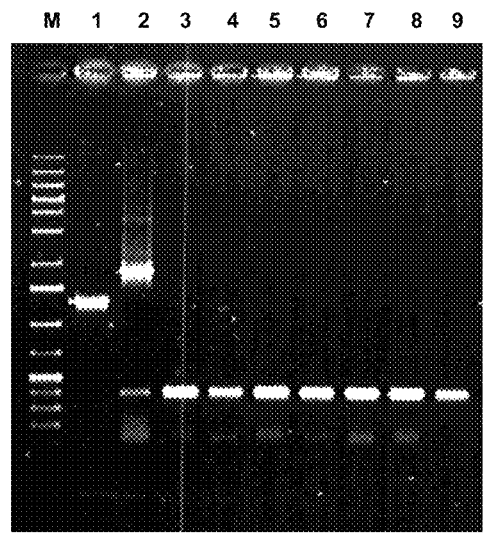
FIG. 81 shows verification of the kanamycin resistance cassette loss in E. coli strain BL21(DE3) msbA L1 ΔlpxL ΔkdsD (Km⁻)/pFLP2.
Figure 82:
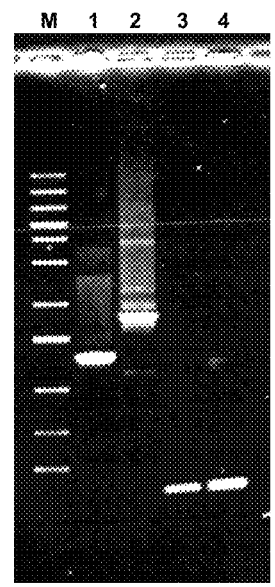
FIG. 82 shows verification of the kanamycin resistance cassette loss in E. coli strain BL21(DE3) msbA L14 ΔlpxL ΔkdsD (Km⁻)/pFLP2.

The PCR products were analyzed by agarose gel electrophoresis (0.8% TBE agarose) using 1-µl samples. The results are shown in FIGS. 81 and 82.

The pFLP2 was removed from *E. coli* strains BL21(DE3) msbA L1 ΔlpxL ΔkdsD/pFLP2 4 and BL21(DE3) msbA L14 ΔlpxL ΔkdsD/pFLP2 29. The strains were streaked on LB agar plates containing 5% sucrose to obtain single colonies at 37° C. Each single colony (8 per strain) was streaked on both LB agar plates+5% sucrose and LB agar plates+100 µg/ml ampicillin. The plates were incubated at 37° C. Growth was assessed on LB agar plates+5% sucrose but not on LB agar plates+100 µg/ml ampicillin. The following new strains were obtained:

1. *E. coli* BL21(DE3) msbA L1 ΔlpxL ΔkdsD
2. *E. coli* BL21(DE3) msbA L14 ΔlpxL ΔkdsD The strains grew on LB agar+5% sucrose but not on LB agar+100 µg/ml ampicillin. Thus, the plasmid pFLP2 was successfully removed.

Example 8

Construction of GutQ Deficient Strains

An insert cassette was constructed targeting the gutQ gene of *E. coli* strains BL21(DE3) msbA L1 ΔlpxL ΔkdsD and BL21(DE3) msbA L14 ΔlpxL ΔkdsD.

The ΔgutQ::Km targeting cassette was constructed with the template pKD4 and primer pair GQF/GQR2.

GQF primer (gutQ homology region is underlined):
(SEQ ID NO: 21)
<u>GATCGATGTGATCATAACCGGAGAGAGCAATGAGTGAAGCGTGTAGGCTG</u>
GAGCTGCTTC GQR2 primer (gutQ homology region is underlined):
(SEQ ID NO: 22)
<u>CGGCTGGCGAAACGTCTGGGATTGAAGGATTAAATAATCCATTCCGGGGA</u>
TCCGTCGACC The PCR mix (50 µl) included:

| | |
|---|---|
| H₂O | 30 µl |
| 10 × Buffer | 5 µl |
| 25 mM MgSO₄ | 3 µl (1.5 mM) |
| dNTPs (2 mM each) | 5 µl (0.2 mM each) |
| 5'-Primer (10 µM) | 1 µl (0.2 µM) |
| 3'-Primer (10 µM) | 1 µl (0.2 µM) |
| pKD4 | 4 µl (50 ng) |
| KOD Pol. (1 U/µl) | 1 µl (0.02 U/µl) |

The PCR conditions were:
95° C. 2 min
4 cycles:
95° C. 20 sec
55° C. 10 sec
70° C. 30 sec 36 cycles:
95° C. 20 sec
70° C. 30 sec
4° C. ∞

Figure 83:
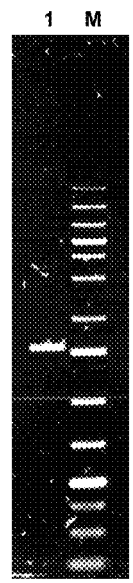
FIG. 83 shows the gel-purified ΔgutQ::Km targeting cassette.

The PCR product was analyzed by agarose gel electrophoresis (0.8% TBE agarose). The PCR product was digested with Dpnl: 1 µl of Dpnl (20 U/µl) was added to the PCR mix, and the reaction was incubated at 37° C. for 3 h. Gel purification of the PCR product was performed using electrophoresis in 1% TAE low melting point agarose (Invitrogen), followed by gel extraction of the PCR product using the Roche Gel Extraction Kit as recommended by the manufacturer. The gel-purified PCR product was analyzed by agarose gel electrophoresis (0.8% TBE agarose) (FIG. 83). The ΔgutQ targeting cassette was concentrated using the DNA Clean & Concentrator TM-5 Kit (Zymo Research) according to the recommendations of the manufacturer; 30 µl of the DNA sample was applied and eluted with 6 µl of nuclease-free water.

For transformation of BL21(DE3) msbA L1 ΔlpxL ΔkdsD/pKD46 and BL21(DE3) msbA L14 ΔlpxL ΔkdsD/pKD46 with the insert cassette targeting the gutQ gene, competent cells of E. coli strains BL21(DE3) msbA L1 ΔlpxL ΔkdsD/pKD46 and BL21(DE3) msbA L14 ΔlpxL ΔkdsD/pKD46 were prepared. Fresh overnight cultures were grown in 5 ml of LB medium containing 100 µg/ml ampicillin (30° C., 220 rpm). The cultures were diluted 1:50 (v/v) in 80 ml pre-warmed LB medium containing 100 µg/ml ampicillin and 10 mM L-arabinose. The cultures were grown to an $OD_{600}$ between 0.3 and 0.4 at 30° C. and 220 rpm. The cultures were placed on ice for 20 min. The cells were pelleted by centrifugation (Beckman JA-14 rotor, 6,000 rpm, 4° C., 20 min. The cells were resuspended in 40 ml $H_2O$ (ice-cold, sterile). The cells were pelleted by centrifugation (Beckman JA-14 rotor, 6,000 rpm, 4° C., 20 min). The cells were resuspended in 20 ml $H_2O$ (ice-cold, sterile). The cells were pelleted by centrifugation (Beckman JA-14 rotor, 6,000 rpm, 4° C., 20 min). The cells were resuspended in 10 ml $H_2O$ (ice-cold, sterile). The cells were pelleted by centrifugation (Beckman JA-14 rotor, 6,000 rpm, 4° C., 20 min). The cells were resuspended in 5 ml 10% glycerol (ice-cold, sterile). The cells were pelleted by centrifugation (Beckman JA-14 rotor, 6,000 rpm, 4° C., 20 min). The cells were resuspended in 100 µl 10% glycerol (ice-cold, sterile). Aliquots (50-µl) were prepared. Competent cells (50 µl) were transformed with 2 µl of the 5× concentrated insert cassette targeting the gutQ gene.

Electroporation was performed, and 1 ml of SOC medium containing 10 mM L-arabinose was added to the transformed cells. The cultures were shaken at 30° C. (220 rpm) for 3 h. The transformed cells were plated on LB agar plates containing 100 µg/ml ampicillin and 30 µg/ml kanamycin. The plates were incubated at 30° C. PCRs were performed on kanamycin-resistant transformants of E. coli strain BL21 (DE3) msbA L1 ΔlpxL ΔkdsD/pKD46 using the primer pair ECgutQctrl1/ECgutQctrl2. Transformation of BL21(DE3) msbA L14 ΔlpxL ΔkdsD/pKD46 with the insert cassette targeting the gutQ gene was not successful.

ECgutQctrl1:
(SEQ ID NO: 23)
GTCGATAAGCTGATTACCGACGC

ECgutQctrl2:
(SEQ ID NO: 24)
GTGAAACTATTCGTCAGGCACTGG

The biomass of the following strains were used as PCR templates:
1. BL21(DE3) msbA L1 ΔlpxL ΔkdsD/pKD46 (control)
2. BL21(DE3) msbA L1 ΔlpxL ΔkdsD (ΔgutQ::Km)/pKD46 1-16

The PCR mix was (20 µl per reaction):
$H_2O$: 13.9 µl
10× Buffer: 2 µl
ECgutQctrl1 (10 µM): 1 µl
ECgutQctrl2 (10 µM): 1 µl
dATP (10 mM): 0.4 µl
dCTP (10 mM): 0.4 µl
dGTP (10 mM): 0.4 µl
dTTP (10 mM): 0.4 µl
Taq (5 U): 0.5 µl The PCR conditions were:
95° C. 2 min
40 cycles:
95° C. 20 sec
60° C. 30 sec
72° C. 1 min 30 sec
4° C. ∞

The PCR products were analyzed by agarose gel electrophoresis (0.8% TBE agarose) using 0.5-µl samples. The results are shown in FIG. 84.

The strain BL21 (DE3) ΔlpxL ΔkdsD msbA L1 (ΔgutQ::Km⁺)/pKD46 3 showed traces of the wild-type gutQ PCR product and was therefore further colony-purified. BL21 (DE3) ΔlpxL ΔkdsD msbA L1 (ΔgutQ::Km⁺)/pKD46 3 was streaked on LB agar plates containing 30 µg/ml kanamycin to obtain single colonies at 30° C. Sixteen colonies were streaked again on LB agar plates+30 µg/ml kanamycin and incubated at 37° C. to remove pKD46. The biomass of the following strains were used as PCR templates:
1. BL21(DE3) msbA L1 ΔlpxL ΔkdsD/pKD46 (control)
2. BL21(DE3) msbA L1 ΔlpxL ΔkdsD (ΔgutQ::Km)/pKD46 (3) 1-16

The PCR mix was (20 µl per reaction):
$H_2O$: 13.9 µl
10× Buffer: 2 µl
ECgutQctrl1 (10 µM): 1 µl
ECgutQctrl2 (10 µM): 1 µl
dATP (10 mM): 0.4 µl
dCTP (10 mM): 0.4 µl
dGTP (10 mM): 0.4 µl
dTTP (10 mM): 0.4 µl
Taq (5 U): 0.5 µl The PCR conditions were:
95° C. 2 min
40 cycles:
95° C. 20 sec
60° C. 30 sec
72° C. 1 min 30 sec
4° C. ∞

The PCR products were analyzed by agarose gel electrophoresis (0.8% TBE agarose) using 1-µl samples. The results are shown in FIG. 85. All tested clones contained the ΔgutQ::Km cassette.

Each clone was streaked on both LB agar plates+30 µg/ml kanamycin and LB agar plates+30 µg/ml kanamycin+100 µg/ml ampicillin. The plates were incubated at 30° C. The growth was checked on LB agar plates+30 µg/ml kanamycin but not on LB agar plates+30 µg/ml kanamycin+100 µg/ml ampicillin. All clones grew on LB agar plates+30 µg/ml kanamycin but not on LB agar plates+30 µg/ml kanamycin+ 100 µg/ml ampicillin, indicating the pKD46 has been successfully removed.

The insert cassette targeting the gutQ gene from *E. coli* strain BL21(DE3) msbA L1 ΔlpxL ΔkdsD ΔgutQ::Km⁺ was removed. Competent cells of *E. coli* strain BL21(DE3) msbA L1 ΔlpxL ΔkdsD ΔgutQ::Km⁺ were prepared. A fresh overnight culture of strain BL21(DE3) msbA L1 ΔlpxL ΔkdsD ΔgutQ::Km⁺ was grown in 5 ml LB medium containing 30 µg/ml kanamycin (37° C., 220 rpm). The culture was diluted 1:50 in 80 ml pre-warmed LB medium+30 µg/ml kanamycin. The culture was grown to OD$_{600}$~0.3-0.4 at 37° C. and 220 rpm. The culture was placed on ice for 20 min and pelleted by centrifugation (Beckman JA-14 rotor, 6,000 rpm, 4° C., 20 min). The cells were resuspended in 40 ml H$_2$O (ice-cold, sterile). The cells were pelleted by centrifugation (Beckman JA-14 rotor, 6,000 rpm, 4° C., 20 min). The cells were resuspended in 25 ml H$_2$O (ice-cold, sterile). The cells were pelleted by centrifugation (Beckman JA-14 rotor, 6,000 rpm, 4° C., 20 min). The cells were resuspended in 10 ml H$_2$O (ice-cold, sterile). The cells were pelleted by centrifugation (Beckman JA-14 rotor, 6,000 rpm, 4° C., 20 min). The cells were resuspended in 5 ml 10% glycerol (ice-cold, sterile). The cells were pelleted by centrifugation (Beckman JA-14 rotor, 6,000 rpm, 4° C., 20 min). The cells were centrifuged in 100 µl 10% glycerol (ice-cold, sterile). The cells were placed on ice and 50-µl aliquots were prepared. 1 µl of pFLP2 was added to 50 µl of competent cells. The cells were incubated on ice for 1 min, and the mixture was transferred to a 2-mm electroporation cuvette (Bio-Rad). The samples were electroporated using a Gene Pulser apparatus (Bio-Rad) with the following settings: 26 µFD, 200 Ω, 2.5 kV. 1 ml of SOC medium was added to the transformed cells, and the solution was transferred to a new tube. The sample was shaken at 37° C. and 220 rpm for 1 h. Serial dilutions of the culture in LB medium were prepared to obtain single colonies (10^0-10^3). There was 100 µl of each dilution plated on LB agar plates containing 100 µg/ml carbenicillin. The plates were incubated at 37° C. Sixteen colonies of BL21(DE3) msbA L1 ΔlpxL ΔkdsD ΔgutQ::Km⁺ (pFLP2) were streaked on LB agar plates+100 µg/ml carbenicillin and LB agar plates+30 µg/ml kanamycin+100 µg/ml ampicillin. The plates were incubated at 37° C. The growth was assessed on LB agar plates+100 µg/ml carbenicillin but not on LB agar plates+30 µg/ml kanamycin+100 µg/ml ampicillin. All tested clones grew on LB agar plates+100 µg/ml carbenicillin but not on LB agar plates+30 µg/ml kanamycin+100 µg/ml ampicillin. Eight transformants of BL21(DE3) msbA L1 ΔlpxL ΔkdsD ΔgutQ (Km⁻) /pFLP2 were chosen for verification of the kanamycin resistance cassette loss by PCR.

The loss of the kanamycin resistance cassette was verified by PCR on carbenicillin resistant transformants using the primer pair ECgutQctrl1/ECgutQctrl2. Biomass of the following strains were used as templates:
1. BL21 (DE3) msbA L1 ΔlpxL ΔkdsD/pKD46 (control 1)
2. BL21 (DE3) msbA L1 ΔlpxL ΔkdsD ΔgutQ::Km⁺3 (control 2)
3. BL21 (DE3) msbA L1 ΔlpxL ΔkdsD ΔgutQ (Km⁻)/pFLP2 9-16

The PCR mix was (20 µl per reaction):
H$_2$O: 13.9 µl
10× Buffer: 2 µl
ECgutQctrl1 (10 µM): 1 µl
ECgutQctrl2 (10 µM): 1 µl
dATP (10 mM): 0.4 µl
dCTP (10 mM): 0.4 µl
dGTP (10 mM): 0.4 µl
dTTP (10 mM): 0.4 µl
Taq (5 U): 0.5 µl The PCR conditions were:
95° C. 2 min
40 cycles:
95° C. 20 sec
60° C. 30 sec
72° C. 1 min 30 sec
4° C. ∞

The PCR products were analyzed by agarose gel electrophoresis (0.8% TBE agarose) using 1-µl samples. The results are shown in FIG. 86.

The pFLP2 was removed from *E. coli* strains BL21(DE3) msbA L1 ΔlpxL ΔkdsD ΔgutQ (Km⁻)/pFLP2 9 and BL21 (DE3) msbA L1 ΔlpxL ΔkdsD ΔgutQ (Km⁻)/pFLP2 10. The strains were streaked on LB agar plates containing 5% sucrose to obtain single colonies at 37° C. Each single colony (8 per strain) was streaked on both LB agar plates+ 5% sucrose and LB agar plates+100 µg/ml ampicillin. The plates were incubated at 37° C. Growth was assessed on LB agar plates+5% sucrose but not on LB agar plates+100 µg/ml ampicillin. The following new strain was obtained: *E. coli* BL21(DE3) msbA L1 ΔlpxL ΔkdsD ΔgutQ The strain grew on LB agar+5% sucrose but not on LB agar+100 µg/ml ampicillin. Thus, the plasmid pFLP2 was successfully removed.

The suppressor mutations were tested with the following additional mutations: ΔlpxL ΔkdsD ΔgutQ. Thus, lipid IV$_A$, lacking any Kdo (and hence lacking any further sugar additions) is produced by the strains tested. The growth rate of each strain was compared in LB, a rich media, and compared under identical culture conditions. Surprisingly, a different ranking of the suppressor alleles was observed in the BL21 background compared with the ranking in the K-12 background. The reason for this difference is unknown, but may point to a significant interaction between the MsbA transporter and some other component(s) in the periplasm of the cell such as the LptA or Waal protein Example 9

Construction of LpxM, LpxP, EptA, PagP Deficient Strains

The best strains in example 7 above were used to derive further host strains that now are defective additionally in LpxM, LpxP, EptA, PagP. The steps used in constructing these series of strains is as described in (first Uwe patent), except that the appropriate BL21 based parental strain was used as a recipient and the and a BL21 derived donor strain was also employed to ensure that the protease deficient properties of the *E. coli* B background were retained. Further suppressor mutations such as frr can be added to improve viability and growth.

In this way are constructed strains such as
*E. coli* BL21(DE3) msbA-S50P frr-D61Y sbA-S50P frr-D61Y ΔkdsD ΔgutQ ΔlpxL ΔlpxM ΔlpxP ΔpagP ΔeptA
*E. coli* BL21 msbA-S50P frr-D61Y sbA-S50P frr-D61 Y ΔkdsD ΔgutQ ΔlpxL ΔlpxM ΔlpxP ΔpagP ΔeptA Example 10

Purification of DNA

The following method of purification of DNA from an *E. coli* strain is simplified because it does not include any step designed to eliminate LPS, thereby saving time and cost. It relies on the use of a host that not only lacks LPS, but which produces a molecule, lipid IV$_A$, that is homogeneous rather than heterogeneous, simplifying the purification steps.

Example 11

Purification of Protein

The following method of purification of protein from an E. coli strain is simplified because it does not include any step designed to eliminate LPS, thereby saving time and cost. It relies on the use of a host that not only lacks LPS, but which produces a molecule, lipid IV$_A$, that is homogeneous rather than heterogeneous, simplifying the purification steps.

Example 12

Determination of Endotoxin Levels in Strains

BlueSky Biotech determined the endotoxin levels in the bacterial strains. A single colony was used to inoculate a 4 ml LB culture and incubated for 16 h at 37° C. The culture was back-diluted 1:100 in 50 ml LB and incubated at 37° C. until an OD$_{600}$=0.4-0.5 was reached (Table 24). The cells were then incubated on ice for 30 minutes and collected by centrifugation. The pellets were resuspended in 25 ml 0.1 M CaCl$_2$ and incubated on ice for 30 min. The cells were collected by centrifugation again and resuspended in 1 ml CaCl$_2$ plus 15% glycerol. The cells were divided into 50 µl aliquots and immediately stored at −80° C. pcDNA3.1(+) plasmid DNA (0.1 µg) was added to each tube of competent cells. The cells were incubated on ice for 30 minutes. The cells were heat shocked for 45 seconds at 42° C. and placed back on ice for 10 minutes. SOC media (1 mL) was added to each tube and incubated at 37° C. for 1 hr with aeration. Serial dilutions were prepared and colonies were counted. The transformation efficiencies are provided in Table 25.

A single colony was selected from a streaked selective plate and inoculated into 250 ml of LB media with the appropriate antibiotic. The culture was grown at 37° C. for 12-16 h with vigorous shaking (approx. 250-300 rpm). The culture was transferred into plastic centrifuge bottle and spun down for 10 minutes at 9000 rpm. The supernatant was removed, and the bacterial pellet was resuspended with 10 ml of Buffer P1 (this buffer should be have RNAse added into it and be chilled before use). Buffer 2 (10 ml) of Buffer 2 was added, the solution was mixed gently, and incubated at room temperature for 5 minutes. Buffer 3 (10 ml), which should be chilled before use, is added. The solution is mixed immediately but gently by inverting. The QIAfilter Cartridge is set up by screwing on the cap onto the outlet nozzle. The lysate is poured into the barrel of the QIAfilter Cartridge and incubated at room temperature (15-25° C.) for about 10 minutes. The plunger is not inserted until 10 minutes have elapsed. After 10 minutes, the cap is removed from the nozzle, and the plunger is inserted into the QIAfilter MAXI cartridge. The cell lysate is filtered into a 50 ml conical tube. Once the lysate has been filtered, buffer ER (2.5 ml) is added to the lysate. The tube is inverted about 10 times to ensure adequate mixing and incubate the tube on ice for about 30 minutes. When there is about 10 minutes left for incubation, a QIAGEN-tip 500 is set up over an empty, plastic waste bin and equilibrated by adding 10 ml of Buffer QBT; the column is allowed to empty by gravity flow. After both the incubation and Buffer QBT has passed through the QIAGEN-tip 500, the filtered lysate from step 8 is added into the QIAGEN-tip 500. Let the lysate pass through the column until empty by gravity flow into the waste bin. Once the lysate has fully filtered through the column, 30 ml of the wash buffer is added (Buffer QC) into the column. The wash buffer is allowed to pass through the column until empty before proceeding with the next step. This washing step is repeated. Once the column has been washed twice, the column is set over a 50 ml conical tube. The DNA is eluted by adding 15 ml of Buffer QN. Once all of the buffer has passed through, the DNA is precipitated by adding 10.5 ml of room temperature isopropanol to the eluted DNA. The solution is mixed by inversion and incubated on ice for 30 minutes. After incubation, the sample is centrifuged immediately at 9000 rpm for 45 minutes at 4° C. After centrifuging, the pellet is located; it should have a white or glossy color. Pour out the supernatant and make sure not to pour out the pellet. The DNA pellet is washed by adding 5 ml of endotoxin-free, room temperature 70% ethanol into the tube with the pellet. The tube is spun in a swinging bucket for 20 minutes at 3,400 rpm. After the spin, the supernatant is carefully poured without disturbing the pellet. All the liquid is removed so that the pellet will dry. The DNA is redissolved in 250 ml of endotoxin-free Buffer TE.

For endotoxin testing, a Limulus Amebocyte Lysate (LAL) Cartridge (Product code: PTS20) was used in the Endosafe PTS system (Charles River Laboratories). Sample (25 µl) was tested 'undiluted' and at a 1:10, 1:100 or 1:1000 dilution, prepared in endotoxin-free deionized water (based on initial data). The endotoxin data is provided in Table 26.

For the HEK-Blue Assay, one vial of HEK Blue-4 cells was thawed into a T75 flask in 15 ml of DMEM high glucose media containing 10% Non-heat inactivated Hyclone FBS (Hyclone #SH30071-03), 1×Normocin and 1×HEK-Blue selection. The culture was monitored daily and sub-cultured at about 80-90% confluence according to the instructions provided with the kit. The cultures were expanded enough to make a working cell bank of 20 cryovials.

For detecting LPS, HEK Blue assays were executed as per manufacturer's instruction. Assays were performed using HEK Blue cells with passage number lower than ten. The HEK-Blue cells were grown up to 60-80% confluence in growth medium supplemented with HEK-Blue selection. Cells were used that hadn't been passaged in at least 48 hours. At 30 minutes prior to the assay, samples and LPS control were warmed at 37° C. The samples were mixed vigorously by vortexing. The LPS control and samples were diluted according to the experiment design. The sample or control (20 µl) was added to each well of a 96-well plate. The cells were harvested and resuspended gently in HEK-Blue Detection media to a density of 1.25×10$^6$ cells/ml. A 200 µl cell suspension (2.5×10$^4$ cells) of was added to each well. The plate(s) were incubated for 18-24 hours at 37° C. in a 5% CO$_2$ incubator. The plate was read at 620 nm with an M5 µlate reader. Color images of the plates were taken. Tables 27-28 provide the Hek-blue assay data.

Example 13

HEK-Blue™-hTLR4 Cells and Assays from InvivoGen

HEK-Blue™-hTLR4 Cells
SEAP Reporter 293 cells expressing the human TLR4 gene
Product Information
Contents and Storage
 1 vial of HEK-Blue™-hTLR4 cells (5–7×10$^6$ cells) in Freezing Medium.

2 ml HEK-Blue™ Selection (250×). A solution containing several selection antibiotics. HEK-Blue™ Selection can be stored at 4° C. for 6 months or at −20° C. for 12 months.

1 ml Normocin™ (50 mg/ml). Normocin™ is a formulation of three antibiotics active against mycoplasmas, bacteria and fungi. Store at −20° C. Product is stable for 18 months when stored at −20° C.

1 pouch of QUANTI-Blue™, alkaline phosphatase detection medium. Store pouch at room temperature. Store reconstituted QUANTI-Blue™ at 4° C. for 2 weeks.

Product Description

HEK-Blue™-hTLR4 cells are designed for studying the stimulation of human TLR4 (hTLR4) by monitoring the activation of NF-kB. TLR4, the first human TLR identified, is the receptor for bacterial lipopolysaccharide (LPS) (Chow J. et al., 1999, *J Biol Chem* 274: 10689-92) and lipid A, its toxic moiety. However, TLR4 alone is not sufficient to confer LPS responsiveness. TLR4 requires MD-2, a secreted molecule, to functionally interact with LPS (Shimazu r. et al., 1999, *J Exp Med*, 189(11): 1777-82). Furthermore, a third protein, called CD14, was shown to participate in LPS signaling, leading to the activation of NF-kB and the production of proinflammatory cytokines (Shuto t. et al., 2005, *Biochem Biophys Res Commun* 338: 1402-9).

HEK-Blue™-hTLR4 cells were obtained by co-transfection of the hTLR4, MD-2/CD14 co-receptor genes and a secreted embryonic alkaline phosphatase (SEAP) reporter gene into HEK293 cells. The SEAP reporter gene is placed under the control of an IL-12 p40 minimal promoter fused to five NF-kB and AP-1-binding sites. Stimulation with a TLR4 ligand activates NF-kB and AP-1 which induce the production of SEAP. Levels of SEAP can be easily determined with HEK-Blue™ Detection or QUANTI-Blue™, detection media that turn purple/blue in the presence of alkaline phosphatase. HEK-Blue™ Detection is designed for high throughput detection of SEAP, while QUANTI-Blue™ is more sensitive and designed for the detection and quantification of SEAP.

HEK293 cells express endogenous levels of TLR3, TLR5 and NOD1. Note: The parental cell line for HEK-Blue™-hTLR4 cells is HEK-Blue™-Null2 cells (SEAP reporter cells which do not express hTLR4).

Handling Cells Upon Arrival

It is strongly recommended that the cells be propogated using the provided procedure, as soon as possible. This will ensure the best cell viability and assay performance. Frozen cells may be placed in liquid nitrogen until you are ready to thaw and propagate them, however, this may reduce cell viability.

Cell Line Stability

Cells will undergo genotypic changes resulting in reduced responsiveness over time in normal cell culture conditions. Genetic instability is a biological phenomenon that occurs in all stably transfected cells. Therefore, it is critical to prepare an adequate number of frozen stocks at early passages.

HEK-Blue™-hTLR4 cells should not be passaged more than 20 times to remain fully efficient. HEK-Blue™-hTLR4 cells should be maintained in Growth Medium as described below in the presence of Normocin™ (100 μg/ml) and 1×HEK-Blue™ Selection. Antibiotic pressure with HEK-Blue™ Selection is required to maintain the plasmids coding hTLR4, MD-2/CD14 and SEAP.

Quality Control

Expression of TLR4 and MD-2/CD14 genes was confirmed by RT-PCR. HEK-Blue™-hTLR4 Cells were stimulated by TLR4 agonists. As expected, TLR4 agonists induced the production of SEAP. These cells are mycoplasma-free.

Required Cell Culture Medium

Growth Medium: DMEM, 4.5 g/l glucose, 10% (v/v) fetal bovine serum, 50 U/ml penicillin, 50 mg/ml streptomycin, 100 mg/ml Normocin™, 2 mM L-glutamine Freezing Medium: DMEM, 4.5 g/l glucose, 20% (v/v) fetal bovine serum, 50 U/ml penicillin, 50 mg/ml streptomycin, 100 mg/ml Normocin™, 2 mM L-glutamine, 10% (v/v) DMSO Test Medium (for use with QUANTI-Blue™): DMEM, 4.5 g/l glucose, 50 U/ml penicillin, 50 mg/ml streptomycin, 100 mg/ml Normocin™, 2 mM L-glutamine, 10% (v/v) heat-inactivated fetal bovine serum (30 min at 56° C.)

Initial Culture Procedure

The first propagation of cells should be for generating stocks for future use. This ensures the stability and performance of the cells for subsequent experiments.

1—Thaw the vial by gentle agitation in a 37° C. water bath. To reduce the possibility of contamination, keep the O-ring and cap out of the water. Thawing should be rapid.

2—Remove the vial from the water bath as soon as the contents are thawed, and decontaminate by dipping in or spraying with 70% (v/v) ethanol. Note: All steps from this point should be carried out under strict aseptic conditions.

3—Transfer cells into a larger vial containing 15 ml of pre-warmed Growth Medium. Do not add selective antibiotics until the cells have been passaged twice.

4—Centrifuge vial at 1000-1200 RPM (RCF 200-300 g) for 5 minutes.

5—Remove supernatant containing the cryoprotective agent and resuspend cells with 1 ml of Growth Medium without selective antibiotics.

6—Transfer the vial contents to a 25 cm2 tissue culture flask containing 5 ml of Growth Medium without selective antibiotics.

7—Place the flask containing HEK-Blue™-hTLR4 cells at 3° C. in 5% CO2.

Frozen Stock Preparation

1—Resuspend cells at a density of 5–7×10$^6$ cells/ml in Freezing Medium freshly prepared with cold Growth Medium. Note: A T-75 culture flask typically yields enough cells for preparing 3-4 frozen vials.

2—Aliquot 1 ml cells into cryogenic vials.

3—Place vials in a freezing container (Nalgene) and store at −80° C. overnight.

4—Transfer vials to liquid nitrogen for long term storage. Note: If properly stored, cells should remain stable for years.

Cell Maintenance

1—Maintain and subculture the cells in Growth Medium supplemented with 1×HEK-Blue™ Selection.

2—Renew Growth Medium 2 times a week.

3—Cells should be passaged when a 70-80% confluency is reached, detach the cells in presence of PBS by tapping the flask or by using a cell scraper. Do not let the cells grow to 100% confluency. Note: The response of HEK-Blue™-hTLR4 cells can be altered by the action of trypsin. Do not use trypsin to detach HEK-Blue™-hTLR4 cells.

TLR4 Stimulation Determined Using HeK-Blue™ Detection

For real-time detection of SEAP or high-throughput applications we recommend the use of HEK-Blue™ Detection medium (not provided).

1—Add 20 ml of each sample per well of a flat-bottom 96-well plate.
2—Add 20 ml of a positive control (such as LPS-EK Ultrapure, 100 ng/ml) in one well.
3—Add 20 ml of a negative control (such as sterile, endotoxin-free water) in one well.
4—Remove HEK-Blue™-hTLR4 cells from the incubator and discard Growth Medium. Rinse cells with PBS. Add 5-10 ml of PBS to a T-75 flask and place cells at 3° C. for 1-2 min, detach the cells by tapping the flask. Note: At this point in the protocol, care should be taken:
do not add HEK-Blue™ Detection medium
do not centrifuge HEK-Blue™-hTLR4 cells as it can lead to high background or false positive readings.
5—Count cells.
6—Prepare a cell suspension ~140,000 cells per ml in HEK-Blue™ Detection medium and immediately add 180 ml of the cell suspension (~25,000 cells) per well.
7—Incubate the plate at 37° C. in 5% CO2 for 6-16 h. SEAP can be determined with naked eye or using a spectrophotometer at 620-655 nm.

TLR4 Stimulation Determined Using QUAnti-Blue™

QUANTI-Blue™ is 10-times more sensitive than HEK-Blue™ Detection medium and can be used to quantify SEAP activity.

Day one:
1—Add 20 ml of each sample per well of a flat-bottom 96-well plate.
2—Add 20 ml of a positive control (such as LPS-EK Ultrapure, 100 ng/ml) in one well.
3—Add 20 ml of a negative control (such as sterile, endotoxin-free water) in one well.
4—Remove HEK-Blue™-hTLR4 cells from the incubator and discard Growth Medium. Rinse cells with PBS, add PBS (5-10 ml for a T-75 flask) and place cells at 3° C. for 1-2 min, detach the cells by tapping the flask. Note: At this point in the protocol care should be taken, avoid centrifugation of HEK-Blue™-hTLR4 cells, as it can lead to high background or false positive readings.
5—Count cells.
6—Prepare a cell suspension of HEK-Blue™-hTLR4 cells at 140,000 cells per ml in Test Medium which contains 10% (v/v) heat-inactivated fetal bovine serum (FBS). Note: Some fetal bovine serum (FBS) may contain alkaline phosphatases that can interfere with SEAP quantification. To ensure that these thermosensitive enzymes are inactive, use heat-inactivated FBS (30 min at 56° C.). Heat-inactivated FBS is also commercially available.
7—Add 180 ml of the cell suspension (~25,000 cells) per well.
8—Incubate the plate at 37° C. in a $CO_2$ incubator for 20-24 h.

Day two:
1—Prepare QUANTI-Blue™ following the instructions on the pouch.
2—Add 180 ml of resuspended QUANTI-Blue™ per well of a flat-bottom 96-well plate.
3—Add 20 ml of induced HEK-Blue™-hTLR4 cells supernatant.
4—Incubate the plate at 37° C. incubator for 1-3 h.
5—Determine SEAP levels using a spectrophotometer at 620-655 nm.

Specificity of HeK-Blue™-hTLR4 Cells

As HEK293 cells express endogenous levels of TLR3, TLR5 and NOD1, HEK-Blue™-hTLR4 cells will respond to their cognate ligands, such as poly(I:C), flagellin and iE-DAP, respectively. In order to identify TLR4-specific responses, it is recommended to use HEK-Blue™-Null2 Cells as a control cell line. Furthermore, an anti-hTLR4 neutralizing antibody can be used to ensure the specificity of the TLR4 response. Note: HEK-Blue™-hTLR4 cells may be stimulated in a TLR4-independent manner as NF-kB/AP-1 can be activated by a wide variety of stimuli (e.g. TNF-α and PMA).

The following disclosures of the following patents are incorporated in their entirety by reference herein: WIPO Application No. 2007/084633. References and publications cited herein are incorporated in their entirety by reference herein to the extent that these references are consistent with the present invention.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims.

Further Disclosures of the Invention:

In some embodiments, as used in the present disclosure the language "that substantially lacks a ligand that acts as an agonist of TLR4/MD-2 signalling, wherein the TLR4/MD-2 signalling is substantially abrogated" may be replaced with the language of "where an endotoxic signalling activity is substantially abrogated". For example, the present invention features a viable Gram-negative bacterium with substantially reduced bacterial proteolytic activity, the bacterium comprising an outer membrane where an endotoxic signalling activity is substantially abrogated.

In some embodiments, the endotoxic signalling activity is caused by an agonist ligand of the TLR4/MD-2 pattern recognition receptor.

TABLE 1

| | E. coli strain description. |
|---|---|
| KPM22 L11 | (msbA52 ΔkdsD ΔgutQ) |
| KPM274 | KPM22 ΔeptA::Km⁺; ΔeptA::Km⁺ donor strain |
| KPM279 | KPM22 ΔlpxL::Km⁺; ΔlpxL::Km⁺ donor strain |
| KPM280 | KPM22 ΔlpxM::Km⁺; ΔlpxM::Km⁺ donor strain |
| KPM281 | KPM22 ΔlpxL |
| KPM282 | KPM22 ΔlpxM |
| KPM288 | KPM22 ΔlpxL::Km⁺ |
| KPM290 | (msbA52 ΔkdsD ΔgutQ ΔlpxL::Km⁺) |
| KPM296 | ΔlpxL derivative of KPM22 L11 (msbA52 ΔkdsD ΔgutQ ΔlpxL) |

TABLE 1-continued

*E. coli* strain description.

| | |
|---|---|
| KPM296-6 | 42° C.—resistant derivative of KPM296 |
| KPM300 | (msbA52 ΔkdsD ΔgutQ ΔlpxL ΔlpxM::Km⁺) |
| KPM303 | ΔlpxL ΔlpxM derivative of KPM22 L11 |
| | (msbA52 ΔkdsD ΔgutQ ΔlpxL ΔlpxM) |
| BW30270 ΔlpxP::Km⁺ | *E. coli* K-12 wild type; ΔlpxP::Km⁺ donor strain |
| BW30270 ΔpagP::Km⁺ | *E. coli* K-12 wild type; ΔpagP::Km⁺ donor strain |
| KPM310 | (msbA52 ΔkdsD ΔgutQ ΔlpxL ΔlpxM ΔpagP:: Km⁺) |
| KPM312 | ΔlpxL ΔlpxM ΔpagP derivative of KPM22 L11 |
| | (msbA52 ΔkdsD ΔgutQ ΔlpxL ΔlpxM ΔpagP) |
| KPM314 | (msbA52 ΔkdsD ΔgutQ ΔlpxL ΔlpxM ΔpagP ΔlpxP:: Km⁺) |
| KPM316 | ΔlpxL ΔlpxM ΔpagP ΔlpxP derivative of KPM22 L11 |
| | (msbA52 ΔkdsD ΔgutQ ΔlpxL ΔlpxM ΔpagP ΔlpxP) |
| KPM317 | (msbA52 ΔkdsD ΔgutQ ΔlpxL ΔlpxM ΔpagP ΔlpxP ΔeptA::Km⁺) |
| KPM318 | ΔlpxL ΔlpxM ΔpagP ΔlpxP ΔeptA derivative of KPM22 L11 |
| | (msbA52 ΔkdsD ΔgutQ ΔlpxL ΔlpxM ΔpagP ΔlpxP ΔeptA) |
| KPM334 | Temperature-resistant KPM318 derivative KPM318-42C 9 |
| | (msbA52 ΔkdsD ΔgutQ ΔlpxL ΔlpxM ΔpagP ΔlpxP ΔeptA frr181) |
| KPM335 | Temperature-resistant KPM318 derivative KPM318-42C 10 |
| | (msbA52 ΔkdsD ΔgutQ ΔlpxL ΔlpxM ΔpagP ΔlpxP ΔeptA frr181) |
| KPM336 | Temperature-resistant KPM318 derivative KPM318-42C 19 |
| | (msbA52 ΔkdsD ΔgutQ ΔlpxL ΔlpxM ΔpagP ΔlpxP ΔeptA efp') |
| KPM337 | Temperature-resistant KPM318 derivative KPM318-42C 23 |
| | (msbA52 ΔkdsD ΔgutQ ΔlpxL ΔlpxM ΔpagP ΔlpxP ΔeptA dcd') |
| KPM338 | Temperature-resistant KPM334 derivative |
| | (msbA52 ΔkdsD ΔgutQ ΔlpxL ΔlpxM ΔpagP ΔlpxP ΔeptA frr181ΔendA::Km⁺) |
| KPM339 | Temperature-resistant KPM335 derivative |
| | (msbA52 ΔkdsD ΔgutQ ΔlpxL ΔlpxM ΔpagP ΔlpxP ΔeptA frr181ΔendA::Km⁺) |
| KPM340 | Temperature-resistant KPM336 derivative |
| | (msbA52 ΔkdsD ΔgutQ ΔlpxL ΔlpxM ΔpagP ΔlpxP ΔeptA efp' ΔendA::Km⁺) |
| KPM341 | Temperature-resistant KPM337 derivative |
| | (msbA52 ΔkdsD ΔgutQ ΔlpxL ΔlpxM ΔpagP ΔlpxP ΔeptA dcd' ΔendA::Km⁺) |
| KPM342 | (msbA52 ΔkdsD ΔgutQ ΔlpxL ΔlpxM ΔpagP ΔlpxP ΔeptA ΔendA::Km⁺) |
| KPM343 | Temperature-resistant ΔendA derivative of KPM334 |
| | (msbA52 ΔkdsD ΔgutQ ΔlpxL ΔlpxM ΔpagP ΔlpxP ΔeptA frr181ΔendA) |
| KPM344 | Temperature-resistant ΔendA derivative of KPM335 |
| | (msbA52 ΔkdsD ΔgutQ ΔlpxL ΔlpxM ΔpagP ΔlpxP ΔeptA frr181ΔendA) |
| KPM345 | Temperature-resistant ΔendA derivative of KPM336 |
| | (msbA52 ΔkdsD ΔgutQ ΔlpxL ΔlpxM ΔpagP ΔlpxP ΔeptA efp' ΔendA) |
| KPM346 | Temperature-resistant ΔendA derivative of KPM337 |
| | (msbA52 ΔkdsD ΔgutQ ΔlpxL ΔlpxM ΔpagP ΔlpxP ΔeptA dcd' ΔendA) |
| KPM347 | ΔendA derivative of KPM318 |
| | (msbA52 ΔkdsD ΔgutQ ΔlpxL ΔlpxM ΔpagP ΔlpxP ΔeptA ΔendA) |
| KPM348 | Temperature-resistant derivative of KPM343 |
| | (msbA52 ΔkdsD ΔgutQ ΔlpxL ΔlpxM ΔpagP ΔlpxP ΔeptA frr181ΔendA ΔrecA::Km⁺) |
| KPM349 | Temperature-resistant derivative of KPM344 |
| | (msbA52 ΔkdsD ΔgutQ ΔlpxL ΔlpxM ΔpagP ΔlpxP ΔeptA frr181ΔendA ΔrecA::Km⁺) |
| KPM350 | Temperature-resistant derivative of KPM345 |
| | (msbA52 ΔkdsD ΔgutQ ΔlpxL ΔlpxM ΔpagP ΔlpxP ΔeptA efp' ΔendA ΔrecA::Km⁺) |
| KPM351 | Temperature-resistant derivative of KPM346 |
| | (msbA52 ΔkdsD ΔgutQ ΔlpxL ΔlpxM ΔpagP ΔlpxP ΔeptA dcd' ΔendA ΔrecA::Km⁺) |
| KPM352 | (msbA52 ΔkdsD ΔgutQ ΔlpxL ΔlpxM ΔpagP ΔlpxP ΔeptA ΔendA ΔrecA::Km⁺) |
| KPM353 | Temperature-resistant ΔendA ΔrecA derivative of KPM334 |
| | (msbA52 ΔkdsD ΔgutQ ΔlpxL ΔlpxM ΔpagP ΔlpxP ΔeptA frr181ΔendA ΔrecA) |
| KPM354 | Temperature-resistant ΔendA ΔrecA derivative of KPM335 |
| | (msbA52 ΔkdsD ΔgutQ ΔlpxL ΔlpxM ΔpagP ΔlpxP ΔeptA frr181ΔendA ΔrecA) |
| KPM355 | Temperature-resistant ΔendA ΔrecA derivative of KPM336 |
| | (msbA52 ΔkdsD ΔgutQ ΔlpxL ΔlpxM ΔpagP ΔlpxP ΔeptA efp' ΔendA ΔrecA) |
| KPM356 | Temperature-resistant ΔendA ΔrecA derivative of KPM337 |
| | (msbA52 ΔkdsD ΔgutQ ΔlpxL ΔlpxM ΔpagP ΔlpxP ΔeptA dcd' ΔendA ΔrecA) |
| KPM357 | ΔendA ΔrecA derivative of KPM318 |
| | (msbA52 ΔkdsD ΔgutQ ΔlpxL ΔlpxM ΔpagP ΔlpxP ΔeptA ΔendA ΔrecA) |
| KPM358 | Temperature-resistant KPM334 derivative carrying the plasmid F'121 Tn10 |
| | [msbA52 ΔkdsD ΔgutQ ΔlpxL ΔlpxM ΔpagP ΔlpxP ΔeptA frr181 (F'121 Tn10)] |
| KPM359 | Temperature-resistant KPM335 derivative carrying the plasmid F'121 Tn10 |
| | [msbA52 ΔkdsD ΔgutQ ΔlpxL ΔlpxM ΔpagP ΔlpxP ΔeptA frr181 (F'121 Tn10)] |
| KPM360 | Temperature-resistant KPM336 derivative carrying the plasmid F'121 Tn10 |
| | [msbA52 ΔkdsD ΔgutQ ΔlpxL ΔlpxM ΔpagP ΔlpxP ΔeptA efp' (F'121 Tn10)] |
| KPM361 | Temperature-resistant KPM337 derivative carrying the plasmid F'121 Tn10 |
| | [msbA52 ΔkdsD ΔgutQ ΔlpxL ΔlpxM ΔpagP ΔlpxP ΔeptA dcd' (F'121 Tn10)] |
| KPM362 | KPM318 derivative carrying the plasmid F'121 Tn10 |
| | [msbA52 ΔkdsD ΔgutQ ΔlpxL ΔlpxM ΔpagP ΔlpxP ΔeptA (F'121 Tn10)] |

TABLE 2

ESI FT-ICR MS peak list of glycoforms detected in E. coli KPM318.

| Obs. Mass [u] | Calc. Mass [u] | Chemical Composition | Glycoform |
|---|---|---|---|
| 3544.4065 | 3544.3941 | 1* Gal 3* Glc 4* Hep 2* Kdo 4* P 1* P—EtN | II |
| 3556.4395 | 3556.3975 | 1* Gal 2* Glc 3* Hep 3* Kdo 4* P 1* P—EtN 1* Rha | IV |
| 3566.3995 | | 1* Gal 3* Glc 4* Hep 2* Kdo 4* P 1* P—EtN 1*Na | II |
| 3578.3653 | | 1* Gal 2* Glc 3* Hep 3* Kdo 4* P 1* P—EtN 1* Rha 1* Na | IV |
| 3624.4402 | 3624.3604 | 1* Gal 3* Glc 4* Hep 2* Kdo 5* P 1* P—EtN | I |
| | 3624.465 | 1*GlcNAc 1* Gal 3* Glc 4* Hep 2* Kdo 4* P | II |
| 3646.3195 | | 1* Gal 3* Glc 4* Hep 2* Kdo 5* P 1* P—EtN 1* Na | I |
| | | 1*GlcNAc 1* Gal 3* Glc 4* Hep 2* Kdo 5* P 1* Na | II |
| 3658.3357 | | 1* Gal 2* Glc 3* Hep 3* Kdo 5* P 1* P—EtN 1* Rha 1* Na | IV |
| 3667.4007 | 3667.5072 | 1*GlcNAc 1* Gal 3* Glc 4* Hep 2* Kdo 3* P 1* P—EtN | II |
| | 3704.4313 | 1*GlcNAc 1* Gal 3* Glc 4* Hep 2* Kdo 3* P | II |
| 3748.3038 | | 1*GlcNAc 1* Gal 3* Glc 4* Hep 2* Kdo 3* P 2* Na | II |
| | 3747.4735 | 1*GlcNAc 1* Gal 3* Glc 4* Hep 2* Kdo 4* P 1* P—EtN | II |
| | 3783.4987 | 1* Gal 2* Glc 3* Hep 3* Kdo 4* P 1* P—EtN 1* Rha 1* HexA 1* Ara4N | |
| | 3797.3734 | 1* Gal 2* Glc 3* Hep 3* Kdo 5* P 1* P—EtN 1* HexA 1* Ara4N | |
| | 3798.5426 | 1*GlcNAc 1* Gal 3* Glc 4* Hep 2* Kdo 5* P 1* P—EtN 1* Ara4N | |

TABLE 3

Optical density and cell number of the bacterial suspensions immediately before the induction with IPTG.

| Strain | Optical density ($OD_{600}$) immediately before the induction | Cell number (cfu/ml) |
|---|---|---|
| BW30270/pJexpress404:51149 | 0.519 | N.D. |
| KPM318/pJexpress404:51149 | 0.540 | N.D. |
| KPM318-9/pJexpress404:51149 | 0.603 | $4.7 \times 10^7$ |
| KPM318-10/pJexpress404:51149 | 0.566 | $9.2 \times 10^7$ |
| KPM318-19/pJexpress404:51149 | 0.539 | $1.3 \times 10^8$ |
| BW30270/pJexpress404:51150 | 0.555 | $8.0 \times 10^5$ |
| KPM318/pJexpress404:51150 | 0.548 | $6.4 \times 10^7$ |
| KPM318-9/pJexpress404:51150 | 0.600 | $7.1 \times 10^7$ |
| KPM318-10/pJexpress404:51150 | 0.601 | $8.5 \times 10^7$ |
| KPM318-19/pJexpress404:51150 | 0.633 | $1.5 \times 10^8$ |

TABLE 4

Optical density and cell number of the bacterial suspensions after 3 hr of induction.

| Strain | Optical density ($OD_{600}$) 3 h post-induction | Cell number (cfu/ml) |
|---|---|---|
| BW30270/pJexpress404:51149 | 2.66 | N.D. |
| KPM318/pJexpress404:51149 | 2.89 | N.D. |
| KPM318-9/pJexpress404:51149 | 2.76 | $7.4 \times 10^8$ |
| KPM318-10/pJexpress404:51149 | 2.73 | $7.8 \times 10^8$ |
| KPM318-19/pJexpress404:51149 | 1.73 | $7.8 \times 10^8$ |
| BW30270/pJexpress404:51150 | 1.73 | $1.0 \times 10^8$ |
| KPM318/pJexpress404:51150 | 2.04 | $3.9 \times 10^7$ |
| KPM318-9/pJexpress404:51150 | 1.93 | $4.4 \times 10^7$ |
| KPM318-10/pJexpress404:51150 | 1.86 | $7.2 \times 10^7$ |
| KPM318-19/pJexpress404:51150 | 1.49 | $1.0 \times 10^8$ |

TABLE 5

Optical density and cell number of the bacterial suspensions after 6 hr of induction.

| Strain | Optical density ($OD_{600}$) 6 hr post-induction | Cell number (cfu/ml) |
|---|---|---|
| BW30270/pJexpress404:51149 | 4.85 | N.D. |
| KPM318/pJexpress404:51149 | 4.99 | N.D. |
| KPM318-9/pJexpress404:51149 | 4.77 | $9.6 \times 10^8$ |
| KPM318-10/pJexpress404:51149 | 4.61 | $2.0 \times 10^9$ |
| KPM318-19/pJexpress404:51149 | 3.59 | $2.7 \times 10^8$ |
| BW30270/pJexpress404:51150 | 2.57 | $3.5 \times 10^7$ |
| KPM318/pJexpress404:51150 | 3.32 | $2.1 \times 10^7$ |
| KPM318-9/pJexpress404:51150 | 3.42 | $2.3 \times 10^8$ |
| KPM318-10/pJexpress404:51150 | 3.39 | $1.9 \times 10^7$ |
| KPM318-19/pJexpress404:51150 | 2.38 | $2.3 \times 10^8$ |

TABLE 6

Optical density and cell number of the bacterial suspensions after 12 hr of induction.

| Strain | Optical density ($OD_{600}$) 12 hr post-induction | Cell number (cfu/ml) |
|---|---|---|
| BW30270/pJexpress404:51149 | 8.73 | N.D. |
| KPM318/pJexpress404:51149 | 8.74 | N.D. |
| KPM318-9/pJexpress404:51149 | 9.08 | $6.9 \times 10^8$ |
| KPM318-10/pJexpress404:51149 | 9.10 | $8.7 \times 10^8$ |
| KPM318-19/pJexpress404:51149 | 6.15 | $2.2 \times 10^7$ |
| BW30270/pJexpress404:51150 | 6.80 | $1.0 \times 10^7$ |
| KPM318/pJexpress404:51150 | 7.59 | $1.0 \times 10^5$ |
| KPM318-9/pJexpress404:51150 | 7.44 | $3.1 \times 10^4$ |
| KPM318-10/pJexpress404:51150 | 7.75 | $4.1 \times 10^4$ |
| KPM318-19/pJexpress404:51150 | 4.63 | $5.8 \times 10^7$ |

TABLE 7

Optical density and cell number of the bacterial suspensions after 24 hr of induction.

| Strain | Optical density ($OD_{600}$) 24 hr post-induction | Cell number (cfu/ml) |
|---|---|---|
| BW30270/pJexpress404:51149 | 12.95 | N.D. |
| KPM318/pJexpress404:51149 | 11.85 | N.D. |
| KPM318-9/pJexpress404:51149 | 10.50 | $3.0 \times 10^8$ |
| KPM318-10/pJexpress404:51149 | 10.90 | to the $10^{-6}$ dilut.: - |
| KPM318-19/pJexpress404:51149 | 7.75 | $1.0 \times 10^7$ |
| BW30270/pJexpress404:51150 | 10.00 | $5.0 \times 10^5$ |
| KPM318/pJexpress404:51150 | 13.75 | $4.2 \times 10^4$ |
| KPM318-9/pJexpress404:51150 | 12.30 | $2.4 \times 10^4$ |

TABLE 7-continued

Optical density and cell number of the bacterial suspensions after 24 hr of induction.

| Strain | Optical density ($OD_{600}$) 24 hr post-induction | Cell number (cfu/ml) |
|---|---|---|
| KPM318-10/pJexpress404:51150 | 14.20 | $2.0 \times 10^4$ |
| KPM318-19/pJexpress404:51150 | 7.50 | $2.0 \times 10^5$ |

TABLE 8

Determination of the amount of culture media obtained from cells immediately before the induction with IPTG.

| Strain | Optical density ($OD_{600}$) immediately before the induction | Culture medium (µl) |
|---|---|---|
| BW30270/pJexpress404:51150 | 0.555 | 9.9 |
| KPM318/pJexpress404:51150 | 0.548 | 10.0 |
| KPM318-9/pJexpress404:51150 | 0.600 | 9.1 |
| KPM318-10/pJexpress404:51150 | 0.601 | 9.1 |
| KPM318-19/pJexpress404:51150 | 0.633 | 8.7 |

TABLE 9

Determination of the amount of culture media obtained from cells after 3 hr of induction.

| Strain | Optical density ($OD_{600}$) 3 hr post-induction | Culture medium (µl) |
|---|---|---|
| BW30270/pJexpress404:51150 | 1.73 | 8.6 |
| KPM318/pJexpress404:51150 | 2.04 | 7.3 |
| KPM318-9/pJexpress404:51150 | 1.93 | 7.7 |
| KPM318-10/pJexpress404:51150 | 1.86 | 8.0 |
| KPM318-19/pJexpress404:51150 | 1.49 | 10.0 |

TABLE 10

Determination of the amount of culture media obtained from cells after 6 hr of induction.

| Strain | Optical density ($OD_{600}$) 6 hr post-induction | Culture medium (µl) |
|---|---|---|
| BW30270/pJexpress404:51150 | 2.57 | 9.3 |
| KPM318/pJexpress404:51150 | 3.32 | 7.2 |
| KPM318-9/pJexpress404:51150 | 3.42 | 7.0 |
| KPM318-10/pJexpress404:51150 | 3.39 | 7.0 |
| KPM318-19/pJexpress404:51150 | 2.38 | 10.0 |

TABLE 11

Determination of the amount of culture media obtained from cells after 12 hr of induction.

| Strain | Optical density ($OD_{600}$) 12 hr post-induction | Culture medium (µl) |
|---|---|---|
| BW30270/pJexpress404:51150 | 6.80 | 6.8 |
| KPM318/pJexpress404:51150 | 7.59 | 6.1 |
| KPM318-9/pJexpress404:51150 | 7.44 | 6.2 |
| KPM318-10/pJexpress404:51150 | 7.75 | 6.0 |
| KPM318-19/pJexpress404:51150 | 4.63 | 10.0 |

TABLE 12

Determination of the amount of culture media obtained from cells after 24 hr of induction.

| Strain | Optical density ($OD_{600}$) 24 hr post-induction | Culture medium (µl) |
|---|---|---|
| BW30270/pJexpress404:51150 | 10.00 | 7.5 |
| KPM318/pJexpress404:51150 | 13.75 | 5.4 |
| KPM318-9/pJexpress404:51150 | 12.30 | 6.1 |
| KPM318-10/pJexpress404:51150 | 14.20 | 5.3 |
| KPM318-19/pJexpress404:51150 | 7.50 | 10.0 |

TABLE 13

Number of electrocompetent cells.

| Strain | Cell number (cfu/ml) |
|---|---|
| BW30270 | $7.3 \times 10^8$ |
| KPM318 (LB) | $4 \times 10^9$ |
| KPM318 (LB A5P/G6P) | $1.1 \times 10^9$ |

TABLE 14

Transformation efficiencies for *E. coli* strains BW30270, KPM318 (LB) and KPM318 (LB A5P/G6P).

| Strain | Transformation efficiency (cfu/µg pMAL-c2 DNA) |
|---|---|
| BW30270 | $1.06 \times 10^7$ |
| KPM318 (LB) | $3.64 \times 10^6$ |
| KPM318 (LB A5P/G6P) | $2.51 \times 10^7$ |

TABLE 15

Transformation efficiencies for *E. coli* strains KPM318-9, KPM318-10, KPM318-19, and KPM318-23.

| Strain | Transformation efficiency (cfu/µg pMAL-c2 DNA) | Transformation efficiency (cfu/µg pMAL-p2 DNA) |
|---|---|---|
| KPM318-9 | $3.44 \times 10^7$ | $7.12 \times 10^7$ |
| KPM318-10 | $2.33 \times 10^7$ | $2.78 \times 10^7$ |
| KPM318-19 | $1.29 \times 10^8$ | $1.40 \times 10^8$ |
| KPM318-23 | $1.08 \times 10^4$ | $8.20 \times 10^3$ |

TABLE 16

Yields of plasmids pMAL-c2 and pMAL-p2 isolated from *E. coli* strains BW30270, KPM318, KPM318-9, KPM318-10, KPM318-19, and KPM318-23.

| Strain | Yield of pMAL-c2 (µg DNA/5 ml culture) | Yield of pMAL-p2 (µg DNA/5 ml culture) |
|---|---|---|
| BW30270 | 1.36 | 3.04 |
| KPM318 | 0.76 | 0.92 |
| KPM318-9 | 1.6 | 1.44 |
| KPM318-10 | 1.28 | 1.2 |
| KPM318-19 | 0.88 | 0.92 |
| KPM318-23 | 0.48 | 0.28 |

TABLE 17

Calculation of the amount of the recipient (BW30270 and KPM318) to add to 500 μl of the donor (JC19022 F'121 Tn10).

| Strain | $OD_{600}$ | Amount of the recipient in μl to add to 500 μl of the donor |
|---|---|---|
| JC19022 F'121 Tn10 (25 μl) | 0.019 | — |
| JC19022 F'121 Tn10 (50 μl) | 0.035 | — |
| JC19022 F'121 Tn10 (100 μl) | 0.07 | — |
| JC19022 F'121 Tn10 (200 μl) | 0.111 | — |
| BW30270 (25 μl) | 0.264 | 210 μl |
| BW30270 (50 μl) | 0.432 | — |
| BW30270 (100 μl) | 0.697 | — |
| BW30270 (200 μl) | 1.008 | — |
| KPM318 (25 μl) | 0.055 | — |
| KPM318 (50 μl) | 0.109 | 509 μl |
| KPM318 (100 μl) | 0.212 | — |
| KPM318 (200 μl) | 0.372 | — |

TABLE 18

Calculation of the amount of the recipient (KPM318-9, KPM318-10, KPM318-19, and KPM318-23) to add to 500 μl of the donor (JC19022 F'121 Tn10).

| Strain | $OD_{600}$ | Amount of the recipient in μl to add to 500 μl of the donor |
|---|---|---|
| JC19022 F'121 Tn10 (25 μl) | 0.035 | — |
| JC19022 F'121 Tn10 (50 μl) | 0.048 | — |
| JC19022 F'121 Tn10 (100 μl) | 0.105 | — |
| JC19022 F'121 Tn10 (200 μl) | 0.163 | — |
| KPM318-9 (25 μl) | 0.117 | 449 μl |
| KPM318-9 (50 μl) | 0.226 | — |
| KPM318-9 (100 μl) | 0.352 | — |
| KPM318-9 (200 μl) | 0.654 | — |
| KPM318-10 (25 μl) | 0.134 | 392 μl |
| KPM318-10 (50 μl) | 0.244 | — |
| KPM318-10 (100 μl) | 0.446 | — |
| KPM318-10 (200 μl) | 0.710 | — |
| KPM318-19 (25 μl) | 0.029 | — |
| KPM318-19 (50 μl) | 0.068 | — |
| KPM318-19 (100 μl) | 0.131 | 401 μl |
| KPM318-19 (200 μl) | 0.245 | — |
| KPM318-23 (25 μl) | 0.127 | 413 μl |
| KPM318-23 (50 μl) | 0.241 | — |
| KPM318-23 (100 μl) | 0.430 | — |
| KPM318-23 (200 μl) | 0.737 | — |

TABLE 19

Optical densities ($OD_{600}$) of the strains immediately before the M13KO7 infection.

| Strain | $OD_{600}$ immediately before the M13KO7 infection |
|---|---|
| BW30270 (control) | 0.717 |
| JC19022 (F'121 Tn10) - control | 0.559 |
| KPM318 (control) | 0.344 |
| BW30270 (F'121 Tn10)-1 | 0.581 |
| BW30270 (F'121 Tn10)-2 | 0.574 |
| BW30270 (F'121 Tn10)-3 | 0.600 |
| BW30270 (F'121 Tn10)-4 | 0.623 |
| KPM318 (F'121 Tn10)-4 | 0.410 |
| KPM318 (F'121 Tn10)-6 | 0.178 |
| KPM318 (F'121 Tn10)-7 | 0.174 |
| KPM318 (F'121 Tn10)-8 | 0.157 |
| KPM318-9 (F'121 Tn10)-1 | 0.128 |
| KPM318-9 (F'121 Tn10)-2 | 0.246 |
| KPM318-9 (F'121 Tn10)-3 | 0.098 |
| KPM318-9 (F'121 Tn10)-4 | 0.261 |
| KPM318-10 (F'121 Tn10)-1 | 0.111 |
| KPM318-10 (F'121 Tn10)-3 | 0.289 |
| KPM318-10 (F'121 Tn10)-4 | 0.166 |
| KPM318-10 (F'121 Tn10)-5 | 0.406 |
| KPM318-19 (F'121 Tn10)-6* | 0.136 |
| KPM318-23 (F'121 Tn10)-1 | 0.219 |
| KPM318-23 (F'121 Tn10)-2 | 0.328 |
| KPM318-23 (F'121 Tn10)-3 | 0.280 |
| KPM318-23 (F'121 Tn10)-5 | 0.252 |

TABLE 20

Number of kanamycin-resistant colonies following infection of potential F'121 Tn10 transconjugants with M13KO7 helper phage.

| Strain | Number of kanamycin-resistant colonies (cfu/ml) |
|---|---|
| BW30270 (control) | 0 |
| JC19022 (F'121 Tn10) - control | $2.8 \times 10^8$ |
| KPM318 (control) | $8.5 \times 10^2$ |
| BW30270 (F'121 Tn10)-1 | $2.7 \times 10^8$ |
| BW30270 (F'121 Tn10)-2 | $1.0 \times 10^8$ |
| BW30270 (F'121 Tn10)-3 | $2.1 \times 10^8$ |
| BW30270 (F'121 Tn10)-4 | $1.7 \times 10^8$ |
| KPM318 (F'121 Tn10)-4 | $4.2 \times 10^4$ |
| KPM318 (F'121 Tn10)-6 | $5.5 \times 10^3$ |
| KPM318 (F'121 Tn10)-7 | $4.4 \times 10^3$ |
| KPM318 (F'121 Tn10)-8 | $6.4 \times 10^4$ |
| KPM318-9 (F'121 Tn10)-1 | $1.4 \times 10^5$ |
| KPM318-9 (F'121 Tn10)-2 | $4.1 \times 10^5$ |
| KPM318-9 (F'121 Tn10)-3 | $3.8 \times 10^7$ |
| KPM318-9 (F'121 Tn10)-4 | $5.6 \times 10^7$ |
| KPM318-10 (F'121 Tn10)-1 | $3.6 \times 10^5$ |
| KPM318-10 (F'121 Tn10)-3 | $7.6 \times 10^4$ |
| KPM318-10 (F'121 Tn10)-4 | $6.5 \times 10^7$ |
| KPM318-10 (F'121 Tn10)-5 | $7.8 \times 10^5$ |
| KPM318-19 (F'121 Tn10)-6 | $6.4 \times 10^6$ |
| KPM318-23 (F'121 Tn10)-1 | $9.8 \times 10^5$ |
| KPM318-23 (F'121 Tn10)-2 | $3.7 \times 10^7$ |
| KPM318-23 (F'121 Tn10)-3 | $1.0 \times 10^7$ |
| KPM318-23 (F'121 Tn10)-5 | $2.3 \times 10^4$ |

TABLE 21

Single nucleotide changes are present in KPM316 relative to the parental strain MG1655, in addition to the msbA52 mutation and the deletion/insertion to inactivate LPS synthetic genes. None are known or predicted to result in any distinctive phenotype.

| Reference Base Position (MG1655 ref) | Base in MG1655 | Base in KPM316 | Gene Affected | Predicted effect |
|---|---|---|---|---|
| 547694 | A | G | ylbB | E to E (silent) |
| 3188791 | C | T | yqiI | S to S (silent) |
| 3753464 | G | C | aldB | T to T (silent) |
| 3957957 | C | T | No annotated feature in region | Unknown effect |

TABLE 22

The BW30270 and KPM318 strains were sequenced at the Scripps Core DNA sequencing facility using Illumina sequencing. All the Single Nucleotide Polymorphisms (SNP) and Deletion/Insertion Polymorphisms (DIP) are indicated. These SNPs and DIPs are assigned based on the comparison of these strains to the Blattner's MG1655 strain. Only those detected at 100% of reads are noted. The msbA-P18S suppressor allele in the original KPM22 L11 strain was identified.

A
BW30270
SNP Calls

| Ref Position | Consens. position | Ref. Allele Base | Mut. Allele Base | Freq | # | tot # | Gene | Amino acid change | Effect | Difference from MG1655 |
|---|---|---|---|---|---|---|---|---|---|---|
| 547694 | 532112 | A | G | 100 | 16 | 16 | ylbB | E to E | silent | BW30270 |
| 3753464 | 3683218 | G | C | 100 | 22 | 22 | oldB | T to T | silent | BW30270 |
| 3957957 | 3879611 | C | T | 100 | 9 | 9 | none | ? | no feature annotated | BW30270 |

DIP Calls
del/insertion cost = 2/2

| Ref Position | Consens. position | Ref. Allele Base | Mut. Allele Base | Freq | # | tot # | Gene | Change | Effect | |
|---|---|---|---|---|---|---|---|---|---|---|
| 3558478 | 3490410 | G | — | 100 | 19 | 19 | glpR | 1 bp DEL | frameshift | BW30270 |

B
KPM318
SNP Calls

| Ref Position | Consens. position | Ref. Allele Base | Mut. Allele Base | Freq | # | tot # | Gene | Amino acid change | Effect | |
|---|---|---|---|---|---|---|---|---|---|---|
| 547694 | 532113 | A | G | 100 | 17 | 17 | ylbB | E to E | silent | BW30270 |
| 965895 | 941104 | C | T | 100 | 24 | 24 | msbA | P18S | known suppressor | KPM96 |
| 3188791 | 3128701 | C | T | 100 | 18 | 18 | yqiI | S to S | silent | KPMs |
| 3644838 | 3571752 | G | T | 100 | 15 | 15 | gor | V173F | altered glutathione oxidoreductase activity ?? | KPMs |
| 3753464 | 3678244 | G | C | 100 | 19 | 19 | oldB | T to T | silent | BW30270 |
| 3798895 | 3720343 | T | A | 100 | 12 | 12 | rfoY | T32Y | altered LPS core sugar synthesis ?? | KPMs |
| 3957957 | 3874634 | C | T | 100 | 10 | 10 | none | ? | no feature annotated | BW30270 |

DIP Calls
del/insertion cost = 2/2

| Ref Position | Consens. position | Ref. Allele Base | Mut. Allele Base | Mutant Freq | # | tot # | Gene | Change | Effect | |
|---|---|---|---|---|---|---|---|---|---|---|
| 3558478 | 3490410 | G | — | 100 | 18 | 18 | glpR | 1 bp DEL | frameshift | BW30270 |

TABLE 23

The four KPM-318 temperature-resistant derivatives, KPM334, KPM335, KPM336, and KPM337 were sequenced at the Scripps Core DNA sequencing facility using Illumina sequencing. All the Single Nucleotide Polymorphisms (SNP) and Deletion/Insertion Polymorphisms (DIP) are indicated. These SNPs and DIPs are assigned based on the comparison of these strains to the Blattner's MG1655 strain. Only those detected at 100% of reads are noted. The msbA-P18S suppressor allele in the original KPM22 L11 strain was identified.

A
KPM318-9
SNP Calls

| Ref Position | Consens. position | Ref. Allele Base | Mut. Allele Base | Freq | # | tot # | Gene | Amino acid change | Effect | |
|---|---|---|---|---|---|---|---|---|---|---|
| 193052 | 191000 | G | T | 100 | 30 | 30 | frr | D61Y | altered ribosome recycling factor | UNIQUE to 9 & 10 |

TABLE 23-continued

The four KPM-318 temperature-resistant derivatives, KPM334, KPM335, KPM336, and KPM337 were sequenced at the Scripps Core DNA sequencing facility using Illumina sequencing. All the Single Nucleotide Polymorphisms (SNP) and Deletion/Insertion Polymorphisms (DIP) are indicated. These SNPs and DIPs are assigned based on the comparison of these strains to the Blattner's MG1655 strain. Only those detected at 100% of reads are noted. The msbA-P18S suppressor allele in the original KPM22 L11 strain was identified.

| Ref Position | Consens. position | Ref. Allele Base | Mut. Allele Base | Freq | # | tot # | Gene | Amino acid change | Effect | Lineage |
|---|---|---|---|---|---|---|---|---|---|---|
| 547694 | 532079 | A | G | 100 | 16 | 16 | ylbB | E to E | silent | BW30270 |
| 965895 | 941032 | C | T | 100 | 19 | 19 | msbA | P18S | known suppressor | KPM96 |
| 3188791 | 3128548 | C | T | 100 | 12 | 12 | yqiI | S to S | silent | KPMs |
| 3644838 | 3571599 | G | T | 100 | 17 | 17 | gor | V137F | altered glutathione oxidoreductase activity ?? | KPMs |
| 3753464 | 3678094 | G | C | 100 | 17 | 17 | oldB | T to T | silent | BW30270 |
| 3798895 | 3720172 | T | A | 100 | 10 | 10 | rfoY | T32Y | altered LPS core sugar synthesis ?? | KPMs |
| 3957957 | 3874474 | C | T | 100 | 10 | 10 | none | ? | no feature annotated | BW30270 |

DIP Calls
del/insertion cost = 2/2

| Ref Position | Consens. position | Ref. Allele Base | Mut. Allele Base | Freq | # | tot # | Gene | Change | Effect | |
|---|---|---|---|---|---|---|---|---|---|---|
| 3558478 | 3490169 | G | — | 100 | 20 | 20 | glpR | 1 bp DEL | frameshift | BW30270 |

B
KPM318-10
SNP Calls

| Ref Position | Consens. position | Ref. Allele Base | Mut. Allele Base | Freq | # | tot # | Gene | Amino acid change | Effect | |
|---|---|---|---|---|---|---|---|---|---|---|
| 193052 | 191008 | G | T | 100 | 28 | 28 | frr | D61Y | altered ribosome recycling factor | UNIQUE to 9 & 10 |
| 547694 | 532080 | A | G | 100 | 18 | 18 | ylbB | E to E | silent | BW30270 |
| 965895 | 941034 | C | T | 100 | 27 | 27 | msbA | P18S | known suppressor | KPM96 |
| 3188791 | 3128576 | C | T | 100 | 13 | 13 | yqiI | S to S | silent | KPMs |
| 3644838 | 3571965 | G | T | 100 | 19 | 19 | gor | V173F | altered glutathione oxidoreductase activity ?? | KPMs |
| 3753464 | 3678183 | G | C | 100 | 19 | 19 | oldB | T to T | silent | BW30270 |
| 3798895 | 3720277 | T | A | 100 | 10 | 10 | rfoY | T32Y | altered LPS core sugar synthesis ?? | KPMs |
| 3957957 | 3874571 | C | T | 100 | 6 | 6 | none | ? | no feature annotated | BW30270 |

DIP Calls
del/insertion cost = 2/2

| Ref Position | Consens. position | Ref. Allele Base | Mut. Allele Base | Freq | # | tot # | Gene | Change | Effect | |
|---|---|---|---|---|---|---|---|---|---|---|
| 3558478 | 3490381 | G | — | 100 | 20 | 20 | glpR | 1 bp DEL | frameshift | BW30270 |

C
KPM318-19
SNP Calls

| Ref Position | Consens. Base | Ref. Allele Base | Mut. Allele Base | Freq | # | tot # | Gene | Amino Acid change | Effect | Lineage |
|---|---|---|---|---|---|---|---|---|---|---|
| 547694 | 532090 | A | G | 100 | 20 | 20 | ylbB | E to E | silent | BW30270 |
| 965895 | 941050 | C | T | 100 | 17 | 17 | msbA | P18S | known suppressor | KPM96 |

TABLE 23-continued

The four KPM-318 temperature-resistant derivatives, KPM334, KPM335, KPM336, and KPM337 were sequenced at the Scripps Core DNA sequencing facility using Illumina sequencing. All the Single Nucleotide Polymorphisms (SNP) and Deletion/Insertion Polymorphisms (DIP) are indicated. These SNPs and DIPs are assigned based on the comparison of these strains to the Blattner's MG1655 strain. Only those detected at 100% of reads are noted. The msbA-P18S suppressor allele in the original KPM22 L11 strain was identified.

| | | | | | | | | | | |
|---|---|---|---|---|---|---|---|---|---|---|
| 3188791 | 3128613 | C | T | 100 | 18 | 18 | yqiI | S to S | silent | KPMs |
| 3644838 | 3571682 | G | T | 100 | 16 | 16 | gor | V173F | altered glutathione oxidoreductase ? | KPMs |
| 3753464 | 3678174 | G | C | 100 | 19 | 19 | oldB | T to T | silent | BW30270 |
| 3798895 | 3720279 | T | A | 100 | 10 | 10 | rfoY | T32Y | altered LPS core sugar synthesis ?? | KPMs |
| 3957957 | 3874575 | C | T | 100 | 12 | 12 | none | ? | no feature annotated | BW30270 |

DIP Calls

| Ref pos | Consens pos | Ref Base | Var Base(s) | Freq | # | tot # | Gene | Change | Effect | Lineage |
|---|---|---|---|---|---|---|---|---|---|---|
| 3558478 | 3490283 | G | — | 100 | 21 | 21 | glpR | 1 bp DEL | frameshift | BW30270 |
| 4373919 | 4271896 | — | T | 100 | 38 | 38 | efp | frameshift in elongation factor P | | THIS ISOLATE-BEST CANDIDATE FOR PHENOTYPE |

D
KPM318-23
SNP Calls

| Ref Position | Consens. position | Ref. Allele Base | Mut. Allele Base | Freq | # | tot # | Gene | Amino Acid change | Effect | Lineage |
|---|---|---|---|---|---|---|---|---|---|---|
| 547694 | 532099 | A | G | 100 | 27 | 27 | ylbB | E to E | silent | BW30270 |
| 965895 | 941061 | C | T | 100 | 25 | 25 | msbA | P18S | known suppressor | KM96 |
| 3188791 | 3128668 | C | T | 100 | 8 | 8 | yqiI | S to S | silent | KPMs |
| 3644838 | 3571751 | G | T | 100 | 23 | 23 | gor | V173F | altered glutathione oxidoreductase activity ?? | KPMs |
| 3753464 | 3678248 | G | C | 100 | 35 | 35 | oldB | T to T | silent | BW30270 |
| 3798895 | 3720343 | T | A | 100 | 12 | 12 | rfoY | T32Y | altered LPS core sugar synthesis | KPMs |
| 3957957 | 3874633 | C | T | 100 | 8 | 8 | none | ? | no feature annotated | BW30270 |

DIP Calls

| Ref pos | Consens pos | Ref Base | Var Base(s) | Freq | # | tot # | Gene | Change | Effect | Lineage |
|---|---|---|---|---|---|---|---|---|---|---|
| 2139799 | 2095371 | CAGCGG | — | 100 | 10 | 10 | dcd | PLPLAL to PLAL | 2 AA deletion | UNIQUE |
| 3558478 | 3490307 | G | — | 100 | 35 | 35 | glpR | 1 bp DEL | frameshift | BW30270 |

TABLE 24

Competent Cell Data

| Strain | Final OD$_{600}$ | Incubation time to Final OD$_{600}$ |
|---|---|---|
| BW30270 | 0.415 | 2 h |
| KPM318 | 0.476 | 4 h 20 min |
| KPM418 | 0.444 | 4 h 20 min |

TABLE 25

Transformation Efficiency

| Strain | Transformants per µg DNA |
|---|---|
| BW30270 | $2.15 \times 10^6$ |
| KPM318 | $9.7 \times 10^3$ |
| KPM418 | $1.2 \times 10^4$ |

TABLE 26

| Strain | Culture volume | DNA Yield (mg) | Endotoxin (EU/ml) | Dilution of prep used for Endotoxin test |
|---|---|---|---|---|
| Mock | 250 ml | n/a | 0.581 | 1 |
| BW30270 | 250 ml | 0.775 | 451 | 1/1000 |
| BW30270 | 1 L | 0.700 | 1835 | 1/1000 |
| KPM318 | 250 ml | 0.402 | 1.89 | 1 |
| KPM318 | 1 L | 0.568 | 3.65 | 1/10 |
| KPM418 | 250 ml | 0.329 | 12.9 | 1/10 |
| KPM418 | 1 L | 0.645 | 11.2 | 1/10 |

TABLE 27

| Strain | Culture volume (ml) | Total Prep volume (ml) | Total DNA Yield (mg) | DNA conc (mg/ml) | Total EU | Endotoxin (EU/ml) | Total HEK Blue LPS (ng) | HEK-Blue LPS conc (ng/ml) |
|---|---|---|---|---|---|---|---|---|
| Mock | 250 | 0.5 | n/a | n/a | $1.43 \times 10^3$ | 0.581 | .005 | 0.01 |
| BW30270 | 250 | 0.5 | 0.775 | 1.55 | $1.13 \times 10^5$ | 451 | 5 | 10 |
| BW30270 | 1000 | 0.5 | 0.700 | 1.4 | $1.84 \times 10^6$ | 1835 | 5 | 10 |
| KPM318 | 250 | 0.5 | 0.402 | 0.8 | $4.73 \times 10^2$ | 1.89 | .005 | 0.01 |
| KPM318 | 1000 | 0.5 | 0.568 | 1.14 | $3.65 \times 10^3$ | 3.65 | .005 | 0.01 |
| KPM418 | 250 | 0.5 | 0.329 | .65 | $3.23 \times 10^3$ | 12.9 | .005 | 0.01 |
| KPM418 | 1000 | 0.5 | 0.645 | 1.29 | $11.2 \times 10^3$ | 11.2 | .005 | 0.01 |

TABLE 28

HEK-blue Assay data

| dilution factor | BW-.25 Mean | BW-1 Mean | KPM318-.25 Mean | KPM318-1 Mean | KPM418-.25 Mean | KPM418-1 Mean | Mock Mean | Endo-free water Mean |
|---|---|---|---|---|---|---|---|---|
| 1× | 1.1829 | 1.238367 | 0.174 | 0.1545 | 0.2108 | 0.1192 | 0.232167 | 0.1596 |
| 10× | 1.041633 | 1.0861 | 0.144067 | 0.150033 | 0.1561 | 0.154433 | 0.1502 | |
| 100× | 0.412567 | 0.4602 | 0.143467 | 0.1499 | 0.152067 | 0.161267 | 0.147267 | |
| 1000× | 0.1713 | 0.179867 | | | | | | |
| 10^4× | 0.144333 | 0.1441 | | | | | | |
| 10^5× | 0.139 | 0.143933 | | | | | | |
| 10^6× | 0.145367 | 0.144967 | | | | | | |
| 10^7× | 0.151433 | 0.150767 | | | | | | |

| dilution factor | BW-.25 SD | BW-1 SD | KPM318-.25 SD | KPM318-1 SD | KPM418-.25 SD | KPM418-1 SD | Mock SD | Endo-free water Mean |
|---|---|---|---|---|---|---|---|---|
| 1× | 0.036206 | 0.037146 | 0.005406 | 0.003251 | 0.017954 | 0.018237 | 0.015476 | 0.010966 |
| 10× | 0.013812 | 0.01963 | 0.007061 | 0.003443 | 0.007318 | 0.007051 | 0.003161 | |
| 100× | 0.009306 | 0.014908 | 0.006137 | 0.003027 | 0.006503 | 0.003963 | 0.003496 | |
| 1000× | 0.001345 | 0.003584 | | | | | | |
| 10^4× | 0.001617 | 0.002193 | | | | | | |
| 10^5× | 0.002706 | 0.004594 | | | | | | |
| 10^6× | 0.002974 | 0.004735 | | | | | | |
| 10^7× | 0.002658 | 0.001858 | | | | | | |

TABLE 29

Doubling time of E. coli KPM22 and KPM22-like strains in LB medium at 37° C.

| 1. Strain | 2. Doubling time [min] |
|---|---|
| KPM22 | 40 |
| KPM22 L1 | 37 |
| KPM22 L11 | 39 |
| KPM22 L14 | 44 |
| KPM22 L15 | 40 |
| KPM22 L18 | 36 |

TABLE 30

Doubling time of E. coli BL21 (DE3) ΔlpxL msbA suppressor strains in LB medium at 37° C.

| 3. Strain | 4. Doubling time [min] |
|---|---|
| BL21 (DE3) | 30 |
| BL21 (DE3) ΔlpxL msbA L1 | 46 |
| BL21 (DE3) ΔlpxL msbA L11 | 93 |
| BL21 (DE3) ΔlpxL msbA L14 | 36 |

TABLE 30-continued

Doubling time of E. coli BL21 (DE3) ΔlpxL msbA suppressor strains in LB medium at 37° C.

| 3. Strain | 4. Doubling time [min] |
|---|---|
| BL21 (DE3) ΔlpxL msbA L15 | 115 |
| BL21 (DE3) ΔlpxL msbA L18 | 72 |

TABLE 31

Doubling time of E. coli BL21 (DE3) ΔlpxL msbA suppressor strains in SB medium at 37° C.

| 5. Strain | 6. Doubling time [min] |
|---|---|
| BL21 (DE3) | 33 |
| BL21 (DE3) ΔlpxL msbA L1 | 51 |
| BL21 (DE3) ΔlpxL msbA L11 | 80 |
| BL21 (DE3) ΔlpxL msbA L14 | 41 |
| BL21 (DE3) ΔlpxL msbA L15 | 97 |
| BL21 (DE3) ΔlpxL msbA L18 | 50 |

What is claimed is:

1. An isolated viable Gram-negative bacterium with substantially reduced bacterial proteolytic activity, wherein said bacterium is *Escherichia coli* and comprises (a) a mutation in at least one of the genes selected from the group consisting of kdsA, kdsC, kdsB, and waaA, or a mutation in each of the kdsD and gutQ genes, wherein said mutation results in a disruption in the biosynthesis of $(Kdo)_2$-lipid $IV_A$, (b) a mutation in each of the genes pagP and eptA wherein said mutation substantially inactivates the enzymatic activity of each of the proteins encoded by the pagP and eptA genes, and (c) a suppressor mutation in the msbA gene or the yjhD gene, such that the outer membrane of the bacterium substantially lacks a ligand that acts as an agonist of TLR4/MD-2 signaling, and TLR4/MD-2 signaling is substantially abrogated.

2. The viable Gram-negative bacterium of claim 1, wherein the bacterium comprises a mutation in a protease gene.

3. The viable Gram-negative bacterium of claim 2, wherein the protease gene is ompT.

4. The viable Gram-negative bacterium of claim 2, wherein the mutation comprises an insertion sequence in the promoter region of the protease gene to reduce expression of the protease.

5. The viable Gram-negative bacterium of claim 4, wherein the protease is the Lon protease.

6. The viable Gram-negative bacterium of claim 1, wherein the first mutation comprises the deletion of kdsD and gutQ.

7. The isolated, viable Gram-negative bacterium of claim 1, wherein the second mutation comprises a mutation in the msbA transporter gene which results in an amino acid substitution in MsbA selected from the group consisting of P50S, P18S, T283A, R310S, and L48F.

8. The viable Gram-negative bacterium of claim 1, comprising deletions of the lpxL, lpxM, pagP, lpxP, and eptA genes.

9. The viable Gram-negative bacterium of claim 1, wherein said bacterium comprises a deletion of kdsD and gutQ, a mutation in msbA resulting in the amino acid substitution P50S, and deletions of the lpxL, lpxM, pagP, lpxP, and eptA genes.

10. The viable Gram-negative bacterium of claim 1, wherein the second mutation is in the yhjD gene resulting in the amino acid substitution of R134C.

11. The viable Gram-negative bacterium of claim 1, wherein the bacterium comprises at least one additional suppressor mutation that enables growth at 42 degrees Celsius.

12. The viable Gram-negative bacterium of claim 1, wherein the bacterium is competent to take up extracellular DNA.

13. The viable Gram-negative bacterium of claim 1, wherein the bacterium is electrocompetent.

14. A method of expressing a protein utilizing a viable Gram-negative bacterium, comprising:
  providing a bacterium according to claims 1;
    transfecting the bacterium with a plasmid containing the nucleotide sequence for the protein to be expressed;
    culturing the bacterium in a fermentation medium having a NaCl concentration in the range of 0.1 M to 0.9 M; and
    expressing the protein in said bacterium in the culture.

15. The method of claim 14, wherein the first mutation in the bacterium comprises the deletion of kdsD and gutQ.

16. The method of claim 14, wherein the bacterium comprises deletions of the lpxL, lpxM, pagP, lpxP, and eptA genes.

17. The method of claim 14, wherein the second mutation in the bacterium is in the yhjD gene resulting in the amino acid substitution of R134C.

18. The method of claim 14, wherein the bacterium comprises at least one additional suppressor mutation that enables growth at 42 degrees Celsius.

19. The method of claim 14, wherein the bacterium is competent to take up extracellular DNA.

* * * * *